US012679822B2

(12) United States Patent
Deng et al.

(10) Patent No.: US 12,679,822 B2
(45) Date of Patent: Jul. 14, 2026

(54) ALKENYL PYRIMIDINE COMPOUND, PREPARATION METHOD THEREFOR, AND APPLICATION THEREOF

(71) Applicant: Hongyun Biotech Co., Ltd., Nanjing (CN)

(72) Inventors: Xianming Deng, Xiamen (CN); Wei Huang, Nanjing (CN); Zhenhua Wu, Xiamen (CN); Yachuang Wu, Beijing (CN); Caihong Yun, Beijing (CN); Jianming Zhang, Shanghai (CN); Xin Huang, Nanjing (CN)

(73) Assignee: Hongyun Biotech Co., Ltd., Nanjing (CN)

( * ) Notice: Subject to any disclaimer, the term of this patent is extended or adjusted under 35 U.S.C. 154(b) by 744 days.

(21) Appl. No.: 18/001,004

(22) PCT Filed: Jun. 7, 2021

(86) PCT No.: PCT/CN2021/098539
§ 371 (c)(1),
(2) Date: Dec. 7, 2022

(87) PCT Pub. No.: WO2021/249324
PCT Pub. Date: Dec. 16, 2021

(65) Prior Publication Data

US 2023/0212147 A1 Jul. 6, 2023

(30) Foreign Application Priority Data

Jun. 8, 2020 (CN) ......................... 202010510345.7
May 28, 2021 (CN) ......................... 202110590788.6

(51) Int. Cl.

| | |
|---|---|
| *C07D 401/14* | (2006.01) |
| *A61K 31/506* | (2006.01) |
| *A61K 31/55* | (2006.01) |
| *A61K 31/675* | (2006.01) |
| *A61K 39/395* | (2006.01) |
| *C07D 403/12* | (2006.01) |
| *C07D 403/14* | (2006.01) |
| *C07F 9/53* | (2006.01) |

(52) U.S. Cl.
CPC .......... *C07D 401/14* (2013.01); *A61K 31/506* (2013.01); *A61K 31/55* (2013.01); *A61K 31/675* (2013.01); *A61K 39/3955* (2013.01); *C07D 403/12* (2013.01); *C07D 403/14* (2013.01); *C07F 9/5325* (2013.01)

(58) Field of Classification Search
None
See application file for complete search history.

(56) References Cited

U.S. PATENT DOCUMENTS

2006/0247262 A1 11/2006 Baenteli et al.
2007/0105839 A1 5/2007 Imbach et al.
2012/0316135 A1 12/2012 Dalgarno et al.
2020/0207768 A1 7/2020 Wu et al.
2023/0219986 A1 * 7/2023 Deng .................. C07F 9/65583 514/81

FOREIGN PATENT DOCUMENTS

CN 1882578 A 12/2006
CN 109575045 A 4/2019
CN 112538072 A 3/2021
EP 3656769 A1 5/2020
(Continued)

OTHER PUBLICATIONS

Database Caplus Chemical Abstracts Service, Columbus, Ohio, US; Database Accession No. 1992:73028, AN: 2022:1300369, Abstract of WO 2022100688, May 19, 2022, Nanjing Hongyun Biotechnology; Hongyun Biotech, Deng et al. (Year: 2022).*
(Continued)

*Primary Examiner* — Karl J Puttlitz
(74) *Attorney, Agent, or Firm* — Kilpatrick Townsend & Stockton LLP

(57) ABSTRACT

The present invention relates to an alkenyl pyrimidine compound, a preparation method therefor, and an application thereof. Particularly, the present invention relates to a compound having EGFR inhibitory activity and a pharmaceutically acceptable salt thereof or a pharmaceutically acceptable solvate thereof, a preparation method thereof, a pharmaceutical composition containing the compound, and a use of the compound in the preparation of drugs for preventing and/or treating cancer and other diseases mediated by EGFR kinase.

(A)

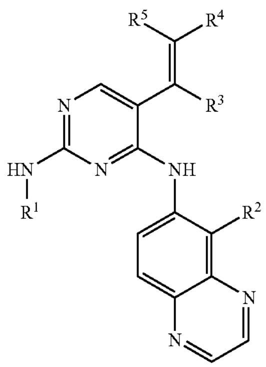

11 Claims, No Drawings

(56) References Cited

FOREIGN PATENT DOCUMENTS

| | | | | | |
|---|---|---|---|---|---|
| EP | 4129996 | A1 | | 2/2023 | |
| JP | 2007505858 | A | | 3/2007 | |
| JP | 2014514348 | A | | 6/2014 | |
| KR | 20190108079 | A | | 9/2019 | |
| TW | 202128670 | A | | 8/2021 | |
| WO | 2018108064 | A1 | | 6/2018 | |
| WO | WO-2019015655 | A1 | * | 1/2019 | .............. A61P 35/00 |
| WO | 2020/216371 | A1 | | 10/2020 | |
| WO | 2021/104305 | A1 | | 6/2021 | |
| WO | WO-2022100688 | A1 | * | 5/2022 | ........... C07D 403/14 |

OTHER PUBLICATIONS

PCT/CN2021/098539, "International Search Report and Written Opinion," Sep. 1, 2021, 26 pages (English translation attached).
European Application No. 21822456.6, Extended European Search Report mailed on Jun. 19, 2024, 8 pages.
Japanese Application No. 2022-565613, Office Action mailed on Nov. 21, 2023, 10 pages (5 pages of Original Document and 5 pages of English Translation).
International Application No. PCT/CN2021/098539, International Preliminary Report on Patentability mailed on Dec. 22, 2022, 20 pages (7 pages of Original Document and 13 pages of English Translation).
Taiwan Application No. 110120527, Office Action mailed on Jun. 24, 2024, 18 pages (9 pages of Original Document and 9 pages of English Translation).
CN200180041038 Office Action, dated Sep. 29, 2024, pp. 1-26, English translation begins on p. 14.

* cited by examiner

ALKENYL PYRIMIDINE COMPOUND, PREPARATION METHOD THEREFOR, AND APPLICATION THEREOF

TECHNICAL FIELD

The present invention relates to the field of medicinal chemistry, and in particular to an alkenylpyrimidine compound and its preparation method and application.

BACKGROUND ART

Epidermal Growth Factor Receptor (EGFR) is a tyrosine kinase that is widely distributed on human cell membranes. When stimulated by endogenous ligands, the EGFR will take dimerization and self-phosphorylation, to activate downstream signal pathways and promote activities such as cell growth, proliferation, migration, etc. After the occurrence of EGFR mutations, for example, most common exon No. 19 deletion (19 Del) or exon No. 20 point mutation (L858R), it will cause the activity of the kinase and the activation of the downstream signal pathways to increase, and further lead to the occurrences of tumors. Researches have shown that at least 10% of patents suffering from non-small cell lung cancer have the EGFR mutations (Nature Reviews Cancer, 2007, 7, 169-181). Hence, targeting the EGFR has been an effective means for treating the non-small cell lung cancer.

Gefitinib and Erlotinib are the earliest ATP competitive EGFR inhibitors that are approved, and they have excellent inhibitory effects on 19Del and L858R mutations. However, after a period of treatments, patients are prone to acquire drug resistance, and the main mechanism resides in that the EGFR further acquires a T790M mutation. Subsequently, researchers have developed second-generation and third-generation inhibitors, e.g., Afatinib and Osimertinib, which, by forming a covalent bond with the Cysteine residue at 797 site of the EGFR, irreversibly block the bonding of the ATP and the EGFR, thereby overcoming the T790M mutation. Moreover, because the third generation inhibitors have weak inhibitory activities on wild EGFR, they can reduce toxic side effects of the second generation inhibitors.

However, the third-generation inhibitors are also confronted to the problem of drug resistance (Nature Medicine, 2015, 21, 560-562), and the main mechanism resides in that the Cysteine residue at 797 site of EGFR is mutated to a Serine residue (C797S), which causes the disappearance of the covalent actions between the Cys and the inhibitors and the reduction of the inhibitory effects.

Hence, the development of fourth-generation EGFR inhibitors which can overcome the C797S mutation will have great significance and clinical values.

SUMMARY OF INVENTION

After extensive and in-depth research, the inventors of the present invention have designed and synthesized a series of small molecule compounds having novel structures, which have good inhibitory effects on a plurality of common EGFR kinase mutants in clinical, including mutants comprising the C797S mutation.

The present invention provides a compound represented by the general formula:

(A)

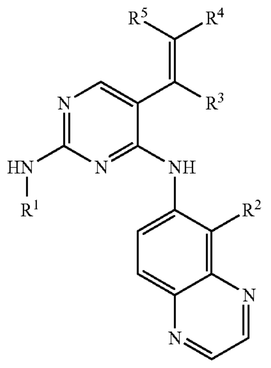

or a stereoisomer, a prodrug, a pharmaceutically acceptable salt or a pharmaceutically acceptable solvate of the above compound.

The definitions of substituents and symbols in the formula are described in detail below.

One object of the present invention is to provide a compound having EGFR kinase inhibitory activity, and a stereoisomer thereof, a prodrug thereof, a pharmaceutically acceptable salt thereof or a pharmaceutically acceptable solvate thereof.

Another object of the present invention is to provide a method of preparing the above compound.

Another object of the present invention is to provide a pharmaceutical composition comprising the above compound.

Another object of the present invention is to provide use of the above compound and the pharmaceutical composition comprising the above compound in the manufacture of a medicament for preventing and/or treating EGFR kinase-mediated cancers or other diseases.

Another object of the present invention is to provide a method of treating cancers, the method comprises administrating an effective amount of the compound or composition of the present invention to a subject.

SPECIFIC MODES FOR CARRYING OUT THE INVENTION

Various specific embodiments, modes and examples are described herein, including exemplary embodiments and definitions, to understand the claimed invention. While the following detailed description sets forth specific preferred embodiments, those skilled in the art will appreciate that these embodiments are illustrative only, and that the present invention can be practiced in other ways. For the purpose of determining infringement, the scope of the present invention will cover any one or more of the appended claims, including equivalents thereof, and elements or limitations equivalent to those recited.

The present invention is achieved by the following technical solutions.

In the first aspect of the present invention, the present invention provides a compound having the following general formula:

(A)

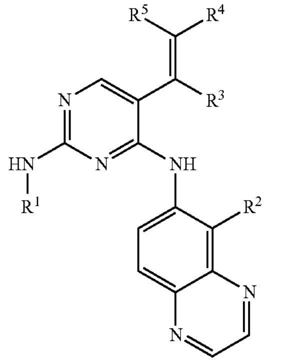

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 3-pyrazolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4-pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

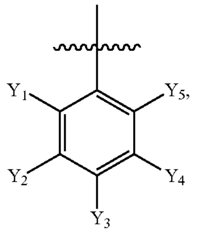

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, mono-halo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, N—(N-methyl-4-piperidyl)piperazinyl, N—(N-ethyl-4-piperidyl)piperazinyl, 4-(N-methylazetidin-3-yl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(piperazinyl-1-)piperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-hydroxyethylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido, (16)

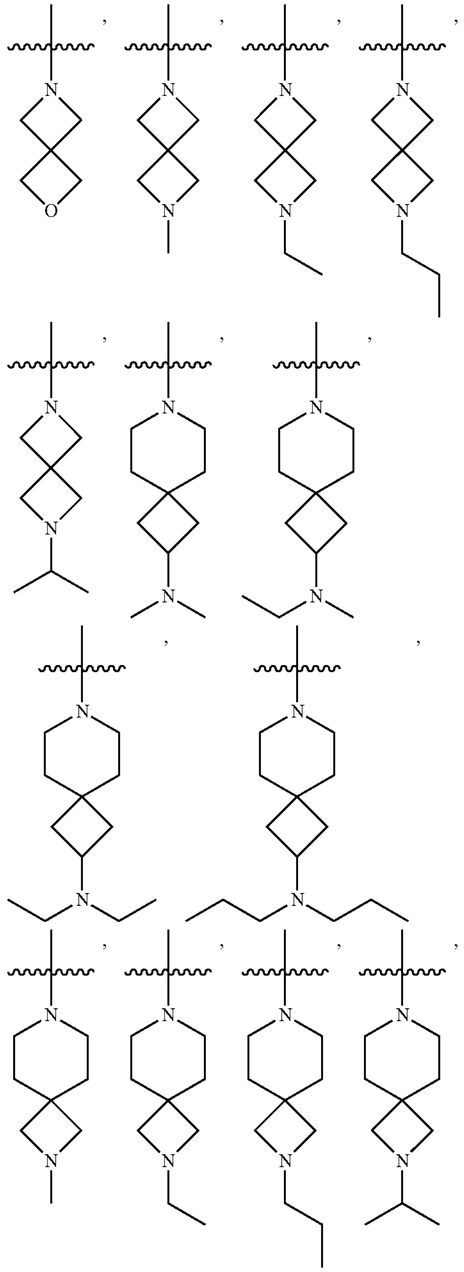

(17) $Y_3$ and $Y_4$ may form an oxygen-containing substituted or unsubstituted 5- to 7-membered ring; the substituent may be selected from the same substituents as described above for $Y_1$,

(18) $Y_3$ and $Y_4$ may form a nitrogen-containing substituted or unsubstituted 5- to 7-membered ring; the substituent may be selected from the same substituents as described above for $Y_1$;

5)

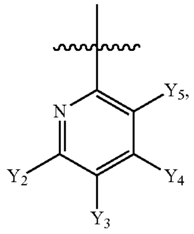

wherein $Y_2$, $Y_3$, $Y_4$, $Y_5$ are the same as defined in 4), and $Y_2$, $Y_3$, $Y_4$, $Y_5$ are not hydrogen at the same time;

6)

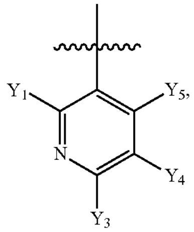

wherein $Y_1$, $Y_3$, $Y_4$, $Y_5$ are the same as defined in 4), and $Y_1$, $Y_3$, $Y_4$, $Y_5$ are not hydrogen at the same time;

7)

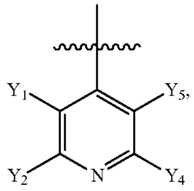

wherein $Y_1$, $Y_2$, $Y_4$, $Y_5$ are the same as defined in 4), and $Y_1$, $Y_2$, $Y_4$, $Y_5$ may be hydrogen at the same time;

8)

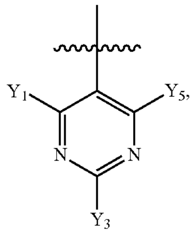

wherein $Y_1$, $Y_3$, $Y_5$ are the same as defined in 4), and $Y_1$, $Y_3$, $Y_5$ are not hydrogen at the same time;

$R^2$ is selected from:

1)

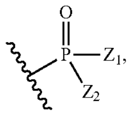

wherein $Z_1$, $Z_2$ each are independently selected from $C_1$-$C_6$ alkyl, or $C_3$-$C_8$ cycloalkyl;

2)

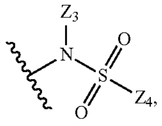

wherein $Z_3$, $Z_4$ each are independently selected from H, $C_1$-$C_6$ alkyl, $C_1$-$C_6$ fluorine-containing alkyl, $C_3$-$C_6$ cycloalkyl, or $C_3$-$C_6$ fluorine-containing cycloalkyl, and $Z_4$ is not H;

3)

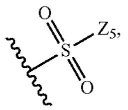

wherein $Z_5$ is selected from $C_1$-$C_6$ alkyl, $C_1$-$C_6$ fluorine-containing alkyl, $C_3$-$C_8$ cycloalkyl, $C_1$-$C_6$ heteroatom-containing alkyl, or $C_3$-$C_8$ heteroatom-containing cycloalkyl;

4)

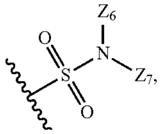

wherein $Z_6$, $Z_7$ each are independently selected from H, $C_1$-$C_6$ alkyl, $C_1$-$C_6$ fluorine-containing alkyl, $C_3$-$C_6$ cycloalkyl, or $C_3$-$C_6$ fluorine-containing cycloalkyl, or, $Z_6$, $Z_7$, together with N may form a 1 to 2 heteroatom-containing substituted or unsubstituted 4- to 8-membered ring, the substituents being selected from halogen, $C_1$-$C_6$ alkyl, or $C_3$-$C_8$ cycloalkyl, preferably, $Z_6$, $Z_7$ each are independently selected from H, or $C_1$-$C_6$ alkyl, more preferably, $Z_6$, $Z_7$ each are independently selected from H, methyl, or isopropyl, most preferably, in $Z_6$ and $Z_7$, one is H, and the other is selected from methyl, or isopropyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, or $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl; and, the compound having the general formula (A) is not selected from

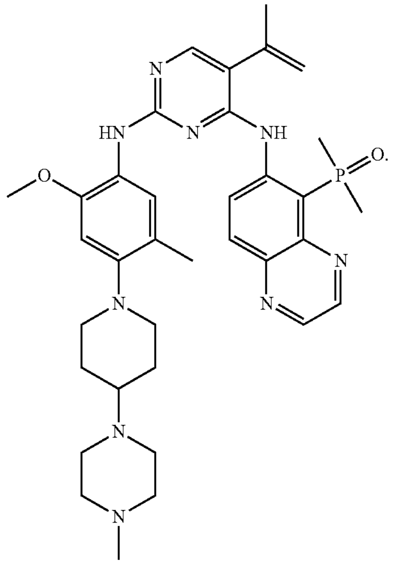

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 3-pyrazolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4- pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl, 1,3-dimethyl-5-pyrazolyl, 1-methyl-4-imidazolyl, 3-methyl-5-isoxazolyl;

4)

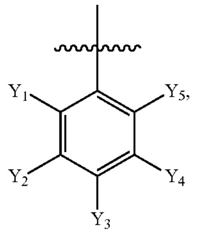

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, N—(N-methyl-4-piperidyl)piperazinyl, N—(N-ethyl-4-piperidyl)piperazinyl, 4-(N-methyl-azetidin-3-yl)piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(piperazinyl-1-)piperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-hydroxyethylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl) piperazinyl-1-sulfonyl, N-(2-N,N-dimethylaminoethyl)piperazinyl-1-sulfonyl, N-(2-N,N-diethylaminoethyl)piperazinyl-1-sulfonyl,

(13) aminoformamido, methylaminoformamido, ethylaminoformamido, propylaminoformamido, isopropylaminoformamido, (14)

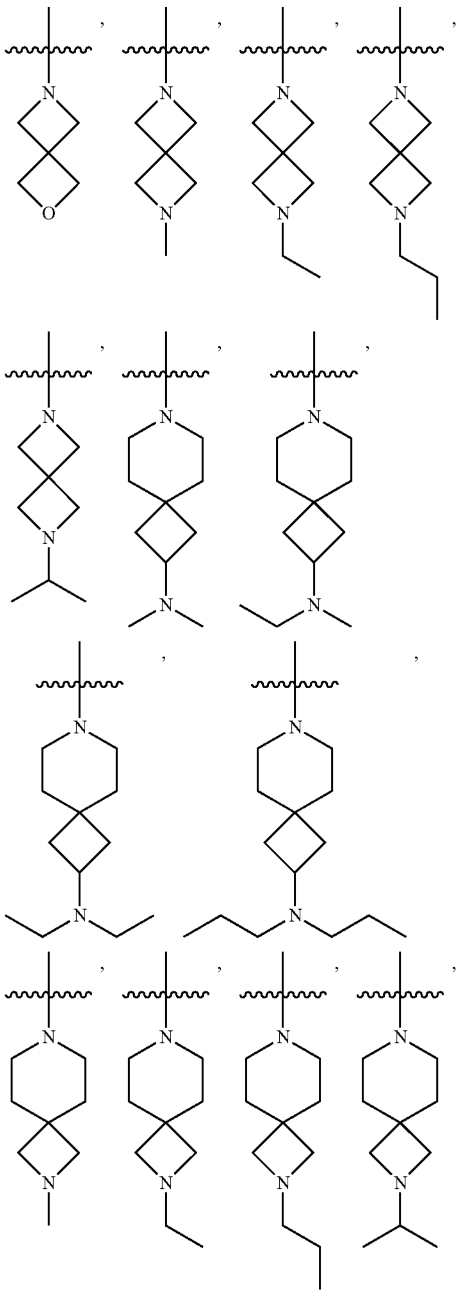

5)

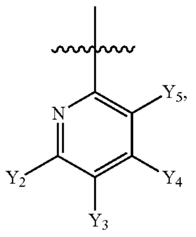

wherein $Y_2$, $Y_3$, $Y_4$, $Y_5$ are the same as defined in 4), and $Y_2$, $Y_3$, $Y_4$, $Y_5$ are not hydrogen at the same time;

6)

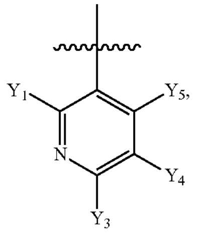

wherein $Y_1$, $Y_3$, $Y_4$, $Y_5$ are the same as defined in 4), and $Y_1$, $Y_3$, $Y_4$, $Y_5$ are not hydrogen at the same time;

7)

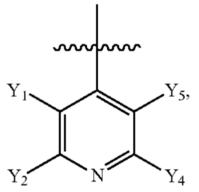

wherein $Y_1$, $Y_2$, $Y_4$, $Y_5$ are the same as defined in 4), and $Y_1$, $Y_2$, $Y_4$, $Y_5$ may be hydrogen at the same time;

8)

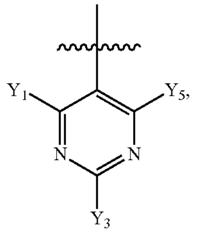

wherein $Y_1$, $Y_3$, $Y_5$ are the same as defined in 4), and $Y_1$, $Y_3$, $Y_5$ are not hydrogen at the same time;

9)

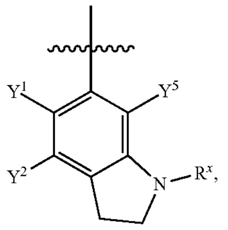

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

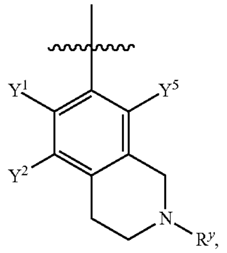

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

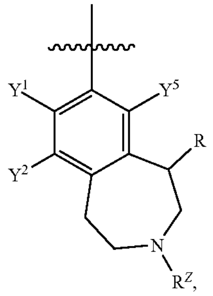

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

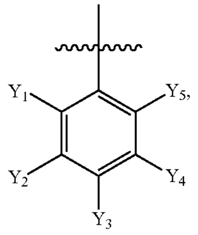

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkyl, $C_1$-$C_6$ fluorine-containing alkoxy, $C_2$-$C_6$ alkenyl, $C_3$-$C_6$ cycloalkyl, (3) piperazinyl, N-methylpiperazinyl, N-ethylpiperazinyl, N-n-propylpiperazinyl, N-isopropylpiperazinyl, N—(N-methyl-4-piperidyl)piperazinyl, N—(N-ethyl-4-piperidyl)piperazinyl, 4-(N-methyl-azetidin-3-yl)piperazinyl, (4) morpholinyl, 2,6-dimethylmorpholinyl, thiomorpholinyl, (5) 3-(N,N-dimethylamino)tetrahydropyrrolyl, 3-(N,N-diethylamino)tetrahydropyrrolyl, (6) 4-N,N-dimethylaminopiperidyl, 4-N,N-diethylaminopiperidyl, 4-N,N-diisopropylaminopiperidyl, 4-(piperazinyl-1-)piperidyl, 4-hydroxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(tetrahydropyrrolyl-1-)piperidyl, (7) piperidin-4-yl, N-methyl-4-piperidyl, N-ethyl-4-piperidyl, N-isopropyl-4-piperidyl, (8) aminoformamido, methylaminoformamido, ethylaminoformamido, propylaminoformamido, isopropylaminoformamido, 2-(N,N-dimethylamino)acetamido, cyclopropylsulfamido, 2-N,N-dimethylaminoethylamino, 3-N,N-dimethylaminopropylamino, 3-N,N-diethylaminopropylamino, 3-N,N-diisopropylaminopropylamino, N-methyl-N-(2-N,N-dimethylamino)ethylamino, (9) 4-methyl-1-piperazinylmethylene, 4-ethyl-1-piperazinylmethylene, 4-propyl-1-piperazinylmethylene, 4-isopropyl-1-piperazinylmethylene, benzyl, cyclopropylmethylene, cyclobutylmethylene, cyclopentylmethylene, cyclohexylmethylene,

(10) 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl,

(11) cyclopropylaminosulfonyl, cyclobutylaminosulfonyl, cyclopentylaminosulfonyl, cyclohexylaminosulfonyl, N-methylpiperazinyl-1-sulfonyl, N-ethylpiperazinyl-1-sulfonyl, N-isopropylpiperazinyl-1-sulfonyl,

(12) amino, N,N-dimethylamino, N,N-diethylamino, N,N-di-n-propylamino, N,N-diisopropylamino, 2-hydroxyethylamino, 2-N,N-dimethylaminoethylamino, 3-N,N-dimethylaminopropylamino, 3-N,N-diethylaminopropylamino, 3-N,N-diisopropylaminopropylamino, N-methyl-N-(2-N,N-dimethylamino)ethylamino, (13)

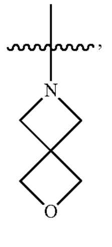,

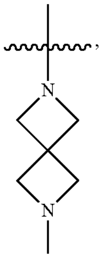,

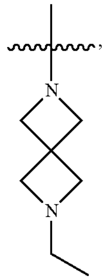,

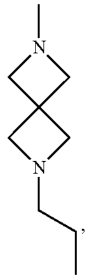,

-continued

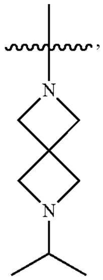,
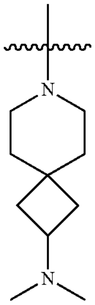,
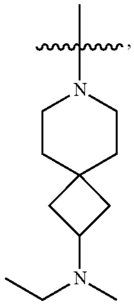,
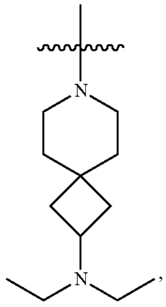,
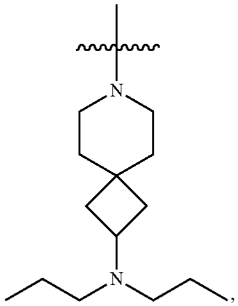,
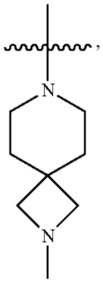,
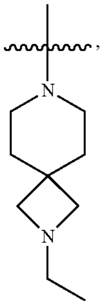,
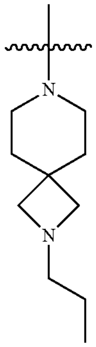,
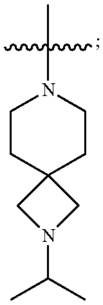;

2)

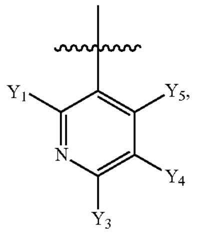

wherein $Y_1$, $Y_3$, $Y_4$, $Y_5$ each are independently selected from H, $C_1$-$C_6$ alkyl, $C_1$-$C_6$ alkoxy, N—(N-methyl-3-tetrahydropyrrolyl)amino, N-methyl-N—(N-methyl-3-tetrahydropyrrolyl)amino, N-methylpiperazinyl, N-ethylpiperazinyl, N-n-propylpiperazinyl, N-isopropylpiperazinyl, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time;

3)

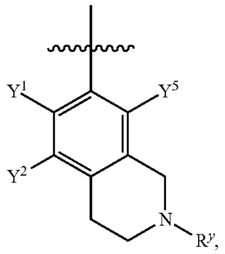

wherein, $Y_1$ is selected from H, $C_1$-$C_6$ alkyl, $C_1$-$C_6$ alkoxy, F, Cl, Br, or $C_1$-$C_6$ fluorine-containing alkoxy, $Y_2$, $Y_5$ each are independently selected from H, or $C_1$-$C_6$ alkyl (preferably, H), $R^y$ is selected from $C_1$-$C_6$ alkyl;

4)

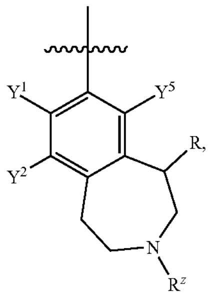

wherein, $Y_1$, $Y_2$, $Y_5$ each are independently selected from H, or $C_1$-$C_6$ alkyl (preferably H), $R^Z$ is selected from $C_1$-$C_6$ alkyl, R is selected from H, or $C_1$-$C_6$ alkyl (preferably selected from H, or methyl);

5) 3-pyrazolyl, 1-methyl-3-pyrazolyl, 1-ethyl-3-pyrazolyl, 1-isopropyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4-pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl.

In some embodiments, $R^1$ is selected from:

1)

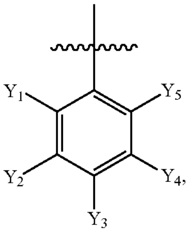

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, ethoxy, iso-propoxy, trifluoromethyl, trifluoromethoxy, vinyl, N-methylpiperazinyl, morpholinyl, 3-(N,N-dimethylamino)tetrahydropyrrolyl, 4-N,N-dimethylaminopiperidyl, 4-hydroxypiperidyl, 4-(N-methylpiperazinyl-1-)piperidyl, 4-(tetrahydropyrrolyl-1-)piperidyl, N-methyl-4-piperidyl, 2-(N,N-dimethylamino)acetamido, cyclopropylsulfamido, 2-hydroxyethylamino, 2-N,N-dimethylaminoethylamino, N-methyl-N-(2-N,N-dimethylamino)ethylamino, 4-methyl-1-piperazinylmethylene, benzyl, cyclopropylmethylene, 4-(N-methyl-1-piperazinyl)piperidyl-1-formyl, N-methylpiperazinyl-1-formyl, cyclopropylaminosulfonyl, N-methylpiperazinyl-1-sulfonyl, 4-(piperazinyl-1-)piperidyl, N—(N-methyl-4-piperidyl)piperazinyl, 4-(N-methyl-azetidin-3-yl)piperazinyl,

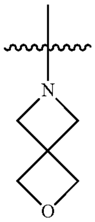, 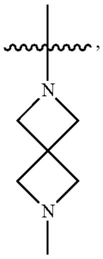, 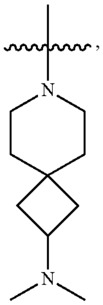, and 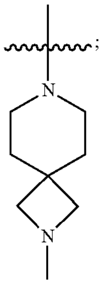;

2)

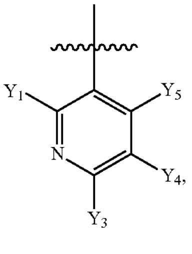

wherein, $Y_1$, $Y_3$, $Y_4$, $Y_5$ each are independently selected from H, methyl, ethyl, methoxy, N—(N-methyl-3-tetrahydropyrrolyl)amino, N-methyl-N—(N-methyl-3-tetrahydropyrrolyl)amino, N-methylpiperazinyl, or 4-(N-methylpiperazinyl-1-)piperidyl, and $Y_1$, $Y_3$, $Y_4$, $Y_5$ are not hydrogen at the same time;

3)

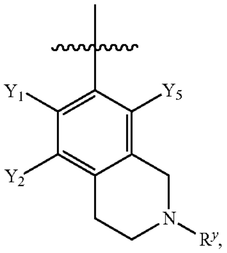

wherein, $Y_1$ is selected from H, methyl, methoxy, F, $C_1$, or trifluoromethoxy, $Y_2$, $Y_5$ are H, $R^y$ is methyl;

4)

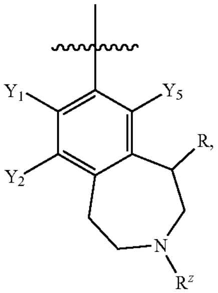

wherein, $Y_1$, $Y_2$, $Y_5$ are H, $R^Z$ is methyl, R is selected from H, or methyl;

5) 3-pyrazolyl, 1-ethyl-3-pyrazolyl, 1-isopropyl-3-pyrazolyl, 1,5-dimethyl-3-pyrazolyl, 1-methyl-5-ethyl-3-pyrazolyl, 4-pyrazolyl, 1-methyl-4-pyrazolyl, 1-ethyl-4-pyrazolyl, 1-isopropyl-4-pyrazolyl, 1-ethyl-3-methyl-4-pyrazolyl.

In some embodiments, $Z_1$, $Z_2$ each are independently selected from $C_1$-$C_6$ alkyl.

In some embodiments, $Z_1$, $Z_2$ are methyl.

In some embodiments, $Z_5$ is selected from $C_1$-$C_6$ alkyl.

In some embodiments, $Z_5$ is selected from methyl, or isopropyl.

In some embodiments, $Z_3$, $Z_4$ each are independently selected from $C_1$-$C_6$ alkyl, $C_1$-$C_6$ fluorine-containing alkyl, or $C_3$-$C_6$ cycloalkyl.

In some embodiments, $Z_3$, $Z_4$ each are independently selected from methyl, ethyl, isopropyl, cyclopropyl, or trifluoromethyl.

In some embodiments, $Z_6$, $Z_7$ each are independently selected from H, or $C_1$-$C_6$ alkyl.

In some embodiments, $Z_6$, $Z_7$ each are independently selected from H, methyl, or isopropyl.

In some embodiments, in $Z_6$ and $Z_7$, one is H, and the other is selected from methyl, or isopropyl.

In some embodiments, $R^3$, $R^4$, $R^5$ each are independently selected from:

1) H, $C_1$-$C_6$ alkyl, $C_1$-$C_6$ alkoxy, $C_3$-$C_6$ cycloalkyl;
2) substituted or unsubstituted aryl, the substituents being selected from halogen, $C_1$-$C_6$ alkyl, or $C_3$-$C_8$ cycloalkyl;
3) $R^3$, $R^4$ and carbon atoms linked thereto together form

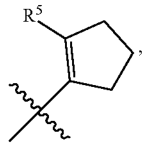

$R^5$ being selected from H, or $C_1$-$C_6$ alkyl.

In some embodiments, $R^3$, $R^4$, $R^5$ each are independently selected from:

1) H, methyl, ethoxy, cyclopropyl;
2) phenyl;
3) $R^3$, $R^4$ and carbon atoms linked thereto together form

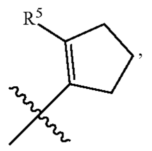

$R^5$ being H.

In the second aspect of the present invention, the present invention provides a compound having the following general formula:

(I)

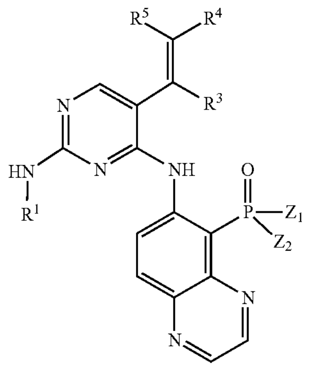

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;
2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;
3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;
4)

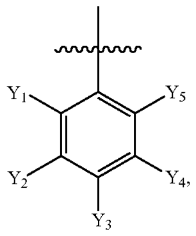

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano,
(2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl,
(3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, mono-halo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl- 1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

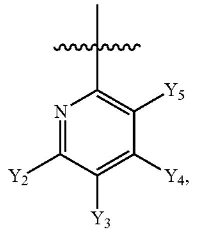

wherein $Y_2$, $Y_3$, $Y_4$, $Y_5$ are the same as defined in 4), and $Y_2$, $Y_3$, $Y_4$, $Y_5$ are not hydrogen at the same time;

6)

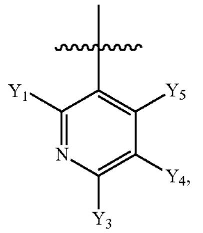

wherein $Y_1$, $Y_3$, $Y_4$, $Y_5$ are the same as defined in 4), and $Y_1$, $Y_3$, $Y_4$, $Y_5$ are not hydrogen at the same time;

7)

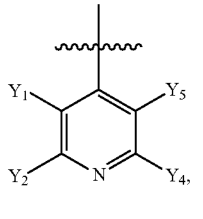

wherein $Y_1$, $Y_2$, $Y_4$, $Y_5$ are the same as defined in 4), and $Y_1$, $Y_2$, $Y_4$, $Y_5$ may be hydrogen at the same time;

8)

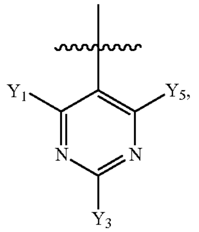

wherein $Y_1$, $Y_3$, $Y_5$ are the same as defined in 4), and $Y_1$, $Y_3$, $Y_5$ are not hydrogen at the same time;

$Z_1$, $Z_2$ each are independently selected from $C_1$-$C_6$ alkyl, or $C_3$-$C_8$ cycloalkyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl;

and, the compound having the general formula (I) is not selected from

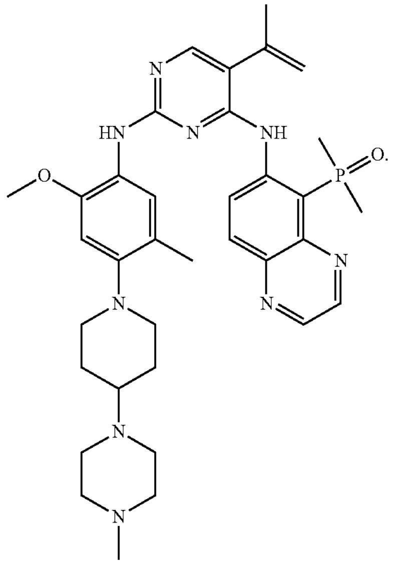

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

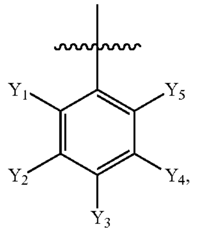

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl) piperazinyl-1-)piperidyl, 4-(N-(2-cyanoethyl) piperazinyl-1-)piperidyl, 4-(N-(3-hydroxypropyl) piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl,

(13) aminoformamido, methylaminoformamido, ethylaminoformamido, propylaminoformamido, isopropylaminoformamido;

5)

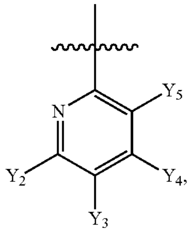

wherein $Y_2$, $Y_3$, $Y_4$, $Y_5$ are the same as defined in 4), and $Y_2$, $Y_3$, $Y_4$, $Y_5$ are not hydrogen at the same time;

6)

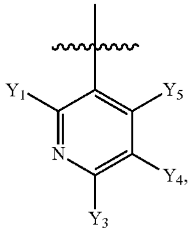

wherein $Y_1$, $Y_3$, $Y_4$, $Y_5$ are the same as defined in 4), and $Y_1$, $Y_3$, $Y_4$, $Y_5$ are not hydrogen at the same time;

7)

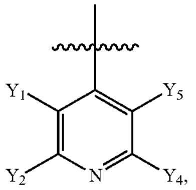

wherein $Y_1$, $Y_2$, $Y_4$, $Y_5$ are the same as defined in 4), and $Y_1$, $Y_2$, $Y_4$, $Y_5$ may be hydrogen at the same time;

8)

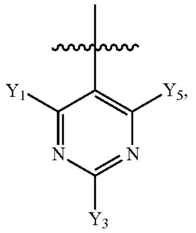

wherein $Y_1$, $Y_3$, $Y_5$ are the same as defined in 4), and $Y_1$, $Y_3$, $Y_5$ are not hydrogen at the same time;

9)

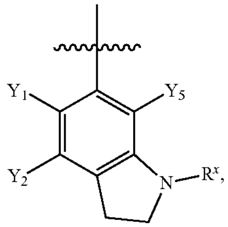

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

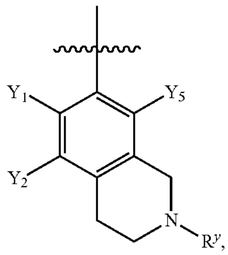

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

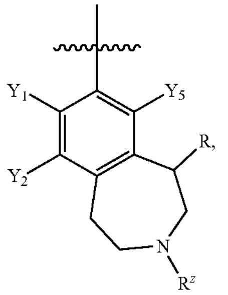

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

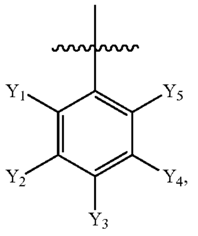

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-)piperidyl, 4-(N-ethylpiperazinyl-1-)piperidyl, 4-(N-isopropylpiperazinyl-1-)piperidyl, (6) cyclopropylmethylene, cyclobutylmethylene, cyclopentylmethylene, cyclohexylmethylene, (7) piperidin-4-yl, N-methyl-4-piperidyl, N-ethyl-4-piperidyl, N-isopropyl-4-piperidyl;

2)

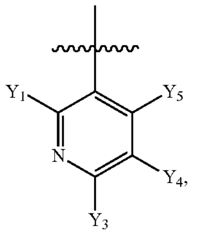

wherein $Y_1$, $Y_3$, $Y_4$, $Y_5$ each are independently selected from H, $C_1$-$C_6$ alkyl, $C_1$-$C_6$ alkoxy, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time;

3)

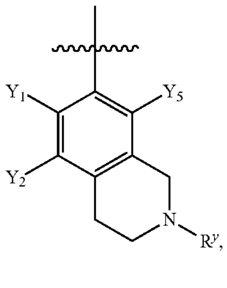

wherein, $Y_1$ is selected from F, $C_1$, or Br, $Y_2$, $Y_5$ each are independently selected from H, or $C_1$-$C_6$ alkyl (preferably H), $R^y$ is selected from $C_1$-$C_6$ alkyl;

4)

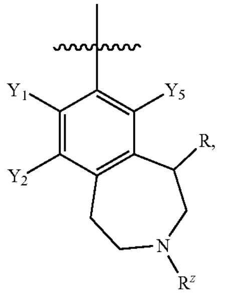

wherein, $Y_1$, $Y_2$, $Y_5$ each are independently selected from H, or $C_1$-$C_6$ alkyl (preferably H), $R^z$ is selected from $C_1$-$C_6$ alkyl, R is selected from H, or $C_1$-$C_6$ alkyl (preferably H).

In some embodiments, $R^1$ is selected from:

1)

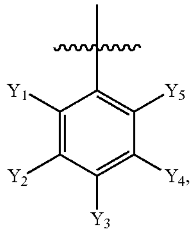

wherein:

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, methyl, ethyl, isopropyl, cyclopropyl, methoxy, trifluoromethoxy, cyclopropylmethylene, N-methylpiperazinyl, 3-(N,N-dimethylamino)tetrahydropyrrolyl, 4-N,N-dimethylaminopiperidyl, 4-(N-methylpiperazinyl-1-)piperidyl, or N-methyl-4-piperidyl;

preferably, $Y_1$, $Y_2$, $Y_4$, $Y_5$ each are independently selected from H, methyl, ethyl, isopropyl, cyclopropyl, methoxy, trifluoromethoxy, cyclopropylmethylene, or N-methyl-4-piperidyl; $Y_3$ is selected from H, N-methylpiperazinyl, 3-(N,N-dimethylamino)tetrahydropyrrolyl, 4-N,N-dimethylaminopiperidyl, or 4-(N-methylpiperazinyl-1-)piperidyl;

2)

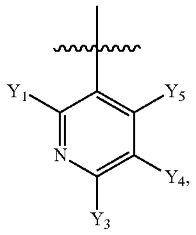

wherein:

$Y_1$, $Y_3$, $Y_4$, $Y_5$ each are independently selected from H, methyl, ethyl, methoxy, or 4-(N-methylpiperazinyl-1-)piperidyl, and $Y_1$, $Y_3$, $Y_4$, $Y_5$ are not hydrogen at the same time, preferably, $Y_1$, $Y_4$, $Y_5$ each are independently selected from H, methyl, ethyl, or methoxy, $Y_3$ is 4-(N-methylpiperazinyl-1-)piperidyl;

3)

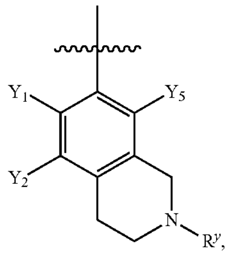

wherein, $Y_1$ is F, $Y_2$, $Y_5$ are H, $R^y$ is methyl;

4)

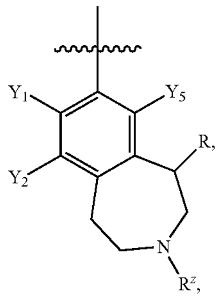

wherein, $Y_1$, $Y_2$, $Y_5$ are H, $R^z$ is methyl, R is H.

In some embodiments, $Z_1$, $Z_2$ each are independently selected from $C_1$-$C_6$ alkyl.

In some embodiments, $Z_1$, $Z_2$ are methyl.

In some embodiments, $R^3$, $R^4$, $R^5$ each are independently selected from:

1) H, $C_1$-$C_6$ alkyl, $C_1$-$C_6$ alkoxy, $C_3$-$C_6$ cycloalkyl;

2) substituted or unsubstituted aryl, the substituents being selected from halogen, $C_1$-$C_6$ alkyl, or $C_3$-$C_8$ cycloalkyl;

3) $R^3$, $R^4$ and carbon atoms linked thereto together form

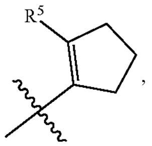

$R^5$ being selected from H, or $C_1$-$C_6$ alkyl.

In some embodiments, $R^3$, $R^4$, $R^5$ each are independently selected from:

1) H, methyl, ethoxy, cyclopropyl;

2) phenyl;

3) $R^3$, $R^4$ and carbon atoms linked thereto together form

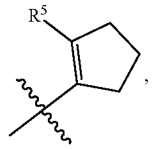

$R^5$ being H.

In some embodiments, $R^3$ is selected from H, or methyl, $R^4$ is selected from H, methyl, ethoxy, cyclopropyl, or phenyl, $R^5$ is selected from H, or methyl; or, $R^3$, $R^4$ and carbon atoms linked thereto together form

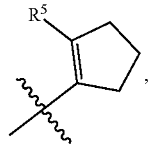

$R^5$ being H.

In the third aspect of the present invention, the present invention provides a compound having the following general formula:

(II)

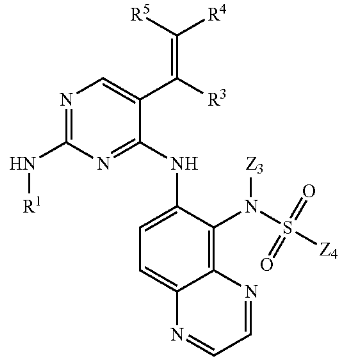

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 3-pyrazolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4-pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

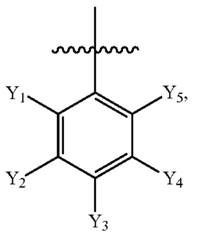

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, mono-halo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, N—(N-methyl-4-piperidyl)piperazinyl, N—(N-ethyl-4-piperidyl)piperazinyl, 4-(N-methyl-azetidin-3-yl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(piperazinyl-1-)piperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-) piperidyl, 4-(N-(2-N,N-dimethylaminoethyl) piperazinyl-1-)piperidyl, 4-(N-(2-N,N-diethylethyl) piperazinyl-1-)piperidyl, 4-(N-(3-N,N-dimethylpropyl) piperazinyl-1-)piperidyl, 4-(N-(3-N,N-diethylpropyl) piperazinyl-1-)piperidyl, 4-(tetrahydropyrrolyl-1-) piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-hydroxyethylamino, 2-N,N-dimethylaminoethylamino, 2-morpholinylethylamino, 2-(N-methylpiperazinyl) ethylamino, 3-N,N-dimethylaminopropylamino, 3-N,N-diethylaminopropylamino, 3-N,N-diisopropylaminopropylamino, 3-morpholinylpropylamino, 3-(N- methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido (16)

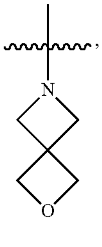,
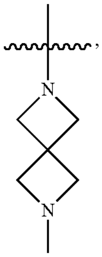,
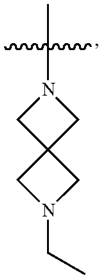,
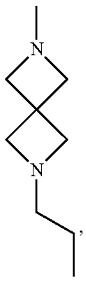,

-continued

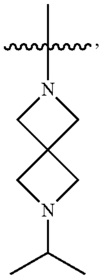,
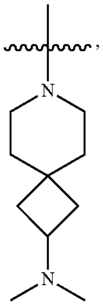,
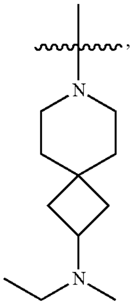,
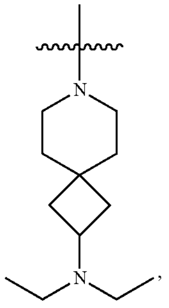,
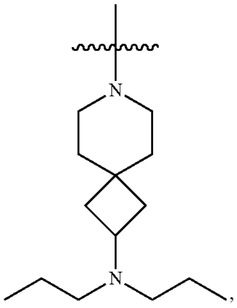,
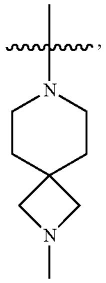,
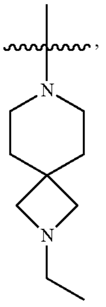,
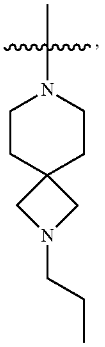,
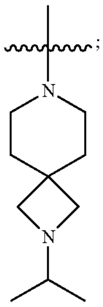;

(17) $Y_3$ and $Y_4$ may form an oxygen-containing substituted or unsubstituted 5- to 7-membered ring; the substituent may be selected from the same substituents as described above for $Y_1$,

(18) $Y_3$ and $Y_4$ may form a nitrogen-containing substituted or unsubstituted 5- to 7-membered ring; the substituent may be selected from the same substituents as described above for $Y_1$;

5)

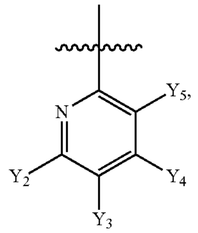

wherein $Y_2$, $Y_3$, $Y_4$, $Y_5$ are the same as defined in 4), and $Y_2$, $Y_3$, $Y_4$, $Y_5$ are not hydrogen at the same time;

6)

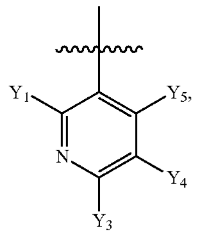

wherein $Y_1$, $Y_3$, $Y_4$, $Y_5$ are the same as defined in 4), and $Y_1$, $Y_3$, $Y_4$, $Y_5$ are not hydrogen at the same time;

7)

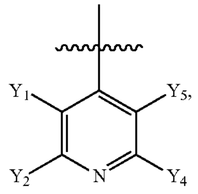

wherein $Y_1$, $Y_2$, $Y_4$, $Y_5$ are the same as defined in 4), and $Y_1$, $Y_2$, $Y_4$, $Y_5$ may be hydrogen at the same time;

8)

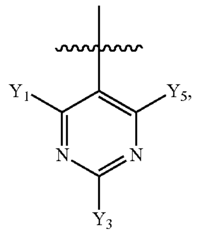

wherein $Y_1$, $Y_3$, $Y_5$ are the same as defined in 4), and $Y_1$, $Y_3$, $Y_5$ are not hydrogen at the same time;

$Z_3$, $Z_4$ each are independently selected from H, $C_1$-$C_6$ alkyl, $C_1$-$C_6$ fluorine-containing alkyl, $C_3$-$C_6$ cycloalkyl, or $C_3$-$C_6$ fluorine-containing cycloalkyl, and $Z_4$ is not H;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl.

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 3-pyrazolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4-pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl, 1,3-dimethyl-5-pyrazolyl, 1-methyl-4-imidazolyl, 3-methyl-5-isoxazolyl;

4)

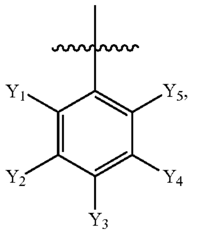

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, N—(N-methyl-4-piperidyl)piperazinyl, N—(N-ethyl-4-piperidyl)piperazinyl, 4-(N-methylazetidin-3-yl)piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(piperazinyl-1-)piperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-hydroxyethylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N, N-diethylaminoethyl)piperazinyl-1-sulfonyl,

(13) aminoformamido, methylaminoformamido, ethylaminoformamido, propylaminoformamido, isopropylaminoformamido, (14)

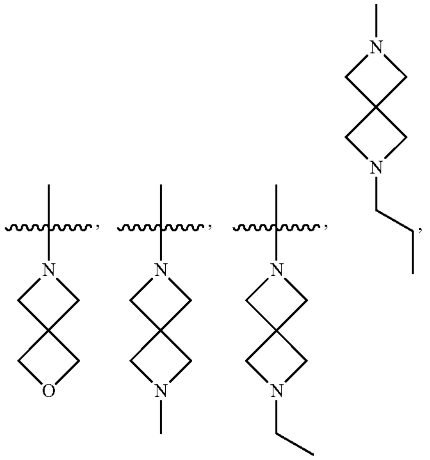

-continued

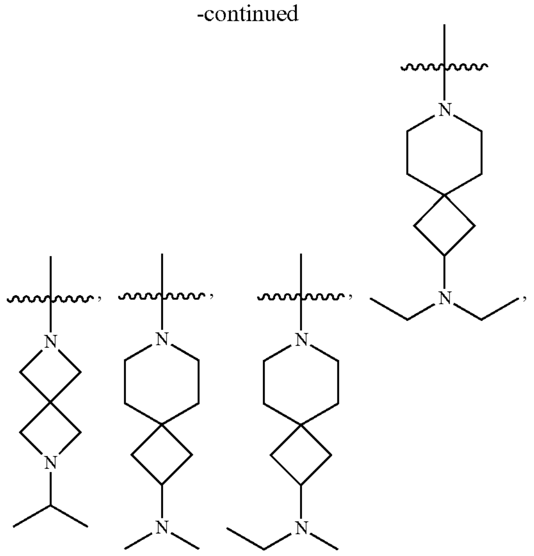

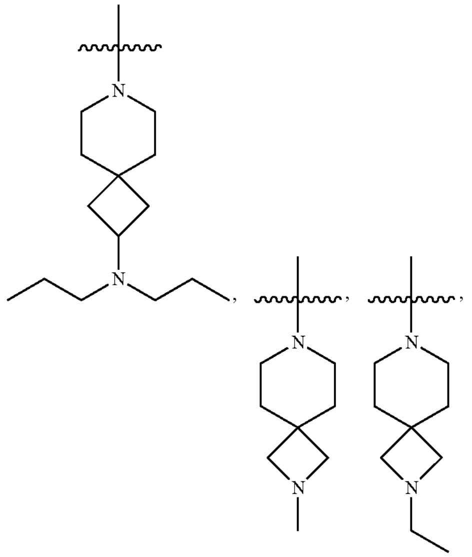

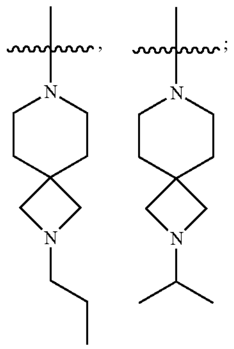

5)

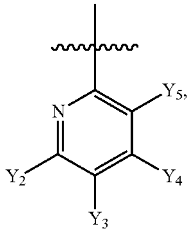

wherein $Y_2$, $Y_3$, $Y_4$, $Y_5$ are the same as defined in 4), and $Y_2$, $Y_3$, $Y_4$, $Y_5$ are not hydrogen at the same time;

6)

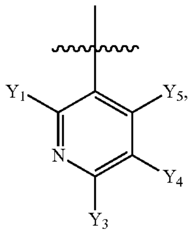

wherein $Y_1$, $Y_3$, $Y_4$, $Y_5$ are the same as defined in 4), and $Y_1$, $Y_3$, $Y_4$, $Y_5$ are not hydrogen at the same time;

7)

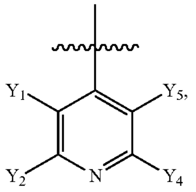

wherein $Y_1$, $Y_2$, $Y_4$, $Y_5$ are the same as defined in 4), and $Y_1$, $Y_2$, $Y_4$, $Y_5$ may be hydrogen at the same time;

8)

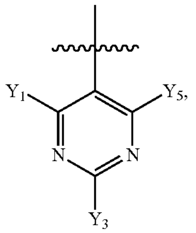

wherein $Y_1$, $Y_3$, $Y_5$ are the same as defined in 4), and $Y_1$, $Y_3$, $Y_5$ are not hydrogen at the same time;

9)

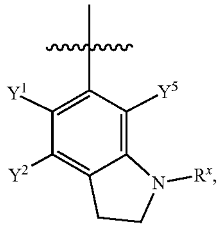

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

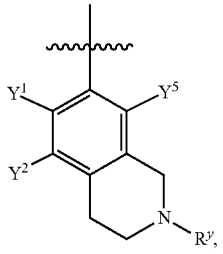

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

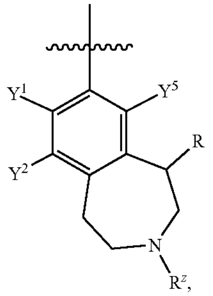

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

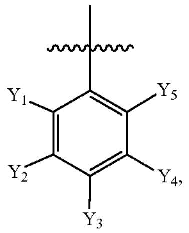

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, N—(N-methyl-4-piperidyl)piperazinyl, N—(N-ethyl-4-piperidyl)piperazinyl, 4-(N-methyl-azetidin-3-yl) piperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(piperazinyl-1-)piperidyl, 4-(N-methylpiperazinyl-1-)piperidyl, 4-(N-ethylpiperazinyl-1-)piperidyl, 4-(N-isopropylpiperazinyl-1-)piperidyl, (6) cyclopropylmethylene, cyclobutylmethylene, cyclopentylmethylene, cyclohexylmethylene, benzyl, (7) 4-(N-methyl-1-piperazinyl)piperidyl-1-formyl, 4-(N-ethyl-1-piperazinyl)piperidyl-1-formyl, (8) amino, N,N-dimethylamino, N,N-diethylamino, N,N-di-n-propylamino, N,N-diisopropylamino, 2-hydroxyethylamino, 2-N,N-dimethylaminoethylamino, 3-N,N-dimethylaminopropylamino, 3-N,N-diethylaminopropylamino, 3-N N-diisopropylaminopropylamino, N-methyl-N-(2-N, N-dimethylamino)ethylamino, (9)

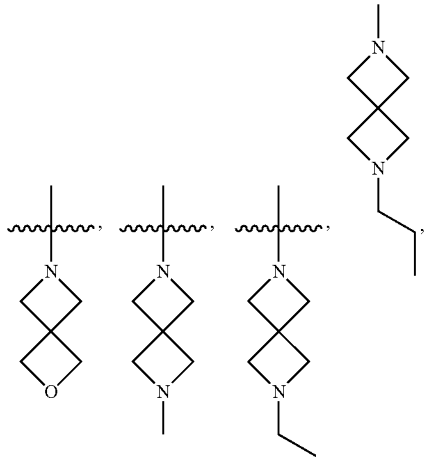

-continued

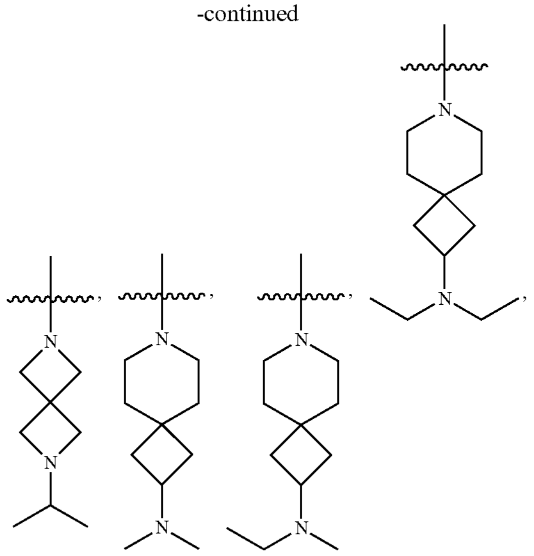

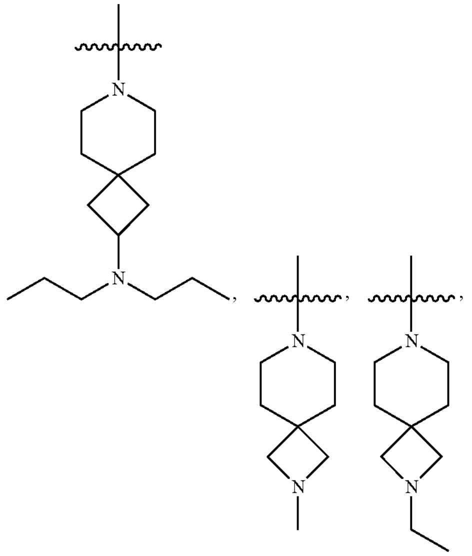

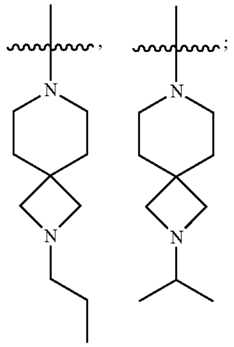

2)

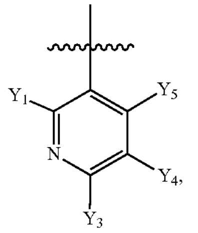

wherein $Y_1$, $Y_3$, $Y_4$, $Y_5$ each are independently selected from H, $C_1$-$C_6$ alkyl, $C_1$-$C_6$ alkoxy, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time;

3)

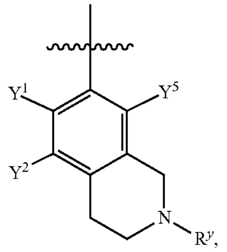

wherein, $Y_1$ is selected from H, $C_1$-$C_6$ alkyl, $C_1$-$C_6$ alkoxy, F, Cl, Br, or $C_1$-$C_6$ fluorine-containing alkoxy, $Y_2$, $Y_5$ are H, $R^y$ is selected from $C_1$-$C_6$ alkyl;

4)

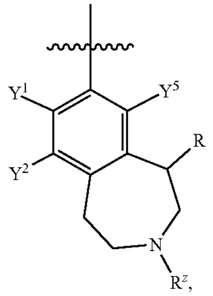

wherein, $Y_1$, $Y_2$, $Y_5$ are H, $R^z$, R each are independently selected from $C_1$-$C_6$ alkyl;

5) 3-pyrazolyl, 1-methyl-3-pyrazolyl, 1-ethyl-3-pyrazolyl, 1-isopropyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4-pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl.

In some embodiments, $R^1$ is selected from:

1)

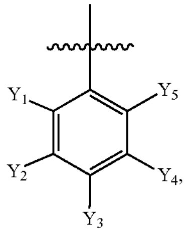

wherein:

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, trifluoromethoxy, cyclopropylmethylene, benzyl, N-methylpiperazinyl, 3-(N,N-dimethylamino)tetrahydropyrrolyl, 4-N,N-dimethylaminopiperidyl, 4-(N-methylpiperazinyl-1-)piperidyl, 4-(N-methyl-1-piperazinyl)piperidyl-1-formyl, 2-hydroxyethylamino, 2-N,N-dimethylaminoethylamino, N-methyl-N-(2-N,N-dimethylamino)ethylamino, 4-(piperazinyl-1-)piperidyl, N—(N-methyl-4-piperidyl)piperazinyl, 4-(N-methyl-azetidin-3-yl)piperazinyl,

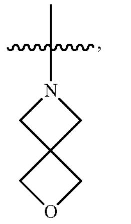

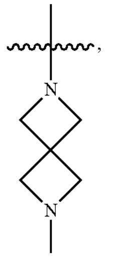

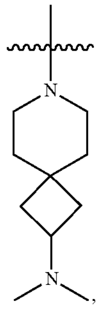

or

-continued

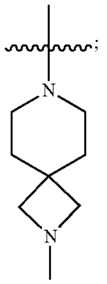

preferably, $Y_1$, $Y_2$, $Y_4$, $Y_5$ each are independently selected from H, F, methyl, ethyl, isopropyl, cyclopropyl, methoxy, trifluoromethoxy, cyclopropylmethylene, or benzyl; $Y_3$ is selected from F, N-methylpiperazinyl, 3-(N,N-dimethylamino)tetrahydropyrrolyl, 4-N,N-dimethylaminopiperidyl, 4-(N-methylpiperazinyl-1-)piperidyl, 4-(N-methyl-1-piperazinyl)piperidyl-1-formyl, 2-hydroxyethylamino, 2-N,N-dimethylaminoethylamino, N-methyl-N-(2-N,N-dimethylamino)ethylamino, 4-(piperazinyl-1-)piperidyl, N—(N-methyl-4-piperidyl)piperazinyl, 4-(N-methyl-azetidin-3-yl)piperazinyl,

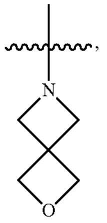

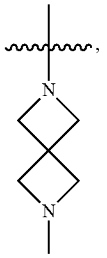

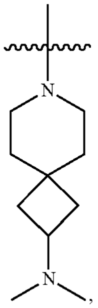

or

-continued

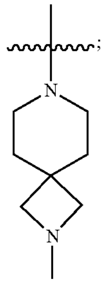

2)

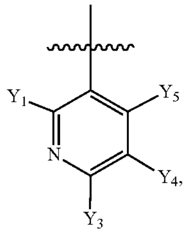

wherein:

$Y_1$, $Y_3$, $Y_4$, $Y_5$ each are independently selected from H, ethyl, methoxy, or 4-(N-methylpiperazinyl-1-)piperidyl, and $Y_1$, $Y_3$, $Y_4$, $Y_5$ are not hydrogen at the same time, preferably, $Y_1$, $Y_4$, $Y_5$ each are independently selected from H, ethyl, or methoxy, $Y_3$ is 4-(N-methylpiperazinyl-1-)piperidyl;

3)

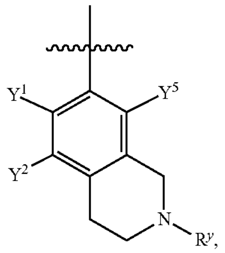

wherein, $Y_1$ is selected from H, methyl, methoxy, F, $C_1$, or trifluoromethoxy, $Y_2$, $Y_5$ are H, $R^y$ is methyl;

4)

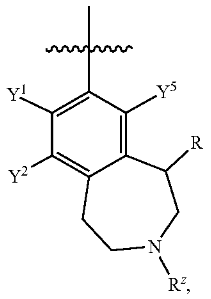

wherein, $Y_1$, $Y_2$, $Y_5$ are H, $R^z$, R are methyl;

5) 3-pyrazolyl, 1-ethyl-3-pyrazolyl, 1-isopropyl-3-pyrazolyl, 1,5-dimethyl-3-pyrazolyl, 1-methyl-5-ethyl-3-pyrazolyl, 4-pyrazolyl, 1-methyl-4-pyrazolyl, 1-ethyl-4-pyrazolyl, 1-isopropyl-4-pyrazolyl, 1-ethyl-3-methyl-4-pyrazolyl.

In some embodiments, $Z_3$, $Z_4$ each are independently selected from H, $C_1$-$C_6$ alkyl, $C_1$-$C_6$ fluorine-containing alkyl, or $C_3$-$C_6$ cycloalkyl.

In some embodiments, $Z_3$, $Z_4$ each are independently selected from H, methyl, ethyl, isopropyl, cyclopropyl, or trifluoromethyl.

In some embodiments, $Z_3$ is selected from H, methyl, ethyl, isopropyl, or cyclopropyl, $Z_4$ is selected from methyl, ethyl, isopropyl, cyclopropyl, or trifluoromethyl.

In some embodiments, $R^3$, $R^4$, $R^5$ each are independently selected from H, $C_1$-$C_6$ alkyl, $C_3$-$C_6$ cycloalkyl, or phenyl; or, $R^3$, $R^4$ and carbon atoms linked thereto together form

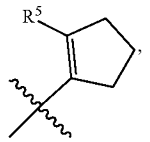

$R^5$ being selected from H, or $C_1$-$C_6$ alkyl.

In some embodiments, $R^3$, $R^4$, $R^5$ each are independently selected from H, methyl, cyclopropyl, or phenyl; or, $R^3$, $R^4$ and carbon atoms linked thereto together form

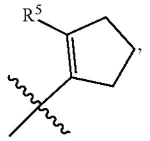

$R^5$ being H.

In some embodiments, $R^3$ is selected from H, or methyl, $R^4$ is selected from H, methyl, cyclopropyl, or phenyl, $R^5$ is selected from H, or methyl; or, $R^3$, $R^4$ and carbon atoms linked thereto together form

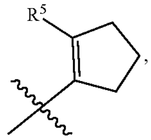

$R^5$ being H.

In the fourth aspect of the present invention, the present invention provides a compound having the following general formula:

(III)

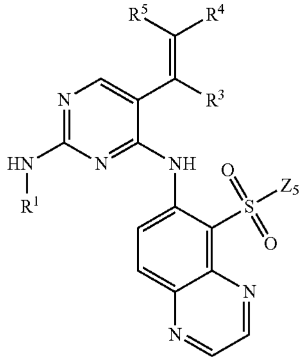

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_6$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

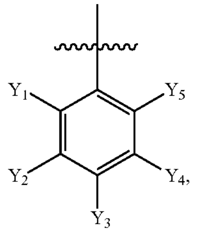

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl)piperazinyl, N-(3-N,N-diethylaminopropyl)piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)

piperazinyl-1-formyl, 4-(N-methyl-4-piperidyl)piperazinyl-1-formyl, 4-(N-ethyl-4-piperidyl)piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

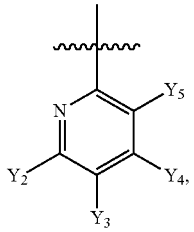

wherein $Y_2$, $Y_3$, $Y_4$, $Y_5$ are the same as defined in 4), and $Y_2$, $Y_3$, $Y_4$, $Y_5$ are not hydrogen at the same time;

6)

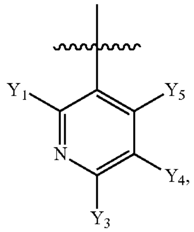

wherein $Y_1$, $Y_3$, $Y_4$, $Y_5$ are the same as defined in 4), and $Y_1$, $Y_3$, $Y_4$, $Y_5$ are not hydrogen at the same time;

7)

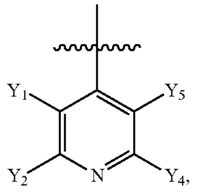

wherein $Y_1$, $Y_2$, $Y_4$, $Y_5$ are the same as defined in 4), and $Y_1$, $Y_2$, $Y_4$, $Y_5$ may be hydrogen at the same time;

8)

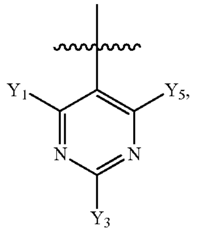

wherein $Y_1$, $Y_3$, $Y_5$ are the same as defined in 4), and $Y_1$, $Y_3$, $Y_5$ are not hydrogen at the same time;

$Z_5$ is selected from $C_1$-$C_6$ alkyl, $C_1$-$C_6$ fluorine-containing alkyl, $C_3$-$C_8$ cycloalkyl, $C_1$-$C_6$ heteroatom-containing alkyl, or $C_3$-$C_8$ heteroatom-containing cycloalkyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl.

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

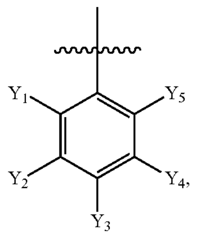

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl) piperazinyl-1-)piperidyl, 4-(N-(2-cyanoethyl) piperazinyl-1-)piperidyl, 4-(N-(3-hydroxypropyl) piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2 6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N, N-diethylaminoethyl)piperazinyl-1-sulfonyl,

(13) aminoformamido, methylaminoformamido, ethylaminoformamido, propylaminoformamido, isopropylaminoformamido;

5)

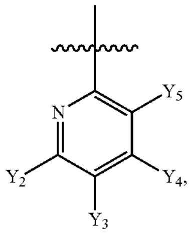

wherein $Y_2$, $Y_3$, $Y_4$, $Y_5$ are the same as defined in 4), and $Y_2$, $Y_3$, $Y_4$, $Y_5$ are not hydrogen at the same time;

6)

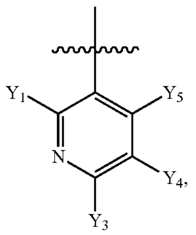

wherein $Y_1$, $Y_3$, $Y_4$, $Y_5$ are the same as defined in 4), and $Y_1$, $Y_3$, $Y_4$, $Y_5$ are not hydrogen at the same time;

7)

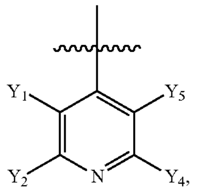

wherein $Y_1$, $Y_2$, $Y_4$, $Y_5$ are the same as defined in 4), and $Y_1$, $Y_2$, $Y_4$, $Y_5$ may be hydrogen at the same time;

8)

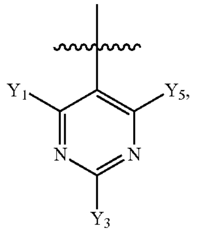

wherein $Y_1$, $Y_3$, $Y_5$ are the same as defined in 4), and $Y_1$, $Y_3$, $Y_5$ are not hydrogen at the same time,

9)

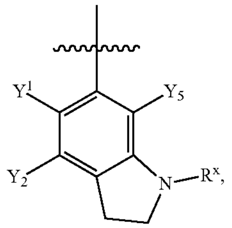

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

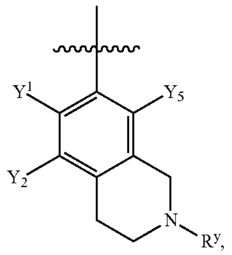

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

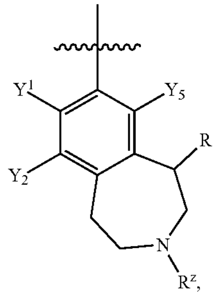

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

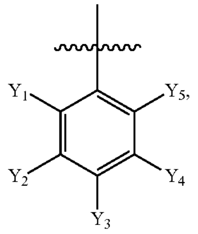

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-)piperidyl, 4-(N-ethylpiperazinyl-1-)piperidyl, 4-(N-isopropylpiperazinyl-1-)piperidyl, (6) cyclopropylmethylene, cyclobutylmethylene, cyclopentylmethylene, cyclohexylmethylene, (7) 4-(N-methyl-1-piperazinyl)piperidyl-1-formyl, 4-(N-ethyl-1-piperazinyl)piperidyl-1-formyl,

2)

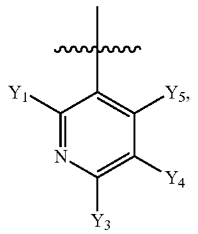

wherein:

$Y_1$, $Y_3$, $Y_4$, $Y_5$ each are independently selected from H, $C_1$-$C_6$ alkyl, $C_1$-$C_6$ alkoxy, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time.

In some embodiments, $R^1$ is selected from:

1)

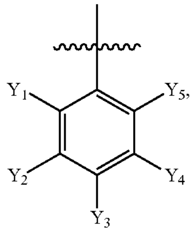

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, trifluoromethoxy, cyclopropylmethylene, N-methylpiperazinyl, 3-(N,N-dimethylamino)tetrahydropyrrolyl, 4-N,N-dimethylaminopiperidyl, 4-(N-methylpiperazinyl-1-)piperidyl, or 4-(N-methyl-1-piperazinyl)piperidyl-1-formyl, preferably, $Y_1$, $Y_2$, $Y_4$, $Y_5$ each are independently selected from H, F, methyl, ethyl, isopropyl, cyclopropyl, methoxy, trifluoromethoxy, or cyclopropylmethylene, $Y_3$ is selected from N-methylpiperazinyl, 3-(N,N-dimethylamino)tetrahydropyrrolyl, 4-N,N-dimethylaminopiperidyl, 4-(N-methylpiperazinyl-1-)piperidyl, or 4-(N-methyl-1-piperazinyl)piperidyl-1-formyl;

2)

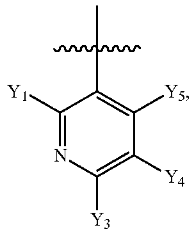

wherein:

$Y_1$, $Y_3$, $Y_4$, $Y_5$ each are independently selected from H, ethyl, methoxy, or 4-(N-methylpiperazinyl-1-)piperidyl, and $Y_1$, $Y_3$, $Y_4$, $Y_5$ are not hydrogen at the same time, preferably, $Y_1$, $Y_4$, $Y_5$ each are independently selected from H, ethyl, or methoxy, $Y_3$ is 4-(N-methylpiperazinyl-1-)piperidyl.

In some embodiments, $Z_5$ is selected from $C_1$-$C_6$ alkyl.

In some embodiments, $Z_5$ is selected from methyl, or isopropyl.

In some embodiments, $R^3$, $R^4$, $R^5$ each are independently selected from H, or $C_1$-$C_6$ alkyl.

In some embodiments, $R^3$, $R^4$, $R^5$ are H.

In the fifth aspect of the present invention, the present invention provides a compound having the following general formula:

(IV)

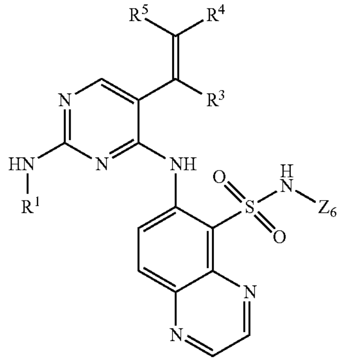

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

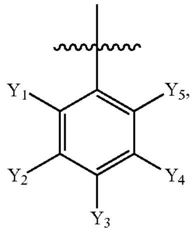

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl)piperazinyl, N-(3-N,N-diethylaminopropyl)piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)

piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2 6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

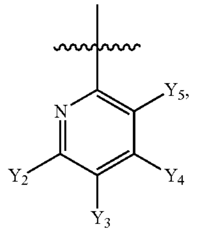

wherein $Y_2$, $Y_3$, $Y_4$, $Y_5$ are the same as defined in 4), and $Y_2$, $Y_3$, $Y_4$, $Y_5$ are not hydrogen at the same time;

6)

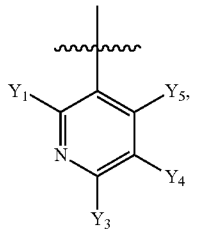

wherein $Y_1$, $Y_3$, $Y_4$, $Y_5$ are the same as defined in 4), and $Y_1$, $Y_3$, $Y_4$, $Y_5$ are not hydrogen at the same time;

7)

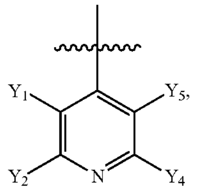

wherein $Y_1$, $Y_2$, $Y_4$, $Y_5$ are the same as defined in 4), and $Y_1$, $Y_2$, $Y_4$, $Y_5$ may be hydrogen at the same time;

8)

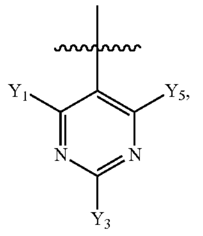

wherein $Y_1$, $Y_3$, $Y_5$ are the same as defined in 4), and $Y_1$, $Y_3$, $Y_5$ are not hydrogen at the same time;

$Z_6$ is selected from $C_1$-$C_6$ alkyl, $C_1$-$C_6$ fluorine-containing alkyl, or $C_3$-$C_6$ cycloalkyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl.

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

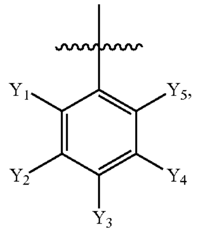

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl) piperazinyl-1-)piperidyl, 4-(N-(2-cyanoethyl) piperazinyl-1-)piperidyl, 4-(N-(3-hydroxypropyl) piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2 6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl) piperazinyl-1-sulfonyl, N-(2-N,N-dimethylaminoethyl)piperazinyl-1-sulfonyl, N-(2-N,N-diethylaminoethyl)piperazinyl-1-sulfonyl,

(13) aminoformamido, methylaminoformamido, ethylaminoformamido, propylaminoformamido, isopropylaminoformamido,

5)

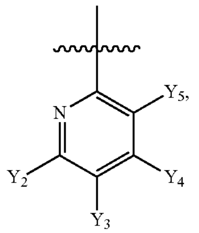

wherein $Y_2$, $Y_3$, $Y_4$, $Y_5$ are the same as defined in 4), and $Y_2$, $Y_3$, $Y_4$, $Y_5$ are not hydrogen at the same time;

6)

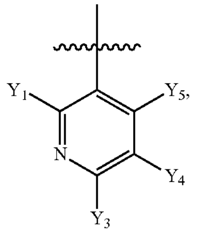

wherein $Y_1$, $Y_3$, $Y_4$, $Y_5$ are the same as defined in 4), and $Y_1$, $Y_3$, $Y_4$, $Y_5$ are not hydrogen at the same time;

7)

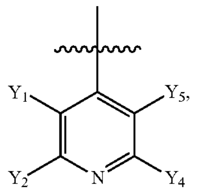

wherein $Y_1$, $Y_2$, $Y_4$, $Y_5$ are the same as defined in 4), and $Y_1$, $Y_2$, $Y_4$, $Y_5$ may be hydrogen at the same time;

8)

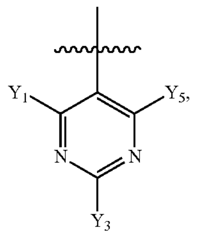

wherein $Y_1$, $Y_3$, $Y_5$ are the same as defined in 4), and $Y_1$, $Y_3$, $Y_5$ are not hydrogen at the same time;

9)

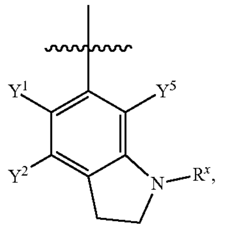

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

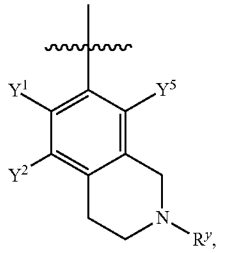

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

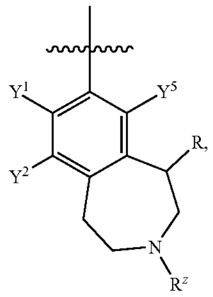

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

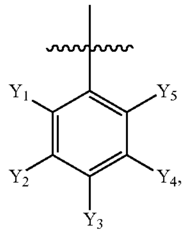

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-)piperidyl, 4-(N-ethylpiperazinyl-1-)piperidyl, 4-(N-isopropylpiperazinyl-1-)piperidyl, (6) cyclopropylmethylene, cyclobutylmethylene, cyclopentylmethylene, cyclohexylmethylene, (7) 4-(N-methyl-1-piperazinyl)piperidyl-1-formyl, 4-(N-ethyl-1-piperazinyl)piperidyl-1-formyl;

2)

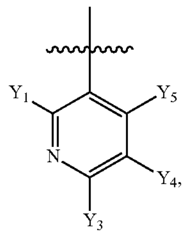

wherein:

$Y_1$, $Y_3$, $Y_4$, $Y_5$ each are independently selected from H, $C_1$-$C_6$ alkyl, $C_1$-$C_6$ alkoxy, 4-(N-methylpiperazinyl-1-)

piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time.

In some embodiments, $R^1$ is selected from:

1)

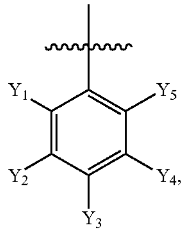

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, trifluoromethoxy, cyclopropylmethylene, N-methylpiperazinyl, 3-(N,N-dimethylamino)tetrahydropyrrolyl, 4-N,N-dimethylaminopiperidyl, 4-(N-methylpiperazinyl-1-)piperidyl, or 4-(N-methyl-1-piperazinyl)piperidyl-1-formyl;

preferably, $Y_1$, $Y_2$, $Y_4$, $Y_5$ each are independently selected from H, F, methyl, ethyl, isopropyl, cyclopropyl, methoxy, trifluoromethoxy, or cyclopropylmethylene; $Y_3$ is selected from N-methylpiperazinyl, 3-(N,N-dimethylamino)tetrahydropyrrolyl, 4-N,N-dimethylaminopiperidyl, 4-(N-methylpiperazinyl-1-)piperidyl, or 4-(N-methyl-1-piperazinyl)piperidyl-1-formyl;

2)

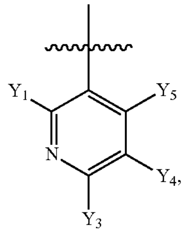

wherein:

$Y_1$, $Y_3$, $Y_4$, $Y_5$ each are independently selected from H, ethyl, methoxy, or 4-(N-methylpiperazinyl-1-)piperidyl, and $Y_1$, $Y_3$, $Y_4$, $Y_5$ are not hydrogen at the same time;

preferably, $Y_1$, $Y_4$, $Y_5$ each are independently selected from H, ethyl, or methoxy, $Y_3$ is 4-(N-methylpiperazinyl-1-)piperidyl.

In some embodiments, $Z_6$ is selected from $C_1$-$C_6$ alkyl.

In some embodiments, $Z_{r}$ is selected from methyl, or isopropyl.

In some embodiments, $R^3$, $R^4$, $R^5$ each are independently selected from H, or $C_1$-$C_6$ alkyl.

In some embodiments, $R^3$, $R^4$, $R^5$ are H.

In the sixth aspect of the present invention, the present invention provides a compound having the following general formula:

(A')

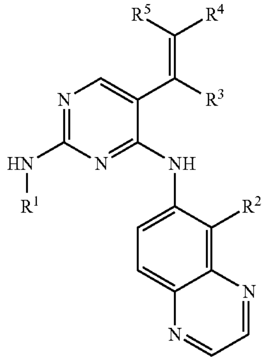

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

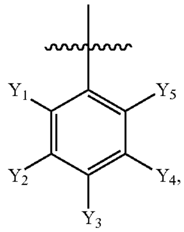

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, mono-halo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl)piperazinyl, N-(3-N,N-diethylaminopropyl)piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)

piperazinyl-1-formyl, 4-(N-methyl-4-piperidyl) piperazinyl-1-formyl, 4-(N-ethyl-4-piperidyl) piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2 6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

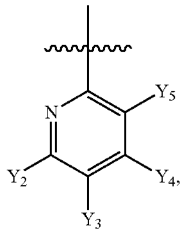

wherein $Y_2$, $Y_3$, $Y_4$, $Y_5$ are the same as defined in 4), and $Y_2$, $Y_3$, $Y_4$, $Y_5$ are not hydrogen at the same time;

6)

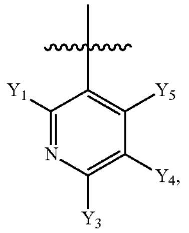

wherein $Y_1$, $Y_3$, $Y_4$, $Y_5$ are the same as defined in 4), and $Y_1$, $Y_3$, $Y_4$, $Y_5$ are not hydrogen at the same time;

7)

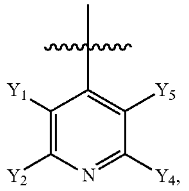

wherein $Y_1$, $Y_2$, $Y_4$, $Y_5$ are the same as defined in 4), and $Y_1$, $Y_2$, $Y_4$, $Y_5$ may be hydrogen at the same time;

8)

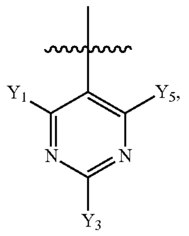

wherein $Y_1$, $Y_3$, $Y_5$ are the same as defined in 4), and $Y_1$, $Y_3$, $Y_5$ are not hydrogen at the same time;

$R^2$ is selected from:

1)

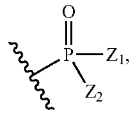

wherein, $Z_1$, $Z_2$ each are independently selected from $C_1$-$C_6$ alkyl, or $C_3$-$C_8$ cycloalkyl;

2)

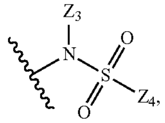

wherein, $Z_3$, $Z_4$ each are independently selected from H, $C_1$-$C_6$ alkyl, $C_1$-$C_6$ fluorine-containing alkyl, $C_3$-$C_6$ cycloalkyl, or $C_3$-$C_6$ fluorine-containing cycloalkyl, and $Z_4$ is not H;

3)

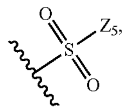

wherein, $Z_5$ is selected from $C_1$-$C_6$ alkyl, $C_1$-$C_6$ fluorine-containing alkyl, $C_3$-$C_8$ cycloalkyl, $C_1$-$C_6$ heteroatom-containing alkyl, or $C_3$-$C_8$ heteroatom-containing cycloalkyl;

4)

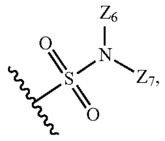

wherein, $Z_6$, $Z_7$ each are independently selected from H, $C_1$-$C_6$ alkyl, $C_1$-$C_6$ fluorine-containing alkyl, $C_3$-$C_6$ cycloalkyl, or $C_3$-$C_6$ fluorine-containing cycloalkyl, or, $Z_6$, $Z_7$, together with N, may form a 1 to 2 heteroatom-containing substituted or unsubstituted 4- to 8-membered ring, the substituents being selected from halogen, $C_1$-$C_6$ alkyl, or $C_3$-$C_8$ cycloalkyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;
2) substituted or unsubstituted aryl or heteroaryl, the substituents being selected from halogen, $C_1$-$C_6$ alkyl, or $C_3$-$C_6$ cycloalkyl;
3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl; and, the compound having the general formula (A') is not selected from

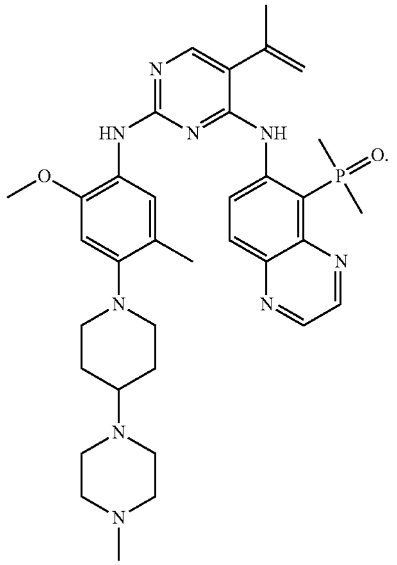

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;
2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;
3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

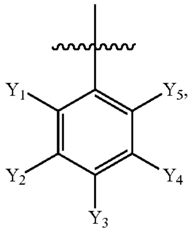

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl) piperazinyl-1-)piperidyl, 4-(N-(2-cyanoethyl) piperazinyl-1-)piperidyl, 4-(N-(3-hydroxypropyl) piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2 6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl) piperazinyl-1-sulfonyl, N-(2-N,N-dimethylaminoethyl)piperazinyl-1-sulfonyl, N-(2-N, N-diethylaminoethyl)piperazinyl-1-sulfonyl,

(13) aminoformamido, methylaminoformamido, ethylaminoformamido, propylaminoformamido, isopropylaminoformamido;

5)

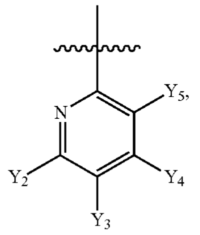

wherein $Y_2$, $Y_3$, $Y_4$, $Y_5$ are the same as defined in 4), and $Y_2$, $Y_3$, $Y_4$, $Y_5$ are not hydrogen at the same time;

6)

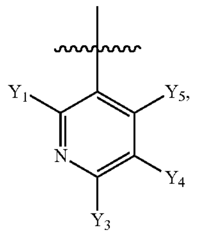

wherein $Y_1$, $Y_3$, $Y_4$, $Y_5$ are the same as defined in 4), and $Y_1$, $Y_3$, $Y_4$, $Y_5$ are not hydrogen at the same time;

7)

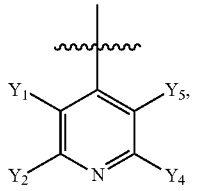

wherein $Y_1$, $Y_2$, $Y_4$, $Y_5$ are the same as defined in 4), and $Y_1$, $Y_2$, $Y_4$, $Y_5$ may be hydrogen at the same time;

8)

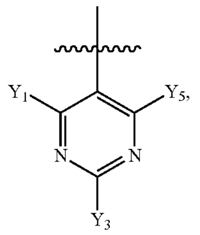

wherein $Y_1$, $Y_3$, $Y_5$ are the same as defined in 4), and $Y_1$, $Y_3$, $Y_5$ are not hydrogen at the same time;

9)

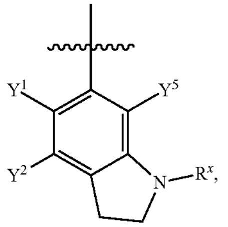

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

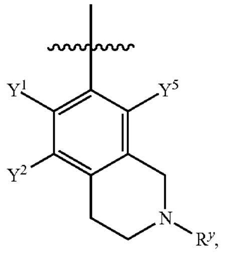

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

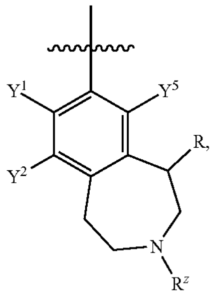

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

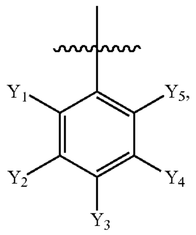

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkyl, $C_1$-$C_6$ fluorine-containing alkoxy, $C_2$-$C_6$ alkenyl, (3) piperazinyl, N-methylpiperazinyl, N-ethylpiperazinyl, N-n-propylpiperazinyl, N-isopropylpiperazinyl, (4) morpholinyl, 2,6-dimethylmorpholinyl, thiomorpholinyl, (5) 3-(N,N-dimethylamino)tetrahydropyrrolyl, 3-(N,N-diethylamino)tetrahydropyrrolyl, (6) 4-N,N-dimethylaminopiperidyl, 4-N,N-diethylaminopiperidyl, 4-N,N-diisopropylaminopiperidyl, 4-hydroxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(tetrahydropyrrolyl-1-)piperidyl, (7) piperidin-4-yl, N-methyl-4-piperidyl, N-ethyl-4-piperidyl, N-isopropyl-4-piperidyl, (8) aminoformamido, methylaminoformamido, ethylaminoformamido, propylaminoformamido, isopropylaminoformamido, 2-(N,N-dimethylamino)acetamido, cyclopropylsulfamido, 2-N,N-dimethylaminoethylamino, 3-N,N-dimethylaminopropylamino, 3-N,N-diethylaminopropylamino, 3-N,N-diisopropylaminopropylamino, N-methyl-N-(2-N,N-dimethylamino) ethylamino, (9) 4-methyl-1-piperazinylmethylene, 4-ethyl-1-piperazinylmethylene, 4-propyl-1-piperazinylmethylene, 4-isopropyl-1-piperazinylmethylene, benzyl, cyclopropylmethylene, cyclobutylmethylene, cyclopentylmethylene, cyclohexylmethylene,

(10) 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl,

(11) cyclopropylaminosulfonyl, cyclobutylaminosulfonyl, cyclopentylaminosulfonyl, cyclohexylaminosulfonyl, N-methylpiperazinyl-1-sulfonyl, N-ethylpiperazinyl-1-sulfonyl, N-isopropylpiperazinyl-1-sulfonyl;

2)

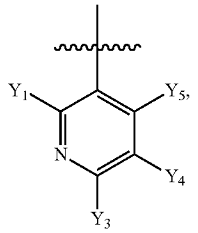

wherein $Y_1$, $Y_3$, $Y_4$, $Y_5$ each are independently selected from H, $C_1$-$C_6$ alkyl, $C_1$-$C_6$ alkoxy, N—(N-methyl-3-tetrahydropyrrolyl)amino, N-methyl-N—(N-methyl-3-tetrahydropyrrolyl)amino, N-methylpiperazinyl, N-ethylpiperazinyl, N-n-propylpiperazinyl, N-isopropylpiperazinyl, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time.

In some embodiments, $R^1$ is selected from:

1)

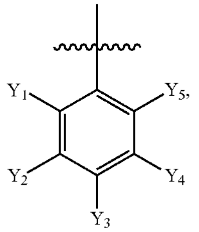

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, methyl, ethyl, methoxy, ethoxy, iso-propoxy, trifluoromethyl, trifluoromethoxy, vinyl, N-methylpiperazinyl, morpholinyl, 3-(N,N-dimethylamino)tetrahydropyrrolyl, 4-N,N-dimethylaminopiperidyl, 4-hydroxypiperidyl, 4-(N-methylpiperazinyl-1-)piperidyl, 4-(tetrahydropyrrolyl-1-)piperidyl, N-methyl-4-piperidyl, 2-(N,N-dimethylamino)acetamido, cyclopropylsulfamido, N-methyl-N-(2-N,N-dimethylamino) ethylamino, 4-methyl-1-piperazinylmethylene, benzyl, cyclopropylmethylene, 4-(N-methyl-1-piperazinyl)piperidyl-1-formyl, N-methylpiperazinyl-1-formyl, cyclopropylaminosulfonyl, or N-methylpiperazinyl-1-sulfonyl;

2)

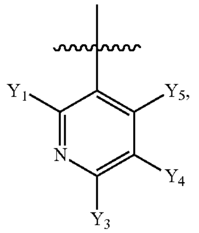

wherein, $Y_1$, $Y_3$, $Y_4$, $Y_5$ each are independently selected from H, methyl, ethyl, methoxy, N—(N-methyl-3-tetrahydropyrrolyl)amino, N-methyl-N—(N-methyl-3-tetrahydropyrrolyl)amino, N-methylpiperazinyl, or 4-(N-methylpiperazinyl-1-)piperidyl, and $Y_1$, $Y_3$, $Y_4$, $Y_5$ are not hydrogen at the same time.

In some embodiments, $Z_1$, $Z_2$ each are independently selected from $C_1$-$C_6$ alkyl.

In some embodiments, $Z_1$, $Z_2$ are methyl.

In some embodiments, $Z_5$ is selected from $C_1$-$C_6$ alkyl.

In some embodiments, $Z_5$ is selected from methyl, or isopropyl.

In some embodiments, $Z_3$, $Z_4$ each are independently selected from $C_1$-$C_6$ alkyl, $C_1$-$C_6$ fluorine-containing alkyl, or $C_3$-$C_6$ cycloalkyl.

In some embodiments, $Z_3$, $Z_4$ each are independently selected from methyl, ethyl, isopropyl, cyclopropyl, or trifluoromethyl.

In some embodiments, $R^3$, $R^4$, $R^5$ each are independently selected from:

1) H, $C_1$-$C_6$ alkyl, $C_1$-$C_6$ alkoxy, $C_3$-$C_6$ cycloalkyl;

2) substituted or unsubstituted aryl, the substituents being selected from halogen, $C_1$-$C_6$ alkyl, or $C_3$-$C_8$ cycloalkyl;

3) $R^3$, $R^4$ and carbon atoms linked thereto together form

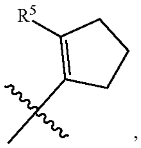

, $R^5$ being selected from:

H, or $C_1$-$C_6$ alkyl.

In some embodiments, $R^3$, $R^4$, $R^5$ each are independently selected from:

1) H, methyl, ethoxy, cyclopropyl;

2) phenyl;

3) $R^3$, $R^4$ and carbon atoms linked thereto together form

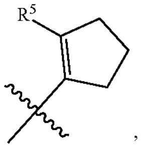

, $R^5$ being H.

In the seventh aspect of the present invention, the present invention provides a compound having the following general formula:

(I')

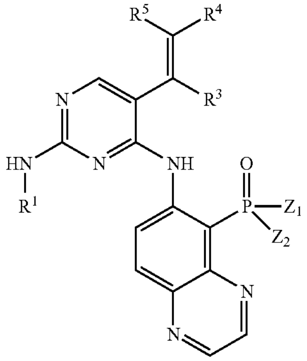

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

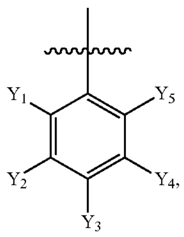

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, monohalo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2 6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

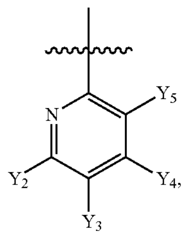

wherein $Y_2$, $Y_3$, $Y_4$, $Y_5$ are the same as defined in 4), and $Y_2$, $Y_3$, $Y_4$, $Y_5$ are not hydrogen at the same time;

6)

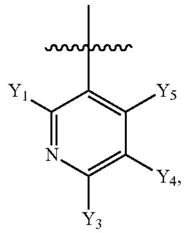

wherein $Y_1$, $Y_3$, $Y_4$, $Y_5$ are the same as defined in 4), and $Y_1$, $Y_3$, $Y_4$, $Y_5$ are not hydrogen at the same time;

7)

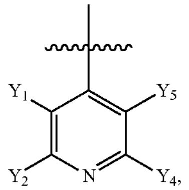

wherein $Y_1$, $Y_2$, $Y_4$, $Y_5$ are the same as defined in 4), and $Y_1$, $Y_2$, $Y_4$, $Y_5$ may be hydrogen at the same time;

8)

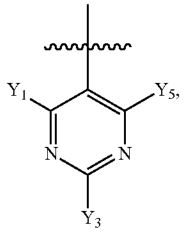

wherein $Y_1$, $Y_3$, $Y_5$ are the same as defined in 4), and $Y_1$, $Y_3$, $Y_5$ are not hydrogen at the same time;

$Z_1$, $Z_2$ each are independently selected from $C_1$-$C_6$ alkyl, or $C_3$-$C_8$ cycloalkyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl;

furthermore, the compound having the general formula (I') is not selected from

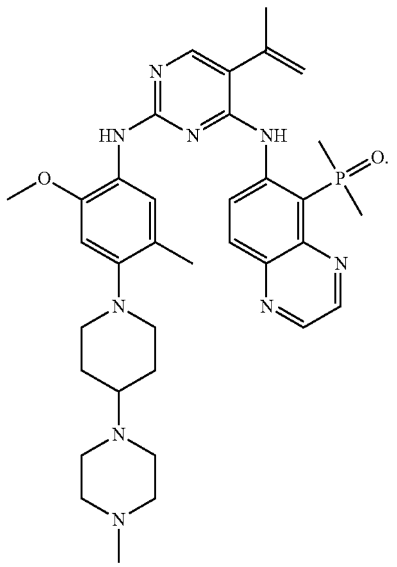

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

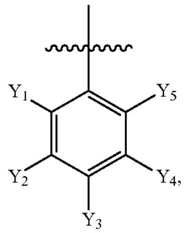

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl) piperazinyl-1-)piperidyl, 4-(N-(2-cyanoethyl) piperazinyl-1-)piperidyl, 4-(N-(3-hydroxypropyl) piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl) piperazinyl-1-formyl, N-(2-N,N-dimethylaminoethyl) piperazinyl-1-formyl, N-(2-N, N-diethylaminoethyl) piperazinyl-1-formyl, 4-(N-methyl-4-piperidyl) piperazinyl-1-formyl, 4-(N-ethyl-4-piperidyl) piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)

piperazinyl-1-sulfonyl, N-(2-N,N-dimethylaminoethyl)piperazinyl-1-sulfonyl, N-(2-N,N-diethylaminoethyl)piperazinyl-1-sulfonyl,

(13) aminoformamido, methylaminoformamido, ethylaminoformamido, propylaminoformamido, isopropylaminoformamido;

5)

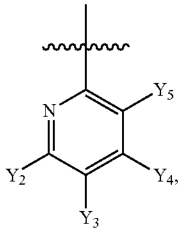

wherein $Y_2$, $Y_3$, $Y_4$, $Y_5$ are the same as defined in 4), and $Y_2$, $Y_3$, $Y_4$, $Y_5$ are not hydrogen at the same time;

6)

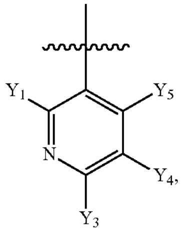

wherein $Y_1$, $Y_3$, $Y_4$, $Y_5$ are the same as defined in 4), and $Y_1$, $Y_3$, $Y_4$, $Y_5$ are not hydrogen at the same time;

7)

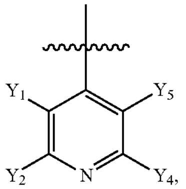

wherein $Y_1$, $Y_2$, $Y_4$, $Y_5$ are the same as defined in 4), and $Y_1$, $Y_2$, $Y_4$, $Y_5$ may be hydrogen at the same time;

8)

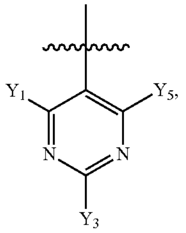

wherein $Y_1$, $Y_3$, $Y_5$ are the same as defined in 4), and $Y_1$, $Y_3$, $Y_5$ are not hydrogen at the same time;

9)

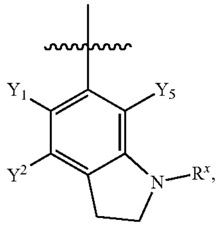

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

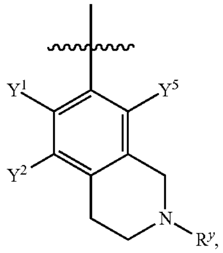

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

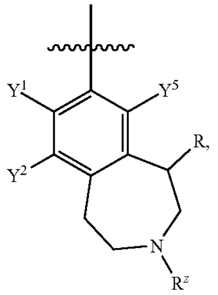

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

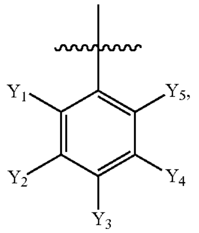

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-)piperidyl, 4-(N-ethylpiperazinyl-1-)piperidyl, 4-(N-isopropylpiperazinyl-1-)piperidyl, (6) cyclopropylmethylene, cyclobutylmethylene, cyclopentylmethylene, cyclohexylmethylene,

2)

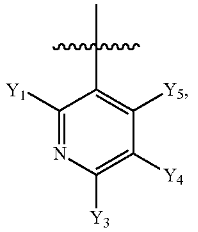

wherein $Y_1$, $Y_3$, $Y_4$, $Y_5$ each are independently selected from H, $C_1$-$C_6$ alkyl, $C_1$-$C_6$ alkoxy, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time.

In some embodiments, $R^1$ is selected from:

1)

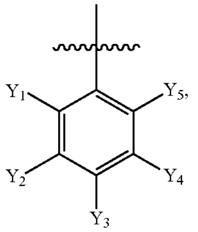

wherein:

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, methyl, ethyl, methoxy, trifluoromethoxy, cyclopropylmethylene, N-methylpiperazinyl, 3-(N,N-dimethylamino)tetrahydropyrrolyl, 4-N,N-dimethylaminopiperidyl, or 4-(N-methylpiperazinyl-1-)piperidyl, preferably, $Y_1$, $Y_2$, $Y_4$, $Y_5$ each are independently selected from H, methyl, ethyl, methoxy, trifluoromethoxy, or cyclopropylmethylene, $Y_3$ is selected from N-methylpiperazinyl, 3-(N,N-dimethylamino)tetrahydropyrrolyl, 4-N,N-dimethylaminopiperidyl, or 4-(N-methylpiperazinyl-1-)piperidyl;

2)

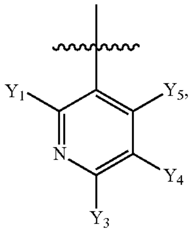

wherein:

$Y_1$, $Y_3$, $Y_4$, $Y_5$ each are independently selected from H, ethyl, methoxy, or 4-(N-methylpiperazinyl-1-)piperidyl, and $Y_1$, $Y_3$, $Y_4$, $Y_5$ are not hydrogen at the same time, preferably, $Y_1$, $Y_4$, $Y_5$ each are independently selected from H, ethyl, or methoxy, $Y_3$ is 4-(N-methylpiperazinyl-1-)piperidyl.

In some embodiments, $Z_1$, $Z_2$ each are independently selected from $C_1$-$C_6$ alkyl.

In some embodiments, $Z_1$, $Z_2$ are methyl.

In some embodiments, $R^3$, $R^4$, $R^5$ each are independently selected from:

1) H, $C_1$-$C_6$ alkyl, $C_1$-$C_6$ alkoxy, $C_3$-$C_6$ cycloalkyl;

2) substituted or unsubstituted aryl, the substituents being selected from halogen, $C_1$-$C_6$ alkyl, or $C_3$-$C_8$ cycloalkyl;

3) $R^3$, $R^4$ and carbon atoms linked thereto together form

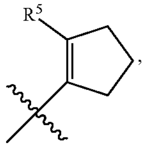

$R^5$ being selected from H, or $C_1$-$C_6$ alkyl.

In some embodiments, $R^3$, $R^4$, $R^5$ each are independently selected from:

1) H, methyl, ethoxy, cyclopropyl;

2) phenyl;

3) $R^3$, $R^4$ and carbon atoms linked thereto together form

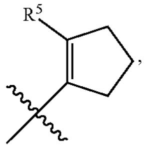

$R^5$ being H.

In some embodiments, $R^3$ is H, $R^4$ is selected from methyl, ethoxy, cyclopropyl, or phenyl, $R^5$ is selected from H, or methyl; or, $R^3$, $R^4$ and carbon atoms linked thereto together form

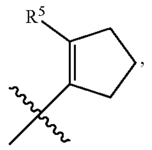

$R^5$ being H.

In the eighth aspect of the present invention, the present invention provides a compound having the following general formula:

(II')

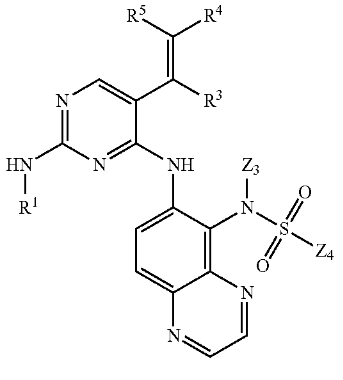

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

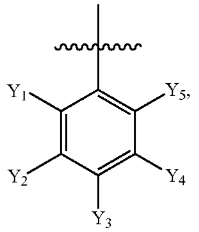

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, mono-halo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl)piperazinyl, N-(3-N,N-diethylaminopropyl)piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

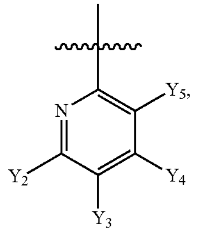

wherein $Y_2$, $Y_3$, $Y_4$, $Y_5$ are the same as defined in 4), and $Y_2$, $Y_3$, $Y_4$, $Y_5$ are not hydrogen at the same time;

6)

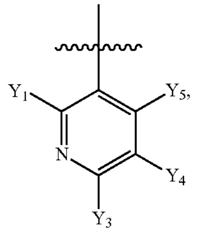

wherein $Y_1$, $Y_3$, $Y_4$, $Y_5$ are the same as defined in 4), and $Y_1$, $Y_3$, $Y_4$, $Y_5$ are not hydrogen at the same time;

7)

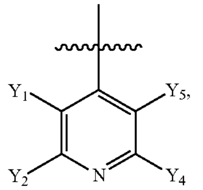

wherein $Y_1$, $Y_2$, $Y_4$, $Y_5$ are the same as defined in 4), and $Y_1$, $Y_2$, $Y_4$, $Y_5$ may be hydrogen at the same time;

8)

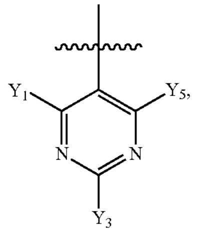

wherein $Y_1$, $Y_3$, $Y_5$ are the same as defined in 4), and $Y_1$, $Y_3$, $Y_5$ are not hydrogen at the same time;

$Z_3$, $Z_4$ each are independently selected from H, $C_1$-$C_6$ alkyl, $C_1$-$C_6$ fluorine-containing alkyl, $C_3$-$C_6$ cycloalkyl, or $C_3$-$C_6$ fluorine-containing cycloalkyl, and $Z_4$ is not H;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl.

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

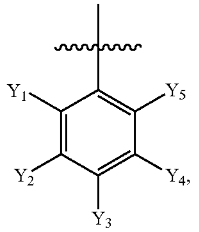

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl)piperazinyl, N-(3-N,N-diethylaminopropyl)piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl,

(13) aminoformamido, methylaminoformamido, ethylaminoformamido, propylaminoformamido, isopropylaminoformamido;

5)

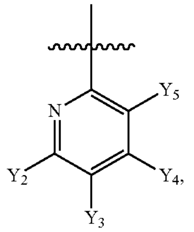

wherein $Y_2$, $Y_3$, $Y_4$, $Y_5$ are the same as defined in 4), and $Y_2$, $Y_3$, $Y_4$, $Y_5$ are not hydrogen at the same time;

6)

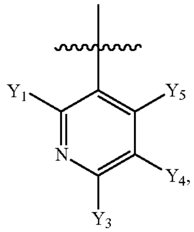

wherein $Y_1$, $Y_3$, $Y_4$, $Y_5$ are the same as defined in 4), and $Y_1$, $Y_3$, $Y_4$, $Y_5$ are not hydrogen at the same time;

7)

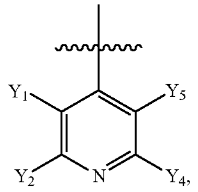

wherein $Y_1$, $Y_2$, $Y_4$, $Y_5$ are the same as defined in 4), and $Y_1$, $Y_2$, $Y_4$, $Y_5$ may be hydrogen at the same time;

8)

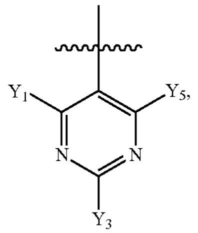

wherein $Y_1$, $Y_3$, $Y_5$ are the same as defined in 4), and $Y_1$, $Y_3$, $Y_5$ are not hydrogen at the same time;

9)

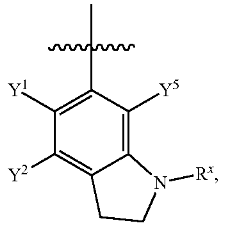

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

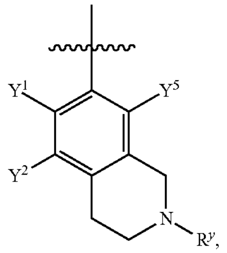

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$;

11)

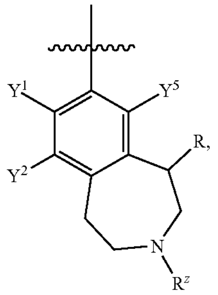

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is selected from:

1)

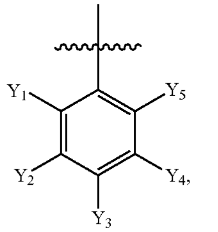

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-)piperidyl, 4-(N-ethylpiperazinyl-1-)piperidyl, 4-(N-isopropylpiperazinyl-1-)piperidyl, (6) cyclopropylmethylene, cyclobutylmethylene, cyclopentylmethylene, cyclohexylmethylene,

2)

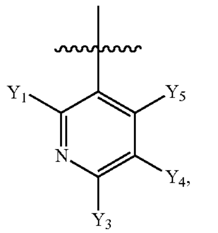

wherein $Y_1$, $Y_3$, $Y_4$, $Y_5$ each are independently selected from H, $C_1$-$C_6$ alkyl, $C_1$-$C_6$ alkoxy, 4-(N-methylpiperazinyl-1-)piperidyl, 4-(N-ethylpiperazinyl-1-)piperidyl, or 4-(N-isopropylpiperazinyl-1-)piperidyl, and $Y_1$, $Y_3$, $Y_4$, $Y_5$ are not hydrogen at the same time.

In some embodiments, $R^1$ is selected from:

1)

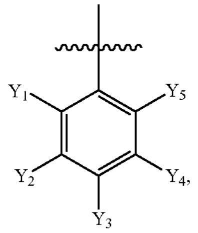

wherein:

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, methyl, ethyl, methoxy, trifluoromethoxy, cyclopropylmethylene, N-methylpiperazinyl, 3-(N,N-dimethylamino)tetrahydropyrrolyl, 4-N,N-dimethylaminopiperidyl, or 4-(N-methylpiperazinyl-1-)piperidyl, preferably, $Y_1$, $Y_2$, $Y_4$, $Y_5$ each are independently selected from H, methyl, ethyl, methoxy, trifluoromethoxy, or cyclopropylmethylene, $Y_3$ is selected from N-methylpiperazinyl, 3-(N,N-dimethylamino)tetrahydropyrrolyl, 4-N,N-dimethylaminopiperidyl, or 4-(N-methylpiperazinyl-1-)piperidyl;

2)

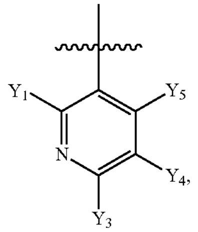

wherein:

$Y_1$, $Y_3$, $Y_4$, $Y_5$ each are independently selected from H, ethyl, methoxy, or 4-(N-methylpiperazinyl-1-)piperidyl, and $Y_1$, $Y_3$, $Y_4$, $Y_5$ are not hydrogen at the same time, preferably, $Y_1$, $Y_4$, $Y_5$ each are independently selected from H, ethyl, or methoxy, $Y_3$ is 4-(N-methylpiperazinyl-1-)piperidyl.

In some embodiments, $Z_3$, $Z_4$ each are independently selected from $C_1$-$C_6$ alkyl, $C_1$-$C_6$ fluorine-containing alkyl, or $C_3$-$C_6$ cycloalkyl.

In some embodiments, $Z_3$, $Z_4$ each are independently selected from methyl, ethyl, isopropyl, cyclopropyl, or trifluoromethyl.

In some embodiments, $Z_3$ is selected from methyl, ethyl, isopropyl, or cyclopropyl, $Z_4$ is selected from methyl, ethyl, isopropyl, cyclopropyl, or trifluoromethyl.

In some embodiments, $R^3$, $R^4$, $R^5$ each are independently selected from H, or $C_1$-$C_6$ alkyl.

In some embodiments, $R^3$, $R^4$, $R^5$ are H.

In the ninth aspect of the present invention, the present invention provides a compound having the following general formula:

(III')

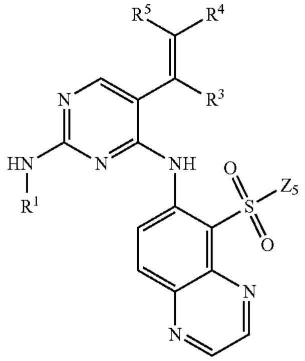

or a stereoisomer, a prodrug, a pharmaceutically acceptable salt or a pharmaceutically acceptable solvate thereof, wherein:

$R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, N-acetyl-4-piperidyl, N-propionyl-4-piperidyl, N-isopropionyl-4-piperidyl, N-cyclopropylformyl-4-piperidyl, N-methylsulfonyl-4-piperidyl, N-ethylsulfonyl-4-piperidyl, N-propylsulfonyl-4-piperidyl, N-isopropylsulfonyl-4-piperidyl, N-cyclopropylsulfonyl-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-acetylaminocyclohexyl, 4-propionylaminocyclohexyl, 4-isopropylformylaminocyclohexyl, 4-methylsulfonylaminocyclohexyl, 4-ethylsulfonylaminocyclohexyl, 4-propylsulfonylaminocyclohexyl, 4-isopropylsulfonylaminocyclohexyl, 4-cyclopropylsulfonylaminocyclohexyl, 4-hydroxycyclohexyl, 4-methoxycyclohexyl, 4-ethoxycyclohexyl, 4-isopropoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1-(N-methyl-4-piperidyl)-4-pyrazolyl, 1-(N-t-butoxycarbonyl-4-piperidyl)-4-pyrazolyl, 1,3-dimethyl-5-pyrazolyl, 1-methyl-4-imidazolyl, 3-methyl-5-isoxazolyl;

4)

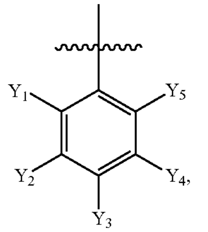

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) 2-N,N-dimethylaminoethoxy, 3-N,N-dimethylaminopropoxy, 2-(N-methylpiperazinyl)ethoxy, 2-(N-acetylpiperazinyl)ethoxy, 2-morpholinylethoxy, 2-thiomorpholinylethoxy, 2-piperidylethoxy, 3-N,N-dimethylaminopropoxy, 3-N,N-diethylaminopropoxy, 3-N,N-diisopropylaminopropoxy, 3-(N-methylpiperazinyl)propoxy, 3-(N-acetylpiperazinyl)propoxy, 3-morpholinylpropoxy, 3-thiomorpholinylpropoxy, 3-piperidylpropoxy, 2-pyridylmethoxy, 3-pyridylmethoxy, 4-pyridylmethoxy, phenylmethoxy, mono-halo-substituted phenylmethoxy, gem-dihalo-substituted phenylmethoxy, hetero-dihalo-substituted phenylmethoxy, (4) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl)piperazinyl, N-(3-N,N-diethylaminopropyl)piperazinyl, N—(N-methyl-4-piperidyl)piperazinyl, N—(N-ethyl-4-piperidyl)piperazinyl, N-t-butoxycarbonylpiperazinyl, N-acetylpiperazinyl, N-propionylpiperazinyl, N-isobutyrylpiperazinyl, N-cyclopropylformylpiperazinyl, N-methylsulfonylpiperazinyl, N-ethylsulfonylpiperazinyl, N-n-propylsulfonylpiperazinyl, N-isopropylsulfonylpiperazinyl, N-cyclopropylsulfonylpiperazinyl, 2-oxo-piperazin-4-yl, (5) morpholinyl, 2,6-dimethylmorpholinyl, thiomorpholinyl, (6) tetrahydropyrrolyl, 3-(N,N-dimethylamino)tetrahydropyrrolyl, 3-(N,N-diethylamino)tetrahydropyrrolyl, (7) imidazolyl, 4-methyl-1-imidazolyl, (8) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-acetylpiperazinyl-1-)piperidyl, 4-(N-t-butoxycarbonylpiperazinyl-1-)piperidyl, 4-(N-methylsulfonylpiperazinyl-1-)piperidyl, 4-(N-(2-hydroxyethyl)piperazinyl-1-)piperidyl, 4-(N-(2-cyanoethyl)piperazinyl-1-)piperidyl, 4-(N-(3-hydroxypropyl)piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (9) piperidin-4-yl, N-methyl-4-piperidyl, N-ethyl-4-piperidyl, N-isopropyl-4-piperidyl, N-acetyl-4-piperidyl, N-t-butoxycarbonyl-4-piperidyl, N-methylsulfonyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl,

(10) amino, N,N-dimethylamino, N,N-diethylamino, N,N-di-n-propylamino, N,N-diisopropylamino, 2-N,N-dimethylaminoethylamino, 2-morpholinylethylamino, 2-(N-methylpiperazinyl)ethylamino, 3-N,N-dimethylaminopropylamino, 3-N,N-diethylaminopropylamino, 3-N,N-diisopropylaminopropylamino, 3-morpholinylpropylamino, 3-(N-methylpiperazinyl)propylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(11) aminomethylene, N,N-dimethylaminomethylene, N,N-diethylaminomethylene, 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(12) aminoformyl, methylaminoformyl, N,N-dimethylaminoformyl, ethylaminoformyl, cyclopropylaminoformyl, cyclobutylaminoformyl, cyclopentylaminoformyl, cyclohexylaminoformyl, aminoacetyl, methylaminoacetyl, 2-(N,N-dimethylamino)acetyl, ethylaminoacetyl, cyclopropylaminoacetyl, cyclobutylaminoacetyl, cyclopentylaminoacetyl, cyclohexylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino)piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)

piperazinyl-1-formyl, 4-(N-methyl-4-piperidyl) piperazinyl-1-formyl, 4-(N-ethyl-4-piperidyl) piperazinyl-1-formyl,

(13) hydroxyformyl, methoxyformyl, ethoxyformyl, propoxyformyl, iso-propoxyformyl, n-butoxyformyl, iso-butoxyformyl, t-butoxyformyl,

(14) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, 4-(N-methyl-1-piperazinyl)piperidyl-1-sulfonyl, 4-(N-ethyl-1-piperazinyl)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N,N-diethylaminoethyl)piperazinyl-1-sulfonyl, 4-(N-methyl-4-piperidyl)piperazinyl-1-sulfonyl, 4-(N-ethyl-4-piperidyl)piperazinyl-1-sulfonyl,

(15) aminoformamido, methylaminoformamido, ethylaminoformamido, propylaminoformamido, isopropylaminoformamido, cyclopropylaminoformamido, cyclobutylaminoformamido, cyclopentylaminoformamido, piperidyl-1-formamido, 4-hydroxypiperidyl-1-formamido, 4-N,N-dimethylpiperidyl-1-formamido, 4-N,N-diethylpiperidyl-1-formamido, tetrahydropyrrolyl-1-formamido, 3-N,N-dimethyltetrahydropyrrolyl-1-formamido, 3-N,N-diethyltetrahydropyrrolyl-1-formamido, N-methylpiperazinyl-1-formamido, N-ethylpiperazinyl-1-formamido, N-acetylpiperazinyl-1-formamido, N-t-butoxycarbonylpiperazinyl-1-formamido, N-(2-hydroxyethyl)piperazinyl-1-formamido, N-(2-cyanoethyl)piperazinyl-1-formamido, N-(2-N,N-dimethylaminoethyl)piperazinyl-1-formamido, N-(2-N,N-diethylaminoethyl)piperazinyl-1-formamido, N-(3-hydroxypropyl)piperazinyl-1-formamido, N-(3-N,N-dimethylpropyl)piperazinyl-1-formamido, N-(3-N,N-diethylpropyl)piperazinyl-1-formamido, morpholinyl-1-formamido, 3,5-dimethylmorpholinyl-1-formamido, 4-(tetrahydropyrrolyl)piperidyl-1-formamido, 4-(N-methyl-1-piperazinyl)piperidyl-1-formamido, 4-(N-ethyl-1-piperazinyl)piperidyl-1-formamido, 4-(N-acetyl-1-piperazinyl)piperidyl-1-formamido, N—(N-methyl-4-piperidyl)piperazinyl-1-formamido,

(16) $Y_3$ and $Y_4$ may form an oxygen-containing substituted or unsubstituted 5- to 7-membered ring; the substituent may be selected from the same substituents as described above for $Y_1$,

(17) $Y_3$ and $Y_4$ may form a nitrogen-containing substituted or unsubstituted 5- to 7-membered ring; the substituent may be selected from the same substituents as described above for $Y_1$;

5)

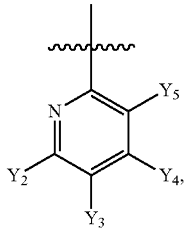

wherein $Y_2$, $Y_3$, $Y_4$, $Y_5$ are the same as defined in 4), and $Y_2$, $Y_3$, $Y_4$, $Y_5$ are not hydrogen at the same time;

6)

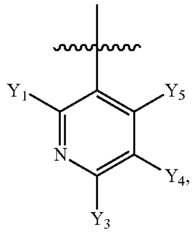

wherein $Y_1$, $Y_3$, $Y_4$, $Y_5$ are the same as defined in 4), and $Y_1$, $Y_3$, $Y_4$, $Y_5$ are not hydrogen at the same time;

7)

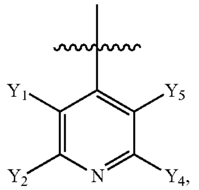

wherein $Y_1$, $Y_2$, $Y_4$, $Y_5$ are the same as defined in 4), and $Y_1$, $Y_2$, $Y_4$, $Y_5$ may be hydrogen at the same time;

8)

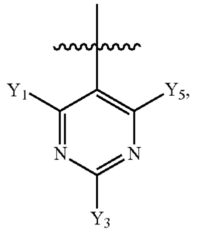

wherein $Y_1$, $Y_3$, $Y_5$ are the same as defined in 4), and $Y_1$, $Y_3$, $Y_5$ are not hydrogen at the same time;

$Z_5$ is selected from $C_1$-$C_6$ alkyl, $C_1$-$C_6$ fluorine-containing alkyl, $C_3$-$C_8$ cycloalkyl, $C_1$-$C_6$ heteroatom-containing alkyl, or $C_3$-$C_8$ heteroatom-containing cycloalkyl;

$R^3$, $R^4$, $R^5$ each are independently selected from:

1) H, $C_1$-$C_6$ alkyl, $C_1$-$C_6$ alkoxy, $C_1$-$C_6$ fluorine-containing alkyl, $C_1$-$C_6$ oxygen-containing alkyl, $C_3$-$C_6$ cycloalkyl, $C_3$-$C_6$ fluorine-containing cycloalkyl, $C_3$-$C_6$ oxygen-containing cycloalkyl;

2) substituted or unsubstituted aryl or heteroaryl, the substituents being selected from halogen, $C_1$-$C_6$ alkyl, or $C_3$-$C_8$ cycloalkyl;

3) $R^3$, $R^4$ and carbon atoms linked thereto together form a substituted or unsubstituted 5- to 7-membered ring, the substituent being selected from halogen, or $C_1$-$C_6$ alkyl, $R^5$ is selected from H, or $C_1$-$C_6$ alkyl.

In some embodiments, $R^1$ is selected from:

1) H, $C_1$-$C_6$ alkyl, $C_1$-$C_6$ fluorine-containing alkyl, $C_3$-$C_8$ cycloalkyl, $C_1$-$C_6$ heteroatom-containing alkyl, $C_3$-$C_8$ heteroatom-containing cycloalkyl;

2) 2-N,N-dimethylaminoethyl, 3-N,N-dimethylaminopropyl, 2-N,N-diethylaminoethyl, 3-N,N-diethylaminopropyl, 2-(N-methylpiperazinyl)ethyl, 2-(N-acetylpiperazinyl)ethyl, 2-morpholinylethyl, 2-thiomorpholinylethyl, 2-piperidylethyl, 2-hydroxyethyl, 3-hydroxypropyl, 2-methoxyethyl, N-methyl-4-piperidyl, N-ethyl-4-piperidyl, N-propyl-4-piperidyl, N-isopropyl-4-piperidyl, N-hydroxyethyl-4-piperidyl, N-cyanomethyl-4-piperidyl, N-(2-cyanoethyl)-4-piperidyl, 3-N,N-dimethylaminocyclopentyl, 3-N,N-diethylaminocyclopentyl, 3-N,N-dipropylaminocyclopentyl, 3-N,N-isopropylaminocyclopentyl, 4-aminocyclohexyl, 4-N,N-dimethylaminocyclohexyl, 4-N,N-diethylaminocyclohexyl, 4-N,N-dipropylaminocyclohexyl, 4-N,N-diisopropylaminocyclohexyl, 4-hydroxycyclohexyl, 4-methoxycyclohexyl, 4-ethoxycyclohexyl, 4-iso-propoxycyclohexyl;

3) 1-methyl-3-pyrrolyl, 1-ethyl-3-pyrrolyl, 1-isopropyl-3-pyrrolyl, 1-cyclopropyl-3-pyrrolyl, 1-methyl-3-pyrazolyl, 1-ethyl-3-pyrazolyl, 1-isopropyl-3-pyrazolyl, 1-cyclopropyl-3-pyrazolyl, 1-hydroxyethyl-3-pyrazolyl, 1-methyl-4-pyrazolyl, 1-ethyl-4-pyrazolyl, 1-isopropyl-4-pyrazolyl, 1-cyclopropyl-4-pyrazolyl, 1-hydroxyethyl-4-pyrazolyl, 1,3-dimethyl-5-pyrazolyl, 1-methyl-4-imidazolyl, 3-methyl-5-isoxazolyl;

4)

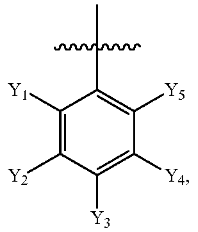

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ oxygen-containing alkyl, $C_1$-$C_6$ fluorine-containing alkyl, $C_1$-$C_6$ fluorine-containing alkoxy, $C_3$-$C_6$ cycloalkyl, $C_2$-$C_6$ alkenyl, (3) piperazinyl, N-methylpiperazinyl, N-ethylpiperazinyl, N-n-propylpiperazinyl, N-isopropylpiperazinyl, N-cyclopropylpiperazinyl, N-(2-hydroxyethyl)piperazinyl, N-(2-N,N-dimethylaminoethyl)piperazinyl, N-(2-N,N-diethylaminoethyl)piperazinyl, N-(2-cyanoethyl)piperazinyl, N-cyanomethylpiperazinyl, N-(3-hydroxypropyl)piperazinyl, N-(3-N,N-dimethylaminopropyl) piperazinyl, N-(3-N,N-diethylaminopropyl) piperazinyl, (4) morpholinyl, 2,6-dimethylmorpholinyl, thiomorpholinyl, (5) tetrahydropyrrolyl, 3-(N,N-dimethylamino)tetrahydropyrrolyl, 3-(N,N-diethylamino)tetrahydropyrrolyl, (6) imidazolyl, 4-methyl-1-imidazolyl, (7) piperidyl, 4-N,N-dimethylaminopiperidyl, 4-N,N-diethylaminopiperidyl, 4-N,N-diisopropylaminopiperidyl, 4-hydroxypiperidyl, 4-methoxypiperidyl, 4-ethoxypiperidyl, 4-(N-methylpiperazinyl-1-)piperidyl, 4-(N-ethylpiperazinyl-1-)piperidyl, 4-(N-isopropylpiperazinyl-1-)piperidyl, 4-(N-(2-hydroxyethyl) piperazinyl-1-)piperidyl, 4-(N-(2-cyanoethyl) piperazinyl-1-)piperidyl, 4-(N-(3-hydroxypropyl) piperazinyl-1-)piperidyl, 4-(N-(2-N,N-dimethylaminoethyl)piperazinyl-1-)piperidyl, 4-(N-(2-N,N-diethylethyl)piperazinyl-1-)piperidyl, 4-(N-(3-N,N-dimethylpropyl)piperazinyl-1-)piperidyl, 4-(N-(3-N,N-diethylpropyl)piperazinyl-1-)piperidyl, 4-(tetrahydropyrrolyl-1-)piperidyl, 4-(3-N,N-dimethylaminotetrahydropyrrolyl-1-)piperidyl, 4-(3-N,N-diethylaminotetrahydropyrrolyl-1-)piperidyl, (8) piperidin-4-yl, N-methyl-4-piperidyl, N-ethyl-4-piperidyl, N-isopropyl-4-piperidyl, N-(2-hydroxyethyl)-4-piperidyl, N-(2-N,N-dimethylaminoethyl)-4-piperidyl, N-(2-N,N-diethylaminoethyl)-4-piperidyl, N-(2-cyanoethyl)-4-piperidyl, N-(3-hydroxypropyl)-4-piperidyl, N-(3-N,N-dimethylaminopropyl)-4-piperidyl, N-(3-N,N-diethylaminopropyl)-4-piperidyl, N-(3-cyanopropyl)-4-piperidyl, N-cyanomethylene-4-piperidyl, (9) amino, N,N-dimethylamino, N,N-diethylamino, N,N-di-n-propylamino, N,N-diisopropylamino, 2-N,N-dimethylaminoethylamino, 3-N,N-dimethylaminopropylamino, 3-N,N-diethylaminopropylamino, 3-N,N-diisopropylaminopropylamino, N-methylpiperidyl-4-amino, N-ethylpiperidyl-4-amino, N-n-propylpiperidyl-4-amino, N-isopropylpiperidyl-4-amino, acetamido, propionamido, 2-(N,N-dimethylamino)acetamido, 2-hydroxyacetamido, 2-methoxyacetamido, methylsulfamido, ethylsulfamido, n-propylsulfamido, isopropylsulfamido, cyclopropylsulfamido, N-methyl-N—(N-methyl-3-tetrahydropyrrolyl)amino, N—(N-methyl-3-tetrahydropyrrolyl)amino, N-methyl-N-(2-N,N-dimethylamino)ethylamino,

(10) 4-methyl-1-piperazinylmethylene, 4-ethyl-1-piperazinylmethylene, 4-propyl-1-piperazinylmethylene, 4-isopropyl-1-piperazinylmethylene, 4-(2-hydroxyethyl)-1-piperazinylmethylene, 4-(2-N,N-dimethylaminoethyl)-1-piperazinylmethylene, piperidyl-1-methylene, 4-(N,N-dimethylamino)-1-piperidylmethylene, 4-hydroxypiperidyl-1-methylene, tetrahydropyrrolyl-1-methylene, 3-(N,N-dimethylamino)-1-tetrahydropyrrolylmethylene, benzyl, cyclopropylmethylene, cyclobutylmethylene, cyclopentylmethylene, cyclohexylmethylene,

(11) aminoformyl, methylaminoformyl, N,N-dimethylaminoformyl, ethylaminoformyl, aminoacetyl, methylaminoacetyl, 2-(N,N-dimethylamino)acetyl, ethylaminoacetyl, tetrahydropyrrolyl-1-formyl, 3-(N,N-dimethylamino)tetrahydropyrrolyl-1-formyl, 3-(N,N-diethylamino)tetrahydropyrrolyl-1-formyl, morpholinyl-4-formyl, thiomorpholinyl-4-formyl, 2,6-dimethylmorpholinyl-4-formyl, piperidyl-1-formyl, 4-hydroxypiperidyl-1-formyl, 4-(N,N-dimethylamino) piperidyl-1-formyl, 4-(N,N-diethylamino)piperidyl-1-formyl, 4-(N-methyl-1-piperazinyl)piperidyl-1-formyl, 4-(N-ethyl-1-piperazinyl)piperidyl-1-formyl, N-methylpiperazinyl-1-formyl, N-ethylpiperazinyl-1-formyl, N-isopropylpiperazinyl-1-formyl, N-(2-hydroxyethyl)piperazinyl-1-formyl, N-(2-N,N-dimethylaminoethyl)piperazinyl-1-formyl, N-(2-N, N-diethylaminoethyl)piperazinyl-1-formyl, 4-(N-methyl-4-piperidyl)piperazinyl-1-formyl, 4-(N-ethyl-4-piperidyl)piperazinyl-1-formyl,

(12) hydroxysulfonyl, aminosulfonyl, methylaminosulfonyl, ethylaminosulfonyl, propylaminosulfonyl, isopropylaminosulfonyl, cyclopropylaminosulfonyl, cyclobutylaminosulfonyl, cyclopentylaminosulfonyl, cyclohexylaminosulfonyl, tetrahydropyrrolyl-1-sulfonyl, 3-(N,N-dimethylamino)tetrahydropyrrolyl-1-sulfonyl, 3-(N,N-diethylamino)tetrahydropyrrolyl-1-sulfonyl, morpholinyl-4-sulfonyl, thiomorpholinyl-4-sulfonyl, 2,6-dimethylmorpholinyl-4-sulfonyl, piperidyl-1-sulfonyl, 4-hydroxypiperidyl-1-sulfonyl, 4-(N,N-dimethylamino)piperidyl-1-sulfonyl, 4-(N,N-diethylamino)piperidyl-1-sulfonyl, N-methylpiperazinyl-1-sulfonyl, N-ethylpiperazinyl-1-sulfonyl, N-isopropylpiperazinyl-1-sulfonyl, N-(2-hydroxyethyl)piperazinyl-1-sulfonyl, N-(2-N,N-dimethylaminoethyl)piperazinyl-1-sulfonyl, N-(2-N, N-diethylaminoethyl)piperazinyl-1-sulfonyl,

(13) aminoformamido, methylaminoformamido, ethylaminoformamido, propylaminoformamido, isopropylaminoformamido;

5)

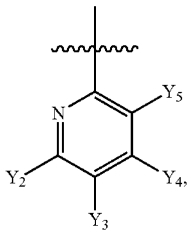

wherein $Y_2$, $Y_3$, $Y_4$, $Y_5$ are the same as defined in 4), and $Y_2$, $Y_3$, $Y_4$, $Y_5$ are not hydrogen at the same time;

6)

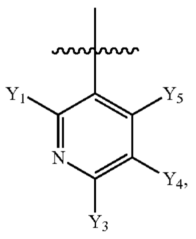

wherein $Y_1$, $Y_3$, $Y_4$, $Y_5$ are the same as defined in 4), and $Y_1$, $Y_3$, $Y_4$, $Y_5$ are not hydrogen at the same time;

7)

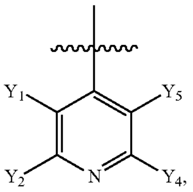

wherein $Y_1$, $Y_2$, $Y_4$, $Y_5$ are the same as defined in 4), and $Y_1$, $Y_2$, $Y_4$, $Y_5$ may be hydrogen at the same time;

8)

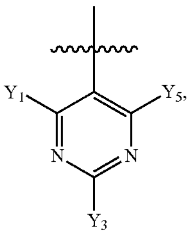

wherein $Y_1$, $Y_3$, $Y_5$ are the same as defined in 4), and $Y_1$, $Y_3$, $Y_5$ are not hydrogen at the same time;

9)

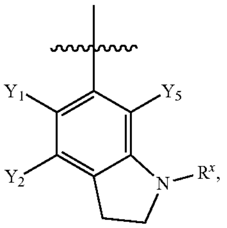

wherein $Y_1$, $Y_2$, $Y_5$ are the same as defined in 4), and $Y_1$, $Y_2$, $Y_5$ may be hydrogen at the same time, $R^x$ is selected from the same substituents as described above for $Y_1$;

10)

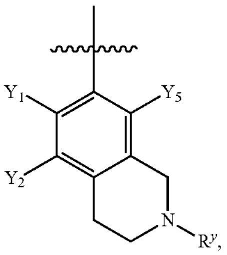

wherein $Y_1$, $Y_2$, $Y_5$ are the same as defined in 4), and $Y_1$, $Y_2$, $Y_5$ may be hydrogen at the same time, $R^y$ is selected from the same substituents as described above for $Y_1$

11)

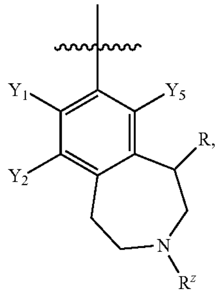

wherein $Y_1$, $Y_2$, $Y_5$ are the same as defined in 4), and $Y_1$, $Y_2$, $Y_5$ may be hydrogen at the same time, $R^z$, R each are independently selected from the same substituents as described above for $Y_1$.

In some embodiments, $R^1$ is

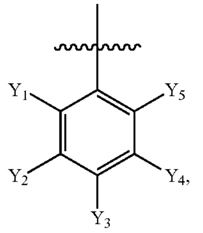

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-)piperidyl, 4-(N-ethylpiperazinyl-1-)piperidyl, 4-(N-isopropylpiperazinyl-1-)piperidyl.

In some embodiments, $R^1$ is

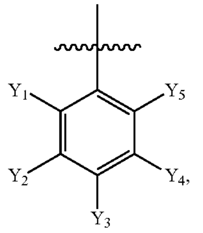

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, ethyl, methoxy, trifluoromethoxy, N-methylpiperazinyl, 3-(N,N-dimethylamino)tetrahydropyrrolyl, 4-N,N-dimethylaminopiperidyl, or 4-(N-methylpiperazinyl-1-)piperidyl;

preferably, $Y_1$, $Y_2$, $Y_4$, $Y_5$ each are independently selected from H, ethyl, methoxy, or trifluoromethoxy, $Y_3$ is selected from N-methylpiperazinyl, 3-(N,N-dimethylamino)tetrahydropyrrolyl, 4-N,N-dimethylaminopiperidyl, or 4-(N-methylpiperazinyl-1-)piperidyl.

In some embodiments, $Z_5$ is selected from $C_1$-$C_6$ alkyl.

In some embodiments, $Z_5$ is selected from methyl, or isopropyl.

In some embodiments, $R^3$, $R^4$, $R^5$ each are independently selected from H, or $C_1$-$C_6$ alkyl.

In some embodiments, $R^3$, $R^4$, $R^5$ are H.

Unless otherwise indicated, the above groups and substituents have the ordinary meanings in the field of medicinal chemistry.

In all parts of the present description, the substituents of the compounds disclosed in the present invention are disclosed according to the kinds or scopes of groups. It is specially specified that the present invention encompasses each independent secondary combination of all members in these kinds and scopes of groups. For example, the term "$C_1$-$C_6$ alkyl" specially refers to independently disclosed methyl, ethyl, $C_3$ alkyl, $C_4$ alkyl, $C_5$ alkyl and $C_6$ alkyl.

The term "$C_1$-$C_6$ alkyl" refers to any straight-chain or branched-chain group containing 1 to 6 carbon atoms, such as methyl, ethyl, n-propyl, isopropyl, n-butyl, isobutyl, t-butyl, sec-butyl, n-pentyl, tert-amyl, n-hexyl and the like.

The term "$C_1$-$C_3$ alkyl" refers to any straight-chain or branched-chain group containing 1 to 3 carbon atoms, such as methyl, ethyl, n-propyl, isopropyl and the like.

The term "oxygen-containing alkyl" refers to a group in which the alkyl skeleton is substituted by one or more alkoxy groups, for example, methoxyethyl, methoxyethoxymethyl and the like.

For example, $C_1$-$C_6$ oxygen-containing alkyl refers to a group in which a $C_1$-$C_6$ alkyl skeleton is substituted by one or more $C_1$-$C_6$ alkoxy groups, for example, methoxyethyl, methoxyethoxymethyl and the like. Similarly, $C_1$-$C_3$ oxygen-containing alkyl refers to a group in which a $C_1$-$C_3$ alkyl skeleton is substituted by one or more $C_1$-$C_6$ alkoxy groups.

The term "$C_2$-$C_6$ alkenyl" refers to any straight-chain or branched-chain group containing 2 to 6 carbon atoms and containing at least one carbon-carbon double bond, such as vinyl, 1-propenyl, 2-propenyl and the like.

The term "$C_3$-$C_8$ cycloalkyl" refers to a hydrocarbon having a 3- to 8-membered monocylic system of saturated ring, and the $C_3$-$C_8$ cycloalkyl may be cyclopropyl, cyclobutyl, cyclopentyl, cyclohexyl and the like.

The term "$C_3$-$C_6$ cycloalkyl" refers to a hydrocarbon having a 3- to 6-membered monocylic system of saturated ring, and the $C_3$-$C_6$ cycloalkyl may be cyclopropyl, cyclobutyl, cyclopentyl, cyclohexyl and the like.

The term "cyano" refers to —CN residue.

The term "nitro" refers to —$NO_2$ group.

The term "heteroatom" refers to N, O or S.

The terms "alkoxy", "cycloalkoxy" and derivatives thereof refer to any of the above groups (such as $C_1$-$C_6$ alkyl, $C_1$-$C_3$ alkyl, etc.), or cycloalkyl (e.g., $C_3$-$C_6$ cycloalkyl), which is attached to the remainder of molecules through oxygen atom (—O—).

The term "heteroaryl" refers to an aromatic heterocyclic ring, which is usually a 5-, 6-, 7-, or 8-membered heterocyclic ring having from 1 to 3 heteroatoms selected from N, O or S; a heteroaryl ring may be optionally further fused or attached to aromatic or non-aromatic carbocyclic rings or heterocyclic rings. Non-limiting examples of the heteroaryl group are, for example, pyridyl, pyrazinyl, pyrimidinyl, pyridazinyl, indolyl, imidazolyl, thiazolyl, isothiazolyl, thioxazolyl, pyrrolyl, phenyl-pyrrolyl, furyl, phenyl-furyl, oxazolyl, isoxazolyl, pyrazolyl, thienyl, benzofuryl, benzothienyl, benzo(1,3-dioxolanyl) (benzodioxolyl), isoindolinyl, benzoimidazolyl, indazolyl, quinolyl, isoquinolyl, 1,2,3-triazolyl, 1-phenyl-1,2,3-triazolyl, 2,3-indolinyl, 2,3-dihydrobenzofuryl, 2,3-dihydrobenzothienyl, benzopyranyl, 2,3-dihydrobenzoxazinyl, 2,3-dihydroquinoxalinyl and the like.

The term "heterocyclyl" (also referred to as "heterocycloalkyl") refers to 3-, 4-, 5-, 6- and 7-membered saturated or partially unsaturated carbocyclic rings, wherein one or more carbon atoms are replaced by heteroatoms such as nitrogen, oxygen and sulfur. Non-limiting examples of the heterocyclic group are, for example, pyranyl, pyrrolidinyl, pyrrolinyl, imidazolinyl, imidazolidinyl, pyrazolidinyl, pyrazolinyl, thiazolinyl, thiazolidinyl, dihydrofuryl, tetrahydrofuryl, 1,3-dioxolanyl, piperidinyl, piperazinyl, morpholine, morpholinyl, tetrahydropyrrolyl, thiomorpholinyl and the like.

For example, "6-membered heterocyclyl" refers to 6-membered saturated or partially unsaturated carbocyclic rings, wherein one or more carbon atoms are replaced by heteroatoms such as nitrogen, oxygen and sulfur. Non-limiting examples of the 6-membered heterocyclyl are, for example, pyranyl, piperidinyl, piperazinyl, morpholine, morpholinyl, thiomorpholinyl and the like.

"5-Membered heterocyclyl" refers to 5-membered saturated or partially unsaturated carbocyclic rings, wherein one or more carbon atoms are replaced by heteroatoms such as nitrogen, oxygen and sulfur. Non-limiting examples of the 5-membered heterocyclyl are, for example, pyrrolidinyl, pyrrolinyl, imidazolinyl, imidazolidinyl, pyrazolidinyl, pyrazolinyl, thiazolinyl, thiazolidinyl, 1,3-dioxolanyl and the like.

The term "optionally substituted heterocyclyl" refers to that the above "heterocyclyl" is substituted with one or more "$C_1$-$C_6$ alkyl", "$C_1$-$C_3$ alkyl", "$C_3$-$C_6$ cycloalkyl" and the like.

"Fluorine-containing alkyl" refers to groups in which an alkyl skeleton is substituted with one or more fluorine groups, such as monofluoromethyl, difluoroethyl, trifluoromethyl and the like.

The term "$C_1$-$C_6$ fluorine-containing alkyl" refers to groups in which a $C_1$-$C_6$ alkyl skeleton is substituted with one or more fluorine groups, such as monofluoromethyl, difluoroethyl, trifluoromethyl and the like.

Similarly, the term "$C_1$-$C_3$ fluorine-containing alkyl" refers to groups in which a $C_1$-$C_3$ alkyl skeleton is substituted with one or more fluorine groups, such as monofluoromethyl, difluoroethyl, trifluoromethyl and the like.

The term "$C_1$-$C_6$ heteroatom-containing alkyl" refers to groups in which one or more carbon atoms in a $C_1$-$C_6$ alkyl skeleton is replaced by one or more heteroatoms, such as N, O or S, such as

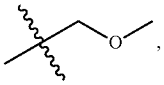,

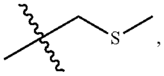,

-continued

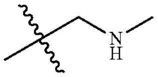

and the like.

The term "$C_3$-$C_8$ heteroatom-containing cycloalkyl" refers to groups in which one or more carbon atoms in a $C_3$-$C_8$ cycloalkyl skeleton is replaced by one or more heteroatoms, such as N, O or S, such as pyrrolidinyl, imidazolidinyl, pyrazolidinyl, thiazolidinyl, piperidinyl, piperazinyl, morpholine, morpholinyl, thiomorpholinyl and the like.

The term "$C_1$-$C_6$ acyl" refers to —C(═O)—H and —C(═O)—$C_1$-$C_5$ alkyl, such as formyl, acetyl, propionyl, butyryl and the like.

The term "sulfonyl" refers to —S(═O)$_2$—.

The term "$C_1$-$C_6$ alkylsulfonyl" refers to —S(═O)$_2$—$C_1$-$C_6$ alkyl, such as methylsulfonyl, ethylsulfonyl, propylsulfonyl, butylsulfonyl and the like.

From all of the above description, it will be apparent to those skilled in the art that any group whose name is a compound name, such as "fluorine-containing oxygen-containing alkyl", shall mean to conventionally construct from the moiety that is derived, such as the oxygen-containing alkyl substituted by the fluorine group, wherein the alkyl is as defined above, and similarly, a "fluorine-containing alkoxy" is further exemplified. Moreover, for example, the "arylamino" shall mean to conventionally construct from the moiety that is derived, such as the amino substituted by the aryl, wherein the aryl is as defined above. Similarly, the meaning of "heteroarylamino" should be understood. Similarly, the meanings of "hydroxysulfonyl", "aminosulfonyl" and the like should be understood.

Similarly, for any terms, for example, composite groups such as alkylamino, dialkylamino, alkoxycarbonyl, alkoxycarbonylamino, heterocyclylcarbonyl, heterocyclylcarbonylamino, cycloalkyloxycarbonyl, alkoxyformyl and the like, moieties of alkyl, alkoxy and the like are as defined above.

The term "$R^3$, $R^4$, $R^5$ each are independently selected from" indicates that groups represented by $R^3$, $R^4$ and $R^5$ may be the same or different, and they are not restricted from each other. For example, $R^3$, $R^4$, $R^5$ each are independently selected from H or methyl, which means that $R^3$ is selected from H or methyl, $R^4$ is selected from H or methyl, and $R^5$ is selected from H or methyl.

According to the invention, unless otherwise indicated, any of the above groups may be optionally substituted by one or more groups at any free position thereof, for example by 1-6 groups, which are independently selected from: halogen atom, nitro, oxo (═O), cyano, $C_1$-$C_6$ alkyl, polyfluoroalkyl, polyfluoroalkoxy, alkenyl, alkynyl, hydroxyalkyl, hydroxyalkylamino, hydroxyheterocyclyl, aryl, aryl-alkyl, heteroaryl, heteroaryl-alkyl, heterocyclyl, heterocyclyl-alkyl, $C_3$-$C_7$ cycloalkyl, cycloalkyl-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkyl-amino, hydroxy, alkoxy, aryloxy, heterocyclyloxy, alkyl-heterocyclyloxy, methylenedioxy, alkylcarbonyloxy, arylcarbonyloxy, cycloalkenyloxy, heterocyclyl carbonyloxy, alkylene aminooxy, carboxy, alkoxycarbonyl, aryloxycarbonyl, cycloalkyloxycarbonyl, heterocyclyl oxycarbonyl, amino, ureido, alkylamino, amino-alkylamino, dialkylamino, dialkylamino-heterocyclyl, dialkylamino-alkylamino, arylamino, arylalkylamino, diarylamino, heterocyclylamino, alkyl-heterocyclylamino, alkyl-heterocyclylcarbonyl, formylamino, alkylcarbonylamino, arylcarbonylamino, heterocyclylcarbonylamino, alkyl-heterocyclylcarbonylamino, aminocarbonyl, alkylaminocarbonyl, dialkylaminocarbonyl, arylaminocarbonyl, heterocyclylaminocarbonyl, alkoxycarbonylamino, alkoxycarbonylamino-alkylamino, alkoxycarbonylheterocyclyl-alkylamino, alkoxy-aryl-alkyl, hydroxyamino-carbonyl, alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclyl aminosulfonyl, arylthio, alkylthio, phosphonate and alkylphosphonate.

Further, if appropriate, each of the above substituents may be further substituted by one or more of the above-exemplified groups.

The term "oxygen-containing substituted or unsubstituted five- to seven-membered ring" or "nitrogen-containing substituted or unsubstituted five- to seven-membered ring" refers to 5-, 6-, or 7-membered saturated or partially unsaturated carbocyclic rings, wherein one or more carbon atoms are replaced by oxygen or nitrogen. Their non-limiting examples are, for example, pyran, pyrrolidine, pyrroline, imidazoline, imidazolidine, pyrazolidine, pyrazoline, dihydrofuran, tetrahydrofuran, 1,3-dioxolane, piperidine, piperazine, morpholine, tetrahydropyrrolyl, hexamethylene imine and the like.

The term "substituted or unsubstituted five- to seven-membered ring" refers to 5-, 6-, or 7-membered saturated or partially unsaturated carbocyclic ring. The non-limiting examples are, for example, cyclopentane, cyclohexane, cyclopentene, cyclopentadiene, cyclohexene, cyclohexadiene (cyclohexa-1,3-diene, cyclohexa-1,4-diene) and the like.

The term "1 to 2 heteroatom-containing substituted or unsubstituted 4- to 8-membered ring" refers to 4-, 5-, 6-, 7- or 8-membered saturated or partially unsaturated carbocyclic rings, wherein one or two carbon atoms are replaced by heteroatoms such as oxygen, nitrogen or sulfur. Their non-limiting examples are, for example, pyran, pyrrolidine, pyrroline, imidazoline, imidazolidine, pyrazolidine, pyrazoline, dihydrofuran, tetrahydrofuran, 1,3-dioxolane, piperidine, piperazine, morpholine, tetrahydropyrrolyl, hexamethylene imine and the like.

As used herein, unless otherwise indicated, the term "prodrug" refers to a derivative that can be hydrolyzed, oxidized or otherwise reacted under biological conditions (in vitro or in vivo) to provide a compound of the invention. Prodrugs can become active compounds only by carrying out the reaction under biological conditions, or they are inactive in their non-reacted form. Prodrugs can be generally prepared using known methods, for example, those methods described in Burger's Medicinal Chemistry and Drug Discovery (1995) 172-178, 949-982 (Manfred E. Wolff, ed. $5^{th}$ edition).

As used herein, examples of the term "pharmaceutically acceptable salt of a compound of formula (A), (I), (II), (III), (IV), (A'), (I'), (II') or (III')" are addition salts formed with organic acids capable of forming pharmaceutically acceptable anions, including, but not limited to, formate, acetate, propionate, benzoate, maleate, fumarate, succinate, tartrate, citrate, ascorbate, α-ketoglutarate, α-glycerophosphate, alkyl sulfonate or aryl sulfonate; preferably, the alkyl sulfonate is methyl sulfonate or ethyl sulfonate; the aryl sulfonate is benzenesulfonate or p-toluenesulfonate. Suitable inorganic salts also can be formed, including, but not limited to, hydrochloride, hydrobromide, hydroiodide, nitrate, bicarbonate and carbonate, sulfate or phosphate.

Pharmaceutically acceptable salts can be obtained using standard procedures well known in the art, for example, by reacting a sufficient amount of a basic compound with a suitable acid that provides a pharmaceutically acceptable anion.

The term "treatment" as used herein generally refers to obtaining the desired pharmacological and/or physiological effect. The effect may be preventive according to complete or partial prevention of disease or its symptoms; and/or may be therapeutic according to partial or complete stabilization or cure of disease and/or side effects due to the disease. The term "treatment" as used herein encompasses any treatment on a patient's disease, including: (a) preventing the disease or symptom that occurs in a patient who is susceptible to the disease or symptom but not yet diagnosed to suffer from the disease; (b) suppressing symptoms of the disease, i.e., stopping its development; or (c) relieving symptoms of the disease, i.e., causing degeneration of the disease or symptom.

According to a specific embodiment of the present invention relating to the compound, a stereoisomer thereof, a prodrug thereof, or a pharmaceutically acceptable salt thereof or a pharmaceutically acceptable solvate thereof, the compound is one of the compounds described in the examples below.

In another aspect, the present invention provides a pharmaceutical composition comprising the compound according to any one of the above embodiments, a stereoisomer thereof, a prodrug thereof, or a pharmaceutically acceptable salt thereof or a pharmaceutically acceptable solvate thereof, and optionally a pharmaceutically acceptable carrier, diluent or excipient.

In some embodiments, the pharmaceutical composition further comprises a EGFR monoclonal antibody.

In some embodiments, the EGFR monoclonal antibody is Cetuximab or biosimilars thereof.

The term "biosimilars" refers to antibody products having the same sequence to Cetuximab and having consistent physicochemical properties, biological activities, and clinical safety and efficiencies to the Cetuximab.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, $19^{th}$ ed. (1995), methods for preparing a pharmaceutical composition comprise incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare into a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, or pressed into a tablet. For the treatment by oral administration, an active compound may be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the active compound in the composition or the preparation can be varied certainly, and the ratio may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc.; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose is used as a sweeting agent, methyl p-hydroxybenzoate or propyl p-hydroxybenzoate is used as a preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersible formulation in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solution or a dispersible formulation or a sterile powder comprising an active ingredient (optionally encapsulated into a liposome) of an immediate preparation such as a solution or a dispersible formulation suitable for sterile injection or infusion. Under all the conditions, the final dosage form shall be sterile, liquid and stable under the production and storage conditions. A liquid carrier may be a solution or a liquid disperse medium, including, for example, water, ethanol, polyols (such as glycerol, propylene glycol, and liquid macrogol, etc.), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc.). In many conditions, an isotonizing agent, such as sugar, buffer agent or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation methods are vacuum drying and freeze drying techniques, which will result in the production of the powder of the active ingredient and any other desired ingredient present in the previous sterile filtration solution.

A useful solid carrier includes crushed solid (such as talc, clay, microcrystalline cellulose, silicon dioxide, and aluminum oxide etc.). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically required amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule(s) or tablet(s). Depending on the particular treatment involved, the amount of an active ingredient in a unit dose may be varied or adjusted between about 0.1 and about 1000 mg or more.

In addition, the present invention further includes use of various new drug dosage forms such as milk liposomes, microspheres and nanospheres, for example, medicaments prepared with the use of a particulate dispersion system including polymeric micelles, nanoemulsions, submicroemulsions, microcapsules, microspheres, liposomes and niosomes (also known as nonionic surfactant vesicles), etc.

In another aspect, the present invention further provides a preparation method of the compound according to any of the above embodiments, comprising the following steps (X denotes halogen):

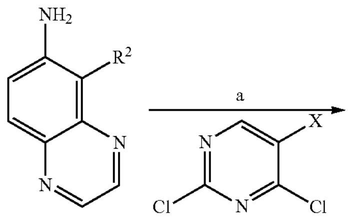

-continued

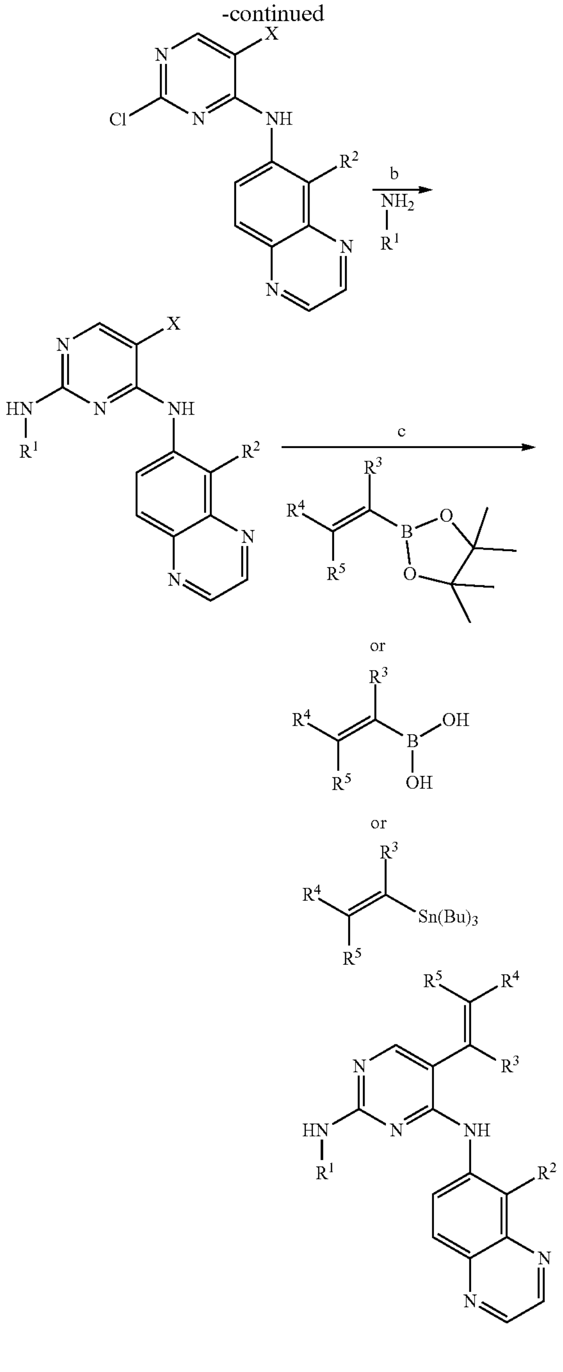

reaction conditions are as follows:

(a) a nucleophilic substitution reaction under acidic or alkaline condition;

(b) a coupling reaction catalyzed by metal palladium, or a nucleophilic substitution reaction under acidic condition;

(c) a coupling reaction catalyzed by metal palladium;

wherein:

the metal palladium catalyst is selected from palladium acetate, tetrakis(triphenylphosphine) palladium, bistriphenylphosphine palladium dichloride, [1,1'-bis(diphenylphosphino)ferrocene] palladium dichloride or tris (dibenzylideneacetone) dipalladium;

the alkaline condition refers to a condition in which any of the following substances exists: triethylamine, diisopropylethylamine, pyridine, sodium bicarbonate, sodium carbonate, potassium carbonate, cesium carbonate, lithium hydroxide, sodium hydroxide, potassium hydroxide, sodium hydride, or potassium hydride;

the acidic condition refers to a condition in which any of the following substances exists: acetic acid, trifluoroacetic acid, hydrochloric acid, methanesulfonic acid, p-toluene sulfonic acid, or camphorsulfonic acid;

see above for the definitions of $R^1$, $R^2$, $R^3$, $R^4$ and $R^5$.

In another aspect, the present invention further provides use of the compound according to any one of the above embodiments, or a stereoisomer thereof, a prodrug thereof, or a pharmaceutically acceptable salt thereof or a pharmaceutically acceptable solvate thereof, and a pharmaceutical composition comprising the compound in the manufacture of a medicament for preventing and/or treating EGFR kinase-mediated cancers and other diseases, especially in the manufacture of a medicament for preventing and/or treating lung cancer (preferably non-small cell lung cancer), particularly in the manufacture of a medicament for preventing and/or treating mutation-type lung cancer (preferably non-small cell lung cancer) with 19Del, L858R, T790M, or C797S mutation or a combination thereof of EGFR kinase, and most preferably in the manufacture of a medicament for preventing and/or treating lung cancer (preferably non-small cell lung cancer) with 19Del single mutation, L858R single mutation, 19Del/T790M dual mutation, L858R/T790M dual mutation, 19Del/T790M/C797S triple mutation or L858R/T790M/C797S triple mutation of EGFR kinase.

In another aspect, the present invention further provides a method of preventing and/or treating EGFR kinase-mediated cancers and other diseases, comprising administering a preventively effective amount and/or a therapeutically effective amount of the above compound or a stereoisomer thereof, a prodrug thereof, or a pharmaceutically acceptable salt thereof or a pharmaceutically acceptable solvate thereof, or the above pharmaceutical composition to a subject in need.

In some embodiments, the method is for preventing and/or treating lung cancer (preferably non-small cell lung cancer).

In some embodiments, the method is for preventing and/or treating mutation-type lung cancer (preferably non-small cell lung cancer) with 19Del, L858R, T790M, or C797S mutation or a combination thereof of EGFR kinase.

In some embodiments, the method is for preventing and/or treating lung cancer (preferably non-small cell lung cancer) with 19Del single mutation, L858R single mutation, 19Del/T790M dual mutation, L858R/T790M dual mutation, 19Del/T790M/C797S triple mutation or L858R/T790M/C797S triple mutation of EGFR kinase.

In another aspect, the present invention further provides the above compound or a stereoisomer thereof, a prodrug thereof, or a pharmaceutically acceptable salt thereof or a pharmaceutically acceptable solvate thereof, or the above pharmaceutical composition, for use in preventing and/or treating EGFR kinase-mediated cancers and other diseases, preferably for use in preventing and/or treating lung cancer (preferably non-small cell lung cancer), more preferably for use in preventing and/or treating mutation-type lung cancer (preferably non-small cell lung cancer) with 19Del, L858R, T790M, or C797S mutation or a combination thereof of EGFR kinase, and most preferably for use in preventing and/or treating lung cancer (preferably non-small cell lung cancer) with 19Del single mutation, L858R single mutation, 19Del/T790M dual mutation, L858R/T790M dual mutation, 19Del/T790M/C797S triple mutation or L858R/T790M/C797S triple mutation of EGFR kinase.

In the present invention, the term "subject" refers to a vertebrate. In some embodiments, the vertebrate refers to a mammal, and the mammal includes, but are not limited to, livestock (such as a cow), pets (such as cat, dog and horse), quadrumana, mouse and rat. In some embodiment, the mammal refers to a human.

In the present invention, the term "effective amount" refers to an amount that can achieve desired treating or preventing effects at necessary doses and time. The "therapeutically effective amount" of the material/molecule of the present invention will vary according to the disease states, ages, sexual distinction and body weights of individuals and the abilities of the material/molecule for initiating desired responses in the individuals. The therapeutically effective amount further covers an amount in which the material/molecule can achieve better beneficial therapeutic effects than any toxic or harmful aftereffects. The "preventively effective amount" refers to an amount that can achieve desired preventive effects at necessary doses and time. Typically but not certainly, since a preventively effective amount is administrated to a subject before disease attacks or at the early stage of diseases, the amount will be lower than the therapeutically effective amount. In the case of cancers, a therapeutically effective amount of a medicine will reduce the number of cancer cells; reduce the volume of tumor; suppress (i.e., retard to an extent, preferably to stop) the infiltration of cancer cells into ambient organs, suppress (i.e., retard to an extent, preferably to stop) tumor metastasis; suppress tumor growths to an extent; and/or relieve one or more symptoms related to cancers to an extent.

Experimental Section

Regarding the examples described below, the compounds of the present invention are synthesized using the methods described herein or other methods well known in the art.

General Methods of Purification and Analysis

Thin layer chromatography was carried out on a silica gel GF254 precoated plate (Qingdao Marine Chemical Plant). Column chromatography was carried out by silica gel (300-400 mesh, Yantai Zhifu Huangwu Silica Gel Development Test Factory) under medium pressure or by a pre-packed silica gel cartridge (ISCO or Welch) with the use of an ISCO Combiflash Rf200 rapid purification system. The ingredient was visualized by UV light (λ: 254 nm) or iodine vapor. When necessary, the compound was purified by preparative HPLC through a Waters Symmetry C18 (19×50 mm, 5 m) column or a Waters×Terra RP 18 (30×150 mm, 5 m) column, and was detected by using of a Waters preparative HPLC 600 equipped with a 996 Waters PDA detector and Micromass mod. ZMD single quadrupole mass spectrometry (electrospray ionization, cationic mode). Method 1: Phase A: 0.1% TFA/MeOH 95/5; Phase B: MeOH/$H_2O$ 95/5. Gradient: proceeding at 10 to 90% B for 8 min, keeping at 90% B for 2 min; flow rate 20 mL/min. Method 2: Phase A: 0.05% $NH_4OH$/MeOH 95/5; Phase B: MeOH/$H_2O$ 95/5. Gradient: proceeding at 10 to 100% B for 8 min, keeping at 100% B for 2 min, flow rate: 20 mL/min.

$^1$H-NMR spectra were recorded via a Bruker Avance 600 spectrometer at 600 MHz. Chemical shift (δ) was reported in parts per million (ppm) and coupling constant (J) was measured in Hz. The tetramethylsilane signal was used as a reference (δ=0 ppm). The following abbreviations were used for peak splitting: s=singlet; br. s.=broad signal; d=doublet; t=triplet; m=multiplet; dd=doublet of doublets.

Electrospray (ESI) mass spectra were obtained via Finnigan LCQ ion trap.

Unless otherwise indicated, all final compounds were homogeneous (with purity not less than 95%), as determined by high performance liquid chromatography (HPLC). HPLC-UV-MS analysis for evaluation of compound purity was performed by combining an ion trap MS device and an HPLC system SSP4000 (Thermo Separation Products) equipped with an autosampler LC Pal (CTC Analytics) and a UV6000LP diode array detector (UV detection 215-400 nm). Device control, data acquisition and processing were performed with Xcalibur 1.2 software (Finnigan). HPLC chromatography was carried out at room temperature and a flow rate of 1 mL/min using a Waters×Terra RP 18 column (4.6×50 mm; 3.5 μm). Mobile phase A was ammonium acetate 5 mM buffer (pH 5.5 obtained with acetic acid): acetonitrile 90:10, mobile phase B was ammonium acetate 5 mM buffer (pH 5.5 obtained with acetic acid):acetonitrile 10:90; proceeding at a gradient of 0 to 100% B for 7 min and then keeping at 100% B for 2 min before rebalancing.

Reagent purification was carried out in accordance with the book Purification of Laboratory Chemicals (Perrin, D. D., Armarego, W. L. F. and Perrins Eds, D. R.; Pergamon Press: Oxford, 1980). Petroleum ether was 60-90° C. fraction, ethyl acetate, methanol and dichloromethane were all analytically pure.

MODE OF CARRYING OUT THE INVENTION

The embodiments of the present invention are described in detail below by way of specific examples, but in any case they cannot be construed as limiting the present invention.

Compounds may be divided into the following four classes:

(I)

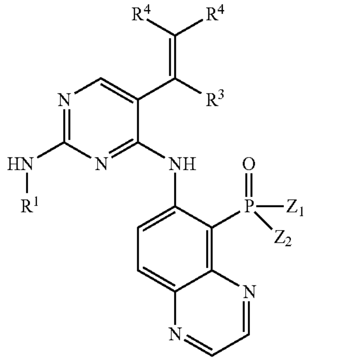

(II)

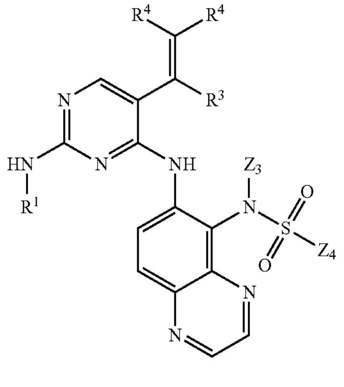

-continued (III)

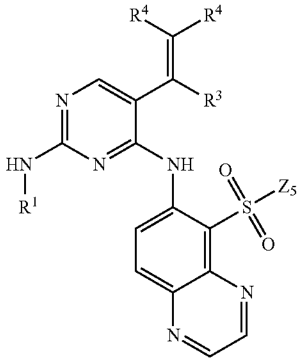

(IV)

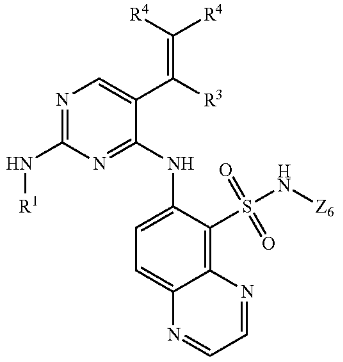

wherein, $R^1$, $R^3$, $R^4$, $R^5$, $Z_1$, $Z_2$, $Z_3$, $Z_4$, $Z_5$ are as above described.

Some of the raw materials and intermediates involved in the synthesis process are described below:

1.

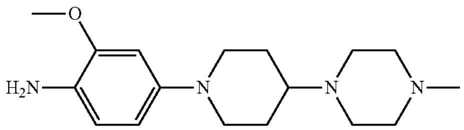

was obtained by the following steps: reacting 5-fluoro-2-nitroanisole (cas: 448-19-1, Bidepharm, Shanghai) with 1-methyl-4-(4-piperidyl)piperazine (cas: 53617-36-0, Aikonchem, Jiangsu) to obtain

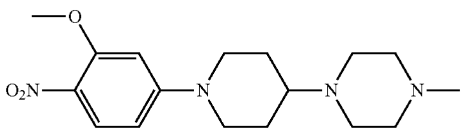

, and then reducing the nitro.

The following intermediates were obtained in a similar manner:

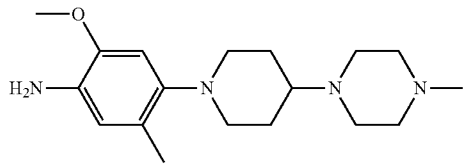

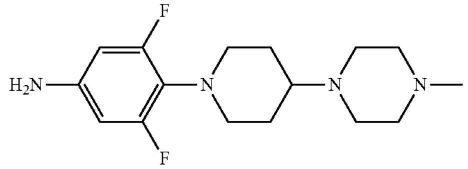

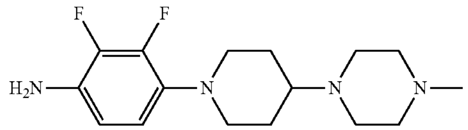

.

The involved raw materials were: 1-fluoro-5-methoxy-2-methyl-4-nitrobenzene (cas: 314298-13-0, Bidepharm, Shanghai), 3,4,5-trifluoronitrobenzene (cas: 66684-58-0, Bidepharm, Shanghai), 2,3,4-trifluoronitrobenzene (cas: 771-69-7, Bidepharm, Shanghai), 1-methyl-4-(4-piperidyl) piperazine (cas: 53617-36-0, Aikonchem, Jiangsu).

2.

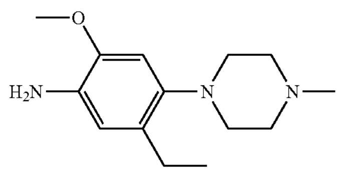

was obtained by the following steps: reducing 2-fluoro-4-hydroxyacetophenone (cas: 98619-07-9, Bidepharm, Shanghai) with palladium carbon and hydrogen gas to obtain 3-fluoro-4-ethylphenol, nitrifying the above reduction product to obtain 3-fluoro-4-ethyl-6-nitrophenol, reacting the above nitrification product with iodomethane (cas: 74-88-4, Xiya Reagent, Shandong) to obtain 3-fluoro-4-ethyl-6-nitroanisole, then reacting the above reaction product with N-methylpiperazine (cas: 109-01-3, Energy, Shanghai) to obtain 3-(N-methylpiperazinyl)-4-ethyl-6-nitroanisole, and finally, reducing the nitro.

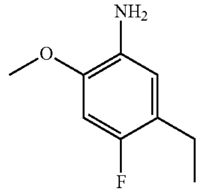

was obtained by reducing the nitro in 3-fluoro-4-ethyl-6-nitroanisole.

The following intermediates were obtained in a similar manner:

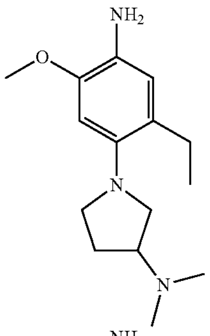
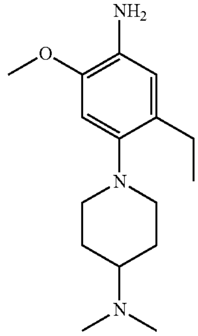
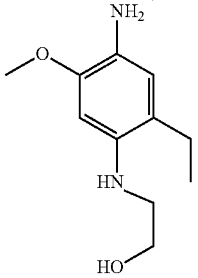
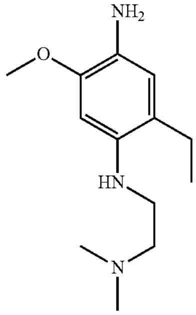
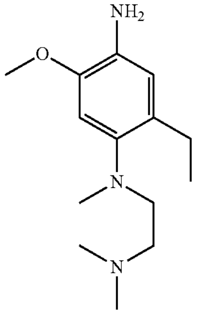
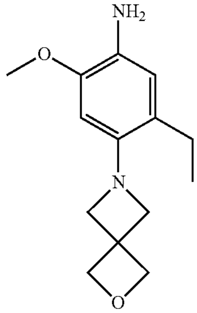
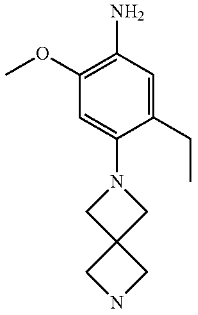
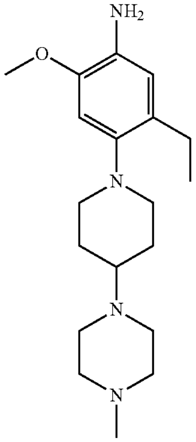

-continued

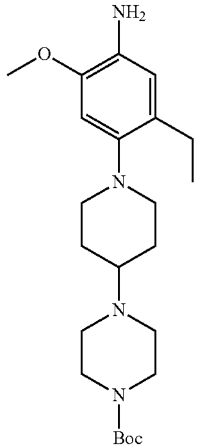
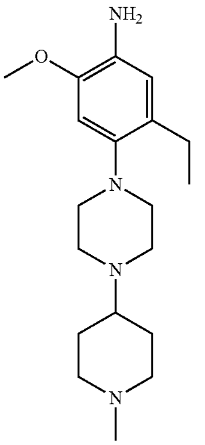
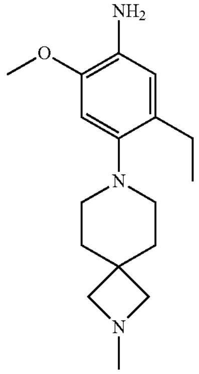
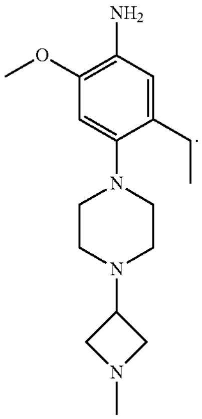

The involved raw materials were: 3-N,N-dimethylamino-pyrrolidine (cas: 64021-83-6, TCI, Shanghai), 4-dimethyl-aminopiperidine (cas: 50533-97-6, Accela ChemBio, Shanghai), ethanolamine (cas: 141-43-5, Aladdin, Shanghai), N,N-dimethylethylenediamine (cas: 108-00-9, Bidepharm, Shanghai), N,N,N'-trimethylethylenediamine (cas: 142-25-6, Bidepharm, Shanghai), 2-oxa-6-azaspiro[3.3]heptane (cas: 174-78-7, Bidepharm, Shanghai), 2-methyl-2,6-diazaspiro[3.3]heptane (cas: 1203567-11-6, Bidepharm, Shanghai), 1-methyl-4-(4-piperidyl)piperazine (cas: 53617-36-0, Aikonchem, Jiangsu), t-butyl 4-(piperidin-4-yl)piperazinyl-1-carboxylate (cas: 205059-24-1, Bidepharm, Shanghai), 1-(1-methylpiperidin-4-yl)piperazine (cas: 23995-88-2, J&K, Shanghai), 2-methyl-2,7-diazaspiro[3.5]nonane dihydrochloride (cas: 1610028-42-6, Bidepharm, Shanghai), 1-(1-methylazetidin-3-yl)piperazine (cas: 864350-81-2, J&K, Shanghai).

3.

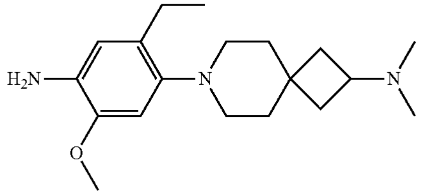 [SMILES: CCc1cc(N)c(OC)cc1N1CCC2(CC1)CC(N(C)C)C2]

was obtained by the following steps: reacting t-butyl 2-oxo-7-azaspiro[3.5]nonane-7-carboxylate (cas: 203661-69-2, Bidepharm, Shanghai) with dimethylamine (cas: 124-40-3, Aladdin, Shanghai) to obtain

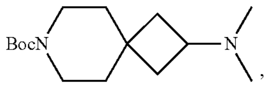 [SMILES: CN(C)C1CC2(CCN(C(=O)OC(C)(C)C)CC2)C1]

after removing t-butoxycarbonyl, reacting the above reaction product with 3-fluoro-4-ethyl-6-nitroanisole in (2) to obtain

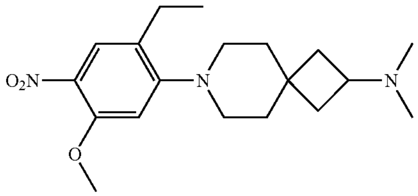

, and then reducing the nitro.

4.

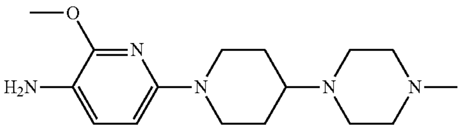

was obtained by the following steps: reacting 2,6-dichloro-3-nitropyridine with sodium methoxide (cas: 124-41-4, Energy, Shanghai) to obtain 2-methoxy-3-nitro-6-chloropyridine, reacting the above reaction product with 1-methyl-4-(4-piperidyl)piperazine (cas: 53617-36-0, Aikonchem, Jiangsu) to obtain

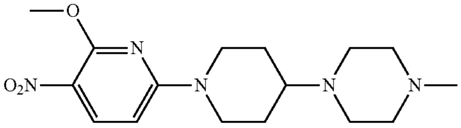

, and further reducing the amino.

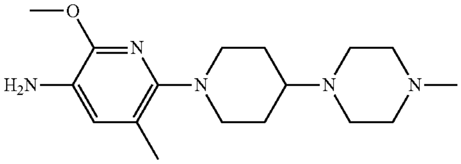

was obtained from 2,6-dichloro-3-nitro-5-methylpyridine according to a similar method.

5.

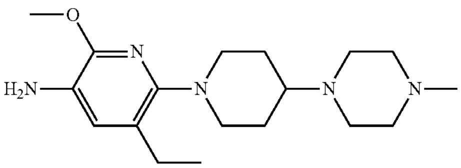

was obtained by the following steps: reacting

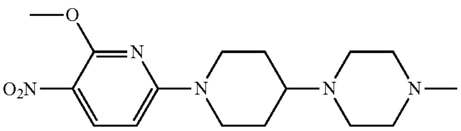

in (3) with liquid bromine (cas: 7726-95-6, Sinopharm, Shanghai) to obtain

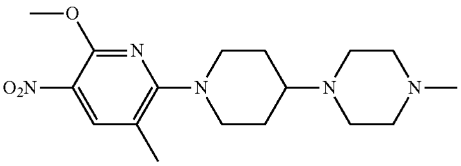

, then reacting the above reaction product with pinacol vinylboronate (cas: 75927-49-0, Bidepharm, Shanghai) to obtain

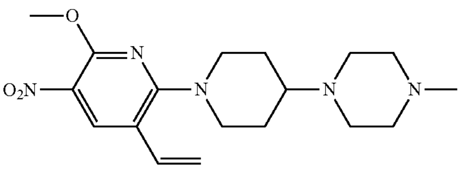

, and further reducing the nitro and the double bond.

6.

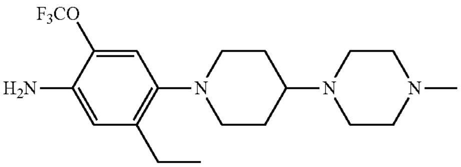 [SMILES: CCc1cc(N)c(OC(F)(F)F)cc1N1CCC(N2CCN(C)CC2)CC1]

was obtained by the following steps: nitrifying 1-bromo-2-fluoro-4-trifluoromethoxybenzene (cas: 168971-68-4, Bidepharm, Shanghai) to obtain 2-trifluoromethoxy-4-fluoro-5-bromonitrobenzene, then reacting the above nitrification product with 1-methyl-4-(4-piperidyl)piperazine (cas: 53617-36-0, Aikonchem, Jiangsu) to obtain

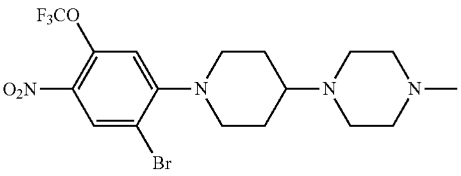

, which was further reacted with pinacol vinylboronate (cas: 75927-49-0, Bidepharm, Shanghai) to obtain

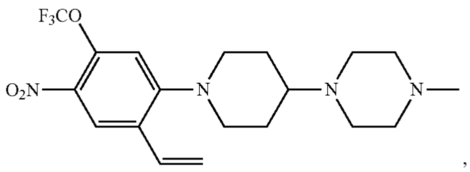 [SMILES: C=Cc1cc([N+](=O)[O-])c(OC(F)(F)F)cc1N1CCC(N2CCN(C)CC2)CC1]

, and further reducing the nitro and the double bond.

7.

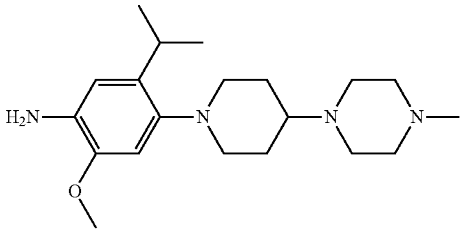 [SMILES: COc1cc(N2CCC(N3CCN(C)CC3)CC2)c(C(C)C)cc1N]

was obtained by the following steps: reacting 1-bromo-2-fluoro-4-methoxy-5-nitrobenzene (cas: 1352244-77-9, Bidepharm, Shanghai) with 1-methyl-4-(4-piperidyl)piperazine (cas: 53617-36-0, Aikonchem, Jiangsu) to obtain

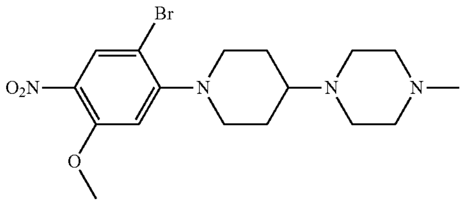

, coupling the above product with isopropenylboronic acid pinacol ester (cas: 126726-62-3, Bidepharm, Shanghai) to obtain

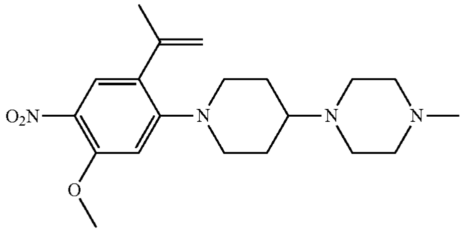

, and further performing a reduction. The following intermediates were obtained in a similar manner:

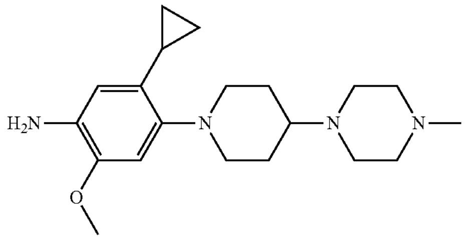

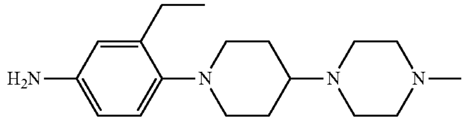

.

The involved raw materials were: 3-bromo-4-fluoronitrobenzene (cas: 701-45-1, Bidepharm, Shanghai), cyclopropylboronic acid pinacol ester (cas: 126689-01-8, Bidepharm, Shanghai), pinacol vinylboronate (cas: 75927-49-0, Bidepharm, Shanghai).

8.

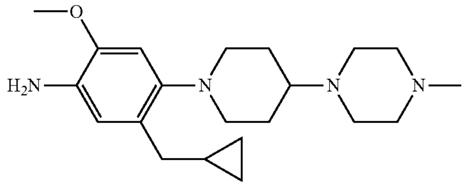 [SMILES: COc1cc(N2CCC(N3CCN(C)CC3)CC2)c(CC2CC2)cc1N]

was obtained by the following steps: nitrifying 2-fluoro-4-methoxybenzaldehyde (cas: 331-64-6) to obtain 2-fluoro-4-methoxy-5-nitrobenzaldehyde, reducing the above nitrification product to obtain 2-fluoro-4-methoxy-5-nitrobenzyl alcohol, further bromating the above reduction product to obtain 2-fluoro-4-methoxy-5-nitrobenzyl bromide, reacting the above bromation product with cyclopropylboronic acid (cas: 411235-57-9, Bidepharm, Shanghai) to obtain

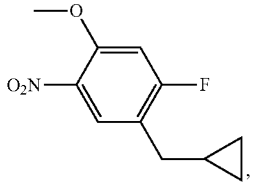 [SMILES: COc1cc(F)c(CC2CC2)cc1[N+](=O)[O-]]

, reacting the above reaction product with 1-methyl-4-(4-piperidyl)piperazine (cas: 53617-36-0, Aikonchem, Jiangsu) to obtain

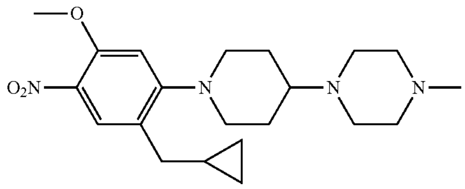

, and finally reducing the nitro.

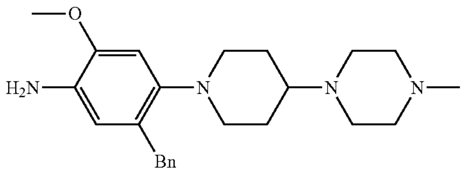 [SMILES: COc1cc(N2CCC(N3CCN(C)CC3)CC2)c(Cc2ccccc2)cc1N]

was obtained according to a similar method by replacing the cyclopropylboronic acid with phenylboronic acid (cas: 98-80-6, Energy, Shanghai).

9.

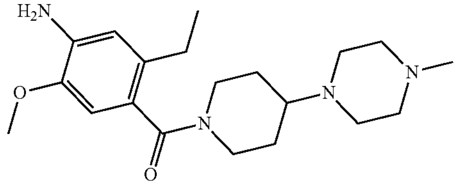

was obtained by the following steps: oxidizing 1-bromo-2-methyl-4-methoxy-5-nitrobenzene (cas: 89978-56-3, Jiuding chem, Shanghai) into 2-bromo-4-nitro-5-methoxybenzoic acid, which was suffered from condensation reaction with 1-methyl-4-(4-piperidyl)piperazine (cas: 53617-36-0, Aikonchem, Jiangsu) to obtain

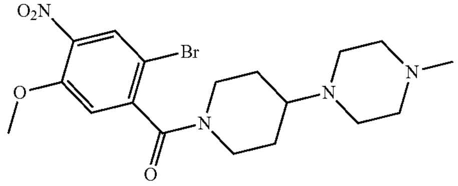

, coupling the above reaction product with potassium vinyltrifluoroborate cas: 13682-77-4, Bidepharm, Shanghai) to obtain

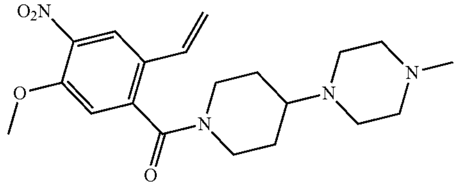

, and performing a reduction.

10.

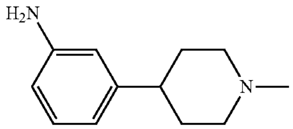

was obtained by the following steps: reacting m-bromonitrobenzene (cas: 585-79-5, Aladdin, Shanghai) with pyridine-4-boronic acid (cas: 1692-15-5, Shuya, Shanghai) to obtain

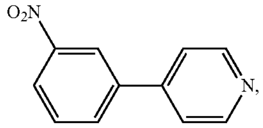 [SMILES: O=[N+]([O-])c1cccc(-c2ccncc2)c1]

further reacting the above reaction product with iodomethane (cas: 74-88-4, Xiya Reagent, Shandong) to obtain

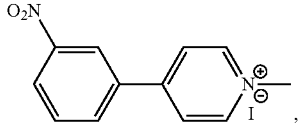

, and

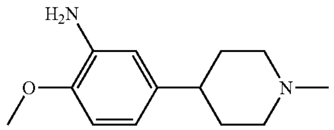

finally, reducing the nitro and the pyridine ring.

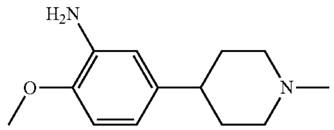

was obtained from 4-bromo-2-nitroanisole (cas: 33696-00-3, Bidepharm, Shanghai) according to a similar method.

11.

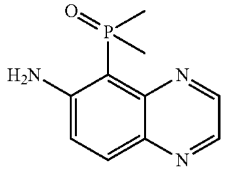

was obtained by the following steps: reacting 6-aminoquinoxaline (cas: 6298-37-9, Bidepharm, Shanghai) with iodine monochloride (cas: 7790-99-0, Aladdin, Shanghai) to obtain

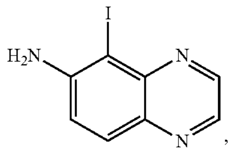

, and further reacting the above reaction product with dimethylphosphine oxide (cas: 7211-39-4, Bidepharm, Shanghai).

12.

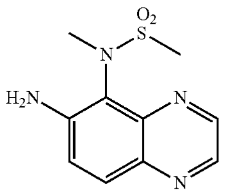 [SMILES: CN(c1c(N)ccc2nccnc12)S(C)(=O)=O]

was obtained by the following steps: reacting 6-nitroquinoxaline (cas: 6639-87-8, Bidepharm, Shanghai) with hydroxyamine hydrochloride (cas: 5470-11-1, Energy, Shanghai) to obtain 5-amino-6-nitro quinoxaline, then converting the above reaction product to 5-chloro-6-nitroquinoxaline, which was further reacted with N-methyl methanesulfonamide (cas: 1184-85-6, Bidepharm, Shanghai) to obtain

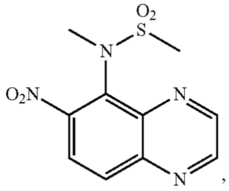 [SMILES: CN(c1c([N+](=O)[O-])ccc2nccnc12)S(C)(=O)=O]

, and finally reducing the nitro. The following intermediates were obtained in a similar manner:

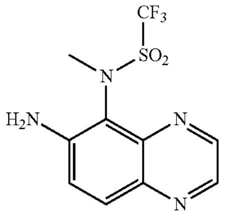

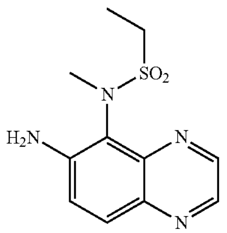

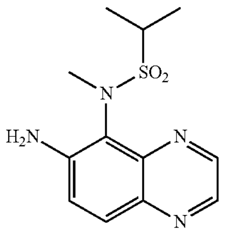

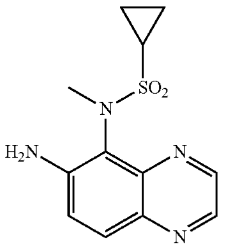

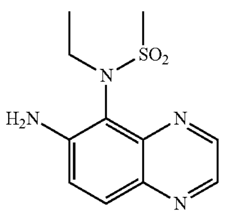

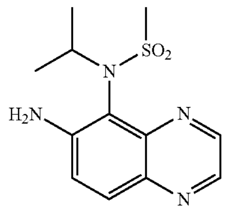

-continued

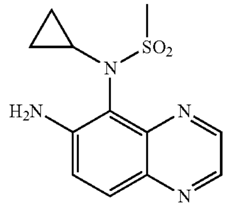

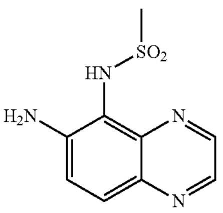

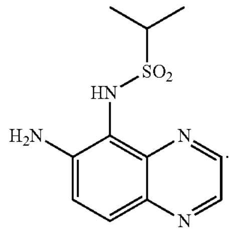

.

The involved raw materials were: methylamine (cas: 74-89-5, Energy, Shanghai), ethylamine (cas: 75-04-7, Aladdin, Shanghai), isopropylamine (cas: 75-31-0, Energy, Shanghai), cyclopropylamine (cas: 765-30-0, Energy, Shanghai), trifluoromethanesulfonyl chloride (cas: 421-83-0, Aladdin, Shanghai), ethylsulfonyl chloride (cas: 594-44-5, Energy, Shanghai), isopropylsulfonyl chloride (cas: 10147-37-2, TCI, Shanghai), cyclopropylsulfonyl chloride (cas: 139631-62-2, Energy, Shanghai), methylsulfamide (cas: 3144-09-0, Bidepharm, Shanghai), isopropylsulfamide (cas: 81363-76-0, Bidepharm, Shanghai).

13.

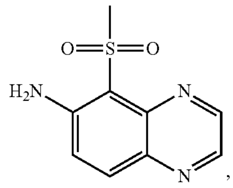

, was obtained by the following steps: reacting 5-chloro-6-nitroquinoxaline in 7) with sodium methylsulfinate (cas: 20277-69-4, Bidepharm, Shanghai) to obtain

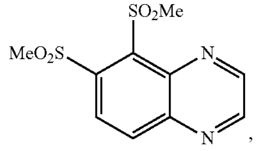 [SMILES: CS(=O)(=O)c1ccc2nccnc2c1S(C)(=O)=O]

, reacting the above reaction product with 2,4-dimethoxybenzylamine (cas: 20781-20-8, Bidepharm, Shanghai) to obtain

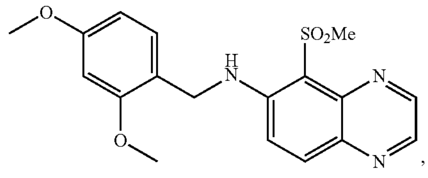 [SMILES: COc1ccc(CNc2ccc3nccnc3c2S(C)(=O)=O)c(OC)c1]

, and further removing 2,4-dimethoxybenzyl.

14.

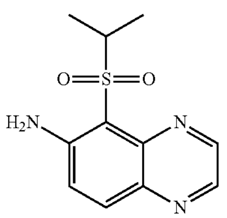 [SMILES: CC(C)S(=O)(=O)c1c(N)ccc2nccnc12]

was obtained by the following steps: reacting 5-chloro-6-nitroquinoxaline in (7) with isopropylmercaptan (cas: 75-33-2, Aladdin Shanghai) to obtain

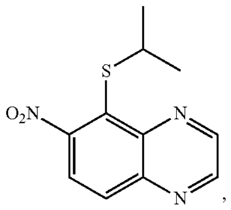 [SMILES: CC(C)Sc1c([N+](=O)[O-])ccc2nccnc12], further oxidizing the above reaction product to obtain

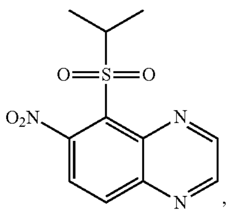 [SMILES: CC(C)S(=O)(=O)c1c([N+](=O)[O-])ccc2nccnc12], and finally reducing the nitro.

15.

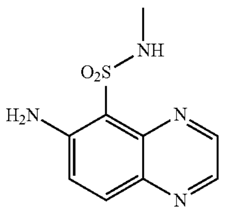 [SMILES: CNS(=O)(=O)c1c(N)ccc2nccnc12]

was obtained by the following steps: reacting 6-amino-5-bromoquinoxaline (cas: 50358-63-9, Bidepharm, Shanghai) with di-tert-butyl dicarbonate (cas: 24424-99-5, Bidepharm, Shanghai) to obtain

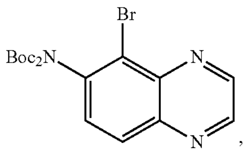, which was converted into

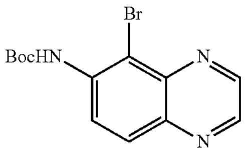 [SMILES: CC(C)(C)OC(=O)Nc1ccc2nccnc2c1Br]

by removing t-butoxycarbonyl, reacting the above conversion product with benzylmercaptan (cas: 100-53-8, Aladdin, Shanghai) to obtain

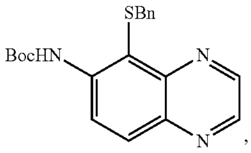, reacting the above reaction product with 1,3-dichloro-5,5-dimethylhydantoin (cas: 118-52-5, Bidepharm, Shanghai) to obtain

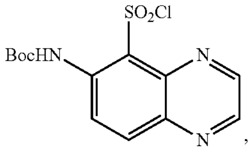 [SMILES: CC(C)(C)OC(=O)Nc1ccc2nccnc2c1S(=O)(=O)Cl], which was converted into

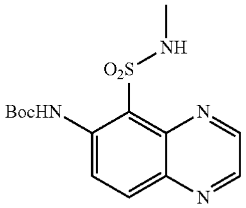 [SMILES: CNS(=O)(=O)c1c(NC(=O)OC(C)(C)C)ccc2nccnc12]

by further reacting with methylamine (cas: 74-89-5, Energy, Shanghai), and finally removing t-butoxycarbonyl.

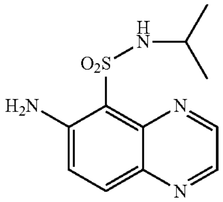 [SMILES: CC(C)NS(=O)(=O)c1c(N)ccc2nccnc12]

was obtained according to a similar method by replacing the methylamine with isopropylamine (cas: 75-31-0, Energy, Shanghai).

16.

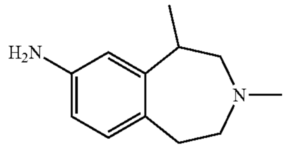

was obtained by the following steps: reacting p-nitrophenylethanol (cas: 100-27-6, Bidepharm, Shanghai) with 1,3-dibromo-5,5-dimethylhydantoin (cas: 77-48-5, Bidepharm, Shanghai) to obtain 2-bromo-4-nitrophenylethanol, reacting the above reaction product with methylsulfonyl chloride (cas: 124-63-0, Xiya Reagent, Shandong) to obtain 2-bromo-4-nitrophenylethyl mesylate, which was continuously reacted with methylallylamine (cas: 627-37-2, Energy, Shanghai) to obtain

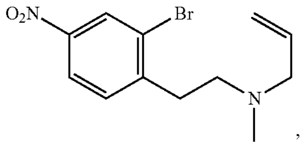 [SMILES: C=CCN(C)CCc1ccc([N+](=O)[O-])cc1Br]

, further converting the above reaction product to

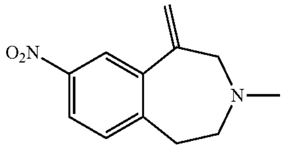 [SMILES: C=C1CN(C)CCc2ccc([N+](=O)[O-])cc21]

via a Heck reaction, and finally reducing the nitro and the double bond.

17.

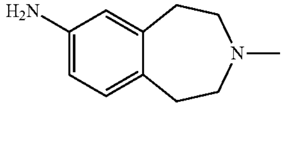

was obtained by the following steps: reacting 2,3,4,5-tetrahydro-1H-benzo[d]azepine (cas: 4424-20-8, Bidepharm, Shanghai) with formaldehyde to obtain

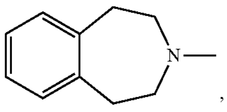

, further nitrifying the above reaction product to obtain

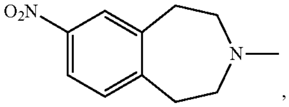

, and finally reducing the nitro.

18.

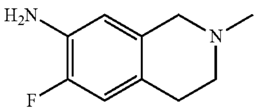

was obtained by the following steps: reacting 6-fluoro-3,4-dihydro-2H-isoquinolin-1-one (cas: 214045-84-8, Bidepharm, Shanghai) with iodomethane (cas: 74-88-4, Xiya Reagent, Shandong) to obtain 2-methyl-6-fluoro-3,4-dihydro-2H-isoquinolin-1-one, reacting the above reaction product with fuming nitric acid (cas: 7697-37-2, Hushi, Shanghai) to obtain 2-methyl-6-fluoro-7-nitro-3,4-dihydro-2H-isoquinolin-1-one, further reducing the carbonyl to obtain 2-methyl-6-fluoro-7-nitro-1,2,3,4-tetrahydroisoquinoline, and finally reducing the nitro.

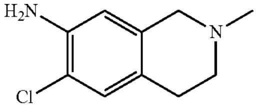

was obtained from 6-chloro-3,4-dihydro-2H-isoquinolin-1-one (cas: 22246-02-2, Bidepharm, Shanghai) according to a similar method.

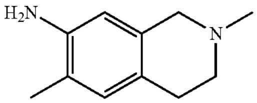

was obtained from 6-methyl-3,4-dihydro-2H-isoquinolin-1-one (cas: 1082041-78-8, Bidepharm, Shanghai) according to a similar method.

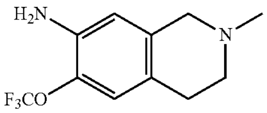

was obtained by the following steps: reducing 3-(trifluoromethoxy)phenylacetonitrile (cas: 108307-56-8, Bidepharm, Shanghai) to obtain 2-(3-trifluoromethoxyphenyl)ethylamine, reacting the above reduction product with ethyl chloroformate (cas: 541-41-3, Xiya Reagent, Shandong) to obtain ethyl 2-(3-trifluoromethoxyphenyl)aminoformate, which was further converted into 6-trifluoromethoxy-3,4-dihydro-2H-isoquinolin-1-one under the action of trifluoromethanesulfonic anhydride (cas: 358-23-6, Energy, Shanghai), and then performing a similar method.

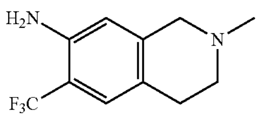

was obtained from m-trifluoromethylphenylacetonitrile (cas: 2338-76-3, Bidepharm, Shanghai) according to a similar method.

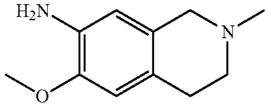

was obtained by the following steps: reacting 2-methyl-6-fluoro-7-nitro-3,4-dihydro-2H-isoquinolin-1-one with methanol (cas: 67-56-1, Hushi, Shanghai) to obtain 2-methyl-6-methoxy-7-nitro-3,4-dihydro-2H-isoquinolin-1-one, and then performing a similar method.

19. 2-Methyl-1,2,3,4-tetrahydroisoquinolin-7-amine (cas: 14097-40-6, Aikonchem, Jiangsu).

20. Pinacol vinylboronate (cas: 75927-49-0, Bidepharm, Shanghai).

21. Isopropenylboronic acid pinacol ester (cas: 126726-62-3, Bidepharm, Shanghai).

22. (E)-2-cyclopropyl boronic acid pinacol ester (cas: 849061-99-0, Bidepharm, Shanghai).

23. (E)-1-ethoxyethene-2-ylboronic acid pinacol ester (cas: 1201905-61-4, Bidepharm, Shanghai).

24. 2,2-Dimethylethenylboronic acid pinacol ester (cas: 126689-00-7, Bidepharm, Shanghai).

25. 1-Cyclopentenylboronic acid pinacol ester (cas: 287944-10-9, Bidepharm, Shanghai).

26. Trans-2-phenylvinylboronic acid pinacol ester (cas: 83947-56-2, Bidepharm, Shanghai).

27. 2,4-Dichloro-5-bromopyrimidine (cas: 36082-50-5, Bidepharm, Shanghai).

28. 1,1'-Bis(diphenylphosphino)ferrocene-palladium(II) dichloride dichloromethane complex (cas: 95464-05-4, Bidepharm, Shanghai).

29. Sodium hydride (cas: 7646-69-7, TCI, Shanghai).

30. 3-Aminopyrazole (cas: 1820-80-0, Bidepharm, Shanghai).

31. 1-Ethyl-3-aminopyrazole (cas: 55361-49-4, Bidepharm, Shanghai).

32. 1-Isopropyl-3-aminopyrazole (cas: 857267-04-0, Bidepharm, Shanghai).

33. 1,5-Dimethyl-3-aminopyrazole (cas: 35100-92-6, Bidepharm, Shanghai).

34.

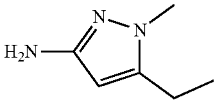

was obtained by reacting 3-oxopentanenitrile (cas: 33279-01-5, Bidepharm, Shanghai) with methylhydrazine (cas: 60-34-4, Xiya Reagent, Shandong).

35. 4-aminopyrazole (cas: 28466-26-4, Bidepharm, Shanghai).

36. 1-methyl-4-aminopyrazole (cas: 69843-13-6, Bidepharm, Shanghai).

37. 1-ethyl-4-aminopyrazole (cas: 876343-24-7, Bidepharm, Shanghai).

38. 1-isopropyl-4-aminopyrazole (cas: 97421-16-4, Bidepharm, Shanghai).

39. 1-ethyl-3-methyl-4-aminopyrazole (cas: 947763-34-0, Bidepharm, Shanghai).

The embodiments of the present invention are described in detail below by way of specific examples, but in any case they cannot be construed as limiting the present invention.

Synthesis of Compound I-1:

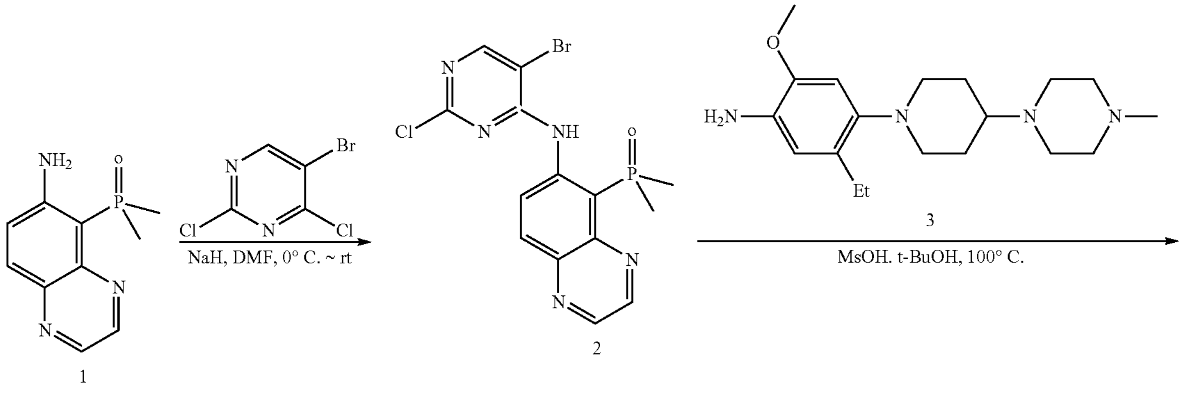

-continued

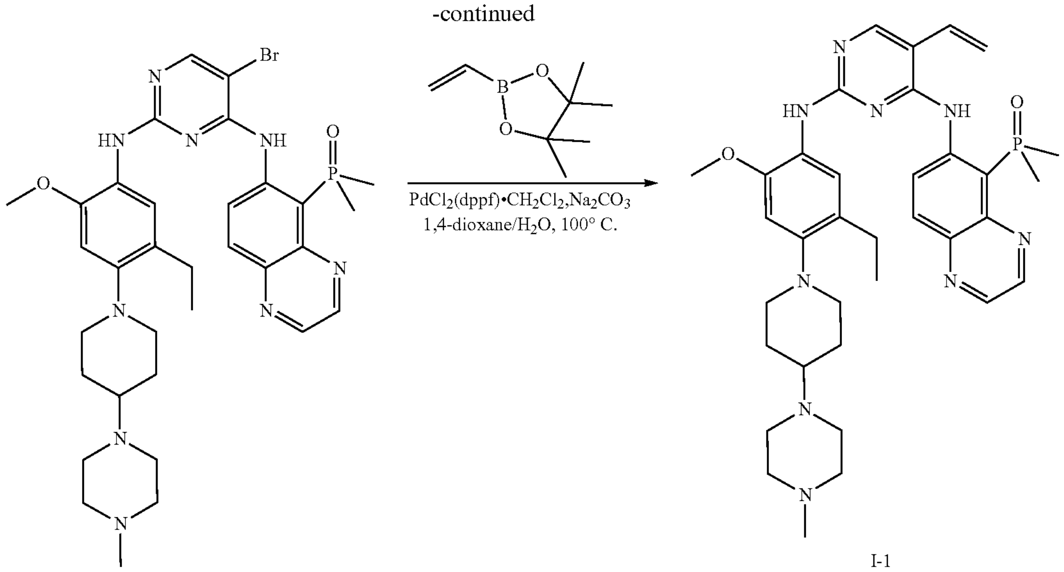

4

I-1

First step: Compound 1 (442 mg, 2 mmol) was dissolved in DMF (5 mL), and, sodium hydride (60% concentration, dispersed in liquid paraffin wax, 160 mg, 4 mmol) was added thereto in batches at 0° C. After 5 minutes, 2,4-dichloro-5-bromopyrimidine (479 mg, 2.1 mmol) was added and reacted by self-heating for 1 hour, the completion of the reaction was detected by TLC and LCMS. 100 mL of water were added to the reaction mixture to precipitate solids. The solids were filtered and dried under reduced pressure to obtain compound 2 (339 mg), which was directly used for the next step reaction.

Second step: Compound 2 (41.3 mg, 0.1 mmol), compound 3 (33.2 mg, 0.1 mmol) and methanesulfonic acid (19 µL, 0.3 mmol) in t-BuOH (2 mL) were heated at 100° C. for 4 h, and the completion of the reaction was detected by TLC and LCMS. After cooling, the reaction mixture was concentrated, and purified by silica gel chromatograph (elution with dichloromethane/methanol), to obtain compound 4 (50 mg).

Third step: Compound 4 (0.042 mmol, 30 mg), pinacol vinylboronate (0.126 mmol, 21 µL), $PdCl_2(dppf)CH_2Cl_2$ (0.0042 mmol, 3.4 mg), and $Na_2CO_3$ (0.126 mmol, 13.4 mg) were dispersed in 1,4-dioxane (1 mL) and water (0.5 mL), and after nitrogen gas replacement, the reaction system solution was heated at 100° C. for 4 hours. The completion of the reaction was detected by TLC and LCMS, and the reaction system was diluted with 50 mL of water and then extracted with DCM. The organic phase was concentrated, and purified by silica gel chromatograph (elution with dichloromethane/methanol), and then further purified by preparative HPLC (aqueous solution containing 0.35% trifluoroacetic acid and methanol as mobile phase), to obtain compound I-1 (15.3 g).

Other such compounds could be synthesized by similar methods.

In the following table, it lists the specific compounds and their structural characterization data.

| No. | Structure | $^1H$ NMR and/or MS data |
|---|---|---|
| I-1 | 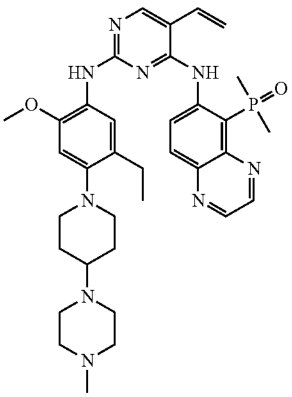 [SMILES: C=Cc1cnc(Nc2cc(CC)c(N3CCC(N4CCN(C)CC4)CC3)cc2OC)nc1Nc1ccc2nccnc2c1P(C)(C)=O] | $^1H$ NMR (400 MHz, MeOD) δ 9.04 (dd, J = 9.6, 4.3 Hz, 1H), 8.81 (d, J = 1.9 Hz, 1H), 8.76 (d, J = 1.9 Hz, 1H), 8.29 (s, 1H), 7.96 (d, J = 9.5 Hz, 1H), 7.72 (s, 1H), 6.89 (dd, J = 17.3, 11.0 Hz, 1H), 6.80 (s, 1H), 5.68 (dd, J = 17.2, 1.3 Hz, 1H), 5.31 (dd, J = 11.0, 1.3 Hz, 1H), 3.85 (s, 3H), 3.16 - 3.06 (m, 2H), 2.80 - 2.68 (m, 2H), 2.68 - 2.56 (m, 8H), 2.52 (q, J = 7.5 Hz, 2H), 2.43 - 2.33 (m, 1H), 2.31 (s, 3H), 2.15 (s, 3H), 2.11 (s, 3H), 2.06 - 1.94 (m, 2H), 1.76 - 1.63 (m, 2H), 0.87 (t, J = 7.5 Hz, 3H); MS (ESI) m/z: 656 [M + H]$^+$. |

-continued

| No. | Structure | $^1$H NMR and/or MS data |
|---|---|---|
| I-2 | 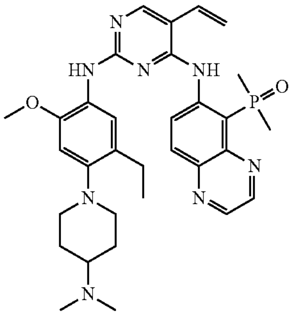 [SMILES: C=Cc1cnc(Nc2cc(CC)c(N3CCC(N(C)C)CC3)cc2OC)nc1Nc1ccc2nccnc2c1P(C)(C)=O] | $^1$H NMR (600 MHz, DMSO-$d_6$) δ 13.61 (s, 1H), 9.95 (s, 1H), 9.03 - 8.89 (m, 3H), 8.43 - 8.22 (m, 1H), 8.02 - 7.79 (m, 1H), 7.32 (s, 1H), 6.97 - 6.87 (m, 2H), 5.86 (d, J = 17.1 Hz, 1H), 5.47 (d, J = 11.0 Hz, 1H), 3.81 (s, 3H), 3.40 - 3.29 (m, 1H), 3.25 - 3.14 (m, 2H), 2.89 - 2.82 (m, 8H), 2.63 - 2.55 (m, 2H), 2.19 - 2.12 (m, 2H), 2.09 (s, 3H), 2.06 (s, 3H), 1.92 - 1.79 (m, 2H), 1.15 - 0.97 (m, 3H); MS (ESI) m/z: 601 $[M + H]^+$. |
| I-3 | 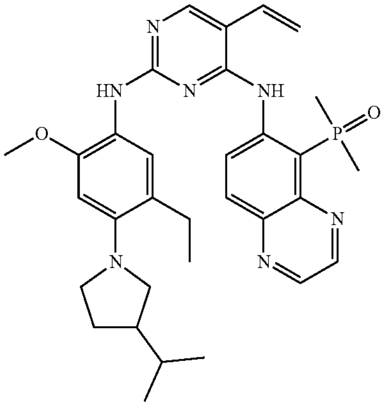 [SMILES: C=Cc1cnc(Nc2cc(CC)c(N3CCC(C(C)C)C3)cc2OC)nc1Nc1ccc2nccnc2c1P(C)(C)=O] | $^1$H NMR (600 MHz, DMSO-$d_6$) δ 13.60 (s, 1H), 10.46 - 10.23 (m, 1H), 9.14 - 8.75 (m, 3H), 8.46 - 8.21 (m, 1H), 7.98 - 7.83 (m, 1H), 7.26 (s, 1H), 6.91 (dd, J = 17.1, 11.0 Hz, 1H), 6.85 (s, 1H), 5.86 (d, J = 17.1 Hz, 1H), 5.46 (d, J = 11.2 Hz, 1H), 4.07 - 3.99 (m, 1H), 3.82 (s, 3H), 3.50 - 3.40 (m, 2H), 3.35 - 3.28 (m, 1H), 3.25 - 3.19 (m, 1H), 2.96 - 2.85 (m, 6H), 2.64 - 2.55 (m, 2H), 2.44 - 2.36 (m, 1H), 2.24 - 2.17 (m, 1H), 2.09 (s, 3H), 2.06 (s, 3H), 1.16 - 0.97 (m, 3H); MS (ESI) m/z: 587 $[M + H]^+$. |
| I-4 | 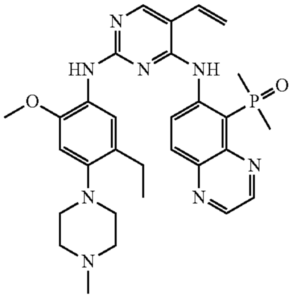 [SMILES: C=Cc1cnc(Nc2cc(CC)c(N3CCN(C)CC3)cc2OC)nc1Nc1ccc2nccnc2c1P(C)(C)=O] | $^1$H NMR (600 MHz, DMSO-$d_6$) δ 13.55 (s, 1H), 10.26 - 10.01 (m, 1H), 9.09 - 8.84 (m, 3H), 8.41 - 8.25 (m, 1H), 8.01 - 7.85 (m, 1H), 7.38 (s, 1H), 6.96 - 6.88 (m, 2H), 5.86 (d, J = 17.1 Hz, 1H), 5.45 (d, J = 11.1 Hz, 1H), 3.83 (s, 3H), 3.62 - 3.53 (m, 2H), 3.36 - 3.25 (m, 2H), 3.24 - 3.19 (m, 2H), 3.15 - 3.07 (m, 2H), 2.93 (s, 3H), 2.58 (q, J = 7.5 Hz, 2H), 2.09 (s, 3H), 2.06 (s, 3H), 1.08 - 0.97 (m, 3H); MS (ESI) m/z: 573 $[M + H]^+$. |
| I-5 | 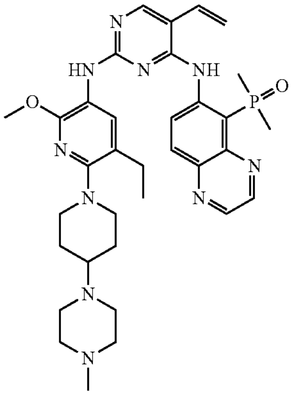 [SMILES: C=Cc1cnc(Nc2cc(CC)c(N3CCC(N4CCN(C)CC4)CC3)nc2OC)nc1Nc1ccc2nccnc2c1P(C)(C)=O] | $^1$H NMR (600 MHz, DMSO-$d_6$) δ 13.39 (s, 1H), 9.82 (s, 1H), 8.97 - 8.93 (m, 2H), 8.92 - 8.90 (m, 1H), 8.35 (s, 1H), 7.98 - 7.84 (m, 1H), 7.71 (s, 1H), 6.92 (dd, J = 17.1, 11.0 Hz, 1H), 5.84 (d, J = 17.1 Hz, 1H), 5.42 (d, J = 11.1 Hz, 1H), 3.87 (s, 3H), 3.82 - 3.64 (m, 8H), 3.61 - 3.54 (m, 2H), 3.50 - 3.42 (m, 1H), 2.94 - 2.91 (m, 2H), 2.90 (s, 3H), 2.55 - 2.52 (m, 2H), 2.19 - 2.14 (m, 2H), 2.08 (s, 3H), 2.06 (s, 3H), 1.89 - 1.76 (m, 2H), 1.04 (t, J = 7.7 Hz, 3H). MS (ESI) m/z: 657 $[M + H]^+$. |

-continued

| No. | Structure | $^1$H NMR and/or MS data |
|---|---|---|
| I-6 | 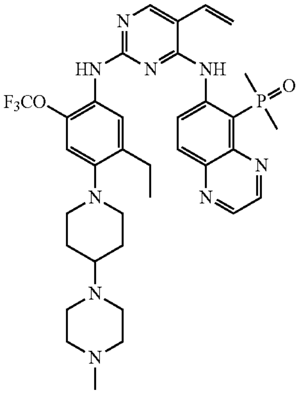 [SMILES: C=Cc1cnc(Nc2cc(CC)c(N3CCC(N4CCN(C)CC4)CC3)cc2OC(F)(F)F)nc1Nc1ccc2nccnc2c1P(C)(C)=O] | $^1$H NMR (600 MHz, DMSO-$d_6$) δ 13.33 (s, 1H), 10.23 - 10.01 (m, 1H), 9.00 - 8.79 (m, 3H), 8.40 (s, 1H), 7.81 - 7.75 (m, 1H), 7.51 (s, 1H), 7.18 (s, 1H), 6.92 (dd, J = 17.0, 11.1 Hz, 1H), 5.83 (d, J = 17.1 Hz, 1H), 5.39 (d, J = 11.2 Hz, 1H), 3.85 - 3.30 (m, 9H), 3.22 - 3.14 (m, 2H), 2.92 (s, 3H), 2.84 - 2.75 (m, 2H), 2.63 (q, J = 7.4 Hz, 2H), 2.26 - 2.15 (m, 2H), 2.07 (s, 3H), 2.04 (s, 3H), 1.90 - 1.79 (m, 2H), 1.07 (t, J = 7.5 Hz, 3H); MS (ESI) m/z: 710 [M + H]$^+$. |
| I-7 | 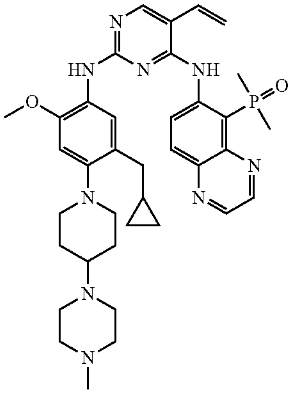 [SMILES: C=Cc1cnc(Nc2cc(CC3CC3)c(N3CCC(N4CCN(C)CC4)CC3)cc2OC)nc1Nc1ccc2nccnc2c1P(C)(C)=O] | $^1$H NMR (600 MHz, DMSO-$d_6$) δ 13.53 (s, 1H), 10.15 - 9.98 (m, 1H), 9.03 - 8.95 (m, 1H), 8.95 (d, J = 1.9 Hz, 1H), 8.93 (d, J = 1.9 Hz, 1H), 8.40 - 8.25 (m, 1H), 7.98 - 7.85 (m, 1H), 7.50 (s, 1H), 6.97 - 6.87 (m, 2H), 5.86 (d, J = 17.2 Hz, 1H), 5.46 (d, J = 11.2 Hz, 1H), 3.82 (s, 3H), 3.75 - 3.47 (m, 8H), 3.45 - 3.37 (m, 1H), 3.21 - 3.14 (m, 2H), 2.92 (s, 3H), 2.87 - 2.77 (m, 2H), 2.45 - 2.41 (m, 2H), 2.24 - 2.17 (m, 2H), 2.09 (s, 3H), 2.07 (s, 3H), 1.88 - 1.77 (m, 2H), 0.85 - 0.74 (m, 1H), 0.38 - 0.28 (m, 2H), 0.02 - -0.04 (m, 2H). MS (ESI) m/z: 682 [M + H]$^+$. |
| I-8 | 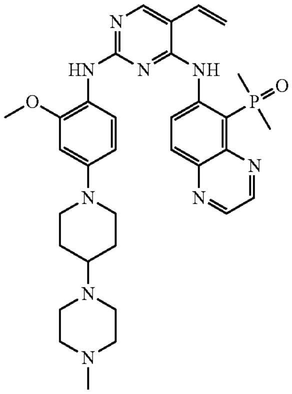 | MS (ESI) m/z: 628 [M + H]$^+$. |
| I-9 | 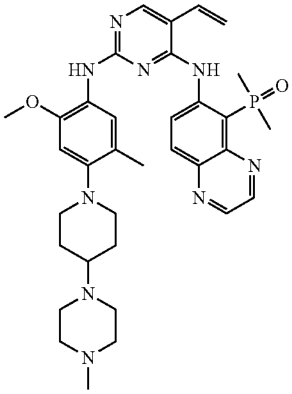 [SMILES: C=Cc1cnc(Nc2cc(C)c(N3CCC(N4CCN(C)CC4)CC3)cc2OC)nc1Nc1ccc2nccnc2c1P(C)(C)=O] | $^1$H NMR (600 MHz, DMSO-$d_6$) δ 13.61 (s, 1H), 10.24 - 10.11 (m, 1H), 8.99 - 8.89 (m, 3H), 8.39 - 8.28 (m, 1H), 8.00 - 7.87 (m, 1H), 7.32 (s, 1H), 6.92 (dd, J = 17.1, 11.1 Hz, 1H), 6.86 (s, 1H), 5.86 (d, J = 17.0 Hz, 1H), 5.46 (d, J = 11.2 Hz, 1H), 3.82 (s, 3H), 3.79 - 3.74 (m, 1H), 3.72 - 3.42 (m, 8H), 3.34 - 3.26 (m, 2H), 2.93 (s, 3H), 2.85 - 2.77 (m, 2H), 2.25 - 2.18 (m, 2H), 2.17 (s, 3H), 2.09 (s, 3H), 2.07 (s, 3H), 1.94 - 1.80 (m, 2H); MS (ESI) m/z: 642 [M + H]$^+$. |

-continued

| No. | Structure | $^1$H NMR and/or MS data |
|---|---|---|
| I-10 | 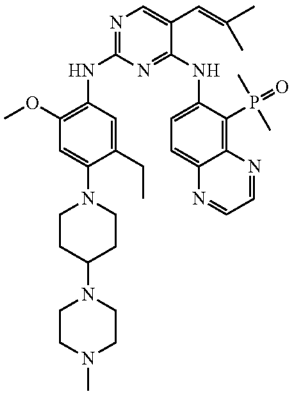 [SMILES: CCc1cc(Nc2ncc(C=C(C)C)c(Nc3ccc4nccnc4c3P(C)(C)=O)n2)c(OC)cc1N1CCC(N2CCN(C)CC2)CC1] | $^1$H NMR (600 MHz, DMSO-$d_6$) δ 13.21 (s, 1H), 10.01 - 9.88 (m, 1H), 8.98 - 8.90 (m, 3H), 8.00 - 7.82 (m, 2H), 7.35 (s, 1H), 6.89 (s, 1H), 6.10 (s, 1H), 3.81 (s, 3H), 3.74 - 3.35 (m, 8H), 3.32 - 3.25 (m, 1H), 3.23 - 3.14 (m, 2H), 2.88 (s, 3H), 2.85 - 2.78 (m, 2H), 2.58 - 2.53 (m, 2H), 2.18 - 2.11 (m, 2H), 2.07 (s, 3H), 2.04 (s, 3H), 1.93 (s, 3H), 1.86 - 1.80 (m, 2H), 1.79 (s, 3H), 1.07 - 0.97 (m, 3H). MS (ESI) m/z: 684 [M + H]$^+$. |
| I-11 | 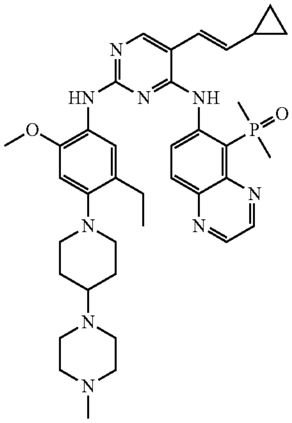 [SMILES: CCc1cc(Nc2ncc(/C=C/C3CC3)c(Nc3ccc4nccnc4c3P(C)(C)=O)n2)c(OC)cc1N1CCC(N2CCN(C)CC2)CC1] | $^1$H NMR (600 MHz, DMSO-$d_6$) δ 13.46 (s, 1H), 10.00 (s, 1H), 9.01 - 8.88 (m, 3H), 8.17 (s, 1H), 7.98 - 7.83 (m, 1H), 7.32 (s, 1H), 6.90 (s, 1H), 6.61 (d, J = 15.2 Hz, 1H), 5.86 (dd, J = 15.3, 9.1 Hz, 1H), 3.81 (s, 3H), 3.73 - 3.44 (m, 8H), 3.34 (d, J = 41.9 Hz, 1H), 3.26 - 3.15 (m, 2H), 2.90 (s, 3H), 2.87 - 2.81 (m, 2H), 2.59 - 2.53 (m, 2H), 2.25 - 2.15 (m, 2H), 2.11 (s, 3H), 2.08 (s, 3H), 1.91 - 1.78 (m, 2H), 1.66 - 1.55 (m, 1H), 1.04 (t, J = 7.6 Hz, 3H), 0.89 - 0.83 (m, 2H), 0.63 - 0.56 (m, 2H). MS (ESI) m/z: 696 [M + H]$^+$. MS (ESI) m/z: 700 [M + H]$^+$. |
| I-12 | 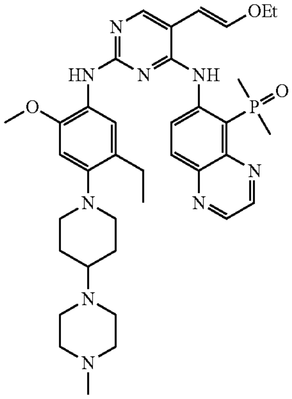 [SMILES: CCO/C=C/c1cnc(Nc2cc(CC)c(N3CCC(N4CCN(C)CC4)CC3)cc2OC)nc1Nc1ccc2nccnc2c1P(C)(C)=O] | MS (ESI) m/z: 700 [M + H]$^+$. $^1$H NMR (600 MHz, DMSO-$d_6$) δ 13.00 (s, 1H), 9.78 (s, 1H), 8.92 (d, J = 6.3 Hz, 2H), 8.79 - 8.60 (m, 1H), 8.19 - 7.87 (m, 2H), 7.35 (s, 1H), 6.85 (s, 1H), 6.22 (s, 1H), 3.81 (s, 3H), 3.73 - 3.38 (m, 8H), 3.31 (s, 1H), 3.19 - 3.10 (m, 2H), 2.89 (s, 3H), 2.83 - 2.75 (m, 2H), 2.71 - 2.64 (m, 2H), 2.49 - 2.43 (m, 4H), 2.20 - 2.12 (m, 2H), 2.03 (s, 3H), 2.01 (s, 3H), 2.00 - 1.96 (m, 2H), 1.89 - 1.77 (m, 2H), 1.03 - 0.78 (m, 3H). MS (ESI) m/z: 696 [M + H]$^+$. |

-continued
| No. | Structure | $^1$H NMR and/or MS data |
|---|---|---|
| I-13 | 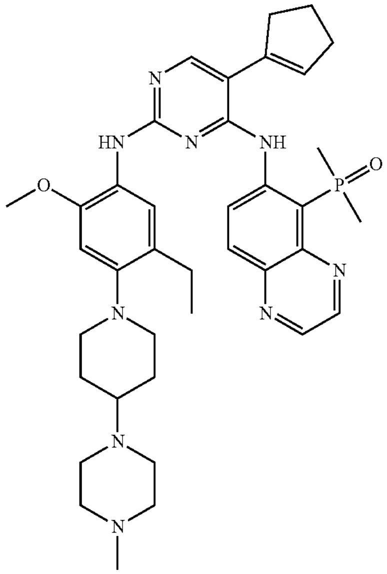 [SMILES: CCc1cc(Nc2ncc(C3=CCCC3)c(Nc3ccc4nccnc4c3P(C)(C)=O)n2)c(OC)cc1N1CCC(N2CCN(C)CC2)CC1] | $^1$H NMR (600 MHz, DMSO-$d_6$) δ 13.00 (s, 1H), 9.78 (s, 1H), 8.92 (d, J = 6.3 Hz, 2H), 8.79 - 8.60 (m, 1H), 8.19 - 7.87 (m, 2H), 7.35 (s, 1H), 6.85 (s, 1H), 6.22 (s, 1H), 3.81 (s, 3H), 3.73 - 3.38 (m, 8H), 3.31 (s, 1H), 3.19 - 3.10 (m, 2H), 2.89 (s, 3H), 2.83 - 2.75 (m, 2H), 2.71 - 2.64 (m, 2H), 2.49 - 2.43 (m, 4H), 2.20 - 2.12 (m, 2H), 2.03 (s, 3H), 2.01 (s, 3H), 2.00 - 1.96 (m, 2H), 1.89 - 1.77 (m, 2H), 1.03 - 0.78 (m, 3H). MS (ESI) m/z: 696 $[M + H]^+$. |
| I-14 | 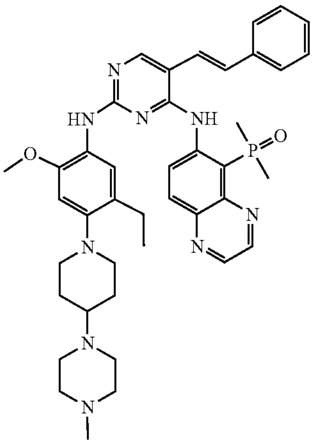 [SMILES: CCc1cc(Nc2ncc(/C=C/c3ccccc3)c(Nc3ccc4nccnc4c3P(C)(C)=O)n2)c(OC)cc1N1CCC(N2CCN(C)CC2)CC1] | $^1$H NMR (600 MHz, DMSO-$d_6$) δ 13.46 (s, 1H), 9.56 (s, 1H), 9.20 - 8.95 (m, 1H), 8.93 - 8.91 (m, 1H), 8.91 - 8.88 (m, 1H), 8.50 (s, 1H), 7.95 - 7.87 (m, 1H), 7.65 (s, 1H), 7.63 (s, 1H), 7.45 - 7.38 (m, 4H), 7.31 (t, J = 7.4 Hz, 1H), 7.21 (d, J = 16.0 Hz, 1H), 6.90 (s, 1H), 3.82 (s, 3H), 3.74 - 3.36 (m, 8H), 3.33 - 3.23 (m, 1H), 3.21 - 3.14 (m, 2H), 2.86 (s, 3H), 2.85 - 2.79 (m, 2H), 2.61 - 2.54 (m, 2H), 2.17 - 2.13 (m, 2H), 2.12 (s, 3H), 2.09 (s, 3H), 1.89 - 1.73 (m, 2H), 1.05 (t, J = 7.7 Hz, 3H). MS (ESI) m/z: 732 $[M + H]^+$. |
| I-15 | 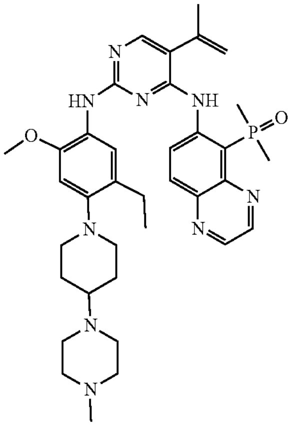 [SMILES: C=C(C)c1cnc(Nc2cc(CC)c(N3CCC(N4CCN(C)CC4)CC3)cc2OC)nc1Nc1ccc2nccnc2c1P(C)(C)=O] | $^1$H NMR (600 MHz, DMSO-$d_6$) δ 13.14 (s, 1H), 10.06 (s, 1H), 8.98 - 8.90 (m, 2H), 8.86 - 8.63 (m, 1H), 8.11 - 7.83 (m, 2H), 7.32 (s, 1H), 6.88 (s, 1H), 5.42 (s, 1H), 5.28 (s, 1H), 3.81 (s, 3H), 3.42 (s, 9H), 3.23 - 3.11 (m, 2H), 2.92 (s, 3H), 2.87 - 2.77 (m, 2H), 2.58 - 2.52 (m, 2H), 2.26 - 2.16 (m, 2H), 2.10 (s, 3H), 2.04 (s, 3H), 2.02 (s, 3H), 1.91 - 1.75 (m, 2H), 0.98 (t, 3H). MS (ESI) m/z: 670 $[M + H]^+$. |

-continued

| No. | Structure | $^1$H NMR and/or MS data |
|---|---|---|
| I-16 | 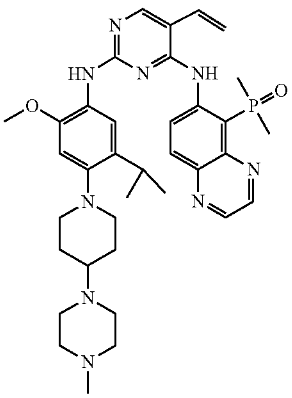 | $^1$H NMR (600 MHz, DMSO-$d_6$) δ 13.52 (s, 1H), 10.13 (s, 1H), 9.03 – 8.94 (m, 1H), 8.93 (d, J = 1.9 Hz, 1H), 8.91 (d, J = 1.8 Hz, 1H), 8.33 (s, 1H), 7.92 – 7.73 (m, 1H), 7.30 (s, 1H), 6.96 (s, 1H), 6.95 – 6.91 (m, 1H), 5.86 (d, J = 17.1 Hz, 1H), 5.43 (d, J = 11.1 Hz, 1H), 3.80 (s, 3H), 3.70 – 3.37 (m, 9H), 3.32 (hept, J = 6.7 Hz, 1H), 3.17 – 3.13 (m, 2H), 2.92 (s, 3H), 2.91 – 2.87 (m, 2H), 2.25 – 2.18 (m, 2H), 2.09 (s, 3H), 2.07 (s, 3H), 1.93 – 1.83 (m, 2H), 1.08 (d, J = 6.8 Hz, 6H). MS (ESI) m/z: 670 $[M + H]^+$. |
| I-17 | 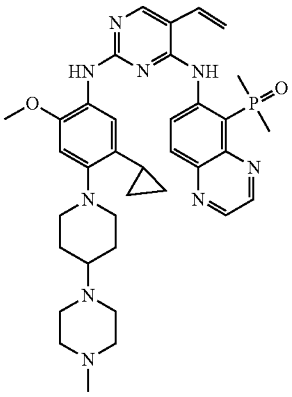 | $^1$H NMR (600 MHz, DMSO-$d_6$) δ 13.54 (s, 1H), 10.10 (s, 1H), 8.96 – 8.93 (m, 1H), 8.92 (d, J = 1.8 Hz, 1H), 8.90 (d, J = 1.8 Hz, 1H), 8.31 (s, 1H), 7.96 – 7.80 (m, 1H), 6.98 – 6.87 (m, 2H), 6.83 (s, 1H), 5.84 (d, J = 17.1 Hz, 1H), 5.43 (d, J = 11.2 Hz, 1H), 3.80 (s, 3H), 3.73 – 3.27 (m, 11H), 2.93 – 2.89 (m, 3H), 2.87 – 2.78 (m, 2H), 2.23 – 2.17 (m, 2H), 2.14 – 2.10 (m, 1H), 2.08 (s, 3H), 2.06 (s, 3H), 1.94 – 1.85 (m, 2H), 0.86 – 0.76 (m, 2H), 0.56 – 0.47 (m, 2H). MS (ESI) m/z: 668 $[M + H]^+$. |
| I-18 | 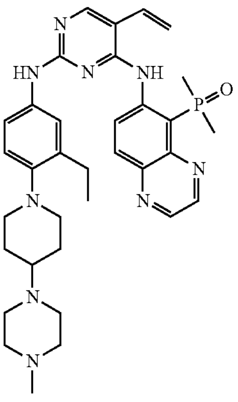 | $^1$H NMR (600 MHz, DMSO-$d_6$) δ 13.56 (s, 1H), 10.65 (s, 1H), 9.94 – 9.88 (m, 1H), 8.95 (d, J = 1.9 Hz, 1H), 8.94 (d, J = 1.9 Hz, 1H), 8.35 (s, 1H), 7.98 (d, J = 9.3 Hz, 1H), 7.37 (dd, J = 8.4, 2.5 Hz, 1H), 7.34 (d, J = 2.5 Hz, 1H), 7.22 (d, J = 8.5 Hz, 1H), 6.93 (dd, J = 17.1, 11.1 Hz, 1H), 5.88 (d, J = 17.1 Hz, 1H), 5.48 (d, J = 11.1 Hz, 1H), 4.00 – 3.62 (m, 4H), 3.56 – 3.48 (m, 1H), 3.45 – 3.25 (m, 4H), 3.21 – 3.15 (m, 2H), 2.95 (s, 3H), 2.83 – 2.76 (m, 2H), 2.68 – 2.60 (m, 2H), 2.26 – 2.17 (m, 2H), 2.10 (s, 3H), 2.07 (s, 3H), 1.90 – 1.82 (m, 2H), 1.08 (t, J = 7.5 Hz, 3H). MS (ESI) m/z: 626 $[M + H]^+$. |

-continued
| No. | Structure | $^1H$ NMR and/or MS data |
| --- | --- | --- |
| I-19 | 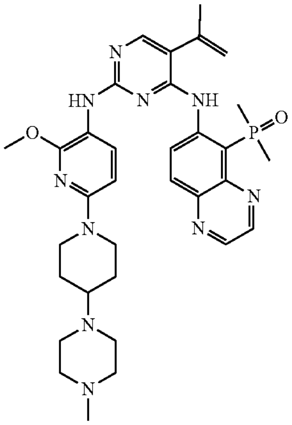 | $^1H$ NMR (600 MHz, DMSO-$d_6$) δ 13.17 (s, 1H), 10.09 (s, 1H), 9.03 - 8.88 (m, 2H), 8.85 - 8.67 (m, 1H), 8.14 - 7.86 (m, 2H), 7.61 (d, J = 8.4 Hz, 1H), 6.56 (d, J = 8.4 Hz, 1H), 5.41 (s, 1H), 5.26 (s, 1H), 4.58 - 4.48 (m, 2H), 3.85 (s, 3H), 3.77 - 3.25 (m, 9H), 2.98 - 2.91 (m, 2H), 2.89 (s, 3H), 2.18 - 2.13 (m, 2H), 2.11 (s, 3H), 2.04 (s, 3H), 2.02 (s, 3H), 1.68 - 1.59 (m, 2H). MS (ESI) m/z: 643 $[M + H]^+$. |
| I-20 | 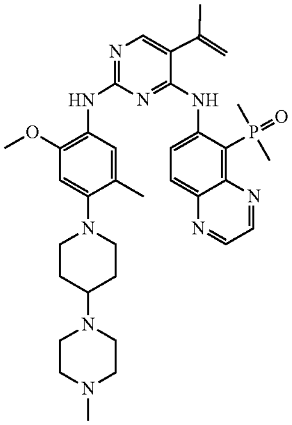 | $^1H$ NMR (600 MHz, DMSO-$d_6$) δ 13.11 (s, 1H), 9.96 (s, 1H), 9.04 - 8.78 (m, 2H), 8.01 (s, 1H), 7.92 - 7.68 (m, 2H), 7.55 (s, 1H), 5.40 (s, 1H), 5.25 (s, 1H), 3.95 (s, 3H), 3.91 - 3.80 (m, 2H), 3.78 - 3.03 (m, 9H), 2.86 (s, 3H), 2.83 - 2.79 (m, 2H), 2.09 (s, 3H), 2.06 (s, 3H), 2.04 (s, 3H), 2.02 (s, 3H), 2.00 - 1.95 (m, 2H), 1.67 - 1.56 (m, 2H). MS (ESI) m/z: 657 $[M + H]^+$. |
| I-21 | 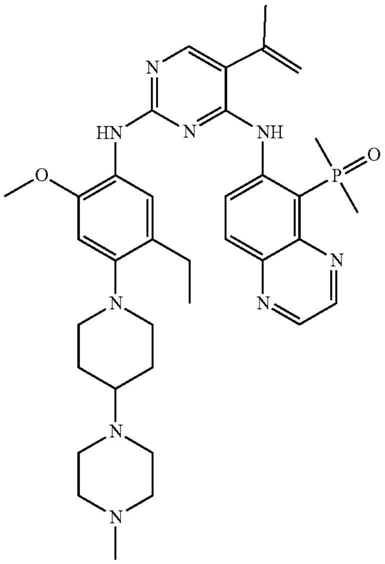 | $^1H$ NMR (600 MHz, DMSO-$d_6$) δ 12.97 (s, 1H), 9.86 (s, 1H), 8.94 - 8.91 (m. 2H), 8.84 - 8.69 (m, 1H), 8.04 (s, 1H), 7.97 - 7.81 (m, 1H), 7.71 (s, 1H), 5.40 (s, 1H), 5.27 (s, 1H), 3.88 (s, 3H), 3.79 - 3.27 (m, 11H), 2.96 - 2.85 (m, 5H), 2.51 - 2.47 (m, 2H), 2.20 - 2.13 (m, 2H), 2.11 (s, 3H), 2.04 (s, 3H), 2.02 (s, 3H), 1.92 - 1.77 (m, 2H), 1.04 - 0.94 (m, 3H). MS (ESI) m/z: 671 $[M + H]^+$. |

-continued

| No. | Structure | $^1$H NMR and/or MS data |
| --- | --- | --- |
| I-22 | 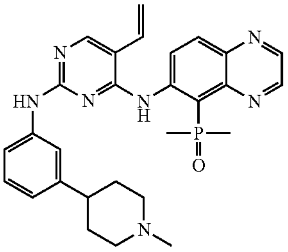 [SMILES: C=Cc1cnc(Nc2cccc(C3CCN(C)CC3)c2)nc1Nc1ccc2nccnc2c1P(C)(C)=O] | $^1$H NMR (600 MHz, DMSO-$d_6$) δ 10.46 (s, 1H), 10.14 (s, 1H), 9.14 - 9.04 (m, 1H), 8.94 - 8.87 (m, 2H), 8.46 (s, 1H), 8.06 (d, J = 9.4 Hz, 1H), 7.58 (d, J = 7.9 Hz, 1H), 7.41 (s, 1H), 7.36 (t, J = 7.9 Hz, 1H), 7.02 (d, J = 7.7 Hz, 1H), 6.93 (dd, J = 17.2, 11.0 Hz, 1H), 5.83 (d, J = 17.1 Hz, 1H), 5.37 (d, J = 11.0 Hz, 1H), 3.51 - 3.45 (m, 2H), 3.07 - 3.00 (m, 2H), 2.82 - 2.71 (m, 3H), 2.42 (s, 3H), 2.08 (s, 3H), 2.06 (s, 3H), 1.98 - 1.88 (m, 2H). MS (ESI) m/z: 514 [M + H]$^+$. |
| I-23 | 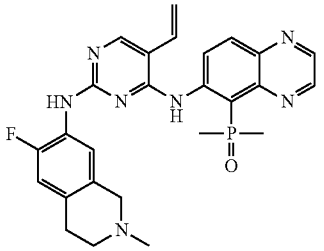 [SMILES: C=Cc1cnc(Nc2cc3c(cc2F)CCN(C)C3)nc1Nc1ccc2nccnc2c1P(C)(C)=O] | $^1$H NMR (400 MHz, Chloroform-d) δ 12.54 (s, 1H), 9.12 (dd, J = 9.5, 4.2 Hz, 1H), 8.76 (d, J = 1.9 Hz, 1H), 8.72 (d, J = 1.9 Hz, 1H), 8.37 (s, 1H), 8.14 (d, J = 9.5 Hz, 1H), 7.94 (d, J = 8.2 Hz, 1H), 7.21 (s, 1H), 6.99 (dd, J = 17.2, 11.0 Hz, 1H), 6.89 (d, J = 11.6 Hz, 1H), 5.70 (dd, J = 17.2, 1.2 Hz, 1H), 5.43 (dd, J = 10.9, 1.2 Hz, 1H), 3.44 (s, 2H), 2.90 (t, J = 6.0 Hz, 2H), 2.71 (t, J = 6.0 Hz, 2H), 2.43 (s, 3H), 2.16 (s, 3H), 2.13 (s, 3H). MS (ESI) m/z: 504 [M + H]$^+$. |
| I-24 | 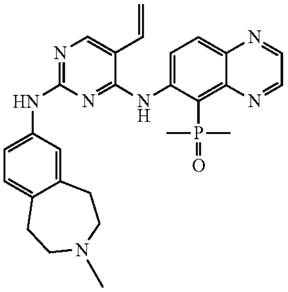 [SMILES: C=Cc1cnc(Nc2ccc3c(c2)CCN(C)CC3)nc1Nc1ccc2nccnc2c1P(C)(C)=O] | $^1$H NMR (600 MHz, DMSO-$d_6$) δ 10.76 (s, 1H), 10.29 (s, 1H), 9.23 - 9.12 (m, 1H), 8.93 - 8.87 (m, 2H), 8.47 (s, 1H), 8.11 (d, J = 9.6 Hz, 1H), 7.53 - 7.45 (m, 2H), 7.21 (d, J = 8.0 Hz, 1H), 6.94 (dd, J = 17.3, 11.2 Hz, 1H), 5.81 (d, J = 17.1 Hz, 1H), 5.34 (d, J = 11.1 Hz, 1H), 3.66 - 3.52 (m, 2H), 3.31 - 3.19 (m, 2H), 3.09 - 2.92 (m, 4H), 2.90 - 2.75 (m, 3H), 2.08 (s, 3H), 2.06 (s, 3H).MS (ESI) m/z: 500 [M + H]$^+$. |
| I-25 | 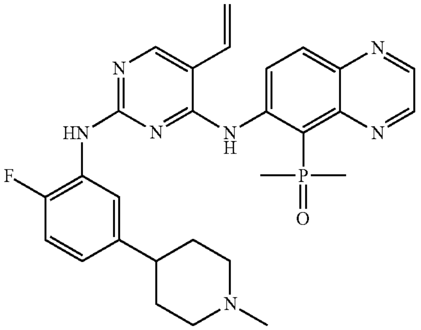 | 1H NMR (600 MHz, DMSO-d6) δ 13.38 (s, 1H), 9.92 - 9.59 (m, 2H), 8.93 (d, J = 1.8 Hz, 1H), 8.92 (d, J = 1.9 Hz, 1H), 8.38 (s, 1H), 7.94 (d, J = 9.6 Hz, 1H), 7.49 (s, 1H), 7.22 - 7.16 (m, 2H), 6.94 (dd, J = 17.1, 11.0 Hz, 1H), 5.83 (d, J = 17.2 Hz, 1H), 5.43 - 5.38 (m, 1H), 3.82 (s, 3H), 3.50 - 3.43 (m, 2H), 3.04 - 2.96 (m, 2H), 2.79 (s, 3H), 2.74 - 2.68 (m, 1H), 2.09 (s, 3H), 2.06 (s, 3H), 2.03 - 1.92 (m, 2H), 1.88 - 1.77 (m, 2H). MS (ESI) m/z: 544 [M + H]+. |
| II-1 | 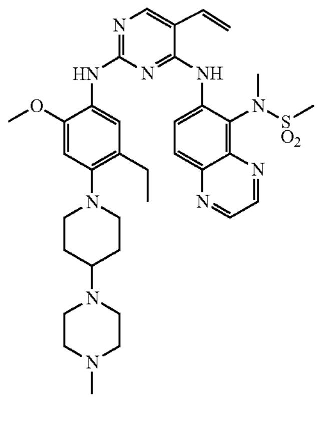 | $^1$H NMR (600 MHz, DMSO-$d_6$) δ 9.94 (s, 1H), 9.70 - 9.53 (m, 1H), 9.08 - 8.99 (m, 2H), 8.40 - 8.26 (m, 1H), 8.19 - 8.03 (m, 2H), 7.18 (s, 1H), 6.87 (dd, J = 17.2, 11.1 Hz, 1H), 6.69 (s, 1H), 5.90 (d, J = 17.3 Hz, 1H), 5.54 (d, J = 11.1 Hz, 1H), 3.76 (s, 3H), 3.65 - 3.30 (m, 11H), 3.27 - 3.20 (m, 3H), 3.11 (s, 3H), 3.00 - 2.92 (m, 2H), 2.90 (s, 3H), 2.73 - 2.60 (m, 2H), 2.19 - 2.06 (m, 2H), 1.80 - 1.67 (m,2H), 1.30 - 1.12 (m, 3H); MS (ESI) m/z: 687 [M + H]$^+$. |

-continued

| No. | Structure | $^1$H NMR and/or MS data |
| --- | --- | --- |
| II-2 | 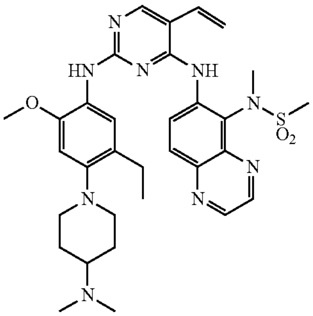 | $^1$H NMR (600 MHz, DMSO-$d_6$) δ 10.02 (s, 1H), 9.86 – 9.75 (m, 1H), 9.58 – 9.41 (m, 1H), 9.10 – 8.99 (m,2H), 8.41 – 8.27 (m, 1H), 8.12 – 8.02 (m, 1H), 7.22 (s, 1H), 6.86 (dd, J = 17.2, 11.0 Hz, 1H), 6.70 (s, 1H), 5.89 (d, J = 17.2 Hz, 1H), 5.52 (d, J = 11.0 Hz, 1H), 3.77 (s, 3H), 3.33 – 3.20 (m, 6H), 3.12 (s, 3H), 2.99 – 2.90 (m, 2H), 2.86 – 2.78 (m,6H), 2.71 – 2.60 (m,2H), 2.11 – 2.02 (m, 2H), 1.79 – 1.65 (m, 2H), 0.70 – 0.41 (m, 3H); MS (ESI) m/z: 632 [M + H]$^+$. |
| II-3 | 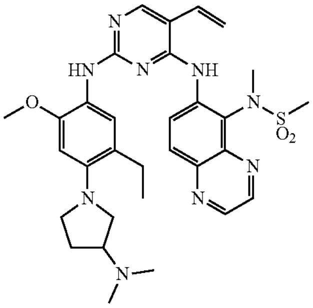 | $^1$H NMR (600 MHz, DMSO-$d_6$) δ 10.61 (s, 1H), 9.86 (s, 1H), 9.68 (s, 1H), 9.09 – 8.99 (m, 2H), 8.42 – 8.26 (m, 1H), 8.11 – 8.02 (m, 1H), 7.16 (d, J = 10.7 Hz, 1H), 6.91 – 6.83 (m, 1H), 6.70 – 6.63 (m, 1H), 5.90 (d, J = 17.3 Hz, 1H), 5.53 (d, J = 11.1 Hz, 1H), 4.00 – 3.91 (m, 1H), 3.77 (s, 3H), 3.45 (q, J = 7.0 Hz, 2H), 3.34 – 3.21 (m, 5H), 3.12 (s, 3H), 3.04 – 2.95 (m, 1H), 2.91 – 2.77 (m, 7H), 2.36 – 2.27 (m, 1H), 2.18 – 2.06 (m, 1H), 1.06 (t, J = 7.0 Hz, 3H); MS (ESI) m/z: 618 [M + H]$^+$. |
| II-4 | 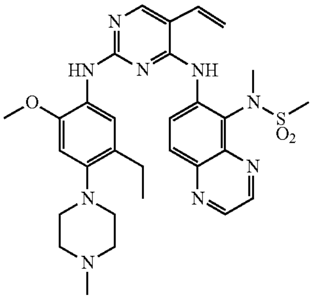 | $^1$H NMR (600 MHz, DMSO-$d_6$) δ 10.18 (s, 1H), 9.71 (s, 1H), 9.37 (s, 1H), 9.03 (d, J =1.9 Hz, 1H), 9.03 (d, J = 1.9 Hz, 1H), 8.35 (s, 1H), 8.08 (d, J = 9.1 Hz, 1H), 7.31 (s, 1H), 6.86 (dd, J = 17.3, 11.1 Hz, 1H), 6.71 (s, 1H), 5.89 (d, J = 17.4 Hz, 1H), 5.51 (d, J = 11.2 Hz, 1H), 3.79 (s, 3H), 3.57 – 3.44 (m, 2H), 3.27 (s, 3H), 3.21 – 3.16 (m, 2H), 3.13 (s, 3H), 3.05 – 2.93 (m, 4H), 2.88 (s, 3H), 2.27 – 1.80 (m, 2H), 0.71 – 0.41 (m, 3H). MS (ESI) m/z: 604 [M + H]$^+$. |
| II-5 | 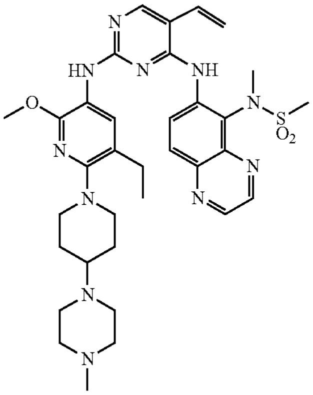 | $^1$H NMR (600 MHz, DMSO-$d_6$) δ 9.82 (s, 1H), 9.55 (s, 1H), 9.04 (d, J = 2.0 Hz, 1H), 9.04 – 9.02 (m, 1H), 8.33 (s, 1H), 8.21 – 8.11 (m, 1H), 8.10 – 8.03 (m, 1H), 7.50 (s, 1H), 6.86 (dd, J = 17.2, 11.1 Hz, 1H), 5.89 (d, J = 17.3 Hz, 1H), 5.52 (d, J = 11.2 Hz, 1H), 3.84 – 3.81 (m, 3H), 3.78 – 3.30 (m, 13H), 3.27 (s, 3H), 3.12 (s, 3H), 2.88 (s, 3H), 2.82 – 2.67 (m, 2H), 2.11 – 2.05 (m, 2H), 1.78 – 1.58 (m, 2H), 0.76 – 0.16 (m, 3H). MS (ESI) m/z: 688 [M + H]$^+$. |

-continued

| No. | Structure | $^1$H NMR and/or MS data |
|---|---|---|
| II-6 | 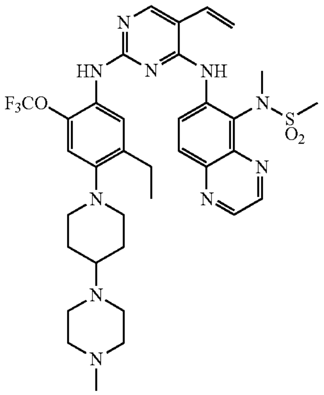 | $^1$H NMR (600 MHz, DMSO-$d_6$) δ 10.09 (s, 1H), 9.71 (s, 1H), 9.08 - 8.96 (m, 2H), 8.37 (s, 1H), 8.22 - 8.13 (m, 1H), 8.04 - 7.97 (m, 1H), 7.31 (s, 1H), 6.95 (s, 1H), 6.85 (dd, J = 17.2, 11.1 Hz, 1H), 5.90 (d, J = 17.4 Hz, 1H), 5.51 (d, J = 11.1 Hz, 1H), 3.91 - 3.31 (m, 9H), 3.20 (s, 3H), 3.12 (s, 3H), 3.03 - 2.96 (m, 1H), 2.91 (s, 3H), 2.88 - 2.81 (m, 1H), 2.71 - 2.61 (m, 1H), 2.60 - 2.53 (m, 1H), 2.33 - 2.23 (m, 1H), 2.20 - 2.10 (m, 2H), 2.07 - 1.93 (m, 1H), 1.82 - 1.70 (m, 2H), 0.74 (s, 3H); MS (ESI) m/z: 741 $[M + H]^+$. |
| II-7 | 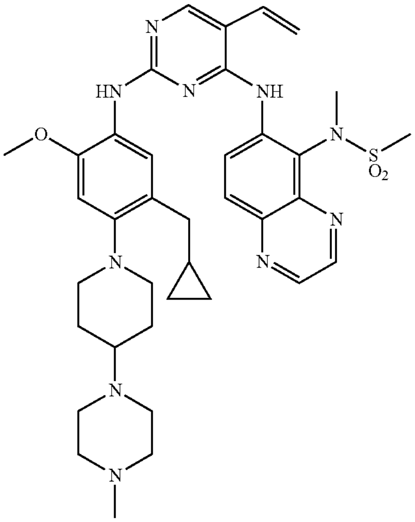 | $^1$H NMR (600 MHz, DMSO-$d_6$) δ 9.81 (s, 1H), 9.61 (s, 1H), 9.07 - 9.01 (m, 2H), 8.39 - 8.27 (m, 1H), 8.23 - 8.14 (m, 1H), 8.05 (s, 1H), 7.32 (s, 1H), 6.85 (dd, J = 17.2, 11.2 Hz, 1H), 6.71 (s, 1H), 5.89 (d, J = 17.3 Hz, 1H), 5.53 (d, J = 11.1 Hz, 1H), 3.76 (s, 3H), 3.67 - 3.21 (m, 11H), 3.17 (s, 3H), 3.10 (s, 3H), 2.99 - 2.84 (m, 5H), 2.72 - 2.57 (m, 2H), 2.15 - 2.05 (m, 2H), 1.75 - 1.60 (m, 2H), 0.13 (s, 2H), -0.16 - -0.35 (m, 3H). MS (ESI) m/z: 713 [M + H]+. |
| II-8 | 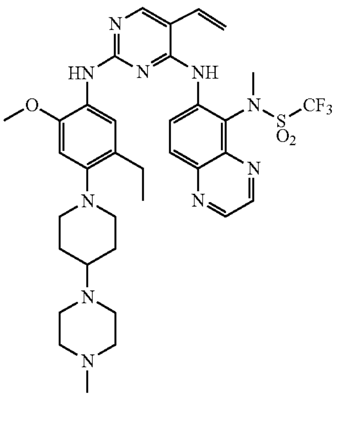 | $^1$H NMR (600 MHz, DMSO-$d_6$) δ 10.29 (s, 1H), 9.39 (s, 1H), 9.12 (d, J = 1.9 Hz, 1H), 9.11 (d, J = 1.9 Hz, 1H), 8.39 (s, 1H), 8.23 (d, J = 9.0 Hz, 1H), 8.02 (d, J = 9.1 Hz, 1H), 7.13 (s, 1H), 6.93 (dd, J = 17.2, 11.1 Hz, 1H), 6.63 (s, 1H), 5.91 (d, J = 17.2 Hz, 1H), 5.52 (d, J = 11.2 Hz, 1H), 3.74 (s, 3H), 3.71 - 3.54 (m, 8H), 3.52 - 3.37 (m, 3H), 3.31 - 3.18 (m, 2H), 2.87 (s, 3H), 2.86 - 2.79 (m, 2H), 2.66 - 2.55 (m, 1H), 2.12 - 2.00 (m, 4H), 1.74 - 1.60 (m, 2H), 0.43 - 0.21 (m, 3H). MS (ESI) m/z: 741 [M + H]+. |

-continued

| No. | Structure | $^1H$ NMR and/or MS data |
|---|---|---|
| II-9 | 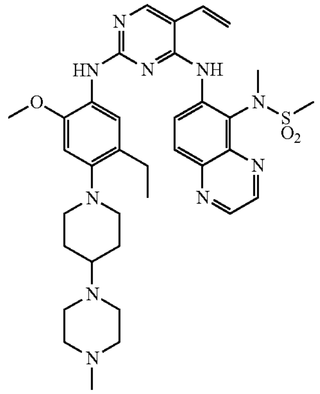 | $^1H$ NMR (600 MHz, DMSO-$d_6$) δ 9.96 (s, 1H), 9.70 (s, 1H), 9.06 – 9.04 (m, 2H), 8.43 – 8.31 (m, 1H), 8.16 – 8.07 (m, 2H), 7.18 (s, 1H), 6.88 (dd, J = 17.2, 11.1 Hz, 1H), 6.69 (s, 1H), 5.92 (d, J = 17.2 Hz, 1H), 5.54 (d, J = 11.2 Hz, 1H), 3.76 (s, 3H), 3.71 – 3.31 (m, 12H), 3.26 (s, 3H), 3.17 – 3.12 (m, 1H), 2.98 – 2.89 (m, 5H), 2.72 – 2.60 (m, 2H), 2.18 – 2.04 (m, 2H), 1.80 – 1.67 (m, 2H), 1.24 (t, J = 7.3 Hz, 3H), 0.64 – 0.40 (m, 3H). MS (ESI) m/z: 701 $[M + H]^+$. |
| II-10 | 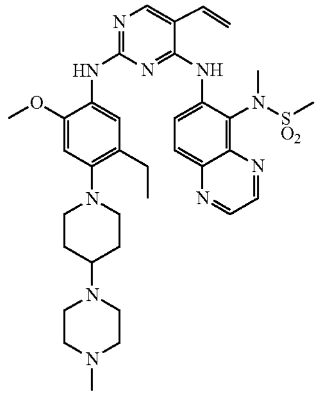 | $^1H$ NMR (600 MHz, DMSO-$d_6$) δ 9.93 (s, 1H), 9.66 (s, 1H), 9.07 (d, J = 1.8 Hz, 1H), 9.05 (d, J = 1.8 Hz, 1H), 8.36 (s, 1H), 8.15 – 8.06 (m, 2H), 7.18 (s, 1H), 6.88 (dd, J = 17.2, 11.1 Hz, 1H), 6.67 (s, 1H), 5.92 (d, J = 17.3 Hz, 1H), 5.54 (d, J = 11.2 Hz, 1H), 3.76 (s, 3H), 3.70 – 3.52 (m, 8H), 3.43 (hept, J = 6.4 Hz, 1H), 3.36 – 3.31 (m, 1H), 3.27 (s, 3H), 2.98 – 2.85 (m, 5H), 2.69 – 2.59 (m, 2H), 2.17 – 2.09 (m, 4H), 1.82 – 1.67 (m, 2H), 1.41 (d, J =6.7 Hz, 3H), 1.17 (d, J = 6.8 Hz, 3H), 0.62 – 0.37 (m, 3H). MS (ESI) m/z: 715 $[M + H]^+$. |
| II-11 | 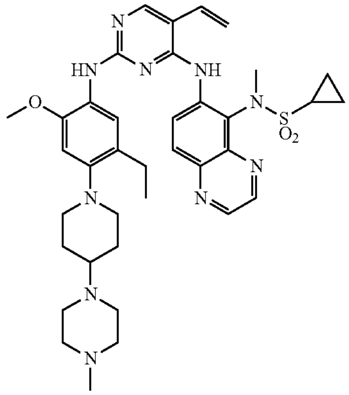 | $^1H$ NMR (600 MHz, DMSO-$d_6$) δ 9.89 (s, 1H), 9.62 (s, 1H), 9.05 – 9.02 (m, 2H), 8.38 – 8.28 (m, 1H), 8.14 (s, 1H), 8.11 – 8.07 (m, 1H), 7.19 (s, 1H), 6.86 (dd, J = 17.2, 11.2 Hz, 1H), 6.70 (s, 1H), 5.90 (d, J = 17.4 Hz, 1H), 5.52 (d, J = 11.2 Hz, 1H), 3.77 (s, 3H), 3.71 – 3.35 (m, 9H), 3.28 (s, 3H), 2.90 (s, 5H), 2.83 – 2.77 (m, 1H), 2.70 – 2.60 (m, 2H), 2.15 – 2.07 (m, 4H), 1.78 – 1.68 (m, 2H), 1.12 – 1.01 (m, 2H), 0.76 – 0.69 (m, 1H), 0.64 – 0.39 (m, 4H). MS (ESI) m/z: 713 $[M + H]^+$. |
| II-12 | 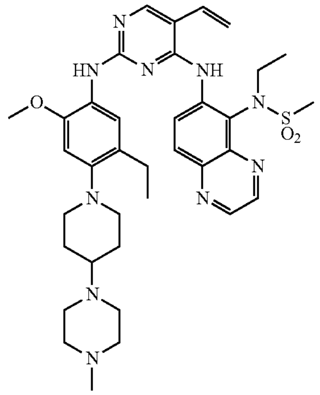 | $^1H$ NMR (600 MHz, DMSO-$d_6$) δ 9.72 (s, 1H), 9.15 (s, 1H), 9.04 – 9.02 (m, 2H), 8.50 – 8.35 (m, 2H), 8.04 (d, J = 9.2 Hz, 1H), 7.33 (s, 1H), 6.79 (s, 1H), 6.75 (dd, J = 17.3, 11.2 Hz, 1H), 5.92 (d, J = 17.4 Hz, 1H), 5.60 (d, J = 11.1 Hz, 1H), 4.03 – 3.93 (m, 1H), 3.81 (s, 3H), 3.70 – 3.45 (m, 9H), 3.42 – 3.31 (m, 1H), 3.21 (s, 3H), 3.11 – 3.00 (m, 2H), 2.93 (s, 3H), 2.79 – 2.70 (m, 2H), 2.32 – 2.21 (m,2H), 2.20 – 2.13 (m,2H), 1.85 – 1.75 (m, 2H), 0.90 (t, J = 7.2 Hz, 3H), 0.77 – 0.62 (m, 3H). MS (ESI) m/z: 701 $[M + H]^+$. |

-continued
| No. | Structure | $^1$H NMR and/or MS data |
|---|---|---|
| II-13 | 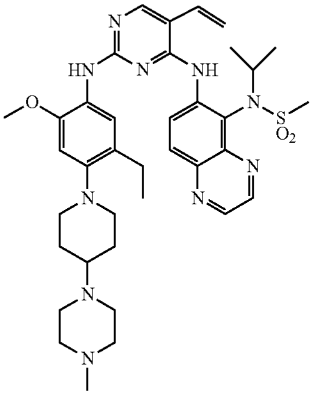 | MS (ESI) m/z: 715 [M + H]$^+$. |
| II-14 | 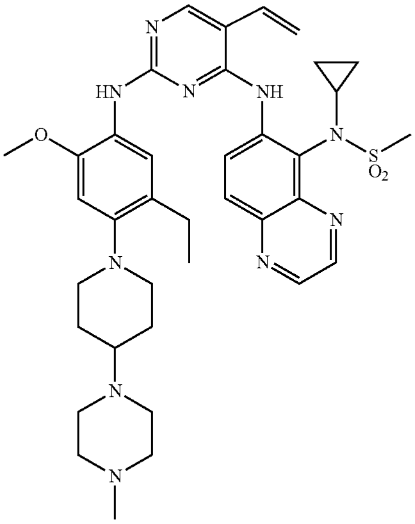 | $^1$H NMR (600 MHz, DMSO-$d_6$) δ 9.65 (s, 1H), 9.04 (d, J = 1.9 Hz, 1H), 9.03 (d, J = 1.8 Hz, 1H), 8.34 (s, 1H), 8.03 (d, J = 9.1 Hz, 1H), 7.30 (s, 1H), 6.79 (s, 1H), 6.74 (dd, J = 17.3, 11.1 Hz, 1H), 5.88 (d, J = 17.4 Hz, 1H), 5.58 (d, J = 11.2 Hz, 1H), 3.81 (s, 3H), 3.73 - 3.44 (m, 9H), 3.41 - 3.35 (m, 2H), 3.33 (s, 3H), 3.10 - 2.99 (m, 2H), 2.92 (s, 3H), 2.80 - 2.68 (m, 2H), 2.26 - 2.10 (m, 3H), 1.84 - 1.75 (m, 2H), 0.90 - 0.78 (m, 2H), 0.72 - 0.54 (m, 3H), 0.44 - 0.31 (m, 2H). MS (ESI) m/z: 713 [M + H]$^+$. |
| II-15 | 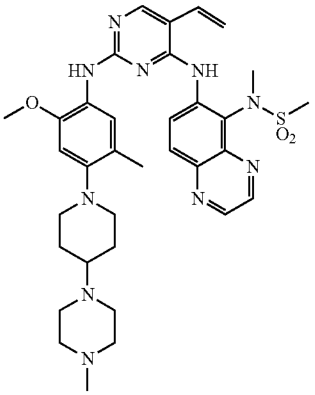 | $^1$H NMR (600 MHz, DMSO-$d_6$) δ 9.99 (s, 1H), 9.77 (s, 1H), 9.11 - 8.96 (m, 2H), 8.44 - 8.26 (m, 1H), 8.20 - 8.05 (m, 2H), 7.10 (s, 1H), 6.87 (dd, J = 17.2, 11.1 Hz, 1H), 6.63 (s, 1H), 5.91 (d, J = 17.3 Hz, 1H), 5.53 (d, J = 11.1 Hz, 1H), 3.76 (s, 3H), 3.67 - 3.35 (m, 9H), 3.29 - 3.20 (m, 3H), 3.12 (s, 3H), 3.08 - 2.98 (m, 2H), 2.92 (s, 3H), 2.66 - 2.58 (m, 2H), 2.55 (s, 3H), 2.20 - 2.09 (m, 2H), 1.83 - 1.69 (m, 2H); MS (ESI) m/z: 673 [M + H]$^+$. |

-continued

| No. | Structure | $^1$H NMR and/or MS data |
| --- | --- | --- |
| II-16 | 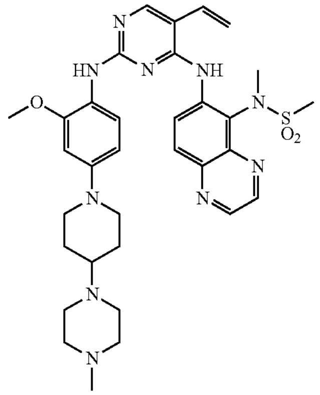 | $^1$H NMR (600 MHz, DMSO-$d_6$) δ 9.81 (s, 1H), 9.76 (s, 1H), 9.07 – 8.99 (m, 2H), 8.29 (d, J = 8.9 Hz, 2H), 8.14 (d, J = 9.1 Hz, 1H), 7.12 (d, J = 8.7 Hz, 1H), 6.83 (dd, J = 17.2, 11.2 Hz, 1H), 6.67 (s, 1H), 6.42 – 6.12 (m, 1H), 5.90 (d, J = 17.3 Hz, 1H), 5.55 (d, J = 11.2 Hz, 1H), 3.89 – 3.79 (m, 2H), 3.77 (s, 3H), 3.71 – 3.33 (m, 9H), 3.29 (s, 3H), 3.14 (s, 3H), 2.90 (s, 3H), 2.75 – 2.65 (m, 2H), 2.22 – 2.09 (m, 2H), 1.79 – 1.63 (m, 2H). MS (ESI) m/z: 659 [M + H]+. |
| II-17 | 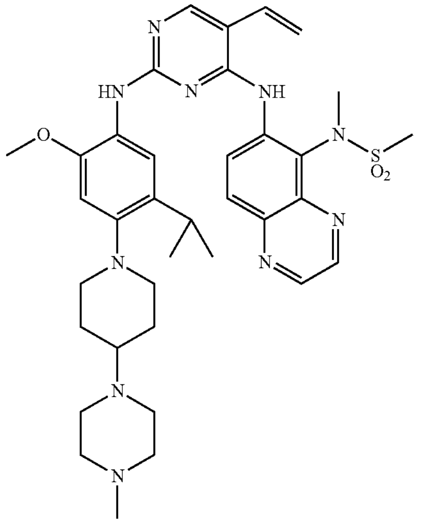 | $^1$H NMR (600 MHz, DMSO-$d_6$) δ 9.87 – 9.77 (m, 2H), 9.02 – 9.00 (m, 2H), 8.41 – 8.24 (m, 1H), 8.18 – 8.01 (m, 2H), 7.17 (s, 1H), 6.85 (dd, J = 17.3, 11.1 Hz, 1H), 6.70 (s, 1H), 5.91 (d, J = 17.3 Hz, 1H), 5.53 (d, J = 11.2 Hz, 1H), 3.73 (s, 3H), 3.67 – 3.30 (m, 9H), 3.22 (s, 3H), 3.10 (s, 3H), 3.04 – 2.96 (m, 1H), 2.91 (s, 3H), 2.87 – 2.79 (m, 2H), 2.72 – 2.61 (m, 2H), 2.16 – 2.08 (m, 2H), 1.80 – 1.68 (m, 2H), 0.90 – 0.67 (m, 3H), 0.65 – 0.38 (m, 3H). MS (ESI) m/z: 701 $[M + H]^+$. |
| II-18 | 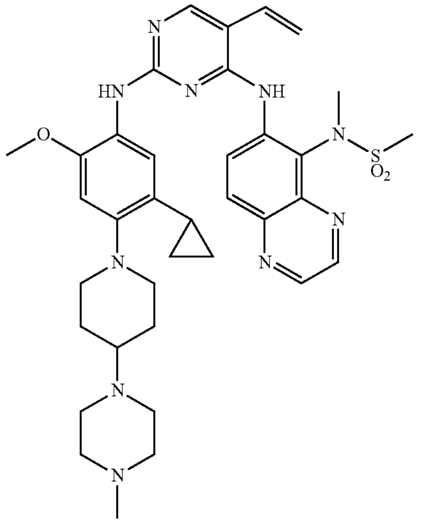 | $^1$H NMR (600 MHz, DMSO-$d_6$) δ 9.78 – 9.67 (m, 2H), 9.02 (d, J = 1.9 Hz, 1H), 9.01 (d, J = 1.8 Hz, 1H), 8.32 – 8.14 (m, 2H), 8.04 (s, 1H), 6.83 (dd, J = 17.3, 11.1 Hz, 1H), 6.73 (s, 1H), 6.64 (s, 1H), 5.89 (d, J = 17.4 Hz, 1H), 5.53 (d, J = 11.2 Hz, 1H), 3.75 (s, 3H), 3.69 – 3.41 (m, 8H), 3.38 – 3.31 (m, 1H), 3.28 – 3.19 (m, 5H), 3.12 (s, 3H), 2.90 (s, 3H), 2.71 – 2.59 (m, 2H), 2.17 – 2.08 (m, 2H), 1.83 – 1.71 (m, 3H), 0.68 – 0.05 (m, 4H). MS (ESI) m/z: 699 $[M + H]^+$. |

-continued

| No. | Structure | $^1$H NMR and/or MS data |
| --- | --- | --- |
| II-19 | 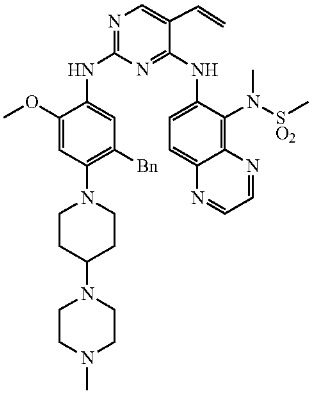 | $^1$H NMR (600 MHz, DMSO-$d_6$) δ 9.86 (s, 1H), 9.80 (s, 1H), 8.99 - 8.93 (m, 2H), 8.41 - 8.28 (m, 1H), 8.17 (s, 1H), 8.05 (d, J = 8.8 Hz, 1H), 7.19 (s, 1H), 7.16 - 7.04 (m, 3H), 6.91 - 6.82 (m, 3H), 6.77 (s, 1H), 5.92 (d, J = 17.4 Hz, 1H), 5.54 (d, J = 11.2 Hz, 1H), 3.76 (s, 3H), 3.69 - 3.39 (m, 8H), 3.37 - 3.30 (m, 1H), 3.26 - 3.20 (m, 5H), 3.11 (s, 3H), 2.92 (s, 3H), 2.85 - 2.73 (m, 2H), 2.69 - 2.59 (m, 2H), 2.14 - 2.03 (m, 2H), 1.78 - 1.65 (m, 2H). MS (ESI) m/z: 749 $[M + H]^+$. |
| II-20 | 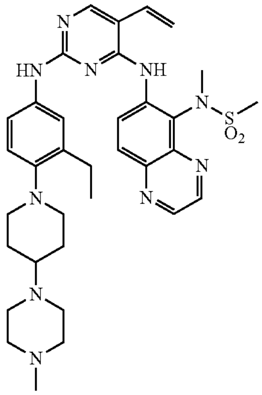 | $^1$H NMR (600 MHz, DMSO-$d_6$) δ 10.52 (s, 1H), 9.67 (s, 1H), 9.07 - 9.01 (m, 2H), 8.39 (s, 1H), 8.36 - 8.28 (m, 1H), 8.15 (d, J = 9.1 Hz, 1H), 7.24 (s, 1H), 7.14 - 7.04 (m, 1H), 6.87 (dd, J = 17.3, 11.2 Hz, 1H), 6.84 - 6.78 (m, 1H), 5.91 (d, J = 17.3 Hz, 1H), 5.50 (d, J = 11.1 Hz, 1H), 3.85 - 3.42 (m, 8H), 3.40 - 3.31 (m, 1H), 3.25 (s, 3H), 3.14 (s, 3H), 2.99 - 2.93 (m, 2H), 2.91 (s, 3H), 2.64 - 2.57 (m, 2H), 2.32 - 2.21 (m, 1H), 2.16 - 2.05 (m, 3H), 1.79 - 1.70 (m, 2H), 0.79 - 0.65 (m, 3H). MS (ESI) m/z: 657 $[M + H]^+$. |
| II-21 | 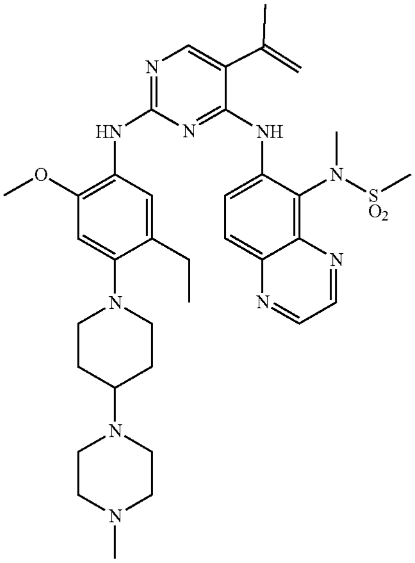 | $^1$H NMR (600 MHz, DMSO-$d_6$) δ 9.56 (s, 1H), 9.31 (s, 1H), 9.01 (d, J = 1.9 Hz, 1H), 8.98 (d, J = 1.9 Hz, 1H), 8.51 (s, 1H), 8.13 - 8.04 (m, 1H), 8.03 - 7.94 (m, 1H), 7.29 (s, 1H), 6.79 (s, 1H), 5.55 (s, 1H), 5.41 (s, 1H), 3.79 (s, 3H), 3.71 - 3.39 (m, 9H), 3.31 (s, 3H), 3.17 (s, 3H), 3.10 - 2.95 (m, 2H), 2.85 (s, 3H), 2.79 - 2.65 (m, 2H), 2.39 - 2.19 (m, 2H), 2.14 (s, 3H), 2.11 - 2.04 (m, 2H), 1.78 - 1.66 (m, 2H), 0.89 - 0.70 (m, 3H). MS (ESI) m/z: 701 $[M + H]^+$. |

-continued

| No. | Structure | $^1H$ NMR and/or MS data |
| --- | --- | --- |
| II-22 | 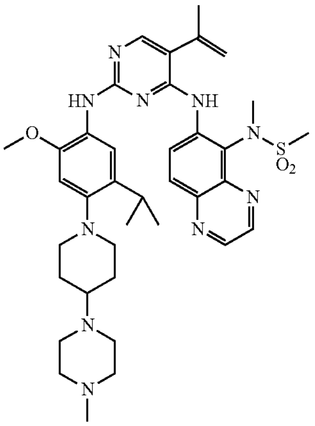 | $^1H$ NMR (600 MHz, DMSO-$d_6$) δ 10.03 (s, 1H), 9.37 (s, 1H), 8.98 (d, J = 1.8 Hz, 1H), 8.96 (d, J = 1.9 Hz, 1H), 8.49 - 8.24 (m, 1H), 8.15 - 8.03 (m, 1H), 7.92 (s, 1H), 7.21 (s, 1H), 6.81 (s, 1H), 5.55 (s, 1H), 5.43 (s, 1H), 3.75 (s, 3H), 3.68 - 3.41 (m, 8H), 3.39 - 3.33 (m, 1H), 3.31 - 3.26 (m, 5H), 3.15 (s, 3H), 3.08 - 2.96 (m, 1H), 2.90 (s, 3H), 2.81 - 2.73 (m, 2H), 2.19 - 2.14 (m, 2H), 2.13 (s, 3H), 1.85 - 1.74 (m, 2H), 1.01 - 0.68 (m, 6H). MS (ESI) m/z: 715 $[M + H]^+$. |
| II-23 | 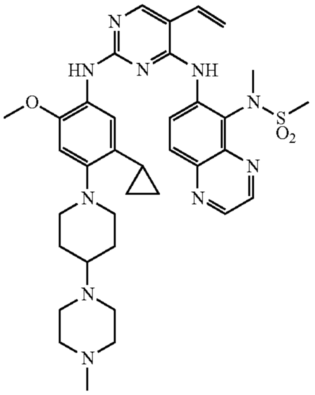 | $^1H$ NMR (600 MHz, DMSO-$d_6$) δ 9.55 (s, 1H), 9.23 (s, 1H), 9.00 (d, J = 1.8 Hz, 1H), 8.96 (d, J = 1.8 Hz, 1H), 8.55 (s, 1H), 8.08 - 8.01 (m, 1H), 7.98 - 7.85 (m, 1H), 6.84 (s, 1H), 6.73 (s, 1H), 5.55 (s, 1H), 5.40 (s, 1H), 3.78 (s, 3H), 3.73 - 3.44 (m, 8H), 3.37 - 3.35 (m, 1H), 3.32 (s, 3H), 3.23 - 3.18 (m, 2H), 3.17 (s, 3H), 2.84 (s, 3H), 2.77 - 2.66 (m, 2H), 2.13 (s, 3H), 2.11 - 2.08 (m, 2H), 2.00 - 1.96 (m, 1H), 1.85 - 1.72 (m, 2H), 0.79 - 0.56 (m, 2H), 0.45 - 0.23 (m, 2H). MS (ESI) m/z: 713 $[M + H]^+$. |
| II-24 | 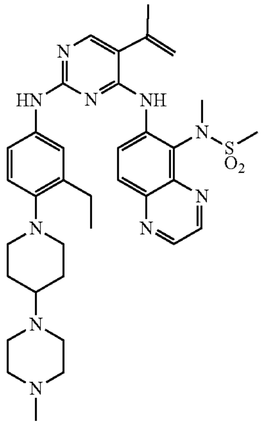 | $^1H$ NMR (600 MHz, DMSO-$d_6$) δ 9.28 (s, 1H), 9.25 (s, 1H), 8.94 (d, J = 1.9 Hz, 1H), 8.88 (d, J = 1.9 Hz, 1H), 8.60 (s, 1H), 8.13 - 8.11 (m, 1H), 8.03 (d, J = 9.4 Hz, 1H), 7.49 - 7.45 (m, 2H), 6.98 (d, J = 8.5 Hz, 1H), 5.47 (s, 1H), 5.29 (s, 1H), 3.34 (s, 3H), 3.22 (s, 3H), 2.97 - 2.90 (m, 2H), 2.62 - 2.52 (m, 8H), 2.46 - 2.35 (m, 4H), 2.32 - 2.26 (m, 1H), 2.20 (s, 3H), 2.12 (s, 3H), 1.85 - 1.79 (m, 2H), 1.59 - 1.49 (m, 2H), 1.07 - 1.01 (m, 3H). MS (ESI) m/z: 671 $[M + H]^+$. |

-continued

| No. | Structure | $^1H$ NMR and/or MS data |
|---|---|---|
| II-25 | 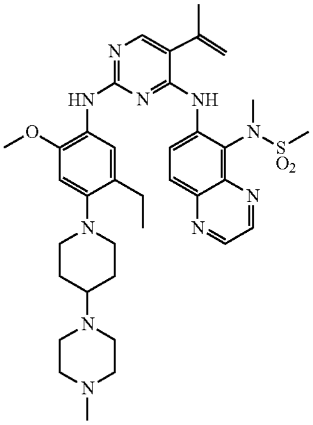 | $^1H$ NMR (600 MHz, DMSO-$d_6$) δ 9.77 (s, 1H), 9.39 (s, 1H), 9.02 (d, J = 1.8 Hz, 1H), 9.00 (d, J = 1.8 Hz, 1H), 8.63 - 8.30 (m, 1H), 8.12 - 8.07 (m, 1H), 8.03 - 7.95 (m, 1H), 7.60 (s, 1H), 5.56 (s, 1H), 5.43 (s, 1H), 3.85 (s, 3H), 3.73 (d, J = 99.4 Hz, 9H), 3.43 (s, 2H), 3.32 (s, 3H), 3.17 (s, 3H), 2.89 (s, 3H), 2.86 - 2.75 (m, 2H), 2.35 - 2.24 (m, 2H), 2.15 (s, 3H), 2.13 - 2.09 (m, 2H), 1.84 - 1.71 (m, 2H), 0.85 - 0.71 (m, 3H). MS (ESI) m/z: 702 [M + H]$^+$. |
| II-26 | 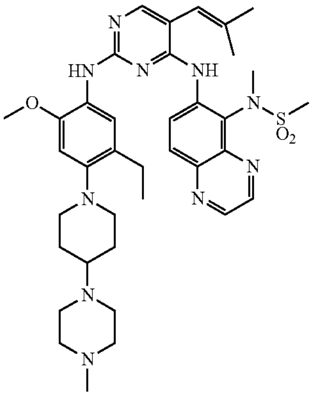 | $^1H$ NMR (600 MHz, DMSO-$d_6$) δ 9.96 (s, 1H), 9.33 (s, 1H), 9.03 (d, J = 1.8 Hz, 1H), 9.01 (d, J = 1.8 Hz, 1H), 8.60 - 8.25 (m, 1H), 8.10 - 8.00 (m, 1H), 7.99 - 7.85 (m, 1H), 7.27 (s, 1H), 6.80 (s, 1H), 5.99 (s, 1H), 3.80 (s, 3H), 3.76 - 3.45 (m, 8H), 3.44 - 3.37 (m, 1H), 3.30 (s, 3H), 3.16 (s, 3H), 3.13 - 3.00 (m, 2H), 2.92 (s, 3H), 2.81 - 2.69 (m, 2H), 2.40 - 2.25 (m, 2H), 2.21 - 2.12 (m, 2H), 1.98 (s, 3H), 1.85 - 1.80 (m, 2H), 1.79 (s, 3H), 0.90 - 0.59 (m, 3H). MS (ESI) m/z: 715 [M + H]$^+$. |
| II-27 | 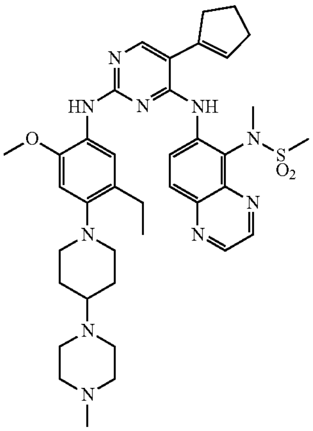 | $^1H$ NMR (600 MHz, DMSO-$d_6$) δ 9.93 (s, 1H), 9.35 (s, 1H), 9.01 (d, J = 1.9 Hz, 1H), 8.99 (d, J = 1.8 Hz, 1H), 8.73 - 8.42 (m, 1H), 8.17 - 8.06 (m, 1H), 8.02 - 7.92 (m, 1H), 7.29 (s, 1H), 6.83 (s, 1H), 6.34 (t, J = 2.2 Hz, 1H), 3.80 (s, 3H), 3.72 - 3.40 (m, 9H), 3.34 (s, 3H), 3.19 (s, 3H), 3.14 - 3.05 (m, 2H), 2.90 (s, 3H), 2.82 - 2.73 (m, 3H), 2.70 - 2.57 (m, 3H), 2.36 (d, J = 34.5 Hz, 2H), 2.22 - 2.12 (m, 2H), 2.01 (q, J =7.6 Hz, 2H), 1.88 - 1.73 (m, 2H), 0.99 - 0.78 (m, 3H). MS (ESI) m/z: 727 [M + H]$^+$. |

-continued

| No. | Structure | $^1$H NMR and/or MS data |
|---|---|---|
| II-28 | 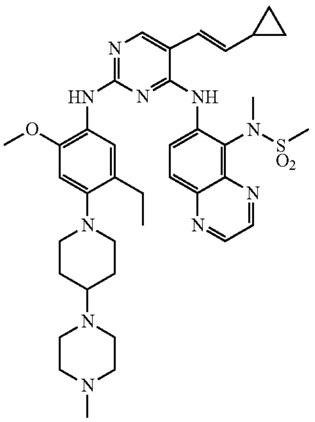 | $^1$H NMR (600 MHz, DMSO-$d_6$) δ 9.89 (s, 1H), 9.63 (s, 1H), 9.09 – 9.02 (m, 2H), 8.23 – 8.03 (m, 3H), 7.17 (s, 1H), 6.69 (s, 1H), 6.53 (d, J = 15.5 Hz, 1H), 5.92 (dd, J = 15.5, 9.2 Hz, 1H), 3.76 (s, 3H), 3.70 – 3.39 (m, 8H), 3.38 – 3.32 (m, 1H), 3.25 (s, 3H), 3.13 (s, 3H), 3.00 – 2.91 (m, 2H), 2.91 (s, 3H), 2.72 – 2.61 (m, 2H), 2.19 – 2.02 (m, 4H), 1.79 – 1.69 (m, 2H), 1.70 – 1.58 (m, 1H), 0.95 – 0.83 (m, 2H), 0.67 – 0.40 (m, 5H). MS (ESI) m/z: 727 [M + H]$^+$. |
| II-29 | 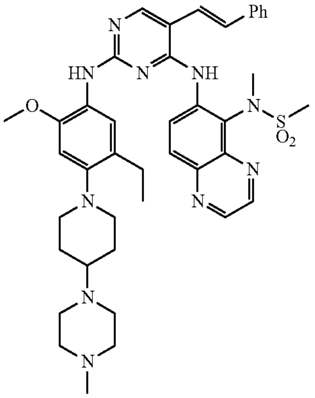 | $^1$H NMR (600 MHz, DMSO-$d_6$) δ 10.07 (s, 1H), 9.54 (s, 1H), 9.11 – 9.01 (m, 2H), 8.50 (s, 1H), 8.26 – 8.10 (m, 2H), 7.71 – 7.61 (m, 2H), 7.48 – 7.40 (m, 2H), 7.38 – 7.26 (m, 3H), 7.20 (s, 1H), 6.69 (s, 1H), 3.77 (s, 3H), 3.70 – 3.28 (m, 9H), 3.23 (s, 3H), 3.13 (s, 3H), 2.97 – 2.90 (m, 2H), 2.89 (s, 3H), 2.73 – 2.58 (m, 2H), 2.25 – 2.01 (m, 5H), 1.79 – 1.64 (m, 1H), 0.74 – 0.46 (m, 3H). MS (ESI) m/z: 763 [M + H]$^+$. |
| II-30 | 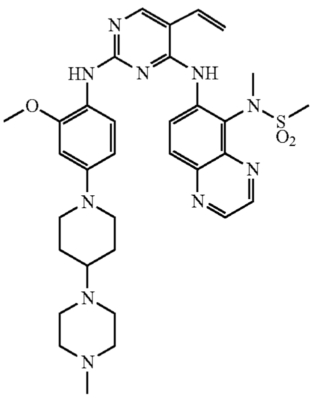 | $^1$H NMR (600 MHz, DMSO-$d_6$) δ 9.88 (s, 1H), 9.76 – 9.65 (m, 2H), 9.06 (d, J = 1.9 Hz, 1H), 9.01 (d, J = 1.8 Hz, 1H), 8.45 – 8.16 (m, 2H), 8.04 (d, J = 9.2 Hz, 1H), 7.21 (d, J = 8.7 Hz, 1H), 6.78 (dd, J = 17.3, 11.1 Hz, 1H), 6.73 – 6.66 (m, 1H), 6.34 – 6.17 (m, 1H), 5.91 (d, J = 17.2 Hz, 1H), 5.56 (d, J = 11.2 Hz, 1H), 3.88 – 3.81 (m, 2H), 3.79 (s, 3H), 3.71 – 3.21 (m, 9H), 3.08 (s, 3H), 2.89 (s, 3H), 2.78 – 2.69 (m, 2H), 2.17 – 2.09 (m, 2H), 1.75 – 1.63 (m, 2H). MS (ESI) m/z: 645 [M + H]$^+$. |

-continued

| No. | Structure | $^1H$ NMR and/or MS data |
|---|---|---|
| II-31 | 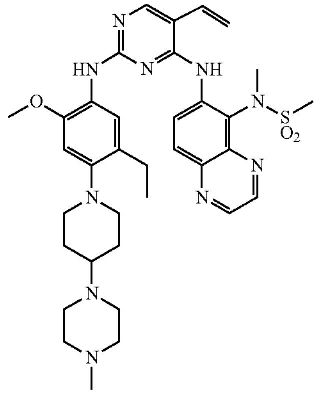 | $^1H$ NMR (600 MHz, DMSO-$d_6$) δ 9.87 (s, 1H), 9.74 (s, 1H), 9.47 (s, 1H), 9.06 (d, J = 1.9 Hz, 1H), 9.01 (d, J = 1.8 Hz, 1H), 8.38 - 8.22 (m, 2H), 8.00 (d, J = 9.2 Hz, 1H), 7.24 (s, 1H), 6.80 (dd, J = 17.2, 11.2 Hz, 1H), 6.69 (s, 1H), 5.90 (d, J = 17.2 Hz, 1H), 5.54 (d, J = 11.2 Hz, 1H), 3.79 (s, 3H), 3.72 - 3.21 (m, 9H), 3.12 - 3.09 (m, 2H), 3.08 (s, 3H), 2.88 (s, 3H), 2.70 - 2.62 (m, 2H), 2.14 - 2.04 (m, 2H), 1.81 - 1.62 (m, 5H). MS (ESI) m/z: 659 $[M + H]^+$. |
| II-32 | 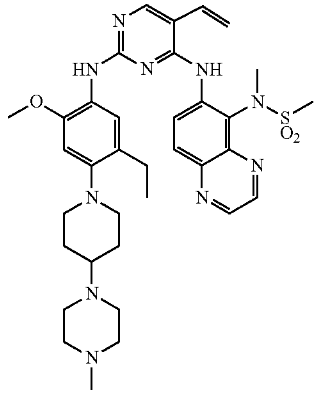 | $^1H$ NMR (600 MHz, DMSO-$d_6$) δ 9.87 (s, 1H), 9.69 (s, 1H), 9.47 (s, 1H), 9.05 (d, J = 1.9 Hz, 1H), 9.01 (d, J = 1.8 Hz, 1H), 8.34 (s, 1H), 8.28 - 8.20 (m, 1H), 7.96 (d, J = 9.1 Hz, 1H), 7.31 (s, 1H), 6.80 (dd, J = 17.3, 11.1 Hz, 1H), 6.76 (s, 1H), 5.90 (d, J = 17.4 Hz, 1H), 5.54 (d, J = 11.1 Hz, 1H), 3.80 (s, 3H), 3.74 - 3.32 (m, 8H), 3.29 - 3.22 (m, 1H), 3.07 (s, 3H), 3.03 - 2.98 (m, 2H), 2.88 (s, 3H), 2.79 - 2.65 (m, 2H), 2.14 - 2.02 (m, 4H), 1.83 - 1.68 (m, 2H), 0.72 - 0.49 (m, 3H). MS (ESI) m/z: 673 $[M + H]^+$. |
| II-33 | 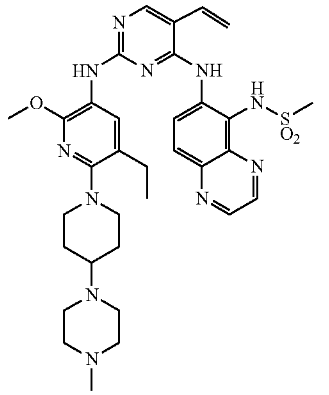 | $^1H$ NMR (600 MHz, DMSO-$d_6$) δ 9.85 (s, 1H), 9.67 (s, 1H), 9.38 (s, 1H), 9.05 (d, J = 1.6 Hz, 1H), 9.01 (d, J = 1.9 Hz, 1H), 8.33 (s, 1H), 8.29 - 8.20 (m, 1H), 7.95 (d, J = 9.0 Hz, 1H), 7.60 (s, 1H), 6.80 (dd, J = 17.2, 11.2 Hz, 1H), 5.89 (d, J = 17.2 Hz, 1H), 5.53 (d, J = 11.2 Hz, 1H), 3.85 (s, 3H), 3.75 - 3.47 (m, 8H), 3.42 - 3.27 (m, 3H), 3.07 (s, 3H), 2.87 (s, 3H), 2.81 - 2.74 (m, 2H), 2.12 - 2.02 (m, 4H), 1.81 - 1.67 (m, 2H), 0.76 - 0.48 (m, 3H). MS (ESI) m/z: 674 $[M + H]^+$. |
| II-34 | 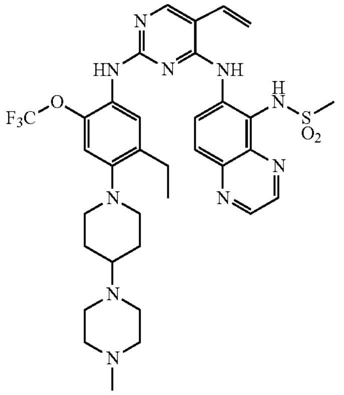 | $^1H$ NMR (600 MHz, DMSO-$d_6$) δ 9.84 (s, 1H), 9.56 (s, 1H), 9.34 (s, 1H), 9.02 (d, J = 1.8 Hz, 1H), 8.96 (d, J = 1.9 Hz, 1H), 8.44 - 8.26 (m, 2H), 7.84 (d, J = 9.3 Hz, 1H), 7.44 (s, 1H), 7.04 (s, 1H), 6.78 (dd, J = 17.3, 11.1 Hz, 1H), 5.87 (d, J = 17.4 Hz, 1H), 5.49 (d, J = 11.2 Hz, 1H), 3.86 - 3.20 (m, 9H), 3.05 (s, 3H), 3.04 - 3.01 (m, 2H), 2.87 (s, 3H), 2.75 - 2.63 (m, 2H), 2.35 (q, J = 7.9 Hz, 2H), 2.13 - 2.04 (m, 2H), 1.80 - 1.70 (m, 2H), 0.82 (t, J = 7.7 Hz, 3H). MS (ESI) m/z: 727 $[M + H]^+$. |

-continued

| No. | Structure | $^1H$ NMR and/or MS data |
|---|---|---|
| II-35 | 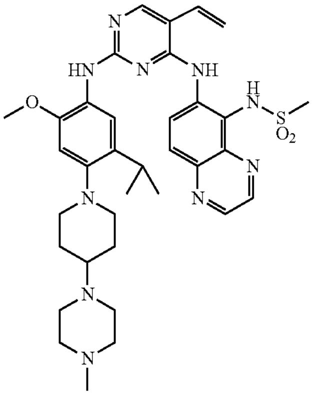 | $^1H$ NMR (600 MHz, DMSO-$d_6$) δ 9.91 (s, 1H), 9.82 - 9.73 (m, 1H), 9.65 (s, 1H), 9.04 (d, J = 1.8 Hz, 1H), 8.99 (d, J = 1.8 Hz, 1H), 8.32 - 8.22 (m, 2H), 7.89 (s, 1H), 7.24 (s, 1H), 6.83 - 6.75 (m, 2H), 5.91 (d, J = 17.3 Hz, 1H), 5.56 (d, J = 11.2 Hz, 1H), 3.78 (s, 3H), 3.75 - 3.24 (m, 10H), 3.06 (s, 3H), 3.03 - 2.98 (m, 2H), 2.90 (s, 3H), 2.81 - 2.73 (m, 2H), 2.18 - 2.11 (m, 2H), 1.82 - 1.72 (m, 2H), 0.87 - 0.66 (m, 6H). MS (ESI) m/z: 687 $[M + H]^+$. |
| II-36 | 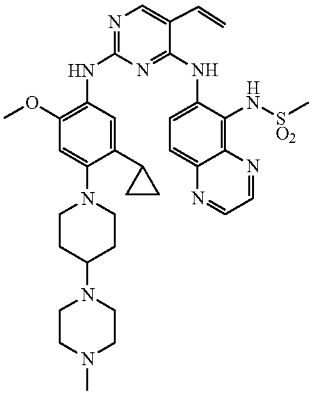 | $^1H$ NMR (600 MHz, DMSO-$d_6$) δ 9.92 (s, 1H), 9.70 - 9.62 (m, 1H), 9.57 (s, 1H), 9.04 (d, J = 1.8 Hz, 1H), 8.98 (d, J = 2.0 Hz, 1H), 8.36 - 8.21 (m, 2H), 7.96 - 7.85 (m, 1H), 6.84 (s, 1H), 6.77 (dd, J = 17.2, 11.2 Hz, 1H), 6.71 (s, 1H), 5.90 (d, J = 17.4 Hz, 1H), 5.55 (d, J = 11.1 Hz, 1H), 3.79 (s, 3H), 3.73 - 3.40 (m, 8H), 3.39 - 3.28 (m, 3H), 3.07 (s, 3H), 2.88 (s, 3H), 2.78 - 2.68 (m, 2H), 2.20 - 2.09 (m, 2H), 1.97 - 1.89 (m, 1H), 1.87 - 1.75 (m, 2H), 0.67 - 0.45 (m, 2H), 0.30 - 0.11 (m, 2H). MS (ESI) m/z: 685 $[M + H]^+$. |
| II-37 | 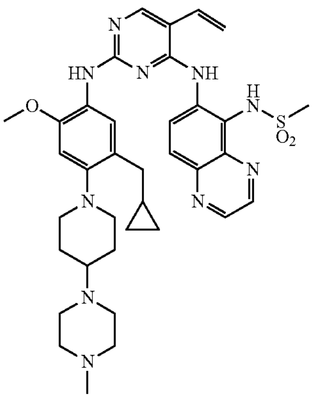 | $^1H$ NMR (600 MHz, DMSO-$d_6$) δ 9.90 (s, 1H), 9.63 (s, 1H), 9.47 - 9.28 (m, 1H), 9.06 (d, J = 1.9 Hz, 1H), 9.00 (d, J = 1.9 Hz, 1H), 8.36 - 8.20 (m, 2H), 7.99 - 7.89 (m, 1H), 7.46 (s, 1H), 6.86 - 6.74 (m, 2H), 5.89 (d, J = 17.3 Hz, 1H), 5.54 (d, J = 11.2 Hz, 1H), 3.80 (s, 3H), 3.75 - 3.19 (m, 9H), 3.06 (s, 3H), 3.04 - 2.96 (m, 2H), 2.86 (s, 3H), 2.75 - 2.65 (m, 2H), 2.13 - 2.04 (m, 4H), 1.75 - 1.65 (m, 2H), 0.53 - 0.35 (m, 1H), 0.22 - 0.06 (m, 2H), - 0.16 - -0.33 (m, 2H). MS (ESI) m/z: 699 $[M + H]^+$. |

-continued

| No. | Structure | $^1$H NMR and/or MS data |
|---|---|---|
| II-38 | 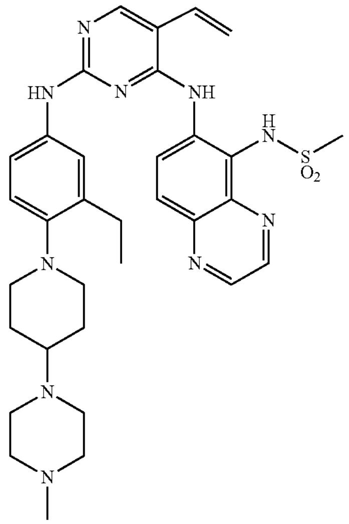 | $^1$H NMR (600 MHz, DMSO-$d_6$) δ 9.85 (s, 1H), 9.73 (s, 1H), 9.18 – 9.06 (m, 1H), 9.03 (d, J = 1.9 Hz, 1H), 9.00 – 8.91 (m, 1H), 8.63 – 8.52 (m, 1H), 8.36 (s, 1H), 8.03 (d, J = 9.2 Hz, 1H), 7.42 – 7.33 (m, 1H), 7.33 – 7.28 (m, 1H), 6.94 – 6.83 (m, 1H), 6.78 (dd, J = 17.3, 11.2 Hz, 1H), 5.84 (d, J = 17.4 Hz, 1H), 5.42 (d, J = 11.2 Hz, 1H), 3.49 – 3.11 (m, 9H), 3.06 (s, 3H), 3.02 – 2.94 (m, 2H), 2.81 (s, 3H), 2.69 – 2.59 (m, 2H), 2.45 – 2.37 (m, 2H), 2.10 – 1.98 (m, 2H), 1.77 – 1.60 (m, 2H), 0.92 – 0.81 (m, 3H). MS (ESI) m/z: 643 [M + H]$^+$. |
| II-39 | 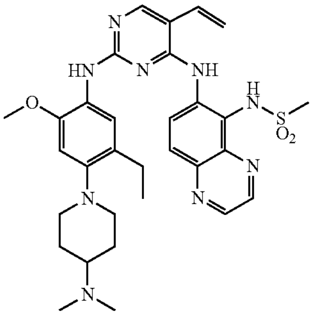 | $^1$H NMR (600 MHz, DMSO-$d_6$) δ 9.88 (s, 1H), 9.75 (s, 1H), 9.52 (s, 1H), 9.06 (d, J = 1.9 Hz, 1H), 9.02 (d, J = 1.9 Hz, 1H), 8.34 (s, 1H), 8.28 – 8.20 (m, 1H), 7.97 (d, J = 9.2 Hz, 1H), 7.31 (s, 1H), 6.81 (dd, J = 17.2, 11.2 Hz, 1H), 6.76 (s, 1H), 5.91 (d, J = 17.3 Hz, 1H), 5.55 (d, J = 11.1 Hz, 1H), 3.80 (s, 3H), 3.29 – 3.21 (m, 1H), 3.07 (s, 3H), 3.04 – 2.96 (m, 2H), 2.82 (s, 3H), 2.81 (s, 3H), 2.74 – 2.64 (m, 2H), 2.20 – 2.10 (m, 2H), 2.11 – 2.04 (m, 2H), 1.80 – 1.68 (m, 2H), 0.71 – 0.45 (m, 3H). MS (ESI) m/z: 618 [M + H]$^+$. |
| II-40 | 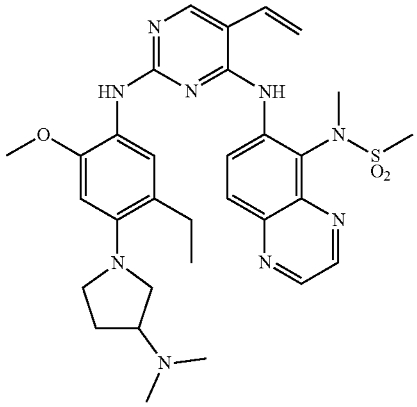 | $^1$H NMR (600 MHz, DMSO-$d_6$) δ 10.12 (s, 1H), 9.88 (s, 1H), 9.62 (s, 1H), 9.05 (d, J = 1.8 Hz, 1H), 9.00 (d, J = 1.8 Hz, 1H), 8.39 – 8.21 (m, 2H), 7.96 (d, J = 9.0 Hz, 1H), 7.28 (s, 1H), 6.79 (dd, J = 17.3, 11.1 Hz, 1H), 6.73 (s, 1H), 5.89 (d, J = 17.3 Hz, 1H), 5.53 (d, J = 11.2 Hz, 1H), 3.80 (s, 3H), 3.31 – 3.25 (m, 2H), 3.16 – 3.12 (m, 1H), 3.07 (s, 3H), 3.05 – 3.00 (m, 2H), 2.89 – 2.80 (m, 6H), 2.36 – 2.27 (m. 1H), 2.22 – 2.08 (m, 3H), 0.76 – 0.55 (m, 3H). MS (ESI) m/z: 604 [M + H]$^+$. |
| II-41 | 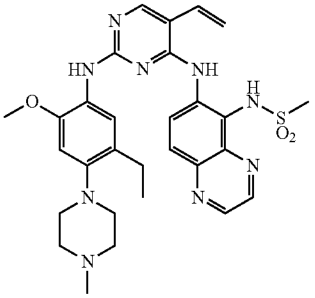 | $^1$H NMR (600 MHz, DMSO-$d_6$) δ 10.14 (s, 1H), 9.88 (s, 1H), 9.74 (s, 1H), 9.06 (d, J = 1.8 Hz, 1H), 9.02 (d, J = 1.9 Hz, 1H), 8.40 – 8.34 (m, 1H), 8.25 (s, 1H), 7.98 (d, J = 9.1 Hz, 1H), 7.37 (s, 1H), 6.81 (dd, J = 17.3, 11.1 Hz, 1H), 6.76 (s, 1H), 5.91 (d, J = 17.2 Hz, 1H), 5.54 (d, J = 11.1 Hz, 1H), 3.82 (s, 3H), 3.54 – 3.44 (m, 2H), 3.24 – 3.17 (m, 2H), 3.08 (s, 3H), 3.06 – 2.95 (m, 4H), 2.89 (s, 3H), 2.23 – 2.06 (m, 2H), 0.73 – 0.44 (m, 3H). MS (ESI) m/z: 590 [M + H]$^+$. |

-continued

| No. | Structure | $^1H$ NMR and/or MS data |
|---|---|---|
| II-42 | 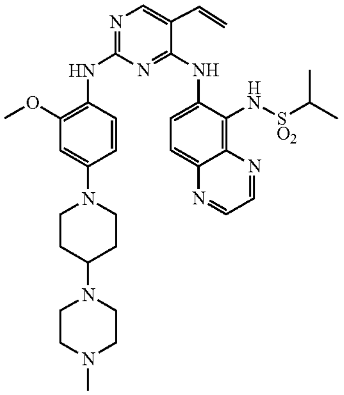 | $^1H$ NMR (600 MHz, DMSO-$d_6$) δ 9.84 (s, 1H), 9.77 (s, 1H), 9.74 (s, 1H), 9.05 (d, J = 1.8 Hz, 1H), 9.01 (d, J = 1.9 Hz, 1H), 8.30 – 8.23 (m, 2H), 8.03 (d, J = 9.1 Hz, 1H), 7.20 (d, J = 8.7 Hz, 1H), 6.81 (dd, J = 17.2, 11.1 Hz, 1H), 6.72 – 6.66 (m, 1H), 6.27 – 6.13 (m, 1H), 5.92 (d, J = 17.3 Hz, 1H), 5.56 (d, J = 11.2 Hz, 1H), 3.85 – 3.80 (m, 2H), 3.79 (s, 3H), 3.67 – 3.16 (m, 10H), 2.89 (s, 3H), 2.76 – 2.66 (m, 2H), 2.18 – 2.11 (m, 2H), 1.75 – 1.64 (m, 2H), 1.35 (d, J = 6.8 Hz, 6H). MS (ESI) m/z: 673 $[M + H]^+$. |
| II-43 | 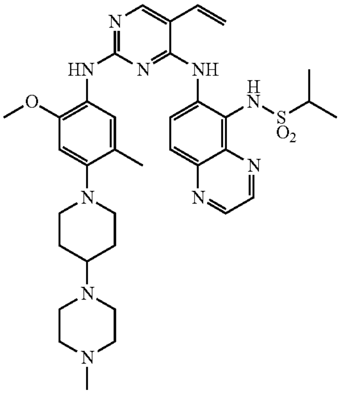 [SMILES: C=Cc1cnc(Nc2cc(C)c(N3CCC(N4CCN(C)CC4)CC3)cc2OC)nc1Nc1ccc2nccnc2c1NS(=O)(=O)C(C)C] | $^1H$ NMR (600 MHz, DMSO-$d_6$) δ 9.93 (s, 1H), 9.73 (s, 1H), 9.64 (s, 1H), 9.05 (d, J = 1.8 Hz, 1H), 9.01 (d, J = 1.9 Hz, 1H), 8.36 (s, 1H), 8.25 – 8.13 (m, 1H), 7.99 (d, J = 9.1 Hz, 1H), 7.22 (s, 1H), 6.84 (dd, J = 17.2, 11.1 Hz, 1H), 6.69 (s, 1H), 5.92 (d, J = 17.3 Hz, 1H), 5.56 (d, J = 11.2 Hz, 1H), 3.79 (s, 3H), 3.71 – 3.49 (m, 8H), 3.44 (hept, J = 6.7 Hz, 1H), 3.38 – 3.29 (m, 1H), 3.12 – 3.05 (m, 2H), 2.91 (s, 3H), 2.71 – 2.61 (m, 2H), 2.15 – 2.08 (m, 2H), 1.80 – 1.72 (m, 2H), 1.63 (s, 3H), 1.34 (d, J = 6.8 Hz, 6H). MS (ESI) m/z: 687 $[M + H]^+$. |
| II-44 | 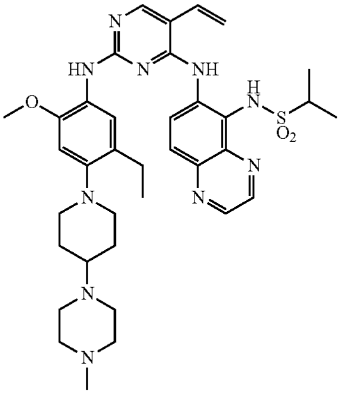 [SMILES: C=Cc1cnc(Nc2cc(CC)c(N3CCC(N4CCN(C)CC4)CC3)cc2OC)nc1Nc1ccc2nccnc2c1NS(=O)(=O)C(C)C] | $^1H$ NMR (600 MHz, DMSO-$d_6$) δ 9.78 (s, 1H), 9.72 (s, 1H), 9.40 – 9.26 (m, 1H), 9.04 (d, J = 1.8 Hz, 1H), 9.00 (d, J = 1.9 Hz, 1H), 8.33 (s, 1H), 8.26 – 8.16 (m, 1H), 7.96 (d, J = 9.1 Hz, 1H), 7.32 (s, 1H), 6.83 (dd, J = 17.2, 11.1 Hz, 1H), 6.74 (s, 1H), 5.90 (d, J = 17.3 Hz, 1H), 5.54 (d, J = 11.1 Hz, 1H), 3.80 (s, 3H), 3.75 – 3.52 (m, 8H), 3.40 (hept, J = 6.8 Hz, 1H), 3.23 – 3.14 (m, 1H), 3.05 – 2.94 (m, 2H), 2.86 (s, 3H), 2.75 – 2.63 (m, 2H), 2.14 – 2.01 (m, 4H), 1.76 – 1.65 (m, 2H), 1.33 (d, J = 6.8 Hz, 6H), 0.66 – 0.46 (m, 3H). MS (ESI) m/z: 701 $[M + H]^+$. |
| II-45 | 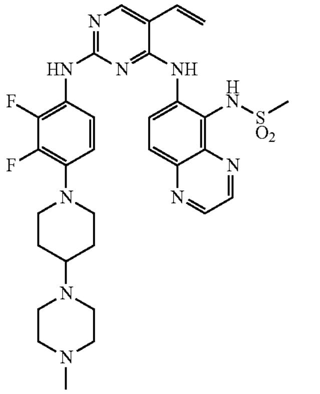 [SMILES: C=Cc1cnc(Nc2ccc(N3CCC(N4CCN(C)CC4)CC3)c(F)c2F)nc1Nc1ccc2nccnc2c1NS(C)(=O)=O] | $^1H$ NMR (600 MHz, DMSO-$d_6$) δ 9.96 (s, 1H), 9.84 (s, 1H), 9.38 (s, 1H), 9.02 (d, J = 1.8 Hz, 1H), 8.96 (d, J = 1.8 Hz, 1H), 8.47 – 8.36 (m, 1H), 8.34 (s, 1H), 7.91 (d, J = 9.2 Hz, 1H), 7.14 (t, J = 8.2 Hz, 1H), 6.77 (dd, J = 17.3, 11.2 Hz, 1H), 6.69 (t, J = 8.9 Hz, 1H), 5.88 (d, J = 17.4 Hz, 1H), 5.50 (d, J = 11.2 Hz, 1H), 3.49 – 3.42 (m, 2H), 3.41 – 3.10 (m, 9H), 3.05 (s, 3H), 2.90 (s, 3H), 2.74 – 2.67 (m,2H), 2.20 – 2.13 (m,2H), 1.81 – 1.71 (m, 2H). MS (ESI) m/z: 651 $[M + H]^+$. |

-continued

| No. | Structure | $^1H$ NMR and/or MS data |
|---|---|---|
| II-46 | 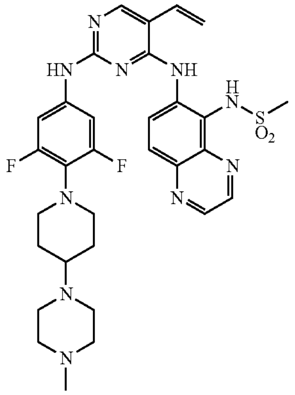 [SMILES: C=Cc1cnc(Nc2cc(F)c(N3CCC(N4CCN(C)CC4)CC3)c(F)c2)nc1Nc1ccc2nccnc2c1NS(C)(=O)=O] | $^1H$ NMR (600 MHz, DMSO-$d_6$) δ 9.95 (s, 1H), 9.86 (s, 1H), 9.06 (s, 1H), 9.03 (d, J = 1.8 Hz, 1H), 8.97 (d, J = 1.9 Hz, 1H), 8.59 - 8.49 (m, 1H), 8.44 (s, 1H), 8.08 (d, J = 9.2 Hz, 1H), 7.28 (d, J = 12.2 Hz, 2H), 6.79 (dd, J = 17.4, 11.2 Hz, 1H), 5.86 (d, J = 17.4 Hz, 1H), 5.43 (d, J = 11.3 Hz, 1H), 3.71 - 3.21 (m, 9H), 3.16 - 3.09 (m, 2H), 3.06 (s, 3H), 3.03 - 2.93 (m, 2H), 2.87 (s, 3H), 2.10 - 1.99 (m, 2H), 1.73 - 1.63 (m, 2H). MS (ESI) m/z: 651 $[M + H]^+$. |
| II-47 | 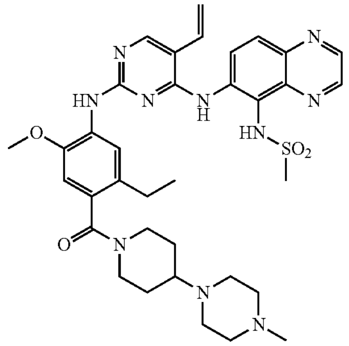 [SMILES: C=Cc1cnc(Nc2cc(CC)c(C(=O)N3CCC(N4CCN(C)CC4)CC3)cc2OC)nc1Nc1ccc2nccnc2c1NS(C)(=O)=O] | $^1H$ NMR (600 MHz, DMSO-$d_6$) δ 9.90 - 9.81 (m, 1H), 9.64 (s, 1H), 9.20 (s, 1H), 9.05 (d, J = 1.9 Hz, 1H), 9.02 - 8.96 (m, 1H), 8.42 (s, 1H), 8.30 (d, J = 9.1 Hz, 1H), 8.10 - 7.96 (m, 1H), 7.53 (d, J = 7.5 Hz, 1H), 6.91 - 6.77 (m, 2H), 5.90 (d, J = 17.3 Hz, 1H), 5.53 (d, J = 11.2 Hz, 1H), 4.68 - 4.56 (m, 1H), 3.86 - 3.79 (m, 3H), 3.73 - 3.12 (m, 8H), 3.08 (s, 3H), 2.97 - 2.91 (m, 2H), 2.84 (s, 3H), 2.76 - 2.69 (m, 2H), 2.20 - 1.76 (m, 5H), 1.66 - 1.40 (m, 1H), 0.63 - 0.41 (m, 3H). MS (ESI) m/z: 701 $[M + H]^+$. |
| II-48 | 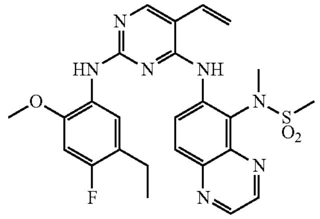 | $^1H$ NMR (600 MHz, Methanol-$d_4$) δ 8.99 (d, J = 1.9 Hz, 1H), 8.96 (d, J = 1.8 Hz, 1H), 8.43 - 8.27 (m, 1H), 8.12 - 8.08 (m, 1H), 8.04 - 7.96 (m, 1H), 7.30 (d, J = 8.0 Hz, 1H), 6.85 (d, J = 11.5 Hz, 1H), 6.82 - 6.73 (m, 1H), 5.90 (d, J = 17.3 Hz, 1H), 5.66 (d, J = 11.1 Hz, 1H), 3.83 (s, 3H), 3.44 (s, 3H), 3.14 (s, 3H), 2.35 - 2.22 (m, 2H), 0.92 - 0.73 (m, 3H). MS (ESI) m/z: 524 $[M + H]^+$. |
| II-49 | 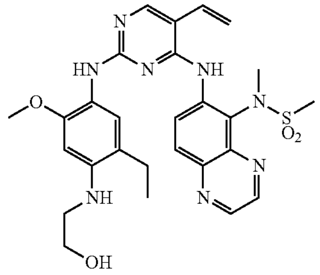 | $^1H$ NMR (600 MHz, DMSO-$d_6$) δ 9.76 (s, 1H), 9.48 (s, 1H), 9.04 (d, J = 1.9 Hz, 1H), 9.03 (d, J = 1.9 Hz, 1H), 8.34 - 8.01 (m, 4H), 7.19 (s, 1H), 6.85 (dd, J = 17.3, 11.1 Hz, 1H), 6.69 (s, 1H), 5.89 (d, J = 17.4 Hz, 1H), 5.52 (d, J = 11.2 Hz, 1H), 4.19 - 4.10 (m, 2H), 3.80 (s, 3H), 3.30 (s, 3H), 3.26 - 3.19 (m, 2H), 3.14 (s, 3H), 2.31 - 1.54 (m, 2H), 0.87 - 0.36 (m, 3H). MS (ESI) m/z: 565 $[M + H]^+$. |
| II-50 | 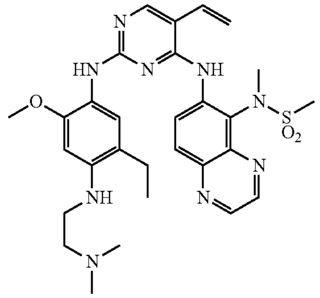 | $^1H$ NMR (600 MHz, DMSO-$d_6$) δ 10.20 (s, 2H), 9.75 (s, 1H), 9.05 - 9.03 (m, 1H), 9.02 (d, J = 1.8 Hz, 1H), 8.41 - 7.95 (m, 3H), 6.97 - 6.91 (m, 1H), 6.84 (dd, J = 17.3, 11.1 Hz, 1H), 6.31 (s, 1H), 5.90 (d, J = 17.3 Hz, 1H), 5.54 (d, J = 11.1 Hz, 1H), 3.79 (s, 3H), 3.59 - 3.47 (m, 2H), 3.34 - 3.27 (m, 5H), 3.14 (s, 3H), 2.88 (s, 6H), 2.08 - 1.72 (m, 2H), 0.76 - 0.50 (m, 3H). MS (ESI) m/z: 592 $[M + H]^+$. |

-continued

| No. | Structure | $^1$H NMR and/or MS data |
|---|---|---|
| II-51 | 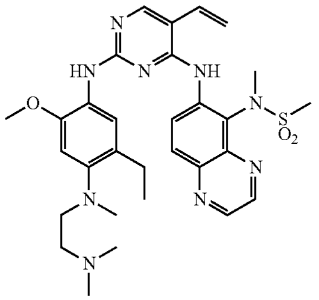 | $^1$H NMR (600 MHz, DMSO-$d_6$) δ 9.97 (s, 1H), 9.67 (s, 1H), 9.06 - 9.03 (m, 2H), 8.42 - 8.33 (m, 1H), 8.18 - 8.13 (m, 1H), 8.12 - 8.07 (m, 1H), 7.24 (s, 1H), 6.88 (dd, J = 17.2, 11.0 Hz, 1H), 6.83 (s, 1H), 5.92 (d, J = 17.4 Hz, 1H), 5.55 (d, J = 11.1 Hz, 1H), 3.80 (s, 3H), 3.28 (s, 3H), 3.21 - 3.14 (m, 4H), 3.12 (s, 3H), 2.78 (s, 6H), 2.49 (s, 3H), 2.31 - 2.05 (m, 2H), 0.67 - 0.28 (m, 3H). MS (ESI) m/z: 606 [M + H]$^+$. |
| II-52 | 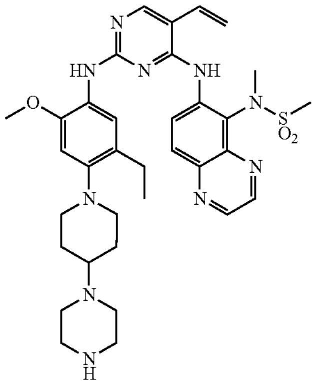 | $^1$H NMR (600 MHz, DMSO-$d_6$) δ 8.96 (d, J = 1.9 Hz, 1H), 8.91 (d, J = 1.9 Hz, 1H), 8.70 (s, 1H), 8.45 (s, 1H), 8.31 (s, 1H), 8.11 - 8.07 (m, 1H), 7.94 (d, J = 9.4 Hz, 1H), 7.49 (s, 1H), 6.80 - 6.72 (m, 2H), 5.76 (d, J = 17.5 Hz, 1H), 5.34 (d, J = 11.2 Hz, 1H), 4.37 - 4.33 (m, 1H), 3.77 (s, 3H), 3.32 (s, 3H), 3.18 (s, 3H), 3.01 - 2.93 (m, 2H), 2.74 - 2.61 (m, 6H), 2.45 (s, 4H), 2.36 - 2.30 (m, 2H), 2.29 - 2.23 (m, 1H), 1.86 - 1.78 (m, 2H), 1.60 - 1.50 (m, 2H), 0.83 - 0.76 (m, 3H). MS (ESI) m/z: 673 [M + H]$^+$. |
| II-53 | 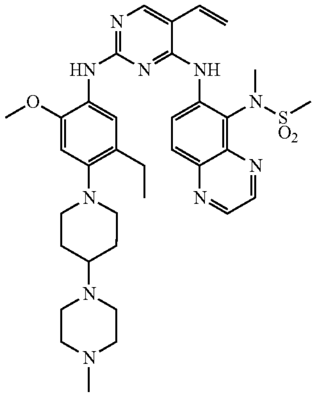 | $^1$H NMR (600 MHz, DMSO-$d_6$) δ 10.21 (s, 1H), 9.92 (s, 1H), 9.12 - 8.98 (m, 2H), 8.37 - 8.27 (m, 1H), 8.20 - 8.03 (m, 2H), 7.17 (s, 1H), 6.87 (dd, J = 17.3, 11.0 Hz, 1H), 6.68 (s, 1H), 5.90 (d, J = 17.2 Hz, 1H), 5.53 (d, J = 11.2 Hz, 1H), 3.75 (s, 3H), 3.73 - 3.67 (m, 1H), 3.24 (s, 3H), 3.11 (s, 3H), 2.73 - 2.68 (m, 8H), 2.68 - 2.59 (m, 3H), 2.27 - 2.15 (m, 2H), 2.13 - 2.06 (m, 2H), 2.04 - 1.91 (m, 2H), 1.71 - 1.59 (m, 4H), 0.77 - 0.33 (m, 3H). MS (ESI) m/z: 687 [M + H]$^+$. |
| II-54 | 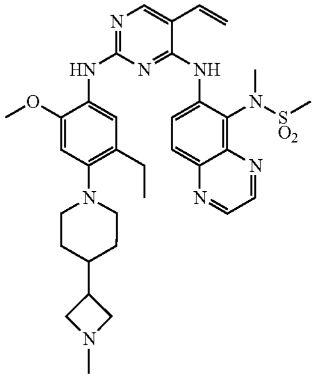 | $^1$H NMR (600 MHz, Methanol-$d_4$) δ 8.99 (d, J = 1.7 Hz, 1H), 8.95 (d, J = 1.8 Hz, 1H), 8.40 - 8.18 (m, 1H), 8.14 - 7.98 (m, 2H), 7.30 (s, 1H), 6.85 (s, 1H), 6.78 (dd, J = 17.3, 11.0 Hz, 1H), 5.90 (d, J = 17.3 Hz, 1H), 5.66 (d, J = 11.0 Hz, 1H), 4.63 - 4.42 (m, 4H), 4.19 - 4.10 (m, 1H), 3.85 (s, 3H), 3.43 (s, 3H), 3.23 - 3.09 (m, 11H), 3.05 (s, 3H), 2.45 - 2.15 (m, 2H), 0.89 - 0.51 (m, 3H). MS (ESI) m/z: 659 [M + H]$^+$. |

-continued
| No. | Structure | $^1H$ NMR and/or MS data |
|---|---|---|
| II-55 | 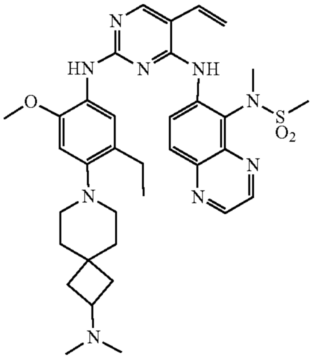 | $^1H$ NMR (600 MHz, DMSO-$d_6$) δ 10.14 (s, 1H), 9.74 (s, 1H), 9.04 (d, J = 1.8 Hz, 1H), 9.03 (d, J = 1.8 Hz, 1H), 8.35 (s, 1H), 8.26 - 8.19 (m, 1H), 8.08 (d, J = 9.0 Hz, 1H), 7.32 (s, 1H), 6.86 (dd, J = 17.3, 11.1 Hz, 1H), 6.69 (s, 1H), 5.89 (d, J = 17.5 Hz, 1H), 5.52 (d, J = 11.2 Hz, 1H), 3.79 (s, 3H), 3.63 (d, J = 12.5 Hz, 6H), 3.52 - 3.46 (m, 1H), 3.28 (s, 3H), 3.23 - 3.17 (m, 2H), 3.13 (s, 3H), 3.02 (s, 6H), 2.45 - 2.35 (m, 2H), 2.28 - 2.03 (m, 2H), 2.01 - 1.80 (m, 2H), 0.69 - 0.37 (m, 3H). MS (ESI) m/z: 672 [M + H]+. |
| II-56 | 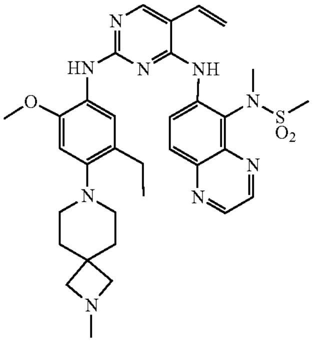 | MS (ESI) m/z: 644 $[M + H]^+$. |
| II-57 | 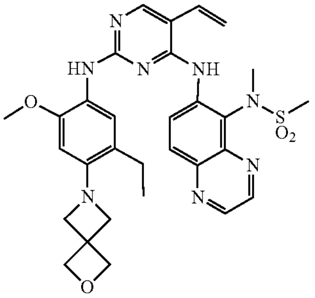 | MS (ESI) m/z: 603 $[M + H]^+$. |
| II-58 | 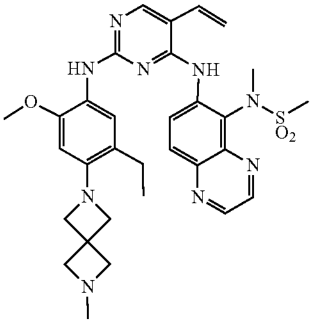 | MS (ESI) m/z: 616 $[M + H]^+$. |
| II-59 | 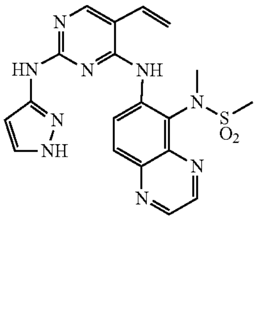 [SMILES: C=Cc1cnc(Nc2cc[nH]n2)nc1Nc1ccc2nccnc2c1N(C)S(C)(=O)=O] | $^1H$ NMR (600 MHz, Methanol-$d_4$) δ 8.96 - 8.95 (m, 1H), 8.94 (d, J = 1.9 Hz, 1H), 8.85 (d, J = 1.8 Hz, 1H), 8.20 (s, 1H), 8.11 (d, J = 9.3 Hz, 1H), 7.55 (d, J =2.3 Hz, 1H), 6.78 (dd, J =17.4, 11.1 Hz, 1H), 6.22 (s, 1H), 5.81 (d, J = 17.4 Hz, 1H), 5.53 (d, J = 11.1 Hz, 1H), 3.46 (s, 3H), 3.19 (s, 3H). MS (ESI) m/z: 438 $[M + H]^+$. |

-continued

| No. | Structure | $^1H$ NMR and/or MS data |
|---|---|---|
| II-60 | 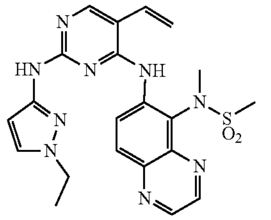 [SMILES: C=Cc1cnc(Nc2ccn(CC)n2)nc1Nc1ccc2nccnc2c1N(C)S(C)(=O)=O] | $^1H$ NMR (600 MHz, DMSO-$d_6$) δ 11.05 (s, 1H), 9.86 (s, 1H), 9.06 (d, J = 1.8 Hz, 1H), 9.04 (d, J = 1.8 Hz, 1H), 8.40 (d, J = 9.2 Hz, 1H), 8.36 (s, 1H), 8.21 (d, J = 9.1 Hz, 1H), 7.78 - 7.45 (m, 1H), 6.88 (dd, J = 17.3, 11.1 Hz, 1H), 6.03 - 5.93 (m, 1H), 5.89 (d, J = 17.3 Hz, 1H), 5.56 (d, J = 11.1 Hz, 1H), 4.16 - 3.99 (m, 2H), 3.36 (s, 3H), 3.15 (s, 3H), 1.44 - 1.30 (m, 3H). MS (ESI) m/z: 466 $[M + H]^+$. |
| II-61 | 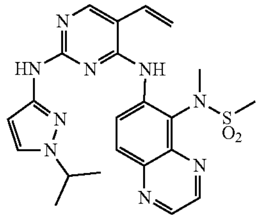 [SMILES: C=Cc1cnc(Nc2ccn(C(C)C)n2)nc1Nc1ccc2nccnc2c1N(C)S(C)(=O)=O] | $^1H$ NMR (600 MHz, DMSO-$d_6$) δ 11.14 (s, 1H), 9.93 (s, 1H), 9.06 (d, J = 1.9 Hz, 1H), 9.04 (d, J = 1.8 Hz, 1H), 8.39 (s, 1H), 8.34 (d, J = 9.1 Hz, 1H), 8.22 (d, J = 9.1 Hz, 1H), 7.89 - 7.58 (m, 1H), 6.89 (dd, J = 17.2, 11.0 Hz, 1H), 5.96 - 5.93 (m, 1H), 5.90 (d, J = 17.3 Hz, 1H), 5.57 (d, J = 11.1 Hz, 1H), 4.58 - 4.38 (m, 1H), 3.36 (s, 3H), 3.14 (s, 3H), 1.50 - 1.34 (m, 6H). MS (ESI) m/z: 480 $[M + H]^+$. |
| II-62 | 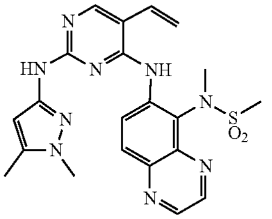 | $^1H$ NMR (600 MHz, DMSO-$d_6$) δ 10.05 (s, 1H), 9.12 - 9.08 (m, 2H), 9.07 (d, J = 1.7 Hz, 1H), 9.06 (d, J = 1.8 Hz, 1H), 8.33 (s, 1H), 8.26 (d, J = 4.6 Hz, 2H), 7.91 (d, J = 8.9 Hz, OH), 6.89 (dd, J = 17.2, 11.0 Hz, 1H), 5.90 (d, J = 17.3 Hz, 1H), 5.57 (d, J = 11.0 Hz, 1H), 3.68 (s, 3H), 3.34 (s, 3H), 3.14 (s, 3H), 2.13 (s, 3H). MS (ESI) m/z: 466 $[M + H]^+$. |
| II-63 | 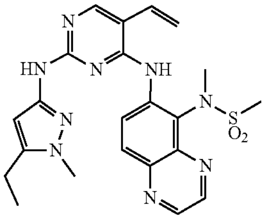 [SMILES: C=Cc1cnc(Nc2cc(CC)n(C)n2)nc1Nc1ccc2nccnc2c1N(C)S(C)(=O)=O] | $^1H$ NMR (600 MHz, DMSO-$d_6$) δ 11.40 - 10.46 (m, 1H), 9.90 (s, 1H), 9.06 (d, J = 1.8 Hz, 1H), 9.04 (d, J = 1.9 Hz, 1H), 8.32 (s, 1H), 8.31 - 8.26 (m, 1H), 8.22 (d, J = 9.0 Hz, 1H), 6.88 (dd, J = 17.3, 11.0 Hz, 1H), 5.88 (d, J = 17.2 Hz, 1H), 5.77 - 5.63 (m, 1H), 5.54 (d, J = 11.1 Hz, 1H), 3.65 (s, 3H), 3.47 - 3.37 (m, 2H), 3.33 (s, 3H), 3.14 (s, 3H), 1.42 - 0.35 (m, 3H). MS (ESI) m/z: 480 $[M + H]^+$. |
| II-64 | 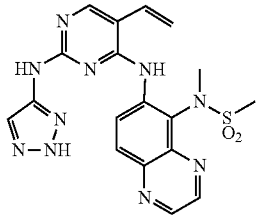 | $^1H$ NMR (600 MHz, DMSO-$d_6$) δ 10.27 (s, 1H), 9.84 - 9.57 (m, 1H), 9.53 - 9.41 (m, 1H), 9.08 - 8.98 (m, 2H), 8.42 - 8.25 (m, 2H), 8.17 (d, J = 9.1 Hz, 1H), 7.84 - 7.68 (m, 1H), 7.44 - 7.30 (m, 1H), 6.82 (dd, J = 17.3, 11.1 Hz, 1H), 5.85 (d, J = 17.3 Hz, 1H), 5.46 (d, J = 11.2 Hz, 1H), 3.32 (s, 3H), 3.17 (s, 3H). MS (ESI) m/z: 438 $[M + H]^+$. |
| II-65 | 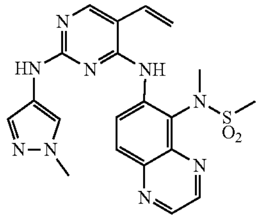 [SMILES: C=Cc1cnc(Nc2cnn(C)c2)nc1Nc1ccc2nccnc2c1N(C)S(C)(=O)=O] | $^1H$ NMR (600 MHz, DMSO-$d_6$) δ 10.64 (s, 1H), 9.79 (s, 1H), 9.13 - 8.98 (m, 2H), 8.36 (s, 1H), 8.29 - 8.17 (m, 2H), 7.23 - 7.05 (m, 2H), 6.93 - 6.78 (m, 1H), 5.88 (d, J = 17.3 Hz, 1H), 5.48 (d, J = 11.2 Hz, 1H), 3.35 - 3.27 (m, 6H), 3.18 (s, 3H). MS (ESI) m/z: 452 [M + H]+. |
| II-66 | 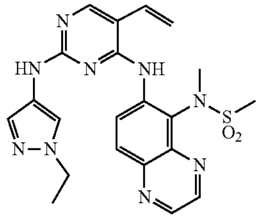 [SMILES: C=Cc1cnc(Nc2cnn(CC)c2)nc1Nc1ccc2nccnc2c1N(C)S(C)(=O)=O] | $^1H$ NMR (600 MHz, DMSO-$d_6$) δ 9.66 (s, 1H), 9.42 (s, 1H), 9.11 - 8.84 (m, 2H), 8.51 - 8.36 (m, 1H), 8.33 (s, 1H), 8.16 (d, J = 9.2 Hz, 1H), 7.58 - 7.43 (m, 1H), 7.27 (s, 1H), 6.85 - 6.72 (m, 1H), 5.79 (d, J = 17.4 Hz, 1H), 5.37 (d, J = 11.2 Hz, 1H), 4.20 - 3.58 (m, 2H), 3.33 (s, 3H), 3.19 (s, 3H), 1.43 - 0.90 (m, 3H). MS (ESI) m/z: 466 $[M + H]^+$. |

-continued

| No. | Structure | $^1$H NMR and/or MS data |
|---|---|---|
| II-67 | 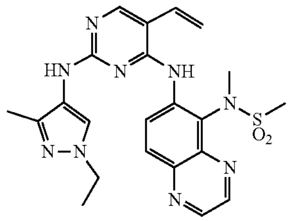 | $^1$H NMR (600 MHz, DMSO-d$_6$) δ 9.95 (s, 1H), 9.15 (s, 1H), 9.06 - 8.94 (m, 2H), 8.42 - 8.29 (m, 2H), 8.17 (d, J = 9.2 Hz, 1H), 7.66 - 7.42 (m, 1H), 7.27 (s, 1H), 6.84 (s, 1H), 5.81 (d, J = 17.4 Hz, 1H), 5.38 (d, J = 11.2 Hz, 1H), 4.02 - 3.80 (m, 1H), 3.33 (s, 3H), 3.19 (s, 3H), 1.04 - 0.87 (m, 6H). MS (ESI) m/z: 480 $[M + H]^+$. |
| II-68 | 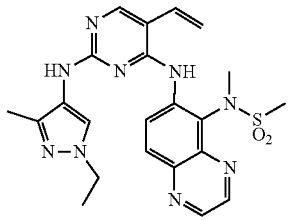 | $^1$H NMR (600 MHz, Methanol-d$_4$) δ 9.00 (d, J = 1.8 Hz, 1H), 8.96 (d, J = 1.9 Hz, 1H), 8.62 (s, 1H), 8.26 - 8.19 (m, 1H), 7.83 - 7.73 (m, 1H), 7.35 (s, 1H), 6.78 (dd, J = 17.3, 11.0 Hz, 1H), 5.90 (d, J = 17.3 Hz, 1H), 5.67 (d, J = 11.0 Hz, 1H), 3.80 - 3.69 (m, 2H), 3.51 (s, 3H), 3.19 - 3.07 (m, 3H), 2.19 - 2.07 (m, 3H), 1.52 - 1.42 (m, 3H). MS (ESI) m/z: 480 $[M + H]^+$. |
| II-69 | 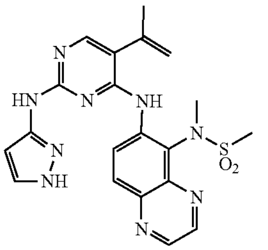 [SMILES: C=C(C)c1cnc(Nc2cc[nH]n2)nc1Nc1ccc2nccnc2c1N(C)S(C)(=O)=O] | $^1$H NMR (600 MHz, Methanol-d$_4$) δ 9.09 (d, J = 9.3 Hz, 1H), 8.95 (d, J = 1.8 Hz, 1H), 8.87 (d, J = 1.9 Hz, 1H), 8.16 (d, J = 9.4 Hz, 1H), 8.02 (s, 1H), 7.64 - 7.60 (m, 1H), 6.24 - 6.16 (m, 1H), 5.63 (s, 1H), 5.41 (s, 1H), 3.46 (s, 3H), 3.18 (s, 3H), 2.19 (s, 3H). MS (ESI) m/z: 452 $[M + H]^+$. |
| II-70 | 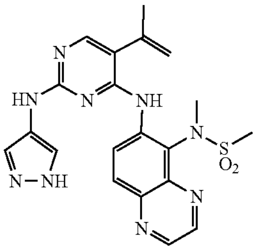 [SMILES: C=C(C)c1cnc(Nc2cn[nH]c2)nc1Nc1ccc2nccnc2c1N(C)S(C)(=O)=O] | $^1$H NMR (600 MHz, DMSO-d$_6$) δ 10.18 (s, 1H), 9.77 (s, 1H), 9.19 - 9.08 (m, 2H), 9.01 (d, J = 1.8 Hz, 1H), 8.98 (s, 1H), 8.69 - 8.52 (m, 1H), 8.14 (s, 1H), 7.88 - 7.66 (m, 1H), 7.65 - 7.49 (m, 1H), 5.53 (s, OH), 5.37 (s, 1H), 3.36 (s, 3H), 3.20 (s, 3H), 2.13 (s, 3H). MS (ESI) m/z: 452 $[M + H]^+$. |
| II-71 | 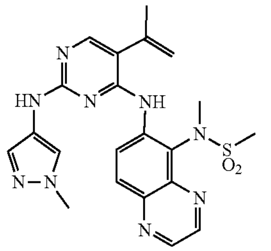 [SMILES: C=C(C)c1cnc(Nc2cnn(C)c2)nc1Nc1ccc2nccnc2c1N(C)S(C)(=O)=O] | $^1$H NMR (600 MHz, DMSO-d$_6$) δ 10.50 (s, 1H), 9.34 (s, 1H), 9.10 - 8.95 (m, 2H), 8.53 (s, 1H), 8.23 (d, J = 9.2 Hz, 1H), 8.18 - 8.00 (m, 1H), 7.64 - 7.31 (m, 2H), 5.57 (s, 1H), 5.43 (s, 1H), 3.93 - 3.52 (m, 3H), 3.39 (s, 3H), 3.24 (s, 3H), 2.18 (s, 3H). MS (ESI) m/z: 466 $[M + H]^+$. |
| II-72 | 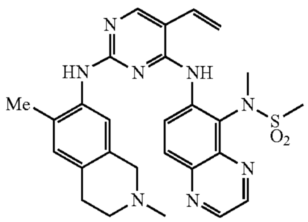 [SMILES: C=Cc1cnc(Nc2cc3c(cc2C)CCN(C)C3)nc1Nc1ccc2nccnc2c1N(C)S(C)(=O)=O] | $^1$H NMR (600 MHz, DMSO-d$_6$) δ 10.50 (s, 1H), 9.78 (s, 1H), 9.02 - 9.00 (m, 1H), 9.00 - 8.97 (m, 1H), 8.48 - 8.38 (m, 1H), 8.30 (s, 1H), 8.07 (d, J = 9.3 Hz, 1H), 7.20 (s, 1H), 7.08 (s, 1H), 6.82 (dd, J = 17.4, 11.2 Hz, 1H), 5.87 (d, J = 17.4 Hz, 1H), 5.50 (d, J = 11.2 Hz, 1H), 4.33 - 4.05 (m, 2H), 4.01 - 3.85 (m, 1H), 3.77 - 3.60 (m, 1H), 3.31 (s, 3H), 3.18 (s, 3H), 3.12 - 2.96 (m, 2H), 2.93 - 2.86 (m, 3H), 2.13 (s, 3H). MS (ESI) m/z: 531 $[M + H]^+$. |

-continued

| No. | Structure | $^1$H NMR and/or MS data |
| --- | --- | --- |
| II-73 | 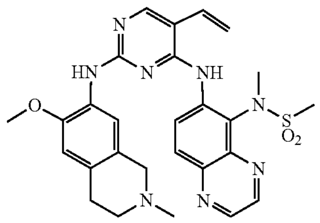 | $^1$H NMR (600 MHz, DMSO-$d_6$) δ 10.46 (s, 1H), 9.37 (s, 1H), 9.15 - 9.05 (m, 2H), 8.48 - 8.38 (m, 2H), 8.23 (d, J = 9.2 Hz, 1H), 7.36 (s, 1H), 6.94 (s, 1H), 6.87 (dd, J = 17.3, 11.1 Hz, 1H), 5.91 (d, J = 17.3 Hz, 1H), 5.53 (d, J = 11.1 Hz, 1H), 3.81 (s, 3H), 3.75 - 3.55 (m, 2H), 3.35 (s, 3H), 3.29 - 3.22 (m, 2H), 3.17 (s, 3H), 3.11 - 2.92 (m, 2H), 2.81 (s, 3H). MS (ESI) m/z: 546 [M + H]$^+$. |
| II-74 | 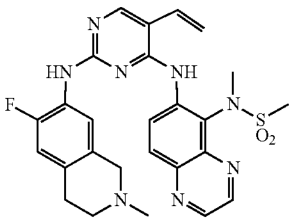 | $^1$H NMR (600 MHz, DMSO-$d_6$) δ 10.34 (s, 1H), 9.50 (s, 1H), 8.99 (d, J = 1.9 Hz, 1H), 8.95 (d, J = 1.8 Hz, 1H), 8.76 - 8.66 (m, 1H), 8.35 (s, 1H), 8.11 (d, J = 9.3 Hz, 1H), 7.45 (d, J = 7.8 Hz, 1H), 7.23 (d, J = 11.2 Hz, 1H), 6.80 (dd, J = 17.5, 11.2 Hz, 1H), 5.84 (d, J = 17.3 Hz, 1H), 5.46 (d, J = 11.2 Hz, 1H), 3.67 (s, 2H), 3.35 (s, 3H), 3.33 - 3.26 (m, 2H), 3.20 (s, 3H), 3.16 - 3.00 (m, 2H), 2.89 (s, 3H). MS (ESI) m/z: 535 [M + H]$^+$. |
| II-75 | 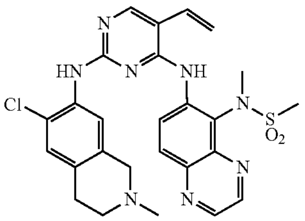 [SMILES: C=Cc1cnc(Nc2cc3c(cc2Cl)CCN(C)C3)nc1Nc1ccc2nccnc2c1N(C)S(C)(=O)=O] | $^1$H NMR (600 MHz, DMSO-$d_6$) δ 10.28 (s, 1H), 9.38 (s, 1H), 9.00 (d, J = 1.9 Hz, 1H), 8.96 (d, 1H), 8.65 - 8.57 (m, 1H), 8.33 (s, 1H), 8.07 (d, J = 9.3 Hz, 1H), 7.49 (s, 1H), 7.48 (s, 1H), 6.80 (dd, J = 17.4, 11.2 Hz, 1H), 5.85 (d, J = 17.5 Hz, 1H), 5.48 (d, J = 11.1 Hz, 1H), 4.30 - 3.95 (m, 2H), 3.35 (s, 3H), 3.32 - 3.26 (m. 2H), 3.19 (s, 3H), 3.14 - 3.03 (m, 2H), 2.89 (s, 3H). MS (ESI) m/z: 551 [M + H]$^+$. |
| II-76 | 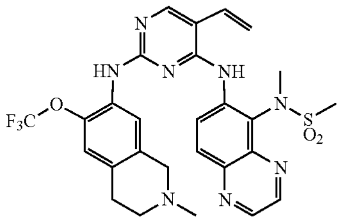 [SMILES: C=Cc1cnc(Nc2cc3c(cc2OC(F)(F)F)CCN(C)C3)nc1Nc1ccc2nccnc2c1N(C)S(C)(=O)=O] | $^1$H NMR (600 MHz, DMSO-$d_6$) δ 10.21 (s, 1H), 9.30 (s, 1H), 8.99 (d, J = 1.9 Hz, 1H), 8.96 - 8.94 (m, 1H), 8.82 - 8.67 (m, 1H), 8.34 (s, 1H), 8.10 (d, J = 8.7 Hz, 1H), 7.58 (s, 1H), 7.38 (s, 1H), 6.80 (dd, J = 17.4, 11.2 Hz, 1H), 5.83 (d, J = 17.5 Hz, 1H), 5.44 (d, J = 11.2 Hz, 1H), 4.42 - 3.87 (m, 2H), 3.68 (s, 2H), 3.36 (s, 3H), 3.20 (s, 3H), 3.14 - 3.05 (m, 2H), 2.89 (s, 3H). MS (ESI) m/z: 601 [M + H]$^+$. |
| II-77 | 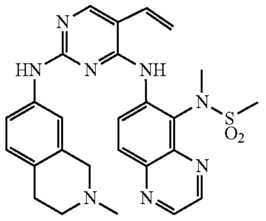 [SMILES: C=Cc1cnc(Nc2ccc3c(c2)CN(C)CC3)nc1Nc1ccc2nccnc2c1N(C)S(C)(=O)=O] | $^1$H NMR (600 MHz, DMSO-$d_6$) δ 10.20 (s, 1H), 10.07 (s, 1H), 9.03 (d, J = 1.9 Hz, 1H), 9.00 (d, J = 1.8 Hz, 1H), 8.81 - 8.56 (m, 1H), 8.41 (s, 1H), 8.22 (d, J = 9.3 Hz, 1H), 7.53 - 7.49 (m, OH), 7.40 (s, 1H), 7.05 - 7.00 (m, 1H), 6.83 (dd, J = 17.5, 11.1 Hz, 1H), 5.86 (dd, J = 17.5, 2.5 Hz, 1H), 5.45 (d, J = 11.2 Hz, 1H), 3.94 - 3.74 (m, 2H), 3.35 (s, 3H), 3.19 (s, 3H), 3.15 - 3.10 (m, 2H), 3.04 - 2.90 (m, 2H), 2.86 (s, 3H). MS (ESI) m/z: 517 [M + H]$^+$. |
| II-78 | 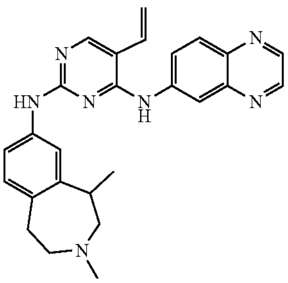 | $^1$H NMR (600 MHz, DMSO-$d_6$) δ 10.07 (s, 1H), 9.93 (s, 1H), 9.01 (d, J = 7.3, 1.6 Hz, 1H), 8.97 (d, J = 4.2, 1.8 Hz, 1H), 8.74 - 8.59 (m, 1H), 8.39 (s, 1H), 8.14 - 8.11 (m, 1H), 7.48 (s, 1H), 7.43 - 7.34 (m, 1H), 7.05 - 6.94 (m, 1H), 6.85 - 6.77 (m, 1H), 5.85 (dd, J = 17.4, 2.5 Hz, 1H), 5.44 (d, J = 11.2 Hz, 1H), 3.35 (s, 3H), 3.28 - 3.21 (m, 3H), 3.19 (s, 3H), 3.14 - 3.10 (m, 1H), 2.92 - 2.81 (m, 3H), 2.80 (s, 3H), 1.07 - 0.94 (m, 3H). MS (ESI) m/z: 545 [M + H]$^+$. |

-continued

| No. | Structure | $^1H$ NMR and/or MS data |
|---|---|---|
| III-1 | 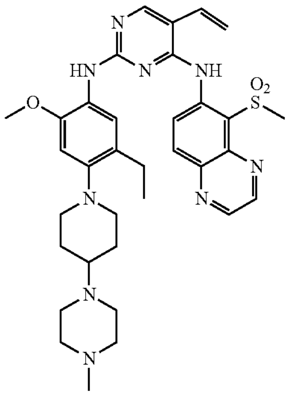 | $^1H$ NMR (600 MHz, DMSO-$d_6$) δ 10.72 (s, 1H), 9.09 - 9.05 (m, 2H), 9.03 - 8.99 (m, 1H), 8.68 - 8.61 (m, 1H), 8.39 (s, 1H), 8.16 (d, J = 9.3 Hz, 1H), 7.35 (s, 1H), 6.82 - 6.74 (m, 2H), 5.85 (d, J = 17.2 Hz, 1H), 5.46 (d, J = 11.2 Hz, 1H), 3.79 (s, 3H), 3.68 (s, 3H), 3.55 - 3.19 (m, 9H), 3.07 - 3.02 (m, 2H), 2.86 (s, 3H), 2.77 - 2.68 (m, 2H), 2.28 (s, 2H), 2.12 - 2.06 (m, 2H), 1.78 - 1.70 (m, 2H), 0.85 - 0.70 (m, 3H). MS (ESI) m/z: 658 $[M + H]^+$. |
| III-2 | 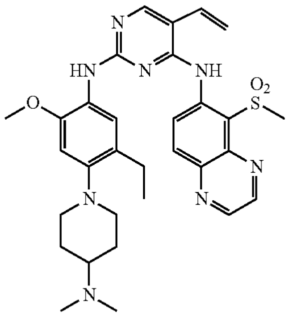 | $^1H$ NMR (600 MHz, DMSO-$d_6$) δ 10.75 (s, 1H), 9.35 (s, 1H), 9.09 (d, J = 1.8 Hz, 1H), 9.05 (d, J = 1.8 Hz, 1H), 8.57 - 8.48 (m, 1H), 8.37 (s, 1H), 8.20 (d, J = 9.4 Hz, 1H), 7.29 (s, 1H), 6.84 - 6.73 (m, 2H), 5.87 (d, J = 17.3 Hz, 1H), 5.50 (d, J = 11.1 Hz, 1H), 3.79 (s, 3H), 3.66 (s, 3H), 3.29 - 3.24 (m, 1H), 3.04 - 3.00 (m, 2H), 2.82 (s, 3H), 2.82 (s, 3H), 2.74 - 2.69 (m, 2H), 2.28 - 2.18 (m, 2H), 2.12 - 2.04 (m, 2H), 1.80 - 1.70 (m, 2H), 0.73 (s, 3H). MS (ESI) m/z: 603 $[M + H]^+$. |
| III- 3 | 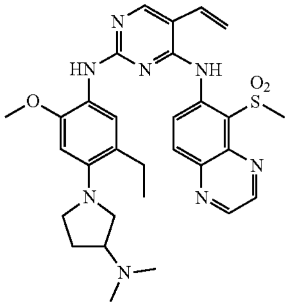 | $^1H$ NMR (600 MHz, DMSO-$d_6$) δ 10.76 (s, 1H), 10.26 (s, 1H), 9.09 (d, J = 1.9 Hz, 1H), 9.03 (d, J = 1.9 Hz, 1H), 8.58 (s, 1H), 8.42 - 8.34 (m, 1H), 8.22 - 8.13 (m, 1H), 7.26 (s, 1H), 6.78 (dd, J = 17.2, 11.1 Hz, 1H), 6.75 (s, 1H), 5.87 (d, J = 17.3 Hz, 1H), 5.48 (d, J = 11.2 Hz, 1H), 3.80 (s, 3H), 3.69 (s, 3H), 3.35 - 3.29 (m, 2H), 3.23 - 3.14 (m, 2H), 3.10 - 3.03 (m, 1H), 2.87 (s, 3H), 2.86 (s, 3H), 2.38 - 2.25 (m, 3H), 2.20 - 2.11 (m, 1H), 0.86 - 0.70 (m, 3H). MS (ESI) m/z: 589 $[M + H]^+$. |
| III-4 | 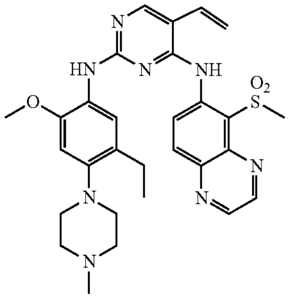 | $^1H$ NMR (600 MHz, DMSO-$d_6$) δ 9.92 (s, 1H), 9.33 (s, 1H), 9.10 (d, J = 1.7 Hz, 1H), 9.05 (d, J = 1.7 Hz, 1H), 8.57 - 8.49 (m, 1H), 8.38 (s, 1H), 8.22 (d, J = 9.3 Hz, 1H), 7.35 (s, 1H), 6.80 (dd, J = 17.2, 10.9 Hz, 1H), 6.77 (s, 1H), 5.88 (d, J = 17.2 Hz, 1H), 5.50 (d, J = 11.1 Hz, 1H), 3.81 (s, 3H), 3.67 (s, 3H), 3.53 - 3.48 (m, 2H), 3.26 - 3.18 (m, 2H), 3.09 - 3.04 (m, 2H), 3.02 - 2.98 (m, 2H), 2.89 (s, 3H), 2.29 - 2.17 (m, 2H), 0.79 - 0.65 (m, 3H). MS (ESI) m/z: 575 $[M + H]^+$. |

-continued

| No. | Structure | ¹H NMR and/or MS data |
|---|---|---|
| III-5 | 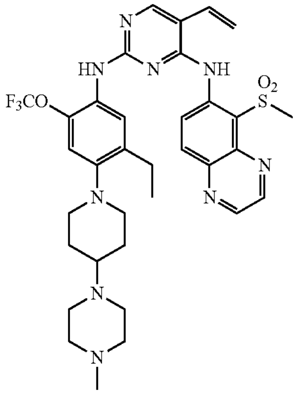 [SMILES: C=Cc1cnc(Nc2cc(CC)c(N3CCC(N4CCN(C)CC4)CC3)cc2OC(F)(F)F)nc1Nc1ccc2nccnc2c1S(C)(=O)=O] | $^1$H NMR (600 MHz, DMSO-$d_6$) δ 10.77 (s, 1H), 9.61 (s, 1H), 9.05 (d, J = 2.0 Hz, 1H), 8.98 (d, J = 1.9 Hz, 1H), 8.69 − 8.63 (m, 1H), 8.42 (s, 1H), 8.04 (d, J = 9.5 Hz, 1H), 7.42 (s, 1H), 7.07 (s, 1H), 6.77 (dd, J = 17.2, 11.2 Hz, 1H), 5.85 (d, J = 17.4 Hz, 1H), 5.45 (d, J = 11.3 Hz, 1H), 3.69 (s, 3H), 3.64 − 3.32 (m, 9H), 3.11 − 3.05 (m, 2H), 2.92 (s, 3H), 2.75 − 2.67 (m, 2H), 2.44 (q, J = 7.6 Hz, 2H), 2.21 − 2.14 (m,2H), 1.87 − 1.75 (m, 2H), 0.93 (t, J = 7.6 Hz, 3H). MS (ESI) m/z: 712 $[M + H]^+$. |
| III-6 | 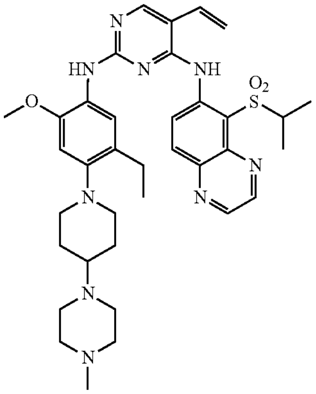 [SMILES: C=Cc1cnc(Nc2cc(CC)c(N3CCC(N4CCN(C)CC4)CC3)cc2OC)nc1Nc1ccc2nccnc2c1S(=O)(=O)C(C)C] | $^1$H NMR (600 MHz, DMSO-$d_6$) δ 10.84 (s, 1H), 9.26 (s, 1H), 9.07 (d, J = 1.9 Hz, 1H), 9.03 (d, J = 1.9 Hz, 1H), 8.72 − 8.52 (m, 1H), 8.40 (s, 1H), 8.19 (d, J = 9.3 Hz, 1H), 7.31 (s, 1H), 6.87 − 6.70 (m, 2H), 5.87 (d, J = 17.3 Hz, 1H), 5.50 (d, J = 11.2 Hz, 1H), 4.44 (p, J = 6.9 Hz, 1H), 3.80 (s, 3H), 3.75 − 3.22 (m, 9H), 3.07 − 2.99 (m, 2H), 2.90 (s, 3H), 2.76 − 2.68 (m, 2H), 2.28 − 2.21 (m, 2H), 2.16 − 2.07 (m, 2H), 1.82 − 1.67 (m, 2H), 1.19 (d, J = 6.8 Hz, 6H), 0.80 − 0.67 (m, 3H). MS (ESI) m/z: 686 $[M + H]^+$. |
| III-7 | 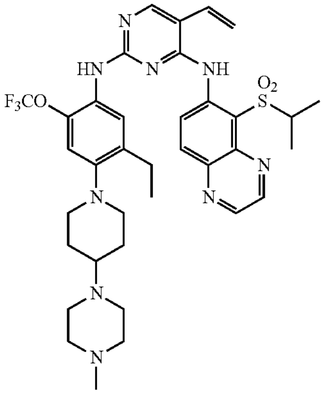 [SMILES: C=Cc1cnc(Nc2cc(CC)c(N3CCC(N4CCN(C)CC4)CC3)cc2OC(F)(F)F)nc1Nc1ccc2nccnc2c1S(=O)(=O)C(C)C] | MS (ESI) m/z: 740 $[M + H]^+$. |
| III-8 | 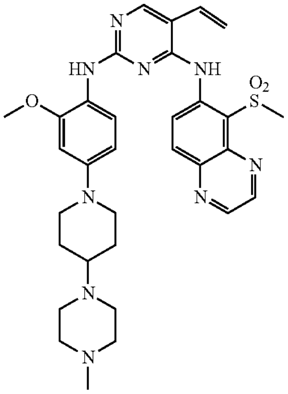 | $^1$H NMR (600 MHz, DMSO-$d_6$) δ 10.86 (s, 1H), 9.50 (s, 1H), 9.08 (d, J = 1.9 Hz, 1H), 9.03 (d, J = 2.0 Hz, 1H), 8.66 (s, 1H), 8.34 − 8.29 (m, 1H), 8.24 (d, J = 9.3 Hz, 1H), 7.26 (d, J = 8.7 Hz, 1H), 6.76 (dd, J = 17.2, 11.2 Hz, 1H), 6.72 (d, J = 2.5 Hz, 1H), 6.46 − 6.38 (m, 1H), 5.86 (d, J = 17.2 Hz, 1H), 5.50 (d, J = 11.3 Hz, 1H), 3.90 − 3.83 (m, 2H), 3.79 (s, 3H), 3.69 (s, 3H), 3.65 − 3.28 (m, 9H), 2.88 (s, 3H), 2.79 − 2.73 (m, 2H), 2.20 − 2.04 (m, 2H), 1.74 − 1.65 (m, 2H). MS (ESI) m/z: 630 $[M + H]^+$. |

-continued

| No. | Structure | $^1$H NMR and/or MS data |
|---|---|---|
| III-9 | 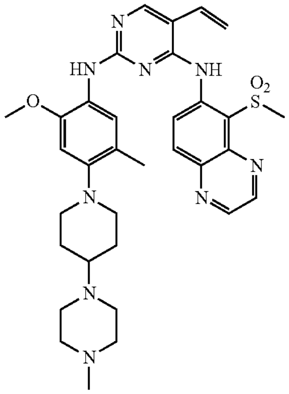 | $^1$H NMR (600 MHz, DMSO-$d_6$) δ 10.78 (s, 1H), 9.22 (s, 1H), 9.08 (d, J = 2.1 Hz, 1H), 9.02 (d, J = 2.0 Hz, 1H), 8.63 (s, 1H), 8.40 - 8.32 (m, 1H), 8.20 (d, J = 9.4 Hz, 1H), 7.28 (s, 1H), 6.78 (dd, J = 17.2, 11.1 Hz, 1H), 6.72 (s, 1H), 5.86 (d, J = 17.4 Hz, 1H), 5.48 (d, J = 11.2 Hz, 1H), 3.78 (s, 3H), 3.67 (s, 3H), 3.61 - 3.22 (m, 9H), 3.15 - 3.09 (m, 2H), 2.88 (s, 3H), 2.72 - 2.64 (m, 2H), 2.14 - 2.07 (m, 2H), 1.85 (s, 3H), 1.80 - 1.71 (m, 2H). MS (ESI) m/z: 644 $[M + H]^+$. |
| III-10 | 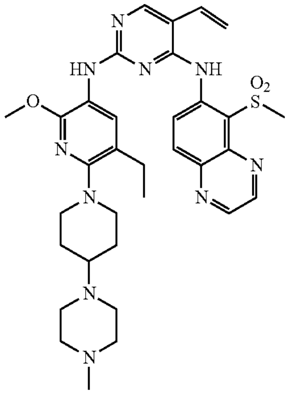 | $^1$H NMR (600 MHz, DMSO-$d_6$) δ 10.75 (s, 1H), 9.35 (s, 1H), 9.09 (d, J = 1.9 Hz, 1H), 9.03 (d, J = 1.9 Hz, 1H), 8.65 - 8.49 (m, 1H), 8.39 (s, 1H), 8.21 - 8.13 (m, 1H), 7.62 (s, 1H), 6.79 (dd, J = 17.2, 11.1 Hz, 1H), 5.87 (d, J = 17.2 Hz, 1H), 5.49 (d, J = 11.3 Hz, 1H), 3.85 (s, 3H), 3.69 (s, 3H), 3.63 - 3.47 (m, 9H), 3.45 - 3.38 (m, 2H), 2.90 (s, 3H), 2.85 - 2.77 (m, 2H), 2.30 - 2.22 (m, 2H), 2.15 - 2.08 (m, 2H), 1.81 - 1.72 (m, 2H), 0.90 - 0.72 (m, 3H). MS (ESI) m/z: 659 $[M + H]^+$. |
| III-11 | 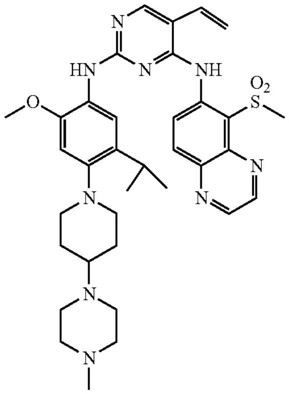 | $^1$H NMR (600 MHz, DMSO-$d_6$) δ 10.78 (s, 1H), 9.51 (s, 1H), 9.06 (d, J = 1.8 Hz, 1H), 9.01 (d, J = 1.8 Hz, 1H), 8.38 - 8.32 (m, 1H), 8.17 - 8.04 (m, 2H), 7.26 (s, 1H), 6.81 (s, 1H), 6.78 (dd, J = 17.3, 11.1 Hz, 1H), 5.87 (d, J = 17.2 Hz, 1H), 5.48 (d, J = 11.2 Hz, 1H), 3.76 (s, 3H), 3.67 (s, 3H), 3.62 - 3.30 (m, 9H), 3.02 - 2.98 (m, 1H), 2.90 (s, 3H), 2.88 - 2.87 (m, 2H), 2.81 - 2.73 (m, 2H), 2.18 - 2.10 (m, 2H), 1.83 - 1.73 (m, 2H), 0.93 - 0.82 (m, 6H). MS (ESI) m/z: 672 $[M + H]^+$. |
| III-12 | 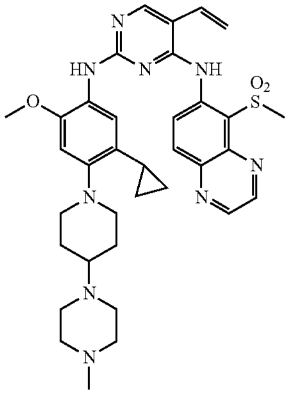 | $^1$H NMR (600 MHz, DMSO-$d_6$) δ 10.76 (s, 1H), 9.25 - 9.09 (m, 1H), 9.06 (d, J = 1.8 Hz, 1H), 9.02 - 8.97 (m, 1H), 8.67 (s, 1H), 8.40 - 8.29 (m, 1H), 8.14 - 8.02 (m, 1H), 6.87 (s, 1H), 6.76 (dd, J = 17.3, 11.1 Hz, 1H), 6.72 (s, 1H), 5.84 (d, J = 17.2 Hz, 1H), 5.46 (d, J = 11.1 Hz, 1H), 3.77 (s, 3H), 3.69 (s, 3H), 3.39 - 3.33 (m, 2H), 3.30 - 2.98 (m, 6H), 2.86 (s, 4H), 2.73 (t, J = 11.7 Hz, 2H), 2.15 - 2.05 (m, 3H), 2.01 - 1.93 (m, 1H), 1.85 - 1.74 (m, 3H), 0.65 (s, 2H), 0.31 (s, 2H). MS (ESI) m/z: 670 $[M + H]^+$. |

-continued

| No. | Structure | $^1$H NMR and/or MS data |
|---|---|---|
| III-13 | 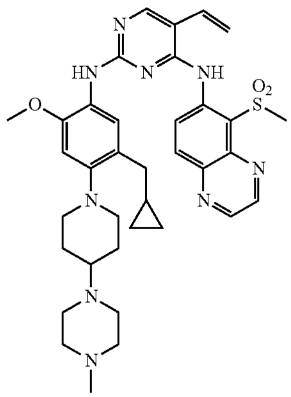 | $^1$H NMR (600 MHz, DMSO-$d_6$) δ 10.56 (s, 1H), 9.25 (s, 1H), 8.89 (d, J = 1.8 Hz, 1H), 8.84 (d, J = 1.8 Hz, 1H), 8.41 – 8.27 (m, 1H), 8.19 – 8.12 (m, 1H), 7.97 (d, J = 8.9 Hz, 1H), 7.23 (s, 1H), 6.63 – 6.53 (m, 2H), 5.68 (d, J = 17.2 Hz, 1H), 5.30 (d, J = 11.3 Hz, 1H), 3.59 (s, 3H), 3.46 (s, 3H), 3.42 – 2.90 (m, 9H), 2.85 – 2.80 (m, 2H), 2.70 (s, 3H), 2.57 – 2.50 (m, 2H), 1.98 – 1.90 (m, 4H), 1.59 – 1.50 (m, 2H), 0.40 – 0.31 (m, 1H), 0.06 – −0.04 (m, 2H), −0.29 – −0.41 (m, 2H). MS (ESI) m/z: 684 $[M + H]^+$. |
| III-14 | 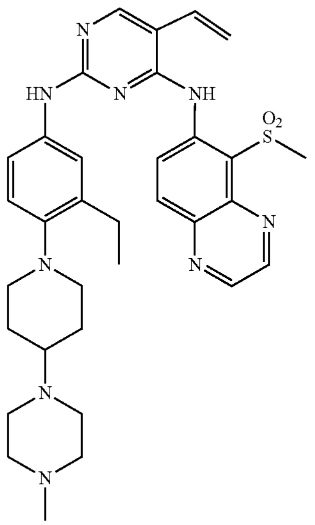 [SMILES: C=Cc1cnc(Nc2ccc(N3CCC(N4CCN(C)CC4)CC3)c(CC)c2)nc1Nc1ccc2nccnc2c1S(C)(=O)=O] | $^1$H NMR (600 MHz, DMSO-$d_6$) δ 10.68 (s, 1H), 9.90 (s, 1H), 9.07 (d, J = 1.8 Hz, 1H), 9.00 (d, J = 1.8 Hz, 1H), 8.89 – 8.75 (m, 1H), 8.44 (s, 1H), 8.25 (d, J = 9.6 Hz, 1H), 7.41 – 7.31 (m, 2H), 6.95 (d, J = 8.8 Hz, 1H), 6.79 (dd, J = 17.3, 11.1 Hz, 1H), 5.85 (d, J = 17.4 Hz, 1H), 5.43 (d, J = 11.3 Hz, 1H), 3.71 (s, 3H), 3.66 – 3.26 (m, 9H), 3.07 – 2.99 (m, 2H), 2.89 (s, 3H), 2.72 – 2.64 (m, 2H), 2.47 – 2.38 (m, 2H), 2.15 – 2.09 (m, 2H), 1.83 – 1.70 (m, 2H), 0.97 – 0.84 (m, 3H). MS (ESI) m/z: 628 $[M + H]^+$. |
| III-15 | 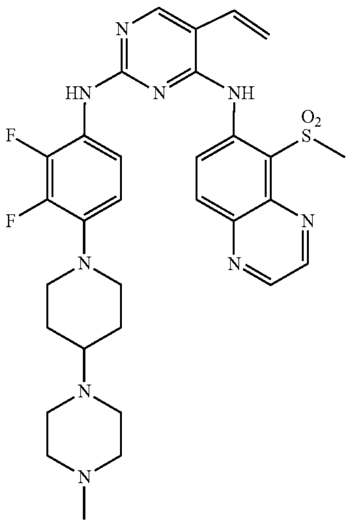 [SMILES: C=Cc1cnc(Nc2ccc(N3CCC(N4CCN(C)CC4)CC3)c(F)c2F)nc1Nc1ccc2nccnc2c1S(C)(=O)=O] | $^1$H NMR (600 MHz, DMSO-$d_6$) δ 10.75 (s, 1H), 9.50 (s, 1H), 9.05 – 9.00 (m, 1H), 8.98 – 8.93 (m, 1H), 8.91 – 8.83 (m, 1H), 8.43 (s, 1H), 8.05 (d, J = 9.5 Hz, 1H), 7.21 (t, J = 8.5 Hz, 1H), 6.84 (t, J = 8.8 Hz, 1H), 6.75 (dd, J = 17.3, 11.1 Hz, 1H), 5.82 (d, J = 17.3 Hz, 1H), 5.41 (d, J = 11.2 Hz, 1H), 3.73 (s, 3H), 3.64 – 3.11 (m, 11H), 2.88 (s, 3H), 2.78 – 2.71 (m, 2H), 2.17 – 2.11 (m, 2H), 1.81 – 1.72 (m, 2H). MS (ESI) m/z: 636 $[M + H]^+$. |

-continued

| No. | Structure | $^1$H NMR and/or MS data |
|---|---|---|
| III-16 | 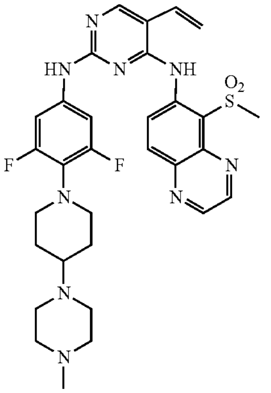 [SMILES: C=Cc1cnc(Nc2cc(F)c(N3CCC(N4CCN(C)CC4)CC3)c(F)c2)nc1Nc1ccc2nccnc2c1S(C)(=O)=O] | $^1$H NMR (600 MHz, DMSO-$d_6$) δ 10.58 (s, 1H), 9.92 (s, 1H), 9.05 (d, J = 1.9 Hz, 1H), 8.98 (d, J = 1.9 Hz, 1H), 8.93 – 8.89 (m, 1H), 8.53 (s, 1H), 8.27 (d, J = 9.4 Hz, 1H), 7.37 (d, J = 12.1 Hz, 2H), 6.79 (dd, J = 17.3, 11.1 Hz, 1H), 5.86 (d, J = 17.4 Hz, 1H), 5.43 (d, J = 11.3 Hz, 1H), 3.76 (s, 3H), 3.58 – 3.22 (m, 9H), 3.19 – 3.13 (m, 2H), 3.05 – 2.99 (m, 2H), 2.86 (s, 3H), 2.07 – 2.01 (m, 2H), 1.73 – 1.64 (m, 2H). MS (ESI) m/z: 636 $[M + H]^+$. |
| III-17 | 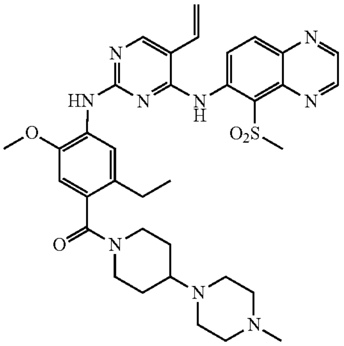 [SMILES: C=Cc1cnc(Nc2cc(CC)c(C(=O)N3CCC(N4CCN(C)CC4)CC3)cc2OC)nc1Nc1ccc2nccnc2c1S(C)(=O)=O] | $^1$H NMR (600 MHz, DMSO-$d_6$) δ 10.75 – 10.65 (m, 1H), 9.06 (d, J = 1.8 Hz, 1H), 9.02 – 8.96 (m, 1H), 8.85 (s, 1H), 8.80 – 8.69 (m, 1H), 8.47 (s, 1H), 8.21 (d, J = 9.4 Hz, 1H), 7.61 (d, J = 8.8 Hz, 1H), 6.88 (d, J = 15.9 Hz, 1H), 6.80 (dd, J = 17.2, 11.2 Hz, 1H), 5.86 (d, J = 17.4 Hz, 1H), 5.46 (d, J = 11.2 Hz, 1H), 4.64 – 4.58 (m, 1H), 3.83 – 3.81 (m, 3H), 3.74 – 3.72 (m, 3H), 3.24 – 2.90 (m, 12H), 2.82 (s, 3H), 2.26 – 1.79 (m, 4H), 1.63 – 1.39 (m, 2H), 0.78 – 0.66 (m, 3H). MS (ESI) m/z: 686 $[M + H]^+$. |
| III-18 | 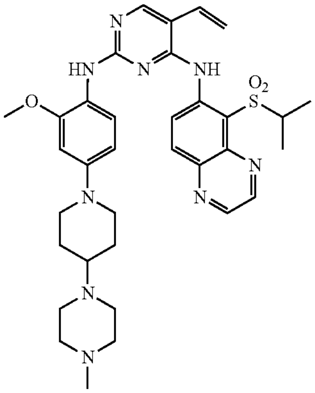 [SMILES: C=Cc1cnc(Nc2ccc(N3CCC(N4CCN(C)CC4)CC3)cc2OC)nc1Nc1ccc2nccnc2c1S(=O)(=O)C(C)C] | $^1$H NMR (600 MHz, DMSO-$d_6$) δ 10.98 (s, 1H), 9.36 (s, 1H), 9.05 (d, J = 1.8 Hz, 1H), 9.01 (d, J = 1.9 Hz, 1H), 8.85 – 8.78 (m, 1H), 8.32 (s, 1H), 8.22 (d, J = 9.3 Hz, 1H), 7.50 (d, J = 7.9 Hz, 1H), 7.32 – 7.27 (m, 1H), 7.13 (d, J = 7.9 Hz, 1H), 6.75 (dd, J = 17.3, 11.0 Hz, 1H), 5.85 (d, J = 17.4 Hz, 1H), 5.50 (d, J = 11.3 Hz, 1H), 4.50 – 4.41 (m, 1H), 3.90 – 3.84 (m, 2H), 3.80 (s, 3H), 3.71 – 3.25 (m, 9H), 2.88 (s, 3H), 2.80 – 2.72 (m, 2H), 2.17 – 2.08 (m, 2H), 1.74 – 1.64 (m, 2H), 1.20 (d, J = 6.9 Hz, 6H). MS (ESI) m/z: 658 $[M + H]^+$. |
| III-19 | 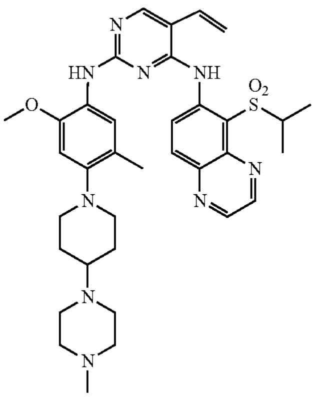 [SMILES: C=Cc1cnc(Nc2cc(C)c(N3CCC(N4CCN(C)CC4)CC3)cc2OC)nc1Nc1ccc2nccnc2c1S(=O)(=O)C(C)C] | $^1$H NMR (600 MHz, DMSO-$d_6$) δ 10.86 (s, 1H), 9.05 (d, J = 2.1 Hz, 1H), 9.01 (d, J = 1.9 Hz, 1H), 8.82 – 8.66 (m, 1H), 8.39 (s, 1H), 8.18 (d, J = 9.4 Hz, 1H), 7.31 (s, 1H), 6.77 (dd, J = 17.3, 11.0 Hz, 1H), 6.72 (s, 1H), 5.85 (d, J = 17.3 Hz, 1H), 5.48 (d, J = 11.2 Hz, 1H), 4.46 (p, J = 6.8 Hz, 1H), 3.79 (s, 3H), 3.73 – 3.19 (m, 9H), 3.16 – 3.07 (m, 2H), 2.88 (s, 3H), 2.72 – 2.64 (m, 2H), 2.13 – 2.05 (m, 2H), 1.86 (s, 3H), 1.81 – 1.69 (m, 2H), 1.20 (d, J = 6.9 Hz, 6H). MS (ESI) m/z: 672 $[M + H]^+$. |

-continued

| No. | Structure | $^1H$ NMR and/or MS data |
| --- | --- | --- |
| III-20 | 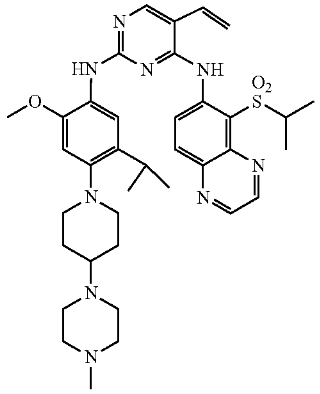 [SMILES: C=Cc1cnc(Nc2cc(C(C)C)c(N3CCC(N4CCN(C)CC4)CC3)cc2OC)nc1Nc1ccc2nccnc2c1S(=O)(=O)C(C)C] | $^1H$ NMR (600 MHz, DMSO-$d_6$) δ 10.87 (s, 1H), 9.25 (s, 1H), 9.03 (d, J = 1.8 Hz, 1H), 8.98 (d, J = 1.9 Hz, 1H), 8.81 – 8.61 (m, 1H), 8.37 (s, 1H), 8.15 – 8.05 (m, 1H), 7.31 (s, 1H), 6.83 (s, 1H), 6.76 (dd, J = 17.3, 11.1 Hz, 1H), 5.86 (d, J = 17.3 Hz, 1H), 5.49 (d, J = 11.2 Hz, 1H), 4.50 – 4.38 (m, 1H), 3.78 (s, 3H), 3.51 (d, J = 232.3 Hz, 9H), 3.22 – 3.12 (m, 1H), 3.07 – 2.99 (m, 2H), 2.89 (s, 3H), 2.84 – 2.72 (m, 2H), 2.19 – 2.07 (m, 2H), 1.86 – 1.70 (m, 2H), 1.23 (d, J = 6.8 Hz, 6H), 0.98 – 0.81 (m, 6H). MS (ESI) m/z: 700 $[M + H]^+$. |
| III-21 | 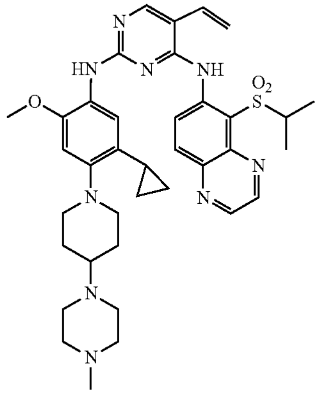 [SMILES: C=Cc1cnc(Nc2cc(C3CC3)c(N3CCC(N4CCN(C)CC4)CC3)cc2OC)nc1Nc1ccc2nccnc2c1S(=O)(=O)C(C)C] | $^1H$ NMR (600 MHz, DMSO-$d_6$) δ 10.99 – 10.82 (m, 1H), 9.21 – 9.08 (m, 1H), 9.07 – 9.02 (m, 1H), 8.99 – 8.97 (m, 1H), 8.89 – 8.64 (m, 1H), 8.48 – 8.30 (m, 1H), 8.19 – 7.92 (m, 1H), 6.90 (s, 1H), 6.82 – 6.62 (m, 2H), 5.85 (dd, J = 17.4, 3.6 Hz, 1H), 5.48 (d, J = 11.2 Hz, 1H), 4.52 – 4.42 (m, 1H), 3.78 (s, 3H), 3.70 – 3.18 (m, 11H), 2.88 (s, 3H), 2.81 – 2.62 (m, 2H), 2.13 (d, J = 11.7 Hz, 2H), 1.88 – 1.71 (m, 2H), 1.57 – 1.48 (m, 1H), 1.28 – 1.21 (m, 6H), 0.69 – 0.58 (m, 2H), 0.37 – 0.27 (m, 2H). MS (ESI) m/z: 698 $[M + H]^+$. |
| IV-1 | 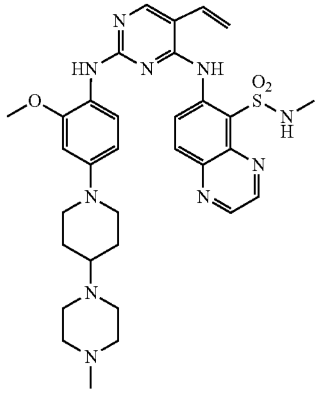 | $^1H$ NMR (600 MHz, DMSO-$d_6$) δ 10.65 (s, 1H), 9.21 (s, 1H), 9.02 – 8.97 (m, 2H), 8.83 – 8.73 (m, 1H), 8.32 (s, 1H), 8.16 (d, J = 9.3 Hz, 1H), 7.55 – 7.46 (m, 1H), 7.33 – 7.25 (m, 1H), 6.76 (dd, J = 17.2, 11.2 Hz, 1H), 6.74 – 6.71 (m, 1H), 6.41 (s, 1H), 5.84 (d, J = 17.2 Hz, 1H), 5.48 (d, J = 11.1 Hz, 1H), 3.88 – 3.81 (m, 2H), 3.79 (s, 3H), 3.65 – 2.95 (m, 9H), 2.85 (s, 3H), 2.79 – 2.71 (m, 2H), 2.44 – 2.40 (m, 3H), 2.13 – 2.06 (m, 2H), 1.72 – 1.64 (m, 2H). MS (ESI) m/z: 645 $[M + H]^+$. |
| IV-2 | 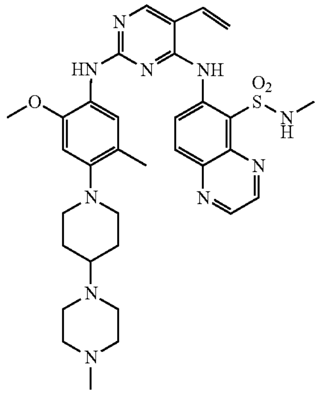 | $^1H$ NMR (600 MHz, DMSO-$d_6$) δ 10.66 (s, 1H), 9.36 (s, 1H), 9.06 (d, J = 1.7 Hz, 1H), 9.04 (d, J = 1.8 Hz, 1H), 8.56 – 8.45 (m, 1H), 8.37 (s, 1H), 8.20 (d, J = 9.2 Hz, 1H), 7.51 – 7.40 (m, 1H), 7.23 (s, 1H), 6.82 (dd, J = 17.1, 11.1 Hz, 1H), 6.70 (s, 1H), 5.88 (d, J = 17.2 Hz, 1H), 5.52 (d, J = 11.2 Hz, 1H), 3.79 (s, 3H), 3.69 – 3.22 (m, 9H), 3.13 – 3.06 (m, 2H), 2.90 (s, 3H), 2.69 – 2.61 (m, 2H), 2.40 – 2.36 (m, 3H), 2.15 – 2.05 (m, 2H), 1.82 – 1.69 (m, 5H). MS (ESI) m/z: 659 $[M + H]^+$. |

-continued

| No. | Structure | $^1H$ NMR and/or MS data |
|---|---|---|
| IV-3 | 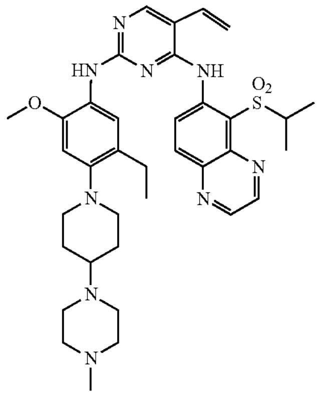 | $^1H$ NMR (600 MHz, DMSO-$d_6$) δ 10.62 (s, 1H), 9.48 (s, 1H), 9.06 (d, J = 1.9 Hz, 1H), 9.04 (d, J = 1.9 Hz, 1H), 8.53 - 8.41 (m, 1H), 8.38 (s, 1H), 8.17 (d, J = 9.3 Hz, 1H), 7.47 (d, J = 5.2 Hz, 1H), 7.26 (s, 1H), 6.82 (dd, J = 17.2, 11.1 Hz, 1H), 6.76 (s, 1H), 5.89 (d, J = 17.3 Hz, 1H), 5.53 (d, J = 11.1 Hz, 1H), 3.80 (s, 3H), 3.74 - 3.26 (m, 9H), 3.04 - 2.97 (m, 2H), 2.91 (s, 3H), 2.77 - 2.66 (m, 2H), 2.42 - 2.36 (m, 3H), 2.24 - 2.07 (m, 4H), 1.85 - 1.71 (m, 2H), 0.81 - 0.62 (m, 3H). MS (ESI) m/z: 673 $[M + H]^+$. |
| IV-4 | 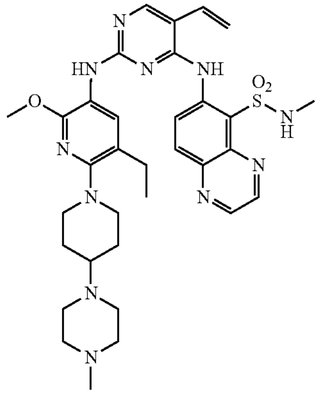 | $^1H$ NMR (600 MHz, DMSO-$d_6$) δ 10.51 (s, 1H), 9.07 (s, 1H), 9.04 - 8.98 (m, 2H), 8.70 - 8.57 (m, 1H), 8.39 (s, 1H), 8.09 (d, J = 9.3 Hz, 1H), 7.64 (s, 1H), 7.49 (q, J = 4.8 Hz, 1H), 6.79 (dd, J = 17.2, 11.1 Hz, 1H), 5.85 (d, J = 17.2 Hz, 1H), 5.47 (d, J = 11.2 Hz, 1H), 3.85 (s, 3H), 3.82 - 3.15 (m, 11H), 2.87 (s, 3H), 2.83 - 2.75 (m, 2H), 2.41 (d, J = 5.0 Hz, 3H), 2.31 - 2.23 (m, 2H), 2.12 - 2.05 (m, 2H), 1.83 - 1.69 (m, 2H), 0.86 - 0.73 (m, 3H). MS (ESI) m/z: 674 $[M + H]^+$. |
| IV-5 | 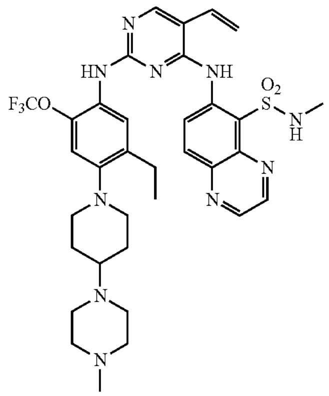 [SMILES: C=Cc1cnc(Nc2cc(CC)c(N3CCC(N4CCN(C)CC4)CC3)cc2OC(F)(F)F)nc1Nc1ccc2nccnc2c1S(=O)(=O)NC] | $^1H$ NMR (600 MHz, DMSO-$d_6$) δ 10.51 (s, 1H), 9.48 (s, 1H), 9.00 - 8.94 (m, 2H), 8.76 - 8.66 (m, 1H), 8.41 (s, 1H), 7.98 (d, J = 9.5 Hz, 1H), 7.49 (q, J = 5.1 Hz, 1H), 7.42 (s, 1H), 7.05 (s, 1H), 6.77 (dd, J = 17.2, 11.1 Hz, 1H), 5.84 (d, J = 17.3 Hz, 1H), 5.45 (d, J = 11.2 Hz, 1H), 3.91 - 3.23 (m, 9H), 3.10 - 3.03 (m, 2H), 2.90 (s, 3H), 2.72 - 2.65 (m, 2H), 2.46 (q, J = 7.5 Hz, 2H), 2.41 (d, J = 5.0 Hz, 3H), 2.16 - 2.10 (m, 2H), 1.83 - 1.73 (m, 2H), 0.94 (t, J = 7.5 Hz, 3H). MS (ESI) m/z: 727 $[M + H]^+$. |
| IV-6 | 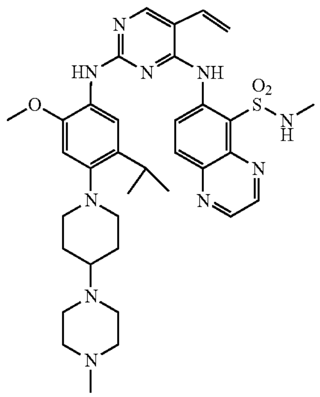 | $^1H$ NMR (600 MHz, DMSO-$d_6$) δ 10.64 (s, 1H), 9.70 (s, 1H), 9.04 - 9.02 (m, 2H), 8.66 - 8.45 (m, 1H), 8.35 (s, 1H), 8.13 - 8.03 (m, 1H), 7.51 (q, J = 5.4 Hz, 1H), 7.24 (s, 1H), 6.84 (s, 1H), 6.80 (dd, J = 17.3, 11.1 Hz, 1H), 5.90 (d, J = 17.1 Hz, 1H), 5.53 (d, J = 11.2 Hz, 1H), 3.79 (s, 3H), 3.70 - 3.24 (m, 9H), 3.16 - 3.08 (m, 1H), 3.05 - 2.99 (m, 2H), 2.92 (s, 3H), 2.84 - 2.75 (m, 2H), 2.43 (d, J = 4.9 Hz, 3H), 2.21 - 2.14 (m, 2H), 1.87 - 1.76 (m, 2H), 0.92 - 0.82 (m, 6H). MS (ESI) m/z: 687 $[M + H]^+$. |

-continued

| No. | Structure | $^1$H NMR and/or MS data |
|---|---|---|
| IV-7 | 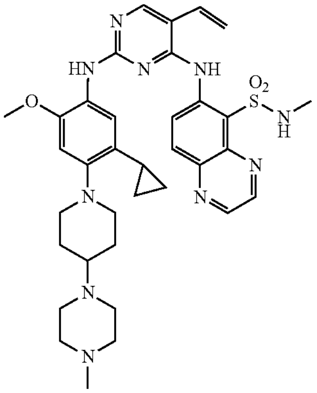 | $^1$H NMR (600 MHz, DMSO-$d_6$) δ 10.64 (s, 1H), 9.57 (s, 1H), 9.07 – 8.89 (m, 2H), 8.67 – 8.47 (m, 1H), 8.40 – 8.25 (m, 1H), 8.18 – 8.01 (m, 1H), 7.16 – 7.11 (m, 1H), 6.83 (s, 1H), 6.78 (dd, J = 17.2, 11.1 Hz, 1H), 6.72 (s, 1H), 5.88 (d, J = 17.4 Hz, 1H), 5.53 (d, J = 11.2 Hz, 1H), 3.78 (s, 3H), 3.75 – 3.25 (m, 11H), 2.91 (s, 3H), 2.77 – 2.69 (m, 2H), 2.43 (d, J = 4.9 Hz, 3H), 2.20 – 2.12 (m, 2H), 2.01 – 1.91 (m, 1H), 1.88 – 1.77 (m, 2H), 0.73 – 0.56 (m, 2H), 0.37 – 0.22 (m, 2H). MS (ESI) m/z: 685 $[M + H]^+$. |
| IV-8 | 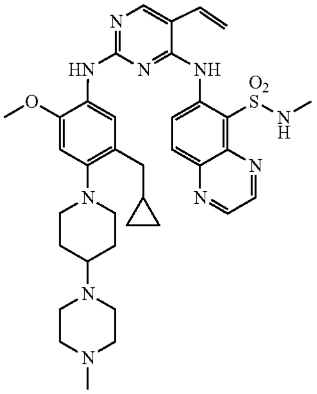 | $^1$H NMR (600 MHz, DMSO-$d_6$) δ 10.41 (s, 1H), 9.32 – 9.20 (m, 1H), 8.86 (d, J = 1.9 Hz, 1H), 8.85 (d, J = 1.9 Hz, 1H), 8.44 – 8.32 (m, 1H), 8.19 (s, 1H), 7.97 – 7.89 (m, 1H), 7.32 (q, J = 4.3 Hz, 1H), 7.25 (s, 1H), 6.68 – 6.57 (m, 2H), 5.70 (d, J = 17.2 Hz, 1H), 5.34 (d, J = 11.2 Hz, 1H), 3.62 (s, 3H), 3.58 – 3.08 (m, 9H), 2.88 – 2.81 (m, 2H), 2.73 (s, 3H), 2.60 – 2.48 (m, 2H), 2.22 (d, J = 5.0 Hz, 3H), 2.03 – 1.89 (m, 4H), 1.64 – 1.51 (m, 2H), 0.37 (s, 1H), 0.03 (d, J = 22.4 Hz, 2H), −0.24 – −0.37 (m, 2H). MS (ESI) m/z: 699 $[M + H]^+$. |
| IV-9 | 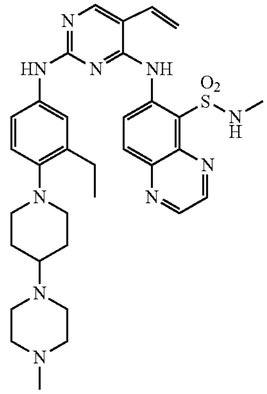 [SMILES: C=Cc1cnc(Nc2ccc(N3CCC(N4CCN(C)CC4)CC3)c(CC)c2)nc1Nc1ccc2nccnc2c1S(=O)(=O)NC] | $^1$H NMR (600 MHz, DMSO-$d_6$) δ 10.48 (s, 1H), 9.98 (s, 1H), 9.04 – 8.99 (m, 2H), 8.89 – 8.68 (m, 1H), 8.43 (s, 1H), 8.21 (d, J = 9.4 Hz, 1H), 7.49 (q, J = 5.2 Hz, 1H), 7.36 (s, 1H), 7.33 – 7.27 (m, 1H), 6.92 (d, J = 8.7 Hz, 1H), 6.80 (dd, J = 17.3, 11.1 Hz, 1H), 5.86 (d, J = 17.2 Hz, 1H), 5.45 (d, J = 11.2 Hz, 1H), 3.83 – 3.24 (m, 9H), 3.04 – 2.97 (m, 2H), 2.89 (s, 3H), 2.70 – 2.62 (m, 2H), 2.41 (d, J = 5.0 Hz, 3H), 2.17 – 2.05 (m, 4H), 1.81 – 1.68 (m, 2H), 0.93 – 0.85 (m, 3H). MS (ESI) m/z: 643 $[M + H]^+$. |
| IV-10 | 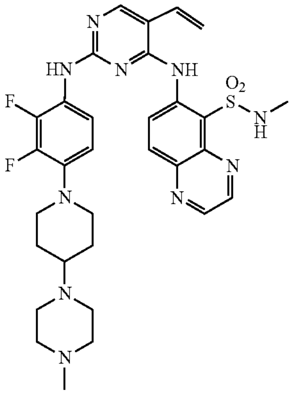 [SMILES: C=Cc1cnc(Nc2ccc(N3CCC(N4CCN(C)CC4)CC3)c(F)c2F)nc1Nc1ccc2nccnc2c1S(=O)(=O)NC] | $^1$H NMR (600 MHz, DMSO-$d_6$) δ 10.49 (s, 1H), 9.48 (s, 1H), 8.97 – 8.95 (m, 1H), 8.95 – 8.94 (m, 1H), 8.93 – 8.87 (m, 1H), 8.40 (s, 1H), 8.01 (d, J = 9.4 Hz, 1H), 7.51 (q, J = 5.0 Hz, 1H), 7.20 (t, J = 8.5 Hz, 1H), 6.83 (t, J = 8.9 Hz, 1H), 6.75 (dd, J = 17.3, 11.1 Hz, 1H), 5.81 (d, J = 17.2 Hz, 1H), 5.42 (d, J = 11.1 Hz, 1H), 3.51 – 3.42 (m, 2H), 3.40 – 2.94 (m, 9H), 2.87 (s, 3H), 2.78 – 2.69 (m, 2H), 2.43 (d, J = 5.1 Hz, 3H), 2.18 – 2.09 (m, 2H), 1.81 – 1.71 (m, 2H). MS (ESI) m/z: 651 [M + H]+. |

-continued

| No. | Structure | ¹H NMR and/or MS data |
|---|---|---|
| IV-11 | 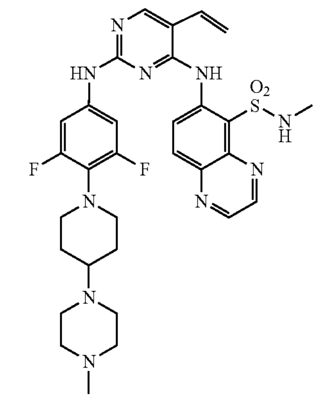 [SMILES: C=Cc1cnc(Nc2cc(F)c(N3CCC(N4CCN(C)CC4)CC3)c(F)c2)nc1Nc1ccc2nccnc2c1S(=O)(=O)NC] | ¹H NMR (600 MHz, DMSO-$d_6$) δ 10.34 (s, 1H), 9.94 (s, 1H), 9.00 (d, J = 1.8 Hz, 1H), 8.99 (d, J = 1.8 Hz, 1H), 8.96 - 8.90 (m, 1H), 8.52 (s, 1H), 8.24 (d, J = 9.5 Hz, 1H), 7.55 (d, J = 5.1 Hz, 1H), 7.37 (d, J = 12.2 Hz, 2H), 6.79 (dd, J = 17.3, 11.1 Hz, 1H), 5.86 (d, J = 17.3 Hz, 1H), 5.45 (d, J = 11.3 Hz, 1H), 3.68 - 3.22 (m, 9H), 3.19 - 3.12 (m, 2H), 3.08 - 2.98 (m. 2H), 2.86 (s, 3H), 2.48 (d, J = 5.1 Hz, 3H), 2.12 - 1.99 (m, 2H), 1.77 - 1.62 (m, 2H). MS (ESI) m/z: 651 $[M + H]^+$. |
| IV-12 | 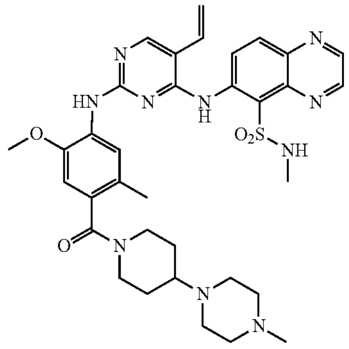 | ¹H NMR (600 MHz, DMSO-d6) δ 10.46 (s, 1H), 9.05 - 8.96 (m, 2H), 8.80 (s, 1H), 8.75 (d, J = 9.2 Hz, 1H), 8.47 (s, 1H), 8.23 - 8.08 (m, 1H), 7.65 - 7.60 (m, 1H), 7.52 - 7.48 (m, 1H), 6.90 - 6.85 (m, 1H), 6.81 (dd, J = 17.3, 11.1 Hz, 1H), 5.86 (d, J = 17.2 Hz, 1H), 5.46 (d, J = 11.2 Hz, 1H), 4.66 - 4.55 (m, 1H), 3.82 (s, 3H), 3.74 - 3.03 (m, 10H), 2.98 - 2.89 (m, 1H), 2.82 (s, 3H), 2.80 - 2.76 (m, 1H), 2.47 - 2.40 (m, 3H), 2.28 - 1.97 (m, 3H), 1.92 - 1.76 (m, 1H), 1.67 - 1.39 (m, 2H), 0.77 - 0.63 (m, 3H). MS (ESI) m/z: 717 $[M + H]^+$. |
| IV-13 | 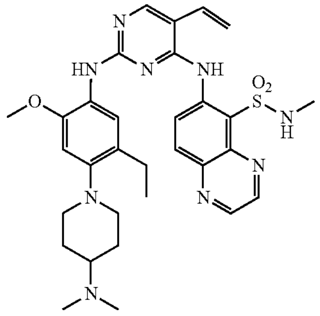 | ¹H NMR (600 MHz, DMSO-d6) δ 10.62 (s, 1H), 10.04 (s, 1H), 9.07 (d, J = 1.9 Hz, 1H), 9.05 (d, J = 1.8 Hz, 1H), 8.53 - 8.43 (m, 1H), 8.38 (s, 1H), 8.17 (d, J = 9.3 Hz, 1H), 7.48 (q, J = 4.8 Hz, 1H), 7.27 (s, 1H), 6.82 (dd, J = 17.2, 11.0 Hz, 1H), 6.77 (s, 1H), 5.89 (d, J = 17.2 Hz, 1H), 5.53 (d, J = 11.1 Hz, 1H), 3.80 (s, 3H), 3.32 - 3.22 (m, 1H), 3.05 - 2.96 (m, 2H), 2.83 (s, 3H), 2.82 (s, 3H), 2.76 - 2.66 (m, 2H), 2.38 (d, J = 4.9 Hz, 3H), 2.23 - 2.13 (m, 2H), 2.11 - 2.04 (m, 2H), 1.82 - 1.67 (m, 2H), 0.78 - 0.61 (m, 3H). MS (ESI) m/z: 618 $[M + H]^+$. |
| IV-14 | 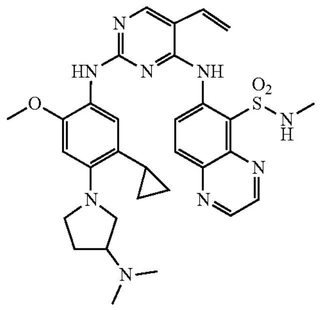 | ¹H NMR (600 MHz, DMSO-d6) δ 10.60 (s, 1H), 10.23 (s, 1H), 9.05 (d, J = 1.9 Hz, 1H), 9.03 (d, J = 1.9 Hz, 1H), 8.58 - 8.47 (m, 1H), 8.36 (s, 1H), 8.14 (d, J = 9.0 Hz, 1H), 7.49 (q, J = 4.8 Hz, 1H), 7.25 (s, 1H), 6.80 (dd, J = 17.2, 11.1 Hz, 1H), 6.74 (s, 1H), 5.88 (d, J = 17.3 Hz, 1H), 5.51 (d, J = 11.2 Hz, 1H), 4.00 - 3.92 (m, 1H), 3.80 (s, 3H), 3.30 (t, J = 5.5 Hz, 2H), 3.19 - 3.13 (m, 1H), 3.07 - 3.01 (m, 1H), 2.89 - 2.83 (m, 6H), 2.41 (d, J = 5.0 Hz, 3H), 2.36 - 2.29 (m, 1H), 2.22 (s, 2H), 2.17 - 2.08 (m, 1H), 0.81 - 0.62 (m, 3H). MS (ESI) m/z: 604 [M + H]+. |

-continued

| No. | Structure | ¹H NMR and/or MS data |
| --- | --- | --- |
| IV-15 | 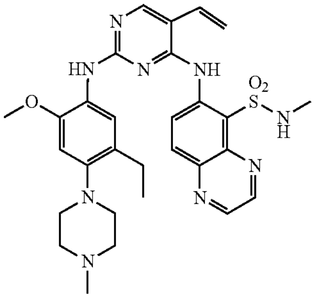 | ¹H NMR (600 MHz, DMSO-d6) δ 10.57 (s, 1H), 10.21 - 10.06 (m, 1H), 9.04 (d, J = 1.9 Hz, 1H), 9.03 (d, J = 1.9 Hz, 1H), 8.59 - 8.49 (m, 1H), 8.40 (s, 1H), 8.16 (d, J = 9.3 Hz, 1H), 7.49 (q, J = 4.5 Hz, 1H), 7.37 (s, 1H), 6.81 (dd, J = 17.2, 11.0 Hz, 1H), 6.77 (s, 1H), 5.88 (d, J = 17.2 Hz, 1H), 5.50 (d, J = 11.2 Hz, 1H), 3.82 (s, 3H), 3.54 - 3.46 (m, 2H), 3.23 - 3.18 (m, 2H), 3.08 - 2.96 (m, 4H), 2.89 (s, 3H), 2.40 (d, J = 5.1 Hz, 3H), 2.26 - 2.16 (m, 2H), 0.81 - 0.62 (m, 3H). MS (ESI) m/z: 590 [M + H]⁺. |
| IV-16 | 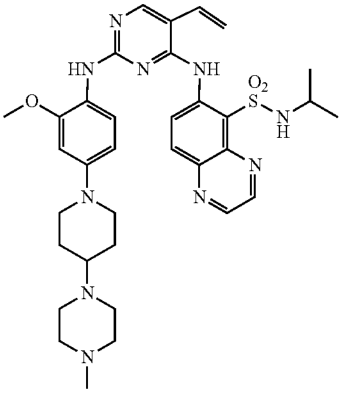 [SMILES: C=Cc1cnc(Nc2ccc(N3CCC(N4CCN(C)CC4)CC3)cc2OC)nc1Nc1ccc2nccnc2c1S(=O)(=O)NC(C)C] | ¹H NMR (600 MHz, DMSO-d6) δ 10.78 (s, 1H), 9.62 (s, 1H), 9.14 - 9.02 (m, 2H), 8.59 (s, 1H), 8.40 - 8.26 (m, 1H), 8.22 (d, J = 9.3 Hz, 1H), 7.54 (d, J = 7.4 Hz, 1H), 7.21 (d, J = 8.7 Hz, 1H), 6.80 (dd, J = 17.1, 11.2 Hz, 1H), 6.75 - 6.69 (m, 1H), 6.42 - 6.24 (m, 1H), 5.89 (d, J = 17.4 Hz, 1H), 5.54 (d, J = 11.1 Hz, 1H), 3.88 - 3.81 (m, 2H), 3.79 (s, 3H), 3.75 - 3.24 (m, 10H), 2.90 (s, 3H), 2.76 - 2.66 (m, 2H), 2.18 - 2.09 (m, 2H), 1.76 - 1.63 (m, 2H), 0.79 (d, J = 6.5 Hz, 6H). MS (ESI) m/z: 673 [M + H]⁺. |
| IV-17 | 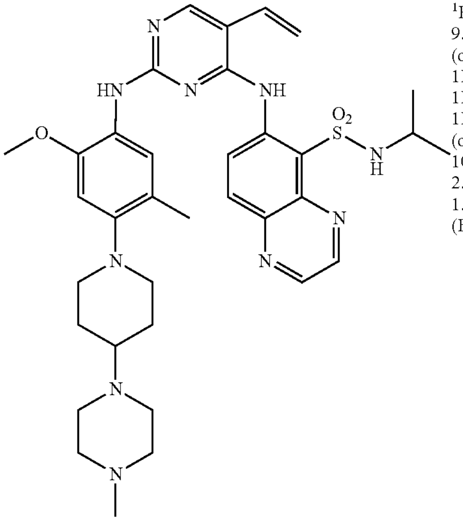 | ¹H NMR (600 MHz, DMSO-d6) δ 10.62 (s, 1H), 9.13 - 9.07 (m, 1H), 9.06 (d, J =1.8 Hz, 1H), 9.02 (d, J = 1.9 Hz, 1H), 8.63 - 8.55 (m, 1H), 8.38 (s, 1H), 8.16 (d, J = 9.3 Hz, 1H), 7.52 (d, J = 7.5 Hz, 1H), 7.28 (s, 1H), 6.81 (dd, J = 17.2, 11.0 Hz, 1H), 6.70 (s, 1H), 5.86 (d, J = 17.2 Hz, 1H), 5.48 (d, J = 11.2 Hz, 1H), 3.79 (s, 3H), 3.70 - 3.16 (m, 10H), 3.12 - 3.04 (m, 2H), 2.86 (s, 3H), 2.72 - 2.60 (m, 2H), 2.13 - 2.02 (m, 2H), 1.78 (s, 3H), 1.75 - 1.71 (m, 2H), 0.78 (d, J = 6.5 Hz, 6H). MS (ESI) m/z: 687 [M + H]⁺. |

-continued

| No. | Structure | $^1H$ NMR and/or MS data |
|---|---|---|
| IV-18 | 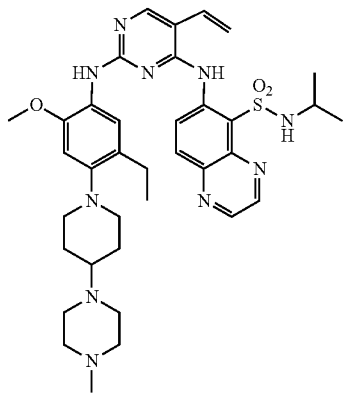 [SMILES: C=Cc1cnc(Nc2cc(CC)c(N3CCC(N4CCN(C)CC4)CC3)cc2OC)nc1Nc1ccc2nccnc2c1S(=O)(=O)NC(C)C] | $^1H$ NMR (600 MHz, DMSO-d6) δ 10.60 (s, 1H), 9.19 (s, 1H), 9.07 - 9.05 (m, 1H), 9.04 - 9.01 (m, 1H), 8.61 - 8.49 (m, 1H), 8.38 (s, 1H), 8.13 (d, J = 9.5 Hz, 1H), 7.53 (d, J = 7.4 Hz, 1H), 7.31 (s, 1H), 6.81 (dd, J = 17.3, 11.1 Hz, 1H), 6.77 (s, 1H), 5.87 (d, J = 17.2 Hz, 1H), 5.50 (d, J = 11.1 Hz, 1H), 3.80 (s, 3H), 3.72 - 3.14 (m, 10H), 3.05 - 2.95 (m, 2H), 2.88 (s, 3H), 2.76 - 2.67 (m, 2H), 2.28 - 2.18 (m, 2H), 2.14 - 2.06 (m, 2H), 1.80 - 1.69 (m, 2H), 0.79 (d, J = 6.6 Hz, 6H), 0.77 - 0.70 (m, 3H). MS (ESI) m/z: 701 $[M + H]^+$. |

Biological Activity Assay:

Growth Inhibitory Activity of Compounds on Cell Lines Stably Transfected with Kinase The activity of compounds against various mutants of kinase EGFR was evaluated by their effect of inhibiting growth of $BaF_3$ cell lines stably transfected with kinase. The specific test method was given as follows:

1) Culture medium: DMEM (Dulbecco's modified eagle medium) or RPMI 1640 (containing 10% fetal bovine serum, 100 μg/mL ampicillin, 100 μg/mL streptomycin).

2) Reagent: MTS reaction solution (containing 2 mg/mL of MTS [3-(4,5-di methylthiazol-2-yl)-5-(3-carboxymethoxyphenyl)-2-(4-sulfophenyl)-2H-tetrazolium, inner Salt]; 100 μg/mL of PES (phenazine methosulfate)).

3) Compound test: cells were incubated into a 96-well culture plate, the volume of cytosol was 90 μL, and then 10 μL of the compound at each gradient concentration was added. That is, the highest concentration was 10 μM, which was diluted stepwise by ⅓, and 8 concentration points were set in total; 0.1% DMSO (dimethyl sulfoxide) was contained in the system. The cell plate with uniformly mixed compound was cultured in a cell culture incubator (37° C.; 5% 002) for 48 h, then 20 μL of MTS reaction solution was added, uniformly mixed and incubated in the cell culture incubator (37° C.; 5% $CO_2$) for 1-4 h; OD values at 490 nm were measured by a microplate reader (VARIOSKAN FLASH, Thermo). Two parallels were set in each group of experiments, with 0.1% (a final concentration) DMSO as a negative control, and a culture medium without cells and compounds as a blank control. The cell growth inhibition rate was calculated by the following formula:

$$\text{Cell growth inhibition rate } \% = 1 - (OD_{experimental\ group} - OD_{blank\ group}) / (OD_{negative\ group} - OD_{blank\ group}) \times 100\%.$$

4) $IC_{50}$ calculation: The semi-inhibitory concentration of the compounds acting on cells was calculated using GradPad Prism 5 software according to the measured cell growth inhibition rate.

The following table lists growth inhibitory activities of compounds on cell lines stably transfected with kinase:

| No. | Del | L858R | Del/T790M | L858R/T790M | Del/T790M/C797S | L858R/T790M/C797S |
|---|---|---|---|---|---|---|
| I-1 | ++++ | ++++ | ++++ | ++++ | ++++ | ++++ |
| I-2 | ++++ | ++++ | ++++ | ++++ | ++++ | ++++ |
| I-3 | +++ | ++++ | ++++ | +++ | ++++ | ++++ |
| I-4 | ++++ | ++++ | ++++ | ++++ | ++++ | ++++ |
| I-5 | ++++ | ++++ | ++++ | ++++ | ++++ | ++++ |
| I-6 | +++ | ++++ | ++++ | ++++ | ++++ | ++++ |
| I-7 | ++++ | ++++ | ++++ | ++++ | ++++ | ++++ |
| I-9 | ++++ | ++++ | ++++ | ++++ | ++++ | ++++ |
| I-10 | ++++ | ++++ | ++ | +++ | +++ | +++ |
| I-11 | ++++ | ++++ | +++ | +++ | +++ | +++ |
| I-13 | ++++ | ++++ | +++ | +++ | +++ | +++ |
| I-14 | +++ | ++++ | +++ | ++ | +++ | +++ |
| I-15 | ++++ | ++++ | ++++ | ++++ | ++++ | ++++ |
| I-16 | +++ | +++ | +++ | +++ | +++ | +++ |
| I-17 | +++ | +++ | +++ | +++ | +++ | +++ |
| I-18 | +++ | ++++ | +++ | +++ | ++++ | ++++ |
| I-19 | ++++ | +++ | +++ | ++++ | ++ | +++ |
| I-20 | ++ | +++ | +++ | +++ | ++ | ++ |
| I-21 | ++++ | ++++ | ++++ | ++++ | ++++ | ++++ |
| I-22 | +++ | +++ | +++ | ++++ | ++ | +++ |
| I-23 | +++ | +++ | +++ | +++ | ++ | +++ |
| I-24 | +++ | ++++ | +++ | +++ | +++ | +++ |
| I-25 | ++++ | ++++ | ++++ | +++ | +++ | ++++ |
| II-1 | ++++ | ++++ | ++++ | ++++ | ++++ | ++++ |
| II-2 | ++++ | ++++ | ++++ | ++++ | ++++ | ++++ |
| II-3 | ++++ | ++++ | ++++ | ++++ | ++++ | ++++ |
| II-4 | ++++ | ++++ | ++++ | ++++ | ++++ | ++++ |

-continued

| No. | Del | L858R | Del/T790M | L858R/T790M | Del/T790M/C797S | L858R/T790M/C797S |
|---|---|---|---|---|---|---|
| II-5 | +++ | +++ | ++++ | ++++ | +++ | +++ |
| II-6 | +++ | +++ | ++++ | +++ | ++++ | +++ |
| II-7 | ++++ | ++++ | ++++ | ++++ | ++++ | ++++ |
| II-8 | +++ | +++ | +++ | +++ | +++ | +++ |
| II-9 | +++ | +++ | ++++ | +++ | +++ | ++++ |
| II-10 | +++ | +++ | +++ | +++ | +++ | +++ |
| II-11 | ++++ | +++ | ++++ | +++ | +++ | +++ |
| II-12 | ++++ | ++++ | ++++ | ++++ | ++++ | ++++ |
| II-14 | ++++ | ++++ | ++++ | ++++ | +++ | ++++ |
| II-15 | ++++ | ++++ | ++++ | ++++ | ++++ | ++++ |
| II-16 | +++ | ++ | +++ | ++ | +++ | +++ |
| II-17 | +++ | ++ | +++ | +++ | +++ | +++ |
| II-18 | +++ | +++ | ++++ | +++ | +++ | +++ |
| II-19 | ++ | ++ | +++ | ++ | ++++ | +++ |
| II-20 | ++++ | ++++ | ++++ | ++++ | ++++ | ++++ |
| II-21 | ++++ | ++++ | ++++ | ++++ | ++++ | ++++ |
| II-22 | +++ | +++ | +++ | +++ | +++ | ++ |
| II-23 | ++++ | ++++ | ++++ | ++++ | +++ | +++ |
| II-24 | ++++ | ++++ | ++++ | ++++ | +++ | +++ |
| II-25 | ++++ | ++++ | ++++ | ++++ | +++ | +++ |
| II-26 | ++++ | +++ | ++ | ++ | ++ | ++ |
| II-27 | ++++ | +++ | ++ | ++ | ++ | ++ |
| II-28 | ++++ | +++ | ++ | ++ | ++ | ++ |
| II-29 | +++ | +++ | ++ | ++ | ++ | ++ |
| II-30 | +++ | +++ | +++ | +++ | ++ | +++ |
| II-31 | ++++ | ++++ | ++++ | +++ | +++ | ++++ |
| II-32 | ++++ | ++++ | ++++ | +++ | +++ | +++ |
| II-33 | ++++ | ++++ | +++ | +++ | +++ | +++ |
| II-34 | +++ | +++ | +++ | +++ | +++ | +++ |
| II-35 | +++ | +++ | +++ | ++ | ++ | +++ |
| II-36 | ++++ | ++++ | ++++ | +++ | +++ | ++++ |
| II-37 | ++++ | ++++ | ++++ | +++ | +++ | ++++ |
| II-38 | ++++ | ++++ | ++++ | ++++ | +++ | ++++ |
| II-39 | ++++ | ++++ | ++++ | ++++ | ++++ | ++++ |
| II-40 | ++++ | ++++ | ++++ | +++ | ++++ | ++++ |
| II-41 | ++++ | ++++ | ++++ | +++ | ++++ | ++++ |
| II-42 | ++ | ++ | ++ | ++ | ++ | +++ |
| II-43 | +++ | +++ | +++ | ++ | +++ | +++ |
| II-44 | +++ | +++ | +++ | ++ | +++ | ++++ |
| II-45 | +++ | +++ | +++ | +++ | ++ | ++ |
| II-46 | +++ | +++ | +++ | ++++ | +++ | +++ |
| II-49 | ++ | ++ | ++ | +++ | +++ | +++ |
| II-50 | ++ | ++ | +++ | +++ | +++ | +++ |
| II-51 | +++ | ++ | +++ | +++ | +++ | +++ |
| II-52 | +++ | +++ | +++ | ++++ | ++++ | ++++ |
| II-53 | +++ | +++ | +++ | +++ | ++++ | ++++ |
| II-54 | ++++ | ++++ | ++++ | +++ | ++++ | ++++ |
| II-55 | +++ | +++ | +++ | +++ | +++ | +++ |
| II-59 | +++ | ++ | ++ | ++ | ++ | ++ |
| II-60 | +++ | +++ | ++ | ++ | +++ | +++ |
| II-61 | ++ | ++++ | ++ | ++ | +++ | +++ |
| II-62 | ++ | ++ | ++ | ++ | +++ | +++ |
| II-63 | +++ | ++ | +++ | +++ | +++ | +++ |
| II-64 | +++ | +++ | +++ | +++ | +++ | +++ |
| II-65 | +++ | +++ | +++ | +++ | +++ | +++ |
| II-66 | ++ | ++ | ++ | ++ | +++ | ++ |
| II-67 | +++ | +++ | +++ | +++ | +++ | +++ |
| II-68 | +++ | +++ | ++ | ++ | +++ | +++ |
| II-69 | +++ | +++ | ++ | +++ | ++ | +++ |
| II-70 | +++ | +++ | +++ | ++++ | ++++ | +++ |
| II-71 | +++ | +++ | ++++ | ++++ | ++++ | +++ |
| II-72 | +++ | +++ | ++ | +++ | +++ | ++++ |
| II-73 | ++ | ++ | ++ | ++ | ++ | +++ |
| II-74 | +++ | ++++ | +++ | +++ | +++ | +++ |
| II-76 | +++ | +++ | ++ | +++ | ++ | +++ |
| II-77 | ++++ | ++++ | ++++ | ++++ | +++ | ++++ |
| II-78 | ++++ | ++++ | +++ | ++++ | +++ | ++++ |
| III-1 | +++ | ++ | +++ | +++ | ++ | ++ |
| III-2 | ++ | ++ | +++ | +++ | ++ | +++ |
| III-3 | ++ | ++ | ++ | +++ | ++ | ++ |
| III-4 | ++ | ++ | ++ | +++ | ++ | ++ |
| III-5 | ++ | ++ | ++ | +++ | ++ | ++ |
| III-6 | +++ | +++ | +++ | +++ | +++ | +++ |
| III-9 | ++ | ++ | ++ | +++ | ++ | ++ |
| III-10 | ++ | ++ | ++ | +++ | ++ | ++ |
| III-11 | ++ | ++ | ++ | +++ | ++ | ++ |
| III-12 | +++ | ++ | +++ | +++ | ++ | +++ |

-continued

| No. | Del | L858R | Del/T790M | L858R/T790M | Del/T790M/C797S | L858R/T790M/C797S |
|---|---|---|---|---|---|---|
| III-13 | +++ | ++ | +++ | +++ | ++ | ++ |
| III-14 | +++ | +++ | +++ | +++ | ++ | +++ |
| III-16 | ++ | ++ | +++ | ++ | ++ | ++ |
| III-18 | ++ | +++ | ++ | +++ | ++ | ++ |
| III-19 | +++ | +++ | +++ | +++ | ++ | +++ |
| III-20 | ++ | +++ | ++ | +++ | ++ | ++ |
| III-21 | +++ | +++ | +++ | +++ | +++ | +++ |
| IV-1 | ++ | ++ | ++ | +++ | ++ | ++ |
| IV-2 | +++ | +++ | +++ | +++ | +++ | +++ |
| IV-3 | +++ | +++ | +++ | +++ | +++ | +++ |
| IV-4 | ++ | ++ | +++ | +++ | ++ | +++ |
| IV-5 | ++ | ++ | +++ | +++ | ++ | ++ |
| IV-6 | ++ | ++ | +++ | +++ | ++ | ++ |
| IV-7 | +++ | +++ | +++ | +++ | +++ | +++ |
| IV-8 | +++ | ++ | +++ | +++ | +++ | +++ |
| IV-9 | +++ | +++ | +++ | ++++ | +++ | +++ |
| IV-10 | +++ | +++ | +++ | ++++ | +++ | +++ |
| IV-11 | +++ | +++ | +++ | ++++ | +++ | +++ |
| IV-12 | ++ | ++ | ++ | +++ | ++ | ++ |
| IV-13 | +++ | +++ | +++ | +++ | +++ | +++ |
| IV-14 | +++ | +++ | +++ | +++ | +++ | +++ |
| IV-15 | +++ | +++ | +++ | +++ | +++ | +++ |
| IV-17 | ++ | +++ | +++ | +++ | ++ | ++ |
| IV-18 | +++ | +++ | +++ | +++ | ++ | ++ |

Note:
"++++" denotes $IC_{50} \leq 50$ nM;
"+++" denotes 50 nM < $IC_{50} \leq 500$ nM;
"++" denotes 500 nM < $IC_{50} \leq 2500$ nM.

The other compounds also have good inhibitory activities on the growth of the above cell lines stably transfected with kinase.

The invention claimed is:

1. A compound having the following general formula:

(II)

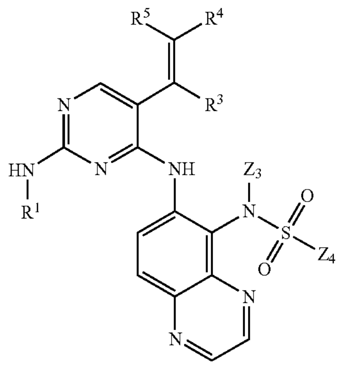

or a stereoisomer, a pharmaceutically acceptable salt or a pharmaceutically acceptable solvate thereof, wherein:

$R^1$ is selected from:

1)

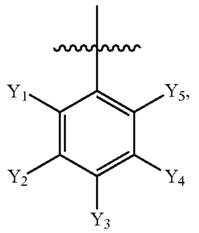

$Y_1$, $Y_2$, $Y_3$, $Y_4$, $Y_5$ each are independently selected from the following groups, and Y, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, N—(N-methyl-4-piperidyl) piperazinyl, N—(N-ethyl-4-piperidyl) piperazinyl, 4-(N-methyl-azetidin-3-yl) piperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(piperazinyl-1-) piperidyl, 4-(N-methylpiperazinyl-1-) piperidyl, 4-(N-ethylpiperazinyl-1-) piperidyl, 4-(N-isopropylpiperazinyl-1-) piperidyl, (6) cyclopropylmethylene, cyclobutylmethylene, cyclopentylmethylene, cyclohexylmethylene, benzyl, (7) 4-(N-methyl-1-piperazinyl) piperidyl-1-formyl, 4-(N-ethyl-1-piperazinyl) piperidyl-1-formyl, (8) amino, N,N-dimethylamino, N,N-diethylamino, N,N-di-n-propylamino, N,N-diisopropylamino, 2-hydroxyethylamino, 2-N,N-dimethylaminoethylamino, 3-N,N-dimethylaminopropylamino, 3-N,N-diethylaminopropylamino, 3-N,N-diisopropylaminopropylamino, N-methyl-N-(2-N,N-dimethylamino)ethylamino, (9)

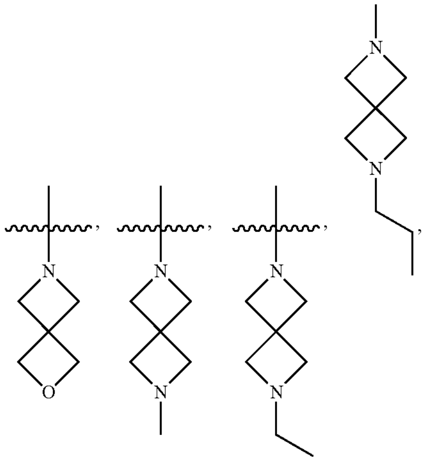

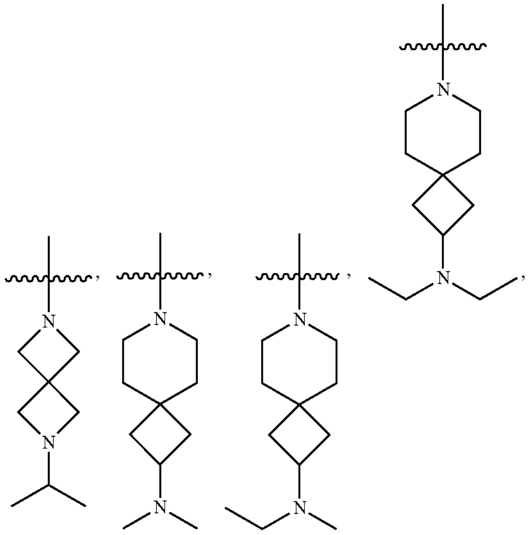

-continued

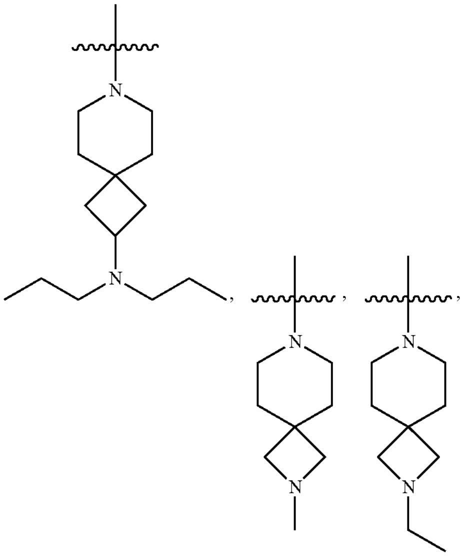

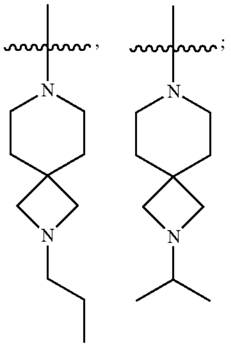

2)

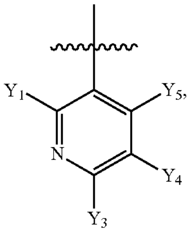

wherein $Y_1$, $Y_3$, $Y_4$, $Y_5$ each are independently selected from H, $C_1$-$C_6$ alkyl, $C_1$-$C_6$ alkoxy, 4-(N-methylpiperazinyl-1-) piperidyl, 4-(N-ethylpiperazinyl-1-) piperidyl, or 4-(N-isopropylpiperazinyl-1-) piperidyl, and Y, $Y_3$, $Y_4$, $Y_5$ are not hydrogen at the same time;

3)

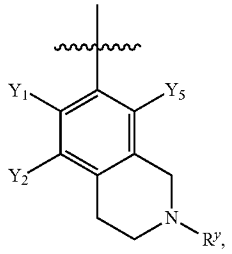

wherein, $Y_1$ is selected from H, $C_1$-$C_6$ alkyl, $C_1$-$C_6$ alkoxy, F, Cl, Br, or $C_1$-$C_6$ fluorine-containing alkoxy, $Y_2$, $Y_5$ are H, $R^y$ is selected from $C_1$-$C_6$ alkyl;

4)

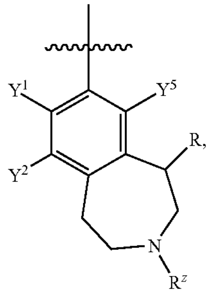

wherein, $Y_1$, $Y_2$, $Y_5$ are H, $R^z$, R each are independently selected from $C_1$-$C_6$ alkyl;

5) 3-pyrazolyl, 1-methyl-3-pyrazolyl, 1-ethyl-3-pyrazolyl, 1-isopropyl-3-pyrazolyl, 1,5-dimethyl-3-pyrazolyl, 1,5-diethyl-3-pyrazolyl, 1,5-diisopropyl-3-pyrazolyl, 1-methyl-5-ethyl-3-pyrazolyl, 1-methyl-5-isopropyl-3-pyrazolyl, 1-ethyl-5-methyl-3-pyrazolyl, 1-ethyl-5-isopropyl-3-pyrazolyl, 1-isopropyl-5-methyl-3-pyrazolyl, 1-isopropyl-5-ethyl-3-pyrazolyl, 4-pyrazolyl, 1-methyl-4-pyrazolyl, 1-ethyl-4-pyrazolyl, 1-isopropyl-4-pyrazolyl, 1,3-dimethyl-4-pyrazolyl, 1,3-diethyl-4-pyrazolyl, 1,3-diisopropyl-4-pyrazolyl, 1-methyl-3-ethyl-4-pyrazolyl, 1-methyl-3-isopropyl-4-pyrazolyl, 1-ethyl-3-methyl-4-pyrazolyl, 1-ethyl-3-isopropyl-4-pyrazolyl, 1-isopropyl-3-methyl-4-pyrazolyl, 1-isopropyl-3-ethyl-4-pyrazolyl;

$Z_3$, $Z_4$ each are independently selected from H, $C_1$-$C_6$ alkyl, $C_1$-$C_6$ fluorine-containing alkyl, or C3-$C_6$ cycloalkyl;

$R^3$, $R^4$, $R^5$ each are independently selected from H, $C_1$-$C_6$ alkyl, $C_3$-$C_6$ cycloalkyl, or phenyl; or, $R^3$, $R^4$ and carbon atoms linked thereto together form

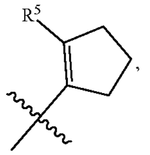

$R^5$ being selected from H, or $C_1$-$C_6$ alkyl.

2. A compound having the following general formula:

(III)

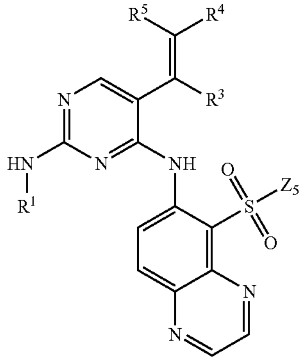

or a stereoisomer, a pharmaceutically acceptable salt or a pharmaceutically acceptable solvate thereof, wherein:

$R^1$ is selected from:

1)

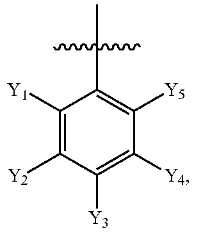

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-) piperidyl, 4-(N-ethylpiperazinyl-1-) piperidyl, 4-(N-isopropylpiperazinyl-1-) piperidyl, (6) cyclopropylmethylene, cyclobutylmethylene, cyclopentylmethylene, cyclohexylmethylene, (7) 4-(N-methyl-1-piperazinyl) piperidyl-1-formyl, 4-(N-ethyl-1-piperazinyl) piperidyl-1-formyl,

2)

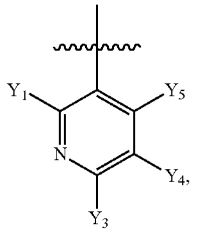

wherein:

$Y_1$, $Y_3$, $Y_4$, $Y_5$ each are independently selected from H, $C_1$-$C_6$ alkyl, $C_1$-$C_6$ alkoxy, 4-(N-methylpiperazinyl-1-) piperidyl, 4-(N-ethylpiperazinyl-1-) piperidyl, or 4-(N-isopropylpiperazinyl-1-) piperidyl, and $Y_1$, $Y_3$, $Y_4$, $Y_5$ are not hydrogen at the same time;

$Z_5$ is selected from $C_1$-$C_6$ alkyl;

$R^3$, $R^4$, $R^5$ each are independently selected from H, or $C_1$-$C_6$ alkyl.

3. A compound having the following general formula:

(IV)

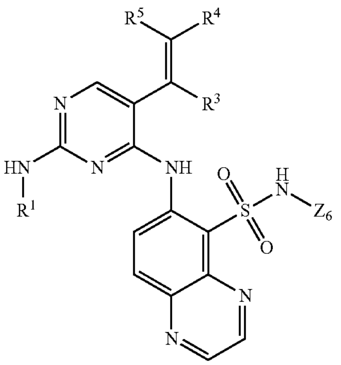

or a stereoisomer, a pharmaceutically acceptable salt or a pharmaceutically acceptable solvate thereof, wherein:

$R^1$ is selected from:

1)

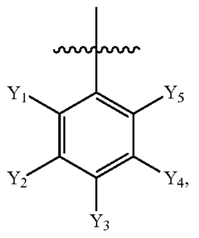

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

(1) H, F, Cl, Br, I, nitro, cyano, (2) $C_1$-$C_6$ alkyl, $C_1$-$C_6$ alkoxy, $C_1$-$C_6$ fluorine-containing alkoxy, $C_3$-$C_6$ cycloalkyl, (3) piperazinyl, N-methylpiperazinyl, N-ethylpiperazinyl, N-n-propylpiperazinyl, N-isopropylpiperazinyl, (4) 3-(N,N-dimethylamino)tetrahydropyrrolyl, 3-(N,N-diethylamino)tetrahydropyrrolyl, (5) 4-N,N-dimethylaminopiperidyl, 4-N,N-diethylaminopiperidyl, 4-N,N-diisopropylaminopiperidyl, 4-(N-methylpiperazinyl-1-) piperidyl, 4-(N-ethylpiperazinyl-1-) piperidyl, 4-(N-isopropylpiperazinyl-1-) piperidyl, (6) cyclopropylmethylene, cyclobutylmethylene, cyclopentylmethylene, cyclohexylmethylene, (7) 4-(N-methyl-1-piperazinyl) piperidyl-1-formyl, 4-(N-ethyl-1-piperazinyl) piperidyl-1-formyl,

2)

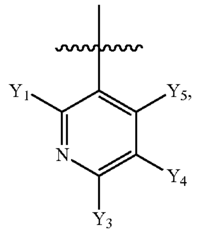

wherein:

$Y_1$, $Y_3$, $Y_4$, $Y_5$ each are independently selected from H, $C_1$-$C_6$ alkyl, $C_1$-$C_6$ alkoxy, 4-(N-methylpiperazinyl-1-) piperidyl, 4-(N-ethylpiperazinyl-1-) piperidyl, or 4-(N-isopropylpiperazinyl-1-) piperidyl, and $Y_1$, $Y_3$, $Y_4$, $Y_5$ are not hydrogen at the same time;

$Z_6$ is selected from $C_1$-C6 alkyl;

$R^3$, $R^4$, $R^5$ each are independently selected from H, or $C_1$-$C_6$ alkyl.

4. A compound selected from:

| No. | Structure |
|---|---|
| I-1 | 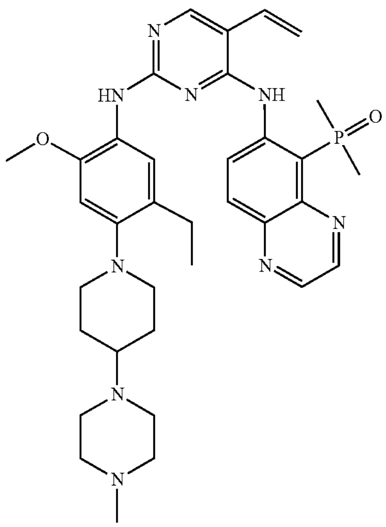 [SMILES: C=Cc1cnc(Nc2cc(CC)c(N3CCC(N4CCN(C)CC4)CC3)cc2OC)nc1Nc1ccc2nccnc2c1P(C)(C)=O] |
| I-2 | 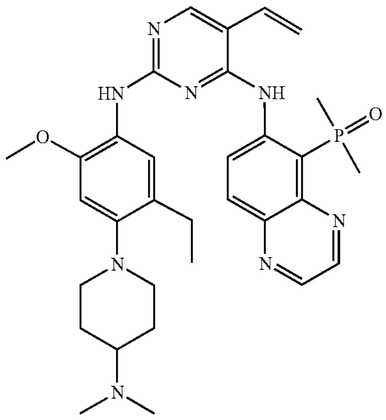 [SMILES: C=Cc1cnc(Nc2cc(CC)c(N3CCC(N(C)C)CC3)cc2OC)nc1Nc1ccc2nccnc2c1P(C)(C)=O] |

-continued
| No. | Structure |
|---|---|
| I-3 | 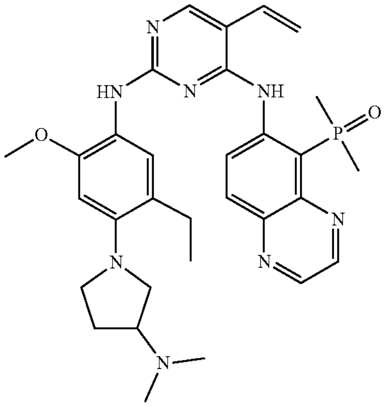 [SMILES: C=Cc1cnc(Nc2cc(CC)c(N3CCC(N(C)C)C3)cc2OC)nc1Nc1ccc2nccnc2c1P(C)(C)=O] |
| I-4 | 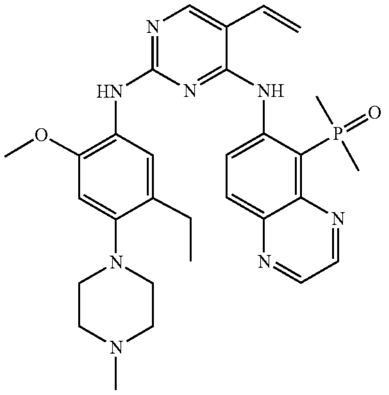 [SMILES: C=Cc1cnc(Nc2cc(CC)c(N3CCN(C)CC3)cc2OC)nc1Nc1ccc2nccnc2c1P(C)(C)=O] |
| I-5 | 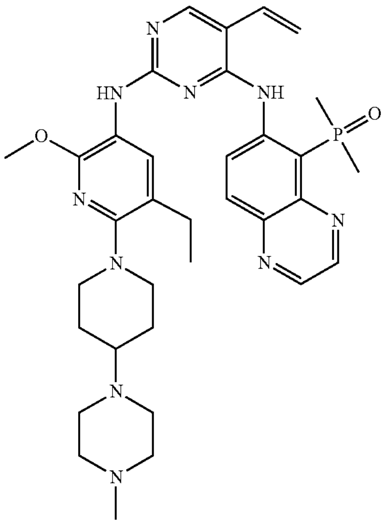 [SMILES: C=Cc1cnc(Nc2cc(CC)c(N3CCC(N4CCN(C)CC4)CC3)nc2OC)nc1Nc1ccc2nccnc2c1P(C)(C)=O] |
-continued
| No. | Structure |
|---|---|
| I-6 | 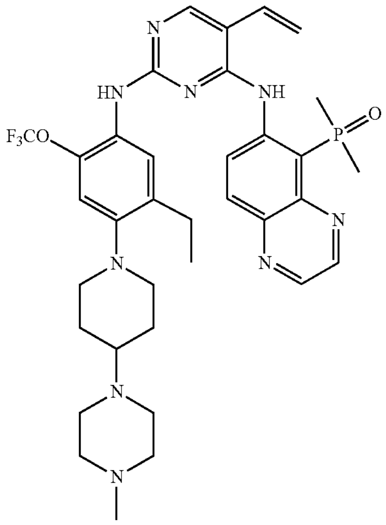 [SMILES: C=Cc1cnc(Nc2cc(CC)c(N3CCC(N4CCN(C)CC4)CC3)cc2OC(F)(F)F)nc1Nc1ccc2nccnc2c1P(C)(C)=O] |
| I-7 | 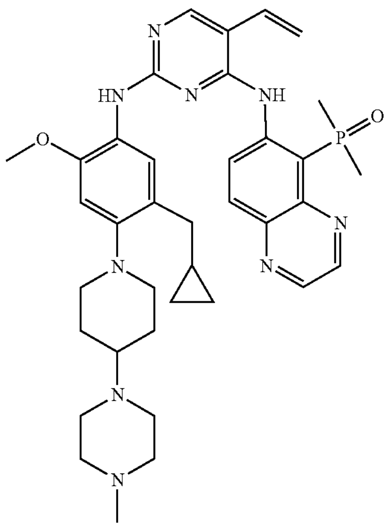 [SMILES: C=Cc1cnc(Nc2cc(CC3CC3)c(N3CCC(N4CCN(C)CC4)CC3)cc2OC)nc1Nc1ccc2nccnc2c1P(C)(C)=O] |
| I-8 | 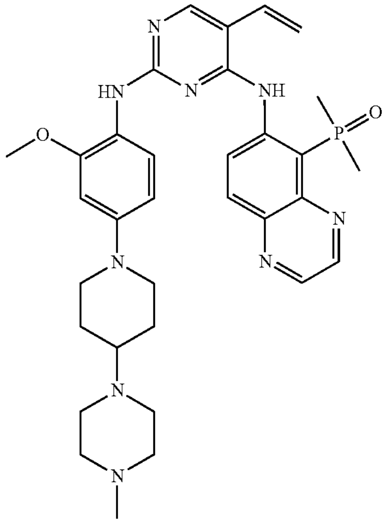 [SMILES: C=Cc1cnc(Nc2ccc(N3CCC(N4CCN(C)CC4)CC3)cc2OC)nc1Nc1ccc2nccnc2c1P(C)(C)=O] |

-continued
| No. | Structure |
|---|---|
| I-9 | 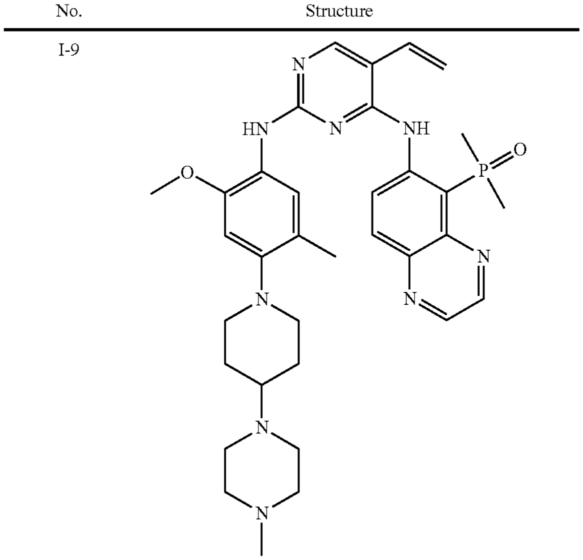 |
| I-10 | 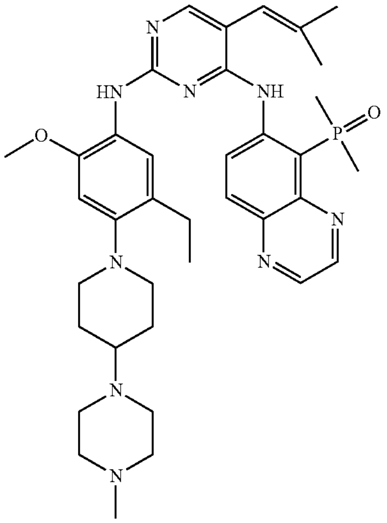 [SMILES: CCc1cc(Nc2ncc(C=C(C)C)c(Nc3ccc4nccnc4c3P(C)(C)=O)n2)c(OC)cc1N1CCC(N2CCN(C)CC2)CC1] |
| I-11 | 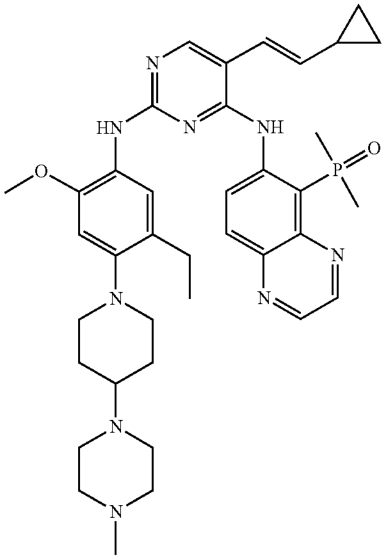 [SMILES: CCc1cc(Nc2ncc(/C=C/C3CC3)c(Nc3ccc4nccnc4c3P(C)(C)=O)n2)c(OC)cc1N1CCC(N2CCN(C)CC2)CC1] |
-continued
| No. | Structure |
|---|---|
| I-12 | 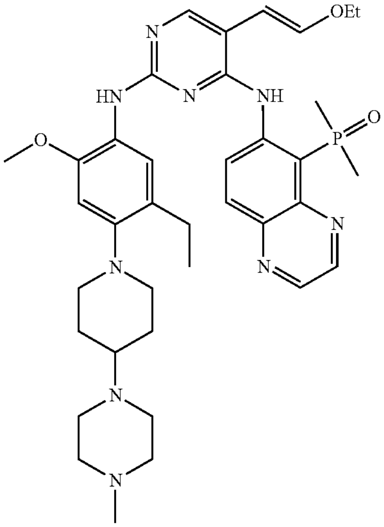 [SMILES: CCO/C=C/c1cnc(Nc2cc(CC)c(N3CCC(N4CCN(C)CC4)CC3)cc2OC)nc1Nc1ccc2nccnc2c1P(C)(C)=O] |
| I-13 | 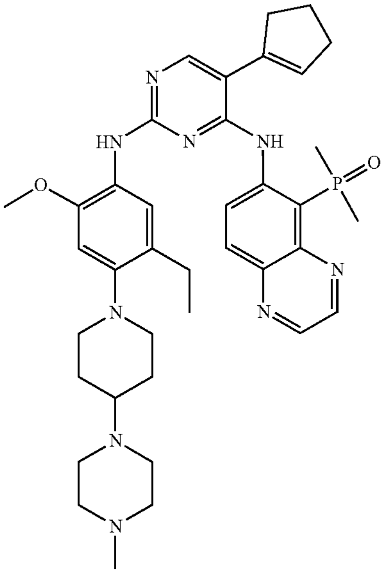 [SMILES: CCc1cc(Nc2ncc(C3=CCCC3)c(Nc3ccc4nccnc4c3P(C)(C)=O)n2)c(OC)cc1N1CCC(N2CCN(C)CC2)CC1] |

-continued
| No. | Structure |
|---|---|
| I-14 | 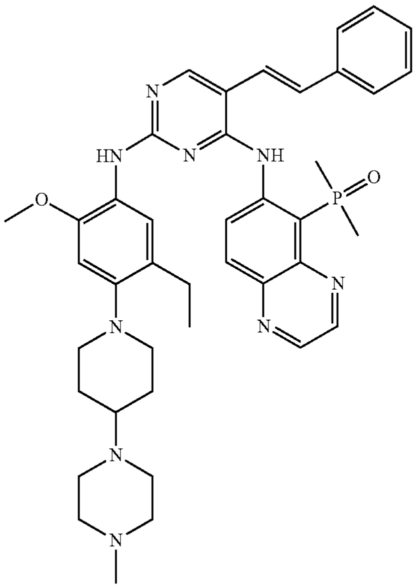 [SMILES: CCc1cc(Nc2ncc(/C=C/c3ccccc3)c(Nc3ccc4nccnc4c3P(C)(C)=O)n2)c(OC)cc1N1CCC(N2CCN(C)CC2)CC1] |
| II-1 | 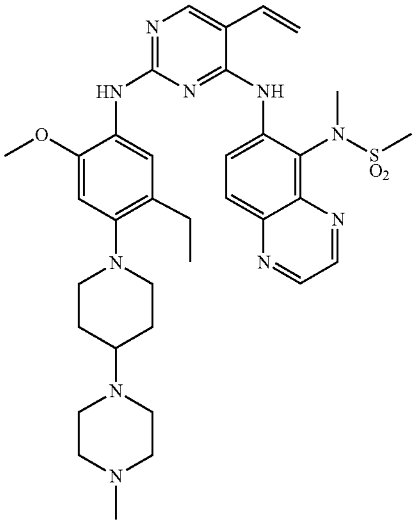 |
| II-2 | 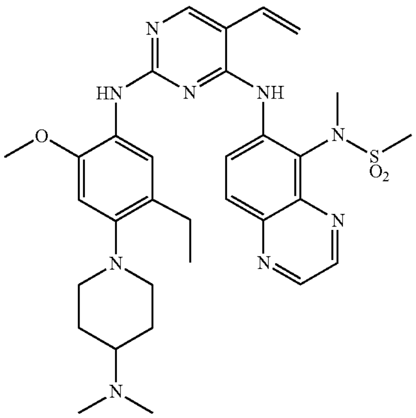 |
-continued
| No. | Structure |
|---|---|
| II-3 | 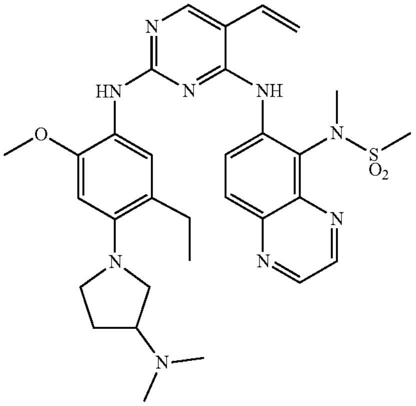 |
| II-4 | 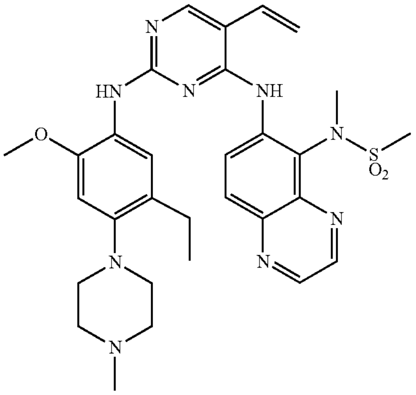 |
| I-15 | 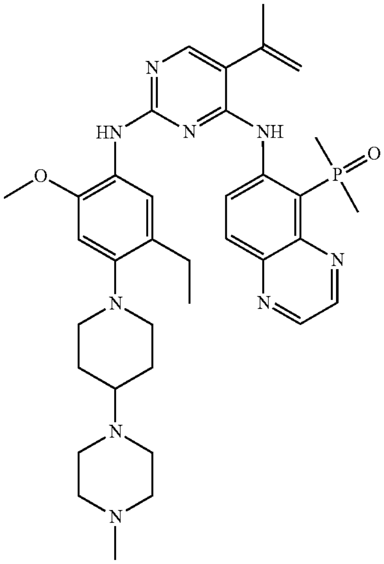 |

-continued
| No. | Structure |
|---|---|
| I-16 | 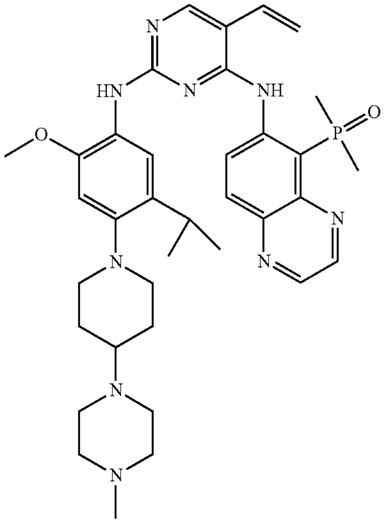 [SMILES: C=Cc1cnc(Nc2cc(C(C)C)c(N3CCC(N4CCN(C)CC4)CC3)cc2OC)nc1Nc1ccc2nccnc2c1P(C)(C)=O] |
| I-17 | 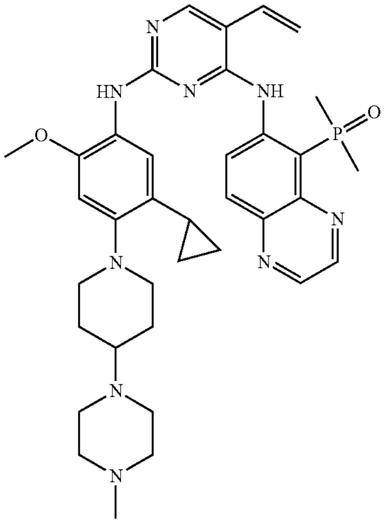 [SMILES: C=Cc1cnc(Nc2cc(C3CC3)c(N3CCC(N4CCN(C)CC4)CC3)cc2OC)nc1Nc1ccc2nccnc2c1P(C)(C)=O] |
| I-18 | 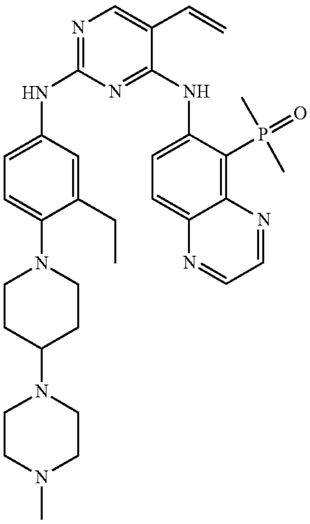 [SMILES: C=Cc1cnc(Nc2ccc(N3CCC(N4CCN(C)CC4)CC3)c(CC)c2)nc1Nc1ccc2nccnc2c1P(C)(C)=O] |
-continued
| No. | Structure |
|---|---|
| I-19 | 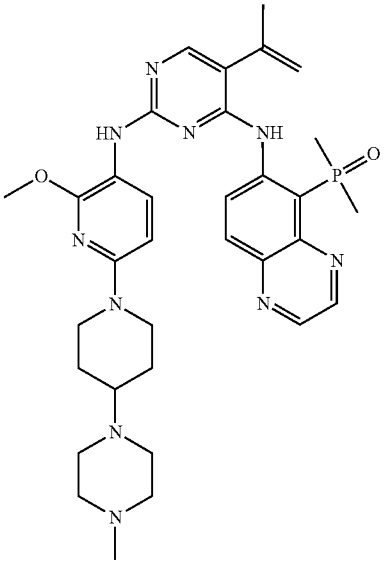 [SMILES: C=C(C)c1cnc(Nc2ccc(N3CCC(N4CCN(C)CC4)CC3)nc2OC)nc1Nc1ccc2nccnc2c1P(C)(C)=O] |
| I-20 | 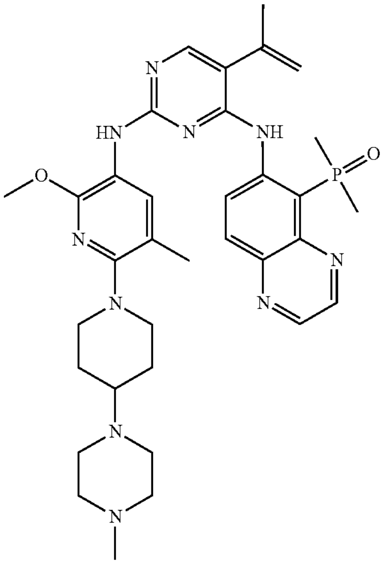 [SMILES: C=C(C)c1cnc(Nc2cc(C)c(N3CCC(N4CCN(C)CC4)CC3)nc2OC)nc1Nc1ccc2nccnc2c1P(C)(C)=O] |

-continued
| No. | Structure |
| --- | --- |
| I-21 | 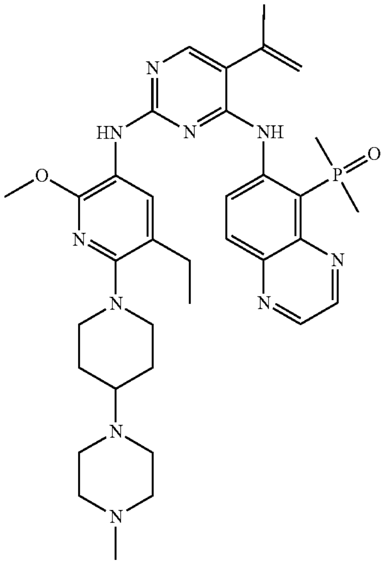 |
| I-22 | 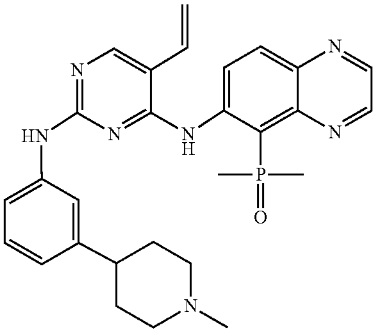 [SMILES: C=Cc1cnc(Nc2cccc(C3CCN(C)CC3)c2)nc1Nc1ccc2nccnc2c1P(C)(C)=O] |
| I-23 | 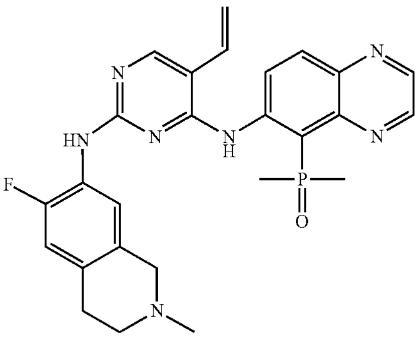 [SMILES: C=Cc1cnc(Nc2cc3c(cc2F)CCN(C)C3)nc1Nc1ccc2nccnc2c1P(C)(C)=O] |
| I-24 | 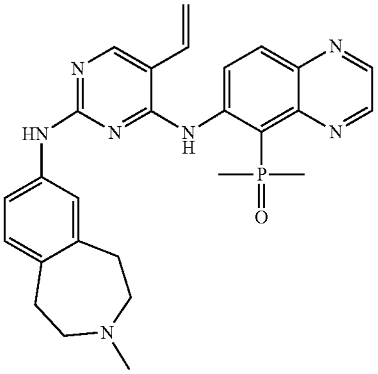 [SMILES: C=Cc1cnc(Nc2ccc3c(c2)CCN(C)CC3)nc1Nc1ccc2nccnc2c1P(C)(C)=O] |
| II-16 | 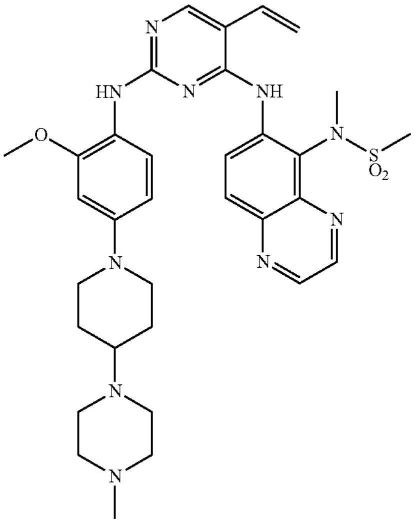 |
| II-17 | 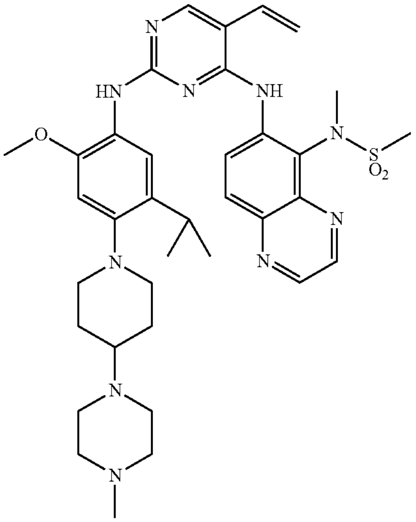 |

-continued
| No. | Structure |
|---|---|
| II-18 | 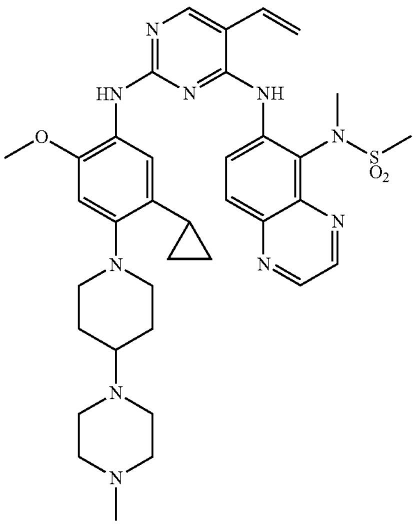 |
| II-19 | 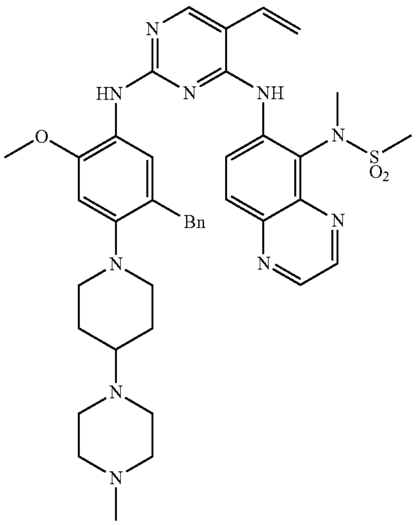 |
| II-20 | 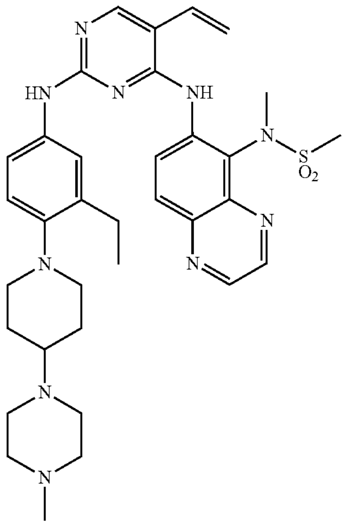 [SMILES: C=Cc1cnc(Nc2ccc(N3CCC(N4CCN(C)CC4)CC3)c(CC)c2)nc1Nc1ccc2nccnc2c1N(C)S(C)(=O)=O] |
-continued
| No. | Structure |
|---|---|
| II-21 | 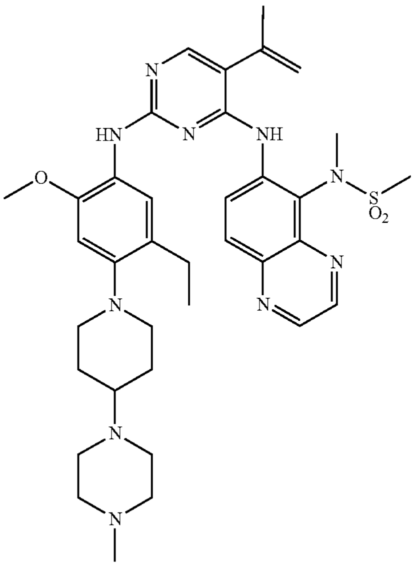 |
| II-22 | 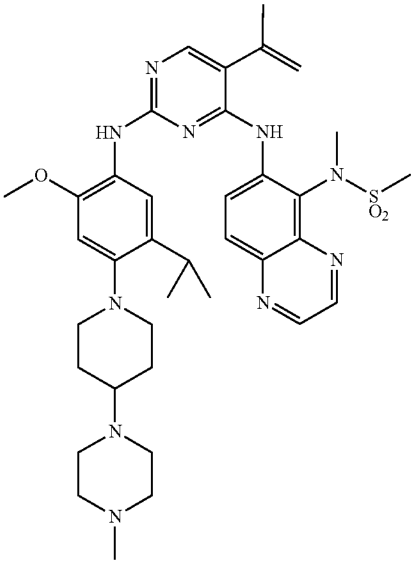 |

-continued
| No. | Structure |
|---|---|
| II-23 | 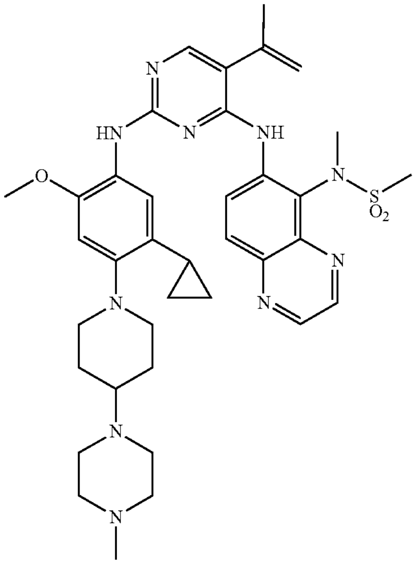 |
| II-24 | 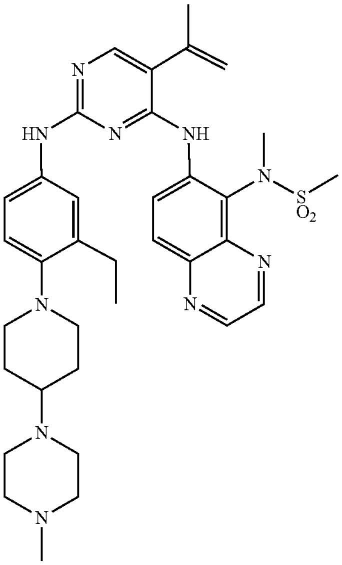 [SMILES: C=C(C)c1cnc(Nc2ccc(N3CCC(N4CCN(C)CC4)CC3)c(CC)c2)nc1Nc1ccc2nccnc2c1N(C)S(C)(=O)=O] |
-continued
| No. | Structure |
|---|---|
| II-25 | 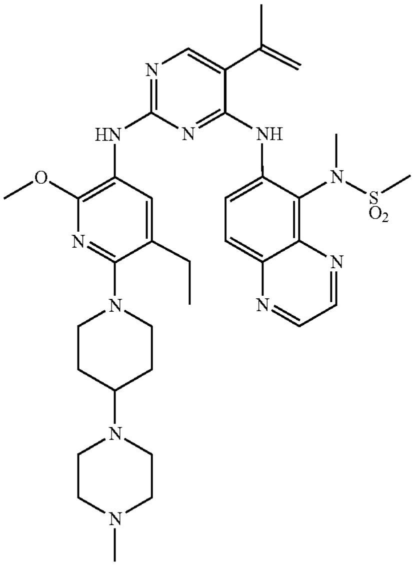 |
| II-26 | 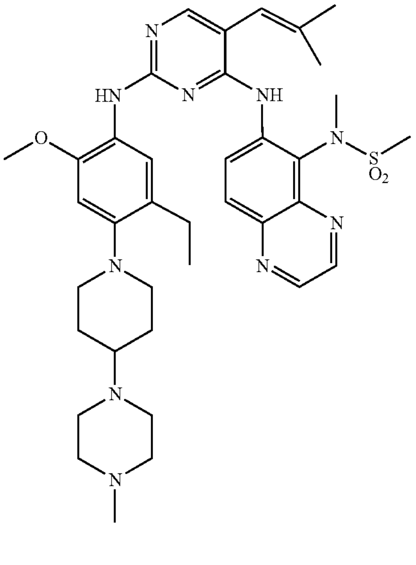 |

-continued
| No. | Structure |
|---|---|
| II-27 | 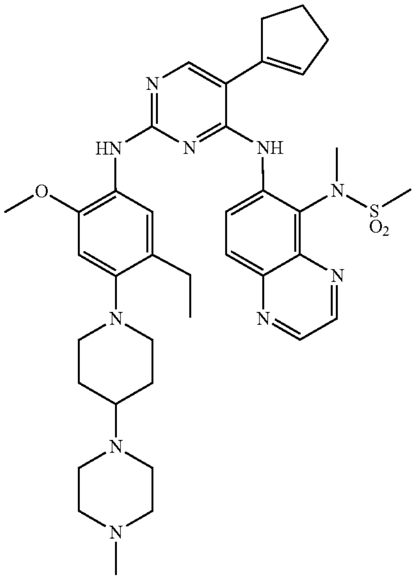 |
| II-28 | 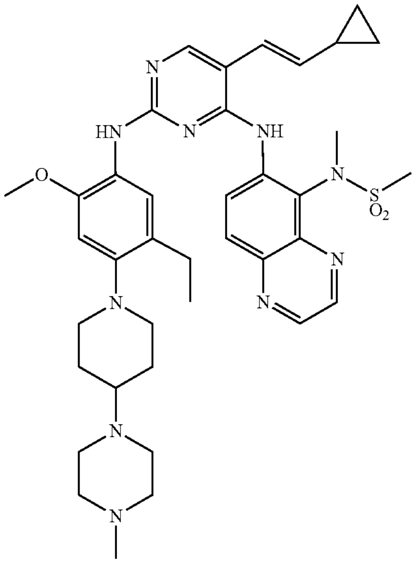 |
-continued
| No. | Structure |
|---|---|
| II-29 | 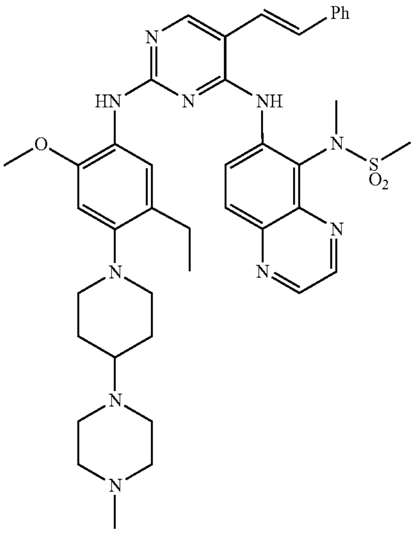 |
| II-30 | 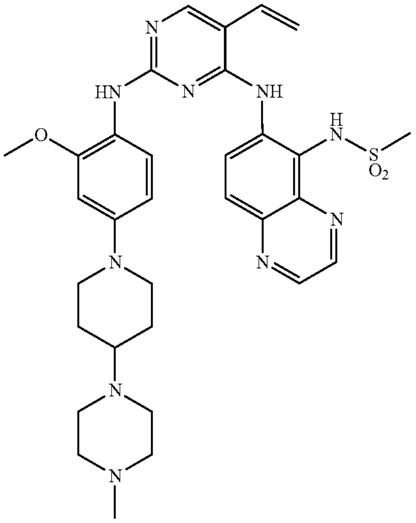 |
| II-31 | 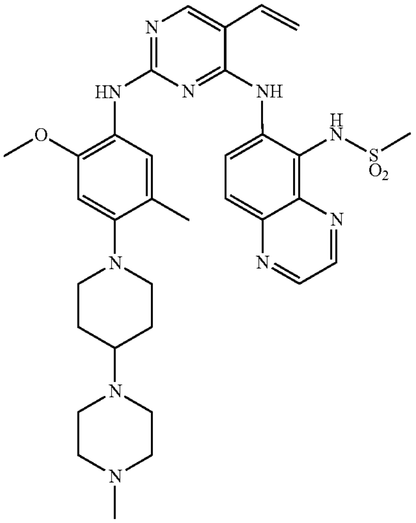 |

-continued
| No. | Structure |
| --- | --- |
| II-32 | 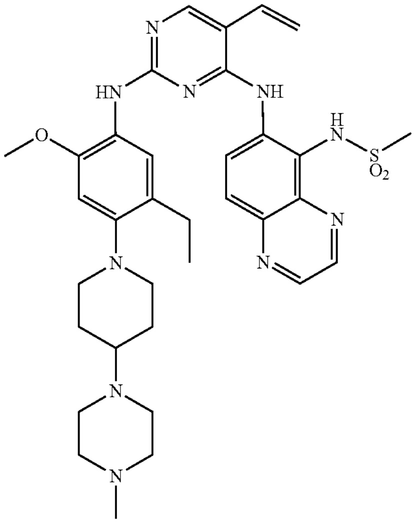 |
| II-33 | 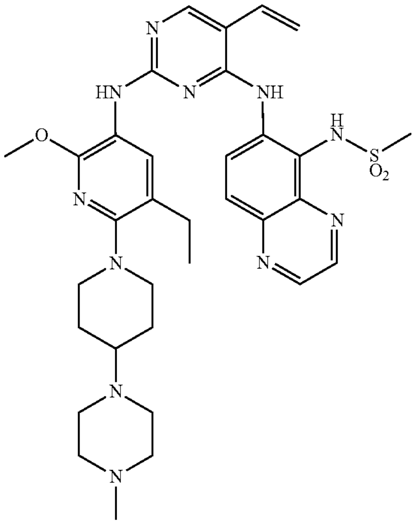 |
| II-34 | 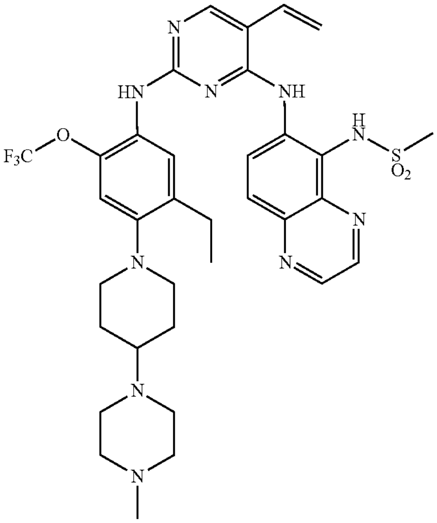 [SMILES: C=Cc1cnc(Nc2cc(CC)c(N3CCC(N4CCN(C)CC4)CC3)cc2OC(F)(F)F)nc1Nc1ccc2nccnc2c1NS(C)(=O)=O] |
-continued
| No. | Structure |
| --- | --- |
| II-35 | 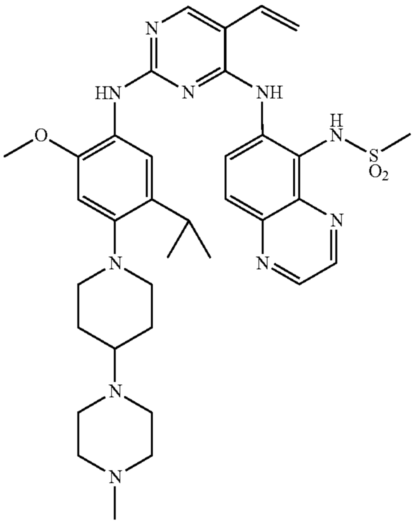 |
| II-36 | 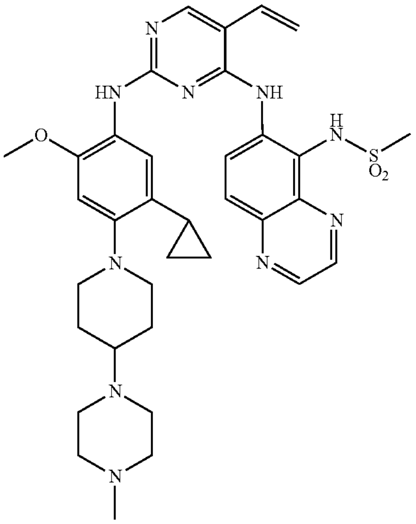 |
| II-37 | 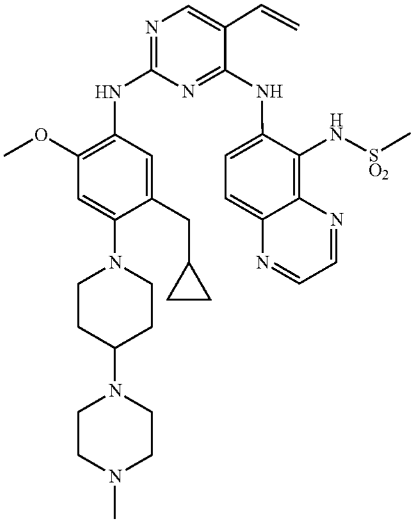 |

-continued
| No. | Structure |
| --- | --- |
| II-38 | 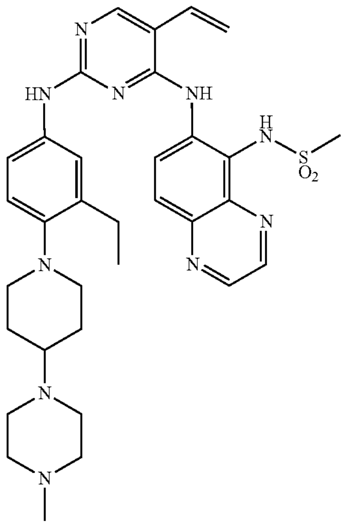 [SMILES: C=Cc1cnc(Nc2ccc(N3CCC(N4CCN(C)CC4)CC3)c(CC)c2)nc1Nc1ccc2nccnc2c1NS(C)(=O)=O] |
| II-39 | 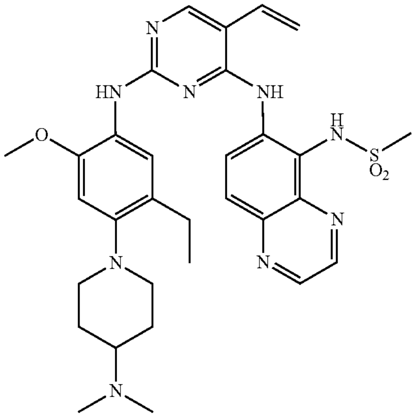 |
| II-40 | 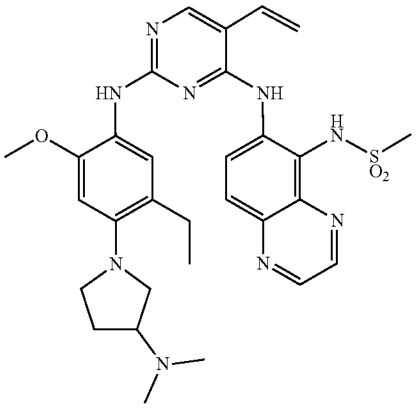 |
-continued
| No. | Structure |
| --- | --- |
| II-41 | 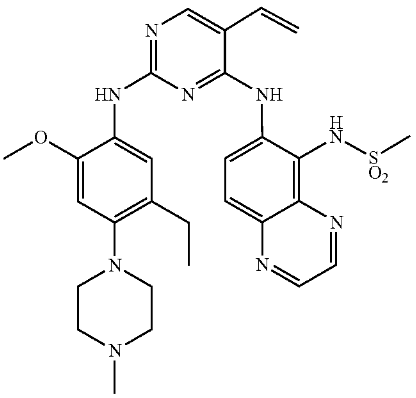 |
| II-42 | 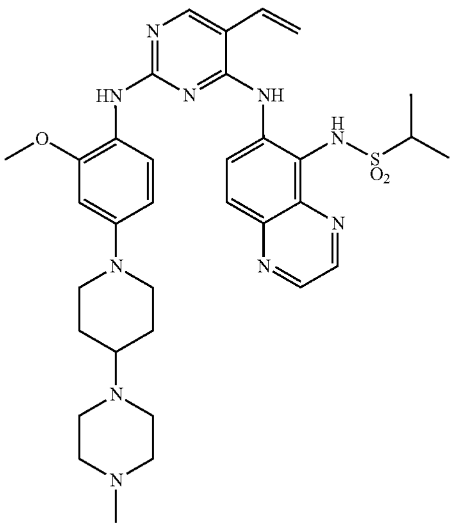 [SMILES: C=Cc1cnc(Nc2ccc(N3CCC(N4CCN(C)CC4)CC3)cc2OC)nc1Nc1ccc2nccnc2c1NS(=O)(=O)C(C)C] |
| II-43 | 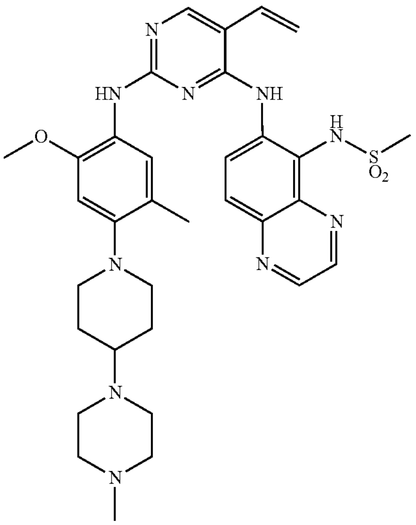 |

-continued
| No. | Structure |
|---|---|
| II-44 | 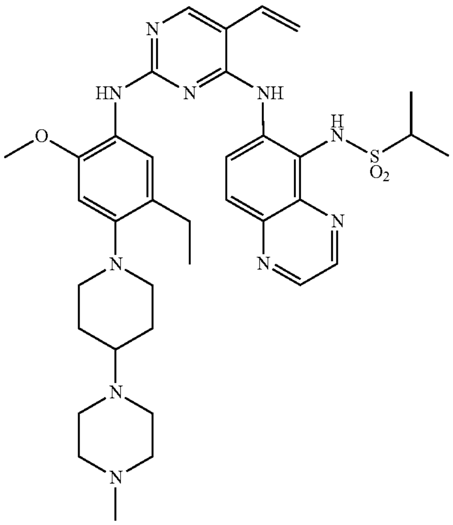 [SMILES: C=Cc1cnc(Nc2cc(CC)c(N3CCC(N4CCN(C)CC4)CC3)cc2OC)nc1Nc1ccc2nccnc2c1NS(=O)(=O)C(C)C] |
| II-45 | 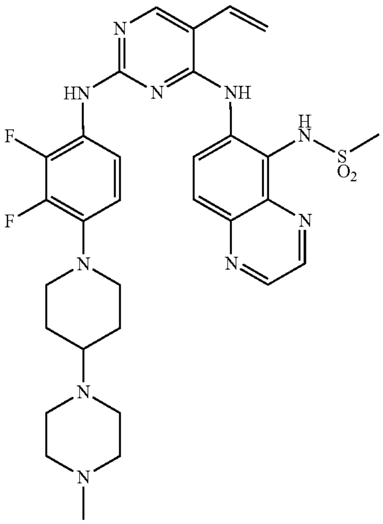 [SMILES: C=Cc1cnc(Nc2ccc(N3CCC(N4CCN(C)CC4)CC3)c(F)c2F)nc1Nc1ccc2nccnc2c1NS(C)(=O)=O] |
| II-46 | 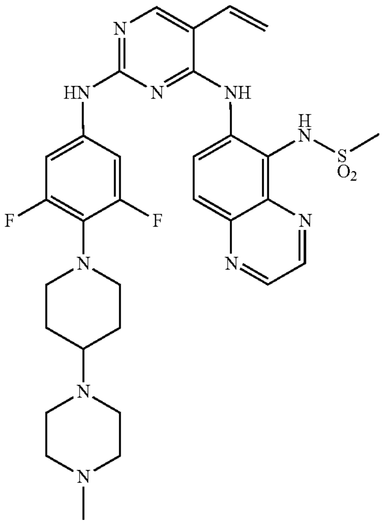 [SMILES: C=Cc1cnc(Nc2cc(F)c(N3CCC(N4CCN(C)CC4)CC3)c(F)c2)nc1Nc1ccc2nccnc2c1NS(C)(=O)=O] |
-continued
| No. | Structure |
|---|---|
| II-47 | 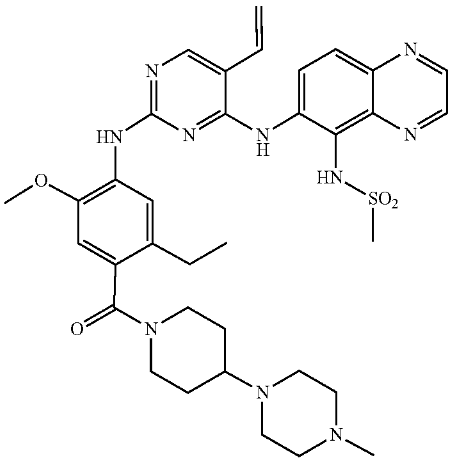 |
| II-48 | 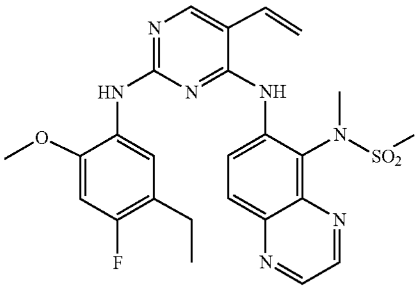 |
| II-49 | 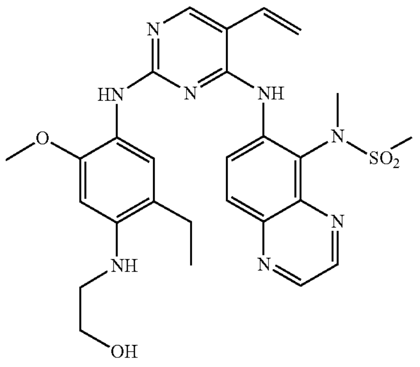 |
| II-50 | 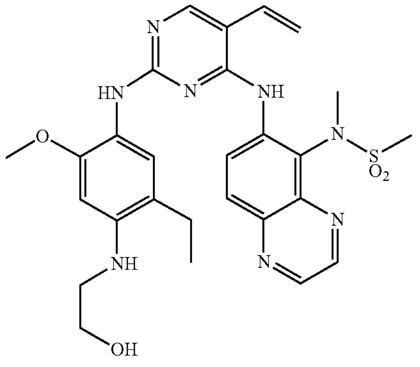 |

-continued
| No. | Structure |
|---|---|
| II-51 | 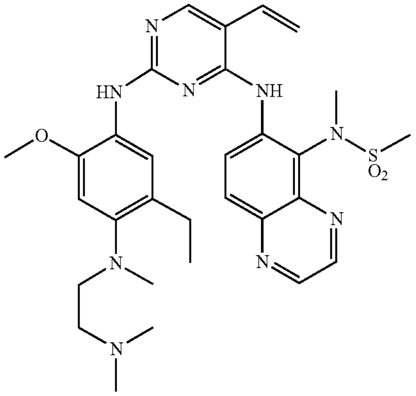 |
| II-52 | 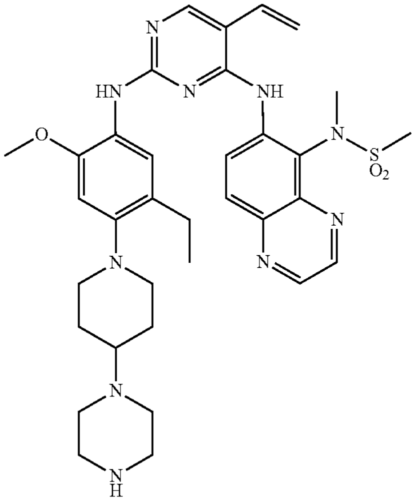 |
| II-53 | 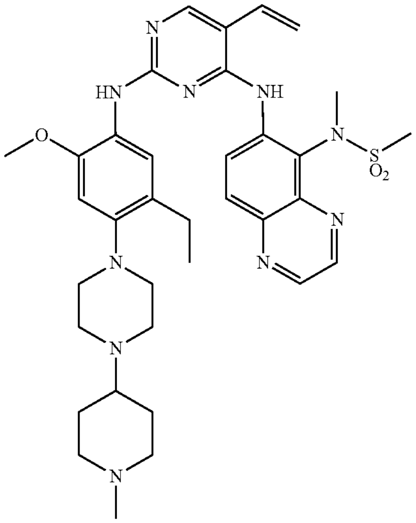 |
| II-54 | 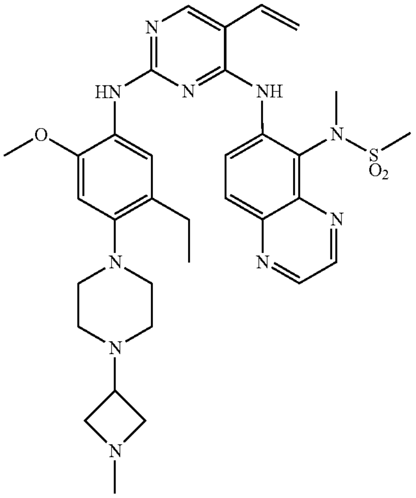 |
| II-55 | 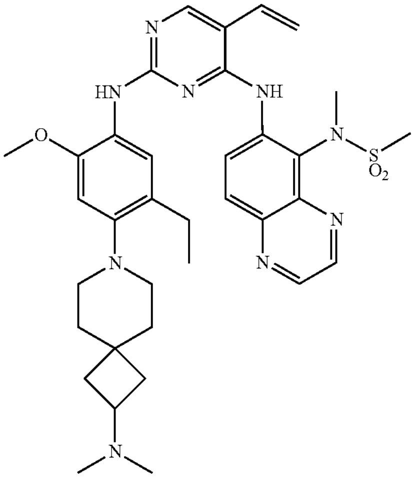 |
| II-56 | 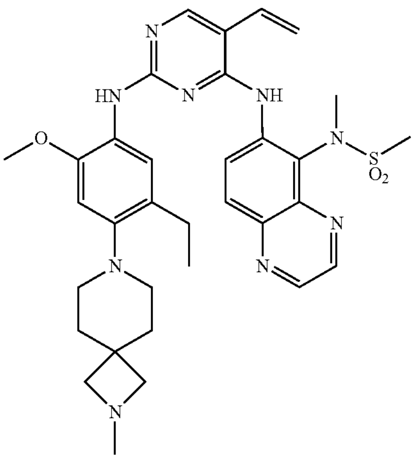 |

-continued
| No. | Structure |
|---|---|
| II-57 | 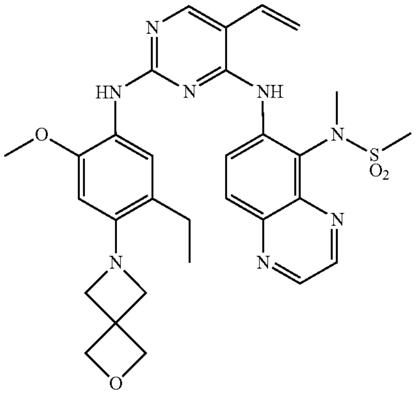 |
| II-58 | 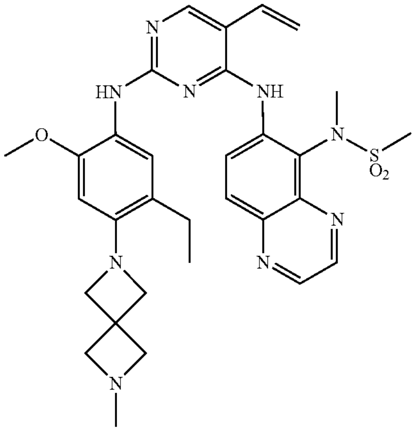 |
| II-5 | 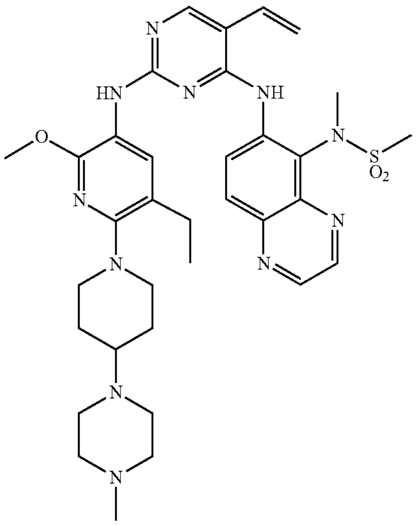 |
-continued
| No. | Structure |
|---|---|
| II-6 | 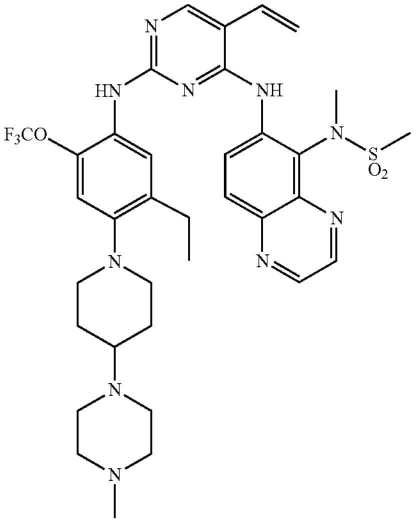 [SMILES: C=Cc1cnc(Nc2cc(CC)c(N3CCC(N4CCN(C)CC4)CC3)cc2OC(F)(F)F)nc1Nc1ccc2nccnc2c1N(C)S(C)(=O)=O] |
| II-7 | 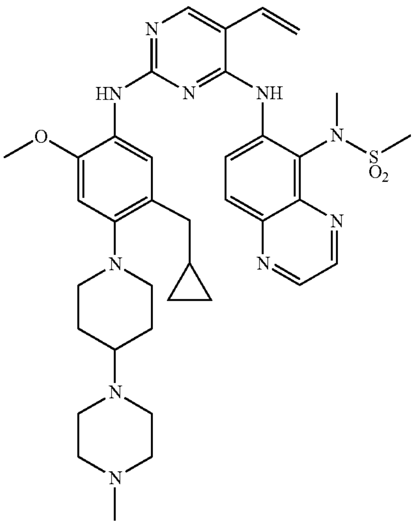 |
| II-8 | 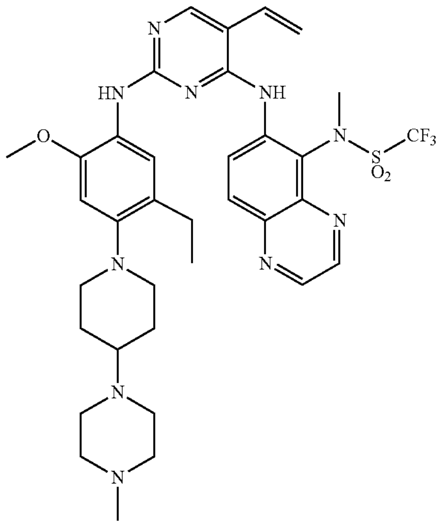 [SMILES: C=Cc1cnc(Nc2cc(CC)c(N3CCC(N4CCN(C)CC4)CC3)cc2OC)nc1Nc1ccc2nccnc2c1N(C)S(=O)(=O)C(F)(F)F] |

-continued
| No. | Structure |
|---|---|
| II-9 | 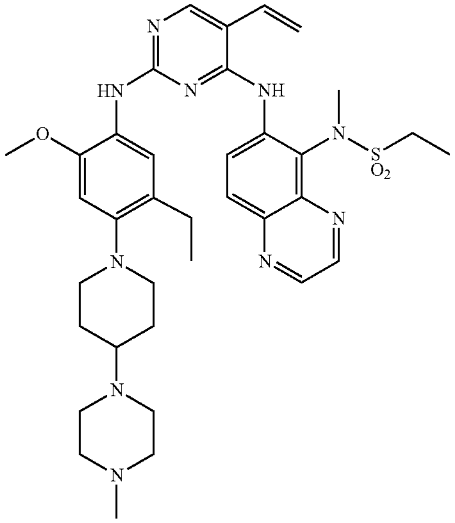 [SMILES: C=Cc1cnc(Nc2cc(CC)c(N3CCC(N4CCN(C)CC4)CC3)cc2OC)nc1Nc1ccc2nccnc2c1N(C)S(=O)(=O)CC] |
| II-10 | 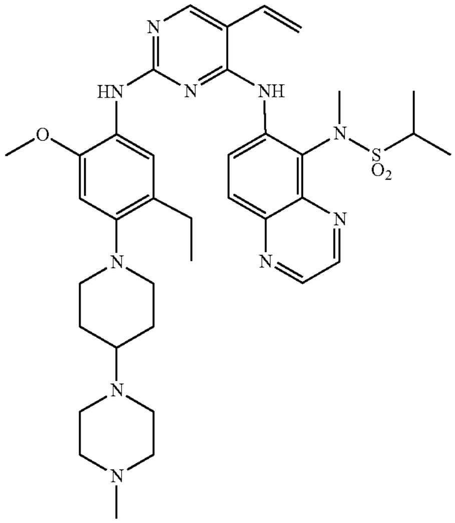 [SMILES: C=Cc1cnc(Nc2cc(CC)c(N3CCC(N4CCN(C)CC4)CC3)cc2OC)nc1Nc1ccc2nccnc2c1N(C)S(=O)(=O)C(C)C] |
| II-11 | 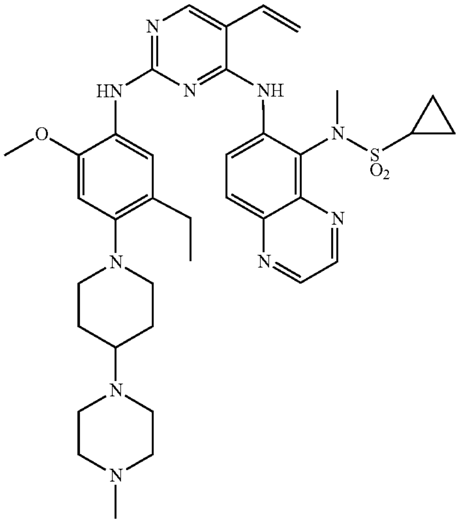 [SMILES: C=Cc1cnc(Nc2cc(CC)c(N3CCC(N4CCN(C)CC4)CC3)cc2OC)nc1Nc1ccc2nccnc2c1N(C)S(=O)(=O)C1CC1] |
-continued
| No. | Structure |
|---|---|
| II-12 | 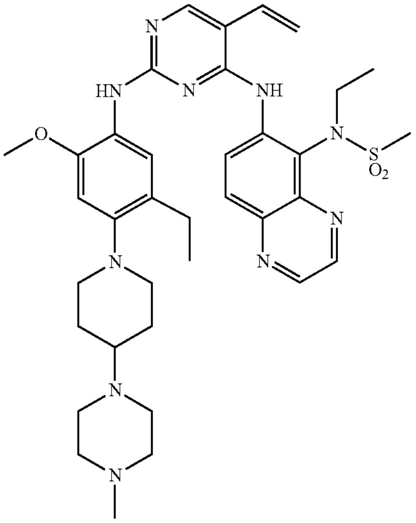 |
| II-13 | 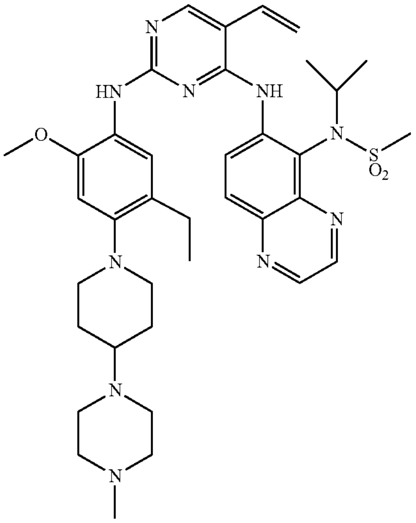 |
| II-14 | 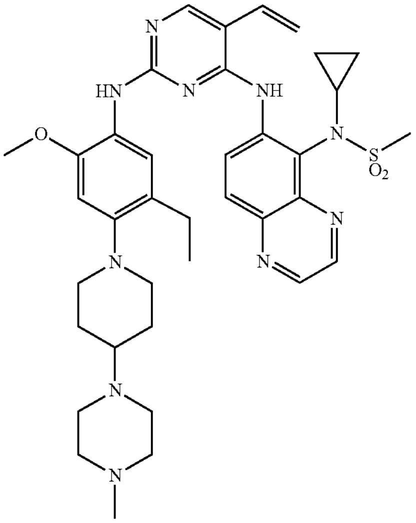 |

-continued
| No. | Structure |
|---|---|
| II-15 | 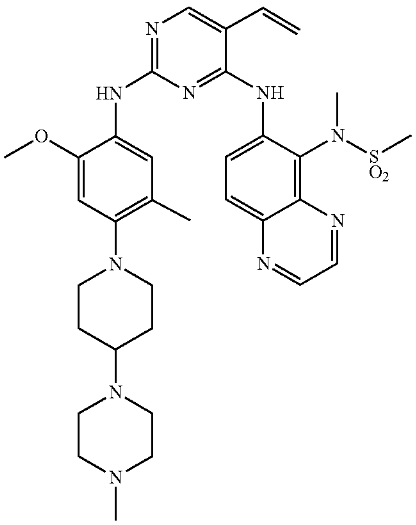 |
| III-1 | 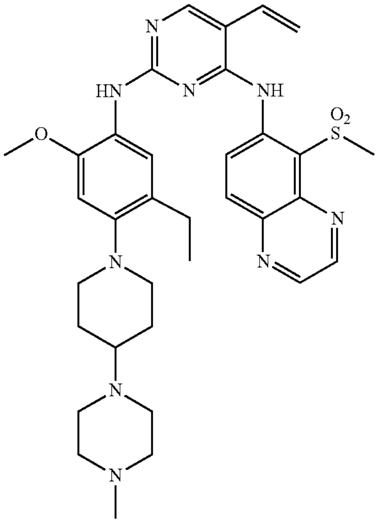 |
| III-2 | 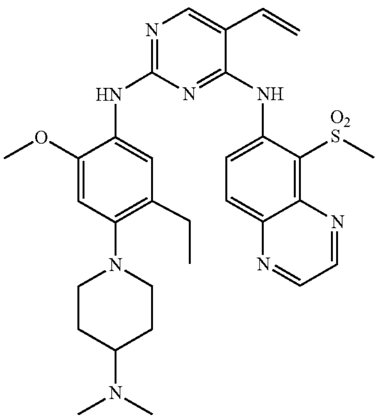 |
-continued
| No. | Structure |
|---|---|
| III-3 | 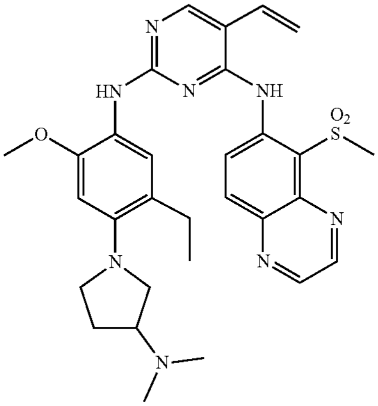 |
| III-4 | 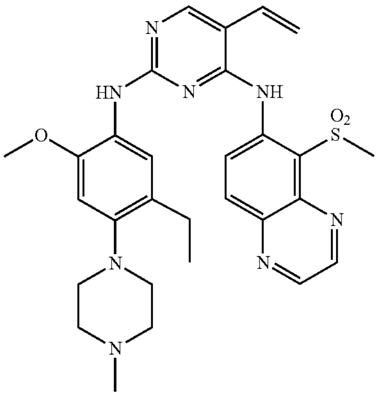 |
| III-5 | 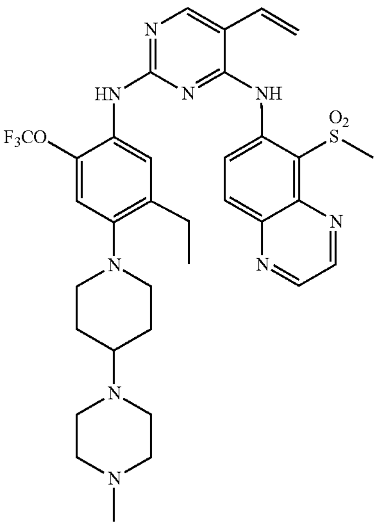 [SMILES: C=Cc1cnc(Nc2cc(CC)c(N3CCC(N4CCN(C)CC4)CC3)cc2OC(F)(F)F)nc1Nc1ccc2nccnc2c1S(C)(=O)=O] |

-continued
| No. | Structure |
|---|---|
| III-6 | 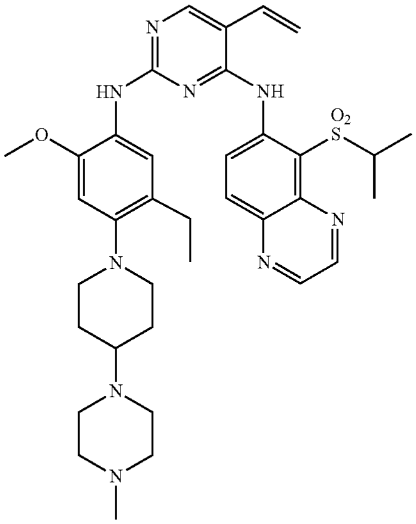 [SMILES: C=Cc1cnc(Nc2cc(CC)c(N3CCC(N4CCN(C)CC4)CC3)cc2OC)nc1Nc1ccc2nccnc2c1S(=O)(=O)C(C)C] |
| III-7 | 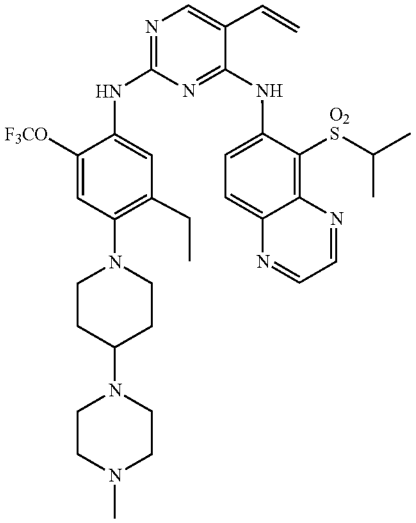 [SMILES: C=Cc1cnc(Nc2cc(CC)c(N3CCC(N4CCN(C)CC4)CC3)cc2OC(F)(F)F)nc1Nc1ccc2nccnc2c1S(=O)(=O)C(C)C] |
| II-59 | 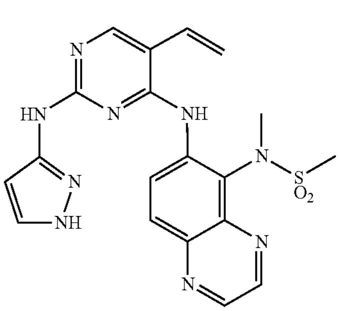 [SMILES: C=Cc1cnc(Nc2cc[nH]n2)nc1Nc1ccc2nccnc2c1N(C)S(C)(=O)=O] |
-continued
| No. | Structure |
|---|---|
| II-60 | 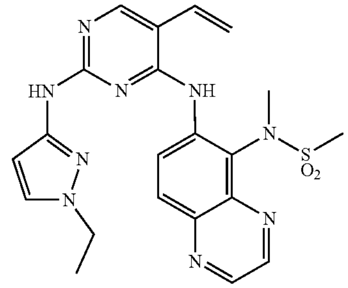 [SMILES: C=Cc1cnc(Nc2ccn(CC)n2)nc1Nc1ccc2nccnc2c1N(C)S(C)(=O)=O] |
| II-61 | 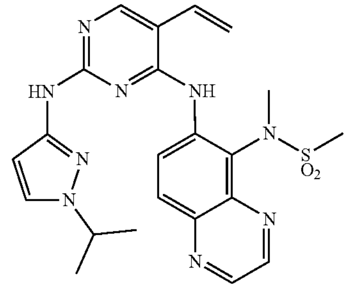 [SMILES: C=Cc1cnc(Nc2ccn(C(C)C)n2)nc1Nc1ccc2nccnc2c1N(C)S(C)(=O)=O] |
| II-62 | 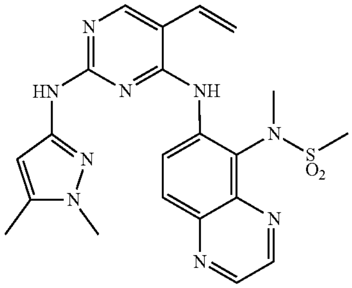 |
| II-63 | 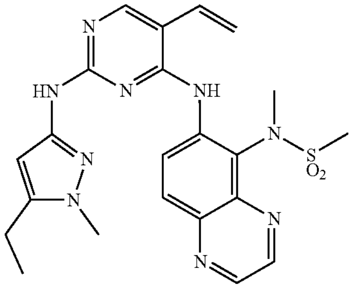 [SMILES: C=Cc1cnc(Nc2cc(CC)n(C)n2)nc1Nc1ccc2nccnc2c1N(C)S(C)(=O)=O] |
| II-64 | 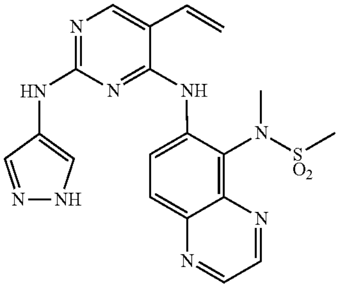 [SMILES: C=Cc1cnc(Nc2cn[nH]c2)nc1Nc1ccc2nccnc2c1N(C)S(C)(=O)=O] |

-continued
| No. | Structure |
|---|---|
| II-65 | 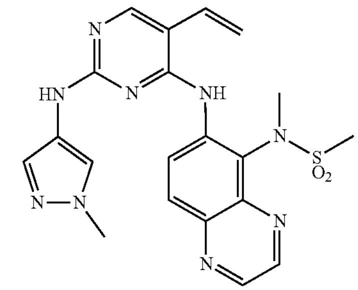 [SMILES: C=Cc1cnc(Nc2cnn(C)c2)nc1Nc1ccc2nccnc2c1N(C)S(C)(=O)=O] |
| II-66 | 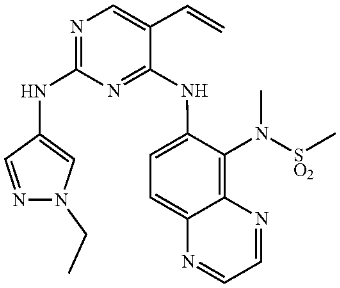 [SMILES: C=Cc1cnc(Nc2cnn(CC)c2)nc1Nc1ccc2nccnc2c1N(C)S(C)(=O)=O] |
| II-67 | 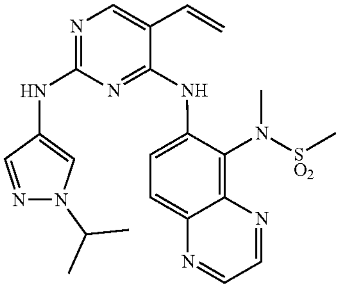 [SMILES: C=Cc1cnc(Nc2cnn(C(C)C)c2)nc1Nc1ccc2nccnc2c1N(C)S(C)(=O)=O] |
| II-68 | 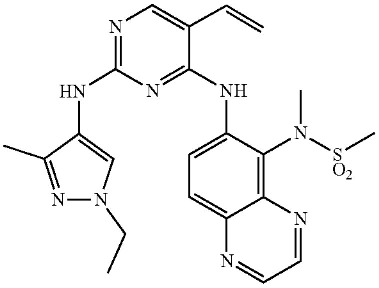 |
| II-69 | 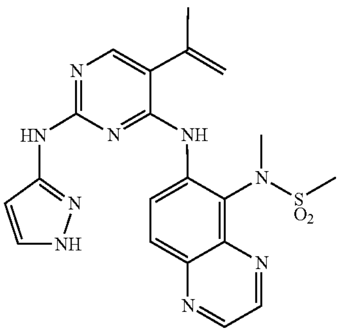 [SMILES: C=C(C)c1cnc(Nc2cc[nH]n2)nc1Nc1ccc2nccnc2c1N(C)S(C)(=O)=O] |
-continued
| No. | Structure |
|---|---|
| II-70 | 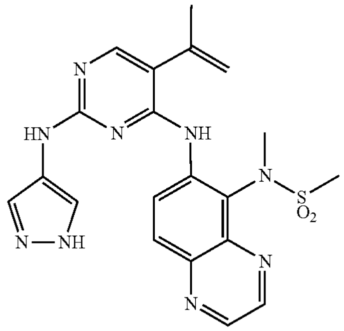 [SMILES: C=C(C)c1cnc(Nc2cn[nH]c2)nc1Nc1ccc2nccnc2c1N(C)S(C)(=O)=O] |
| II-71 | 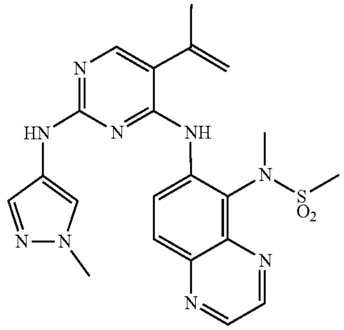 [SMILES: C=C(C)c1cnc(Nc2cnn(C)c2)nc1Nc1ccc2nccnc2c1N(C)S(C)(=O)=O] |
| II-72 | 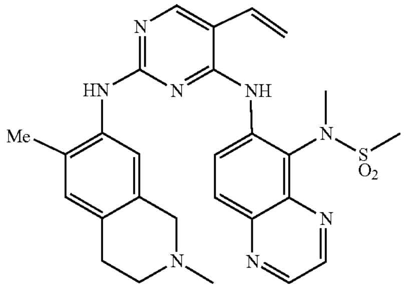 [SMILES: C=Cc1cnc(Nc2cc3c(cc2C)CCN(C)C3)nc1Nc1ccc2nccnc2c1N(C)S(C)(=O)=O] |
| II-73 | 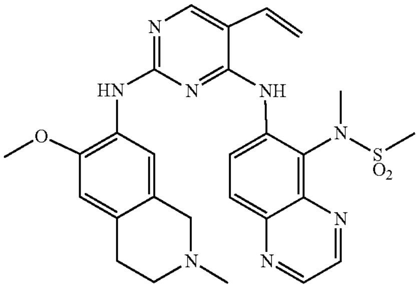 |
| II-74 | 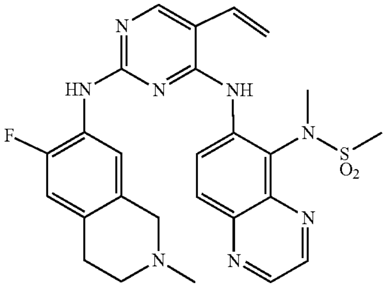 [SMILES: C=Cc1cnc(Nc2cc3c(cc2F)CCN(C)C3)nc1Nc1ccc2nccnc2c1N(C)S(C)(=O)=O] |

-continued
| No. | Structure |
|---|---|
| II-75 | 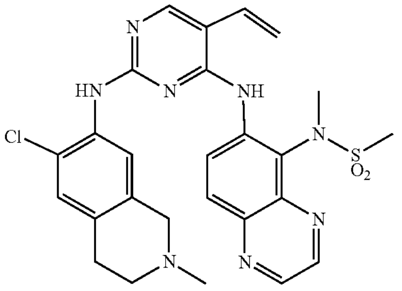 [SMILES: C=Cc1cnc(Nc2cc3c(cc2Cl)CCN(C)C3)nc1Nc1ccc2nccnc2c1N(C)S(C)(=O)=O] |
| II-76 | 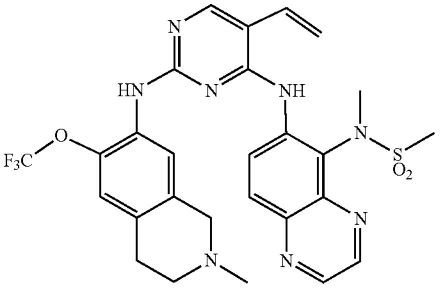 [SMILES: C=Cc1cnc(Nc2cc3c(cc2OC(F)(F)F)CCN(C)C3)nc1Nc1ccc2nccnc2c1N(C)S(C)(=O)=O] |
| II-77 | 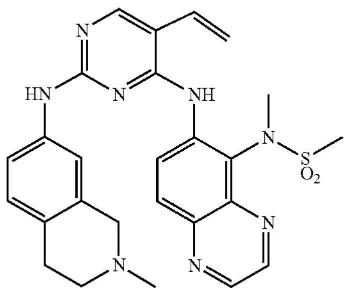 [SMILES: C=Cc1cnc(Nc2ccc3c(c2)CN(C)CC3)nc1Nc1ccc2nccnc2c1N(C)S(C)(=O)=O] |
| II-78 | 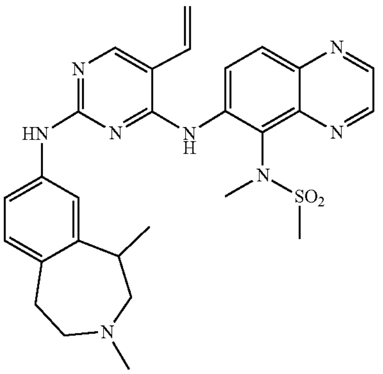 [SMILES: C=Cc1cnc(Nc2ccc3c(c2)C(C)CN(C)CC3)nc1Nc1ccc2nccnc2c1N(C)S(C)(=O)=O] |
-continued
| No. | Structure |
|---|---|
| III-8 | 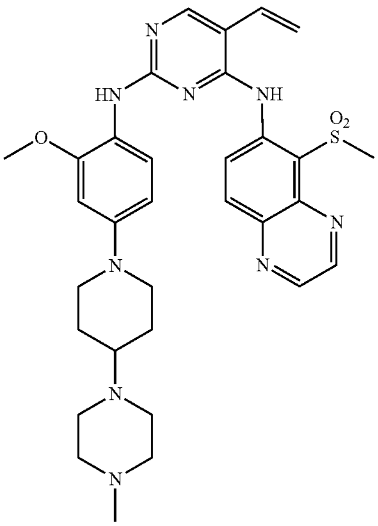 |
| III-9 | 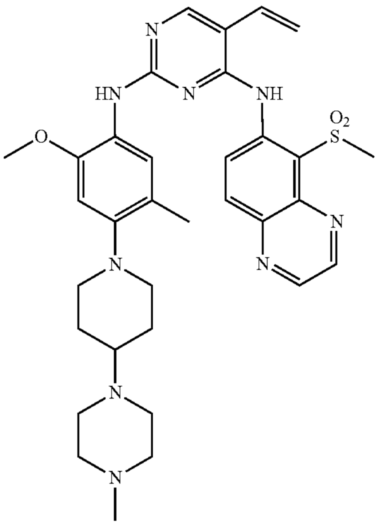 |
| III-10 | 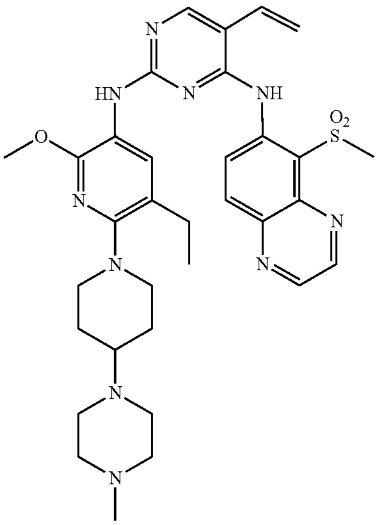 |

-continued
| No. | Structure |
|---|---|
| III-11 | 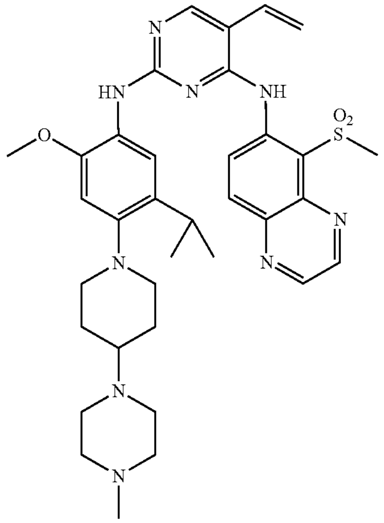 |
| III-12 | 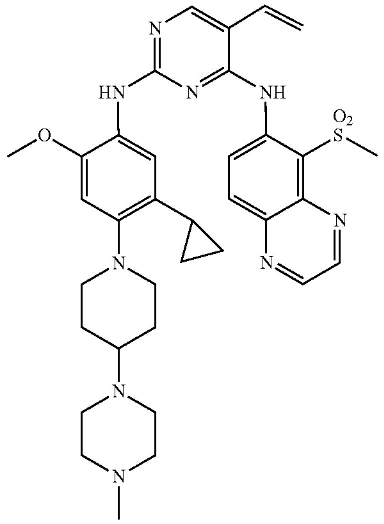 |
| III-13 | 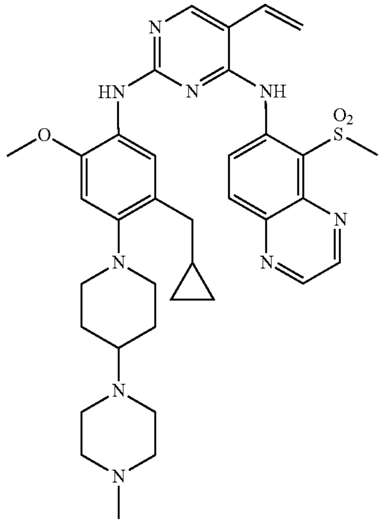 |
-continued
| No. | Structure |
|---|---|
| III-14 | 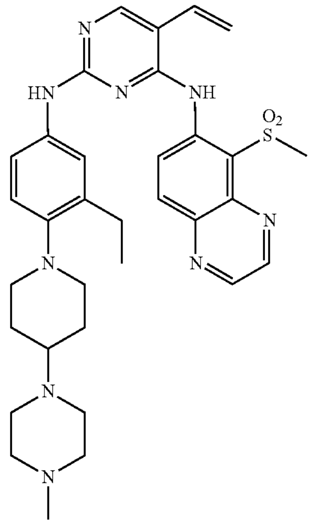 [SMILES: C=Cc1cnc(Nc2ccc(N3CCC(N4CCN(C)CC4)CC3)c(CC)c2)nc1Nc1ccc2nccnc2c1S(C)(=O)=O] |
| III-15 | 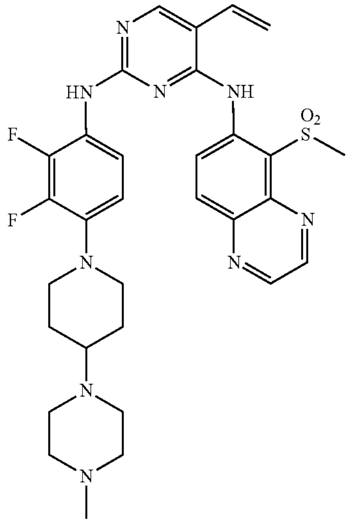 [SMILES: C=Cc1cnc(Nc2ccc(N3CCC(N4CCN(C)CC4)CC3)c(F)c2F)nc1Nc1ccc2nccnc2c1S(C)(=O)=O] |
| III-16 | 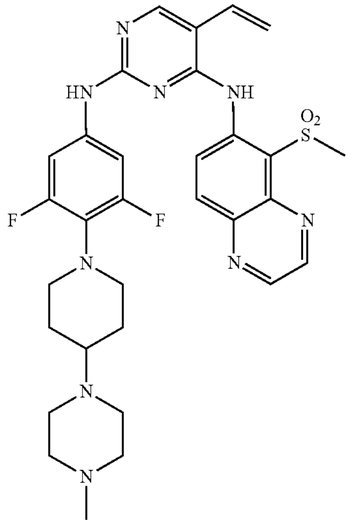 [SMILES: C=Cc1cnc(Nc2cc(F)c(N3CCC(N4CCN(C)CC4)CC3)c(F)c2)nc1Nc1ccc2nccnc2c1S(C)(=O)=O] |

-continued
| No. | Structure |
| --- | --- |
| III-17 | 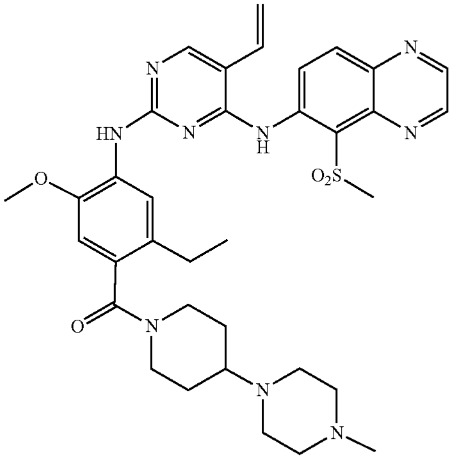 [SMILES: C=Cc1cnc(Nc2cc(CC)c(C(=O)N3CCC(N4CCN(C)CC4)CC3)cc2OC)nc1Nc1ccc2nccnc2c1S(C)(=O)=O] |
| III-18 | 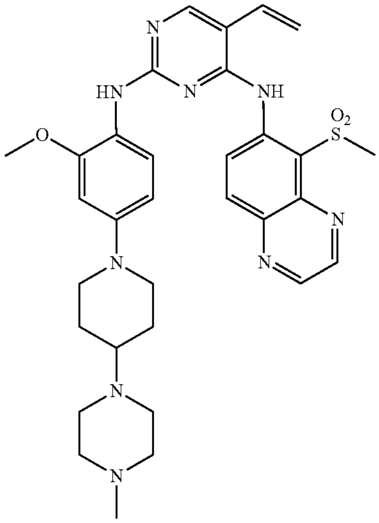 |
| III-19 | 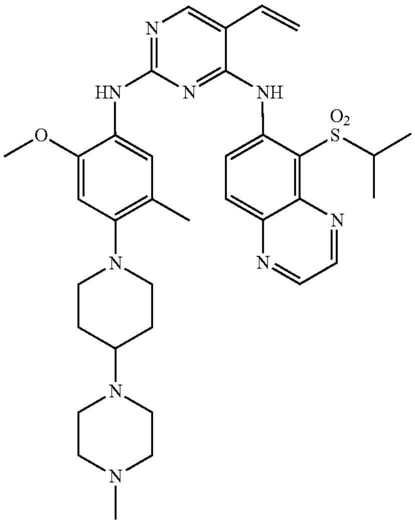 [SMILES: C=Cc1cnc(Nc2cc(C)c(N3CCC(N4CCN(C)CC4)CC3)cc2OC)nc1Nc1ccc2nccnc2c1S(=O)(=O)C(C)C] |
-continued
| No. | Structure |
| --- | --- |
| III-20 | 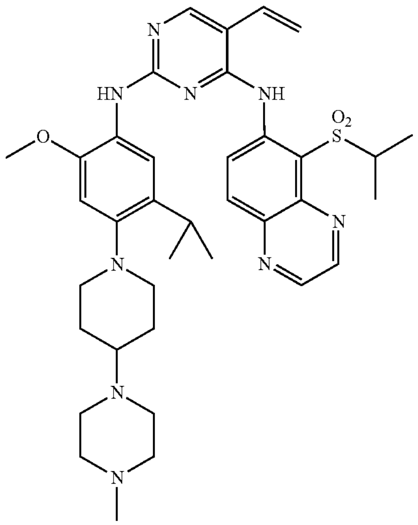 [SMILES: C=Cc1cnc(Nc2cc(C(C)C)c(N3CCC(N4CCN(C)CC4)CC3)cc2OC)nc1Nc1ccc2nccnc2c1S(=O)(=O)C(C)C] |
| III-21 | 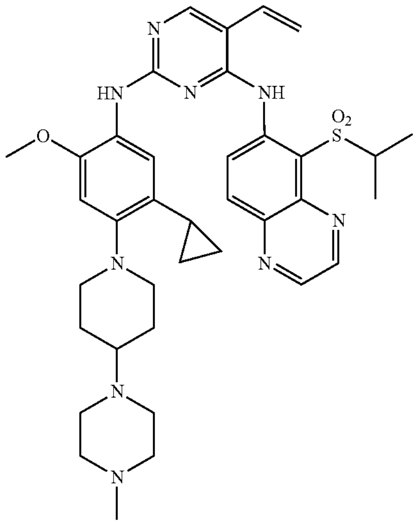 [SMILES: C=Cc1cnc(Nc2cc(C3CC3)c(N3CCC(N4CCN(C)CC4)CC3)cc2OC)nc1Nc1ccc2nccnc2c1S(=O)(=O)C(C)C] |
| IV-1 | 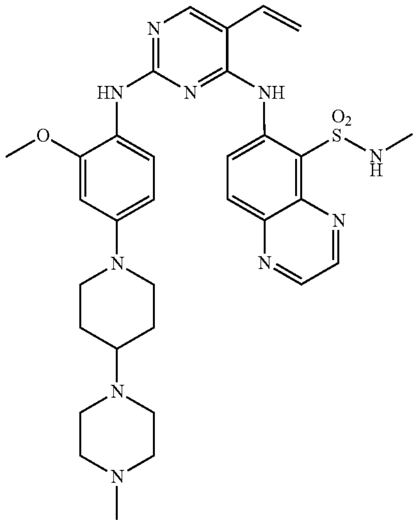 |

-continued
| No. | Structure |
|---|---|
| IV-2 | 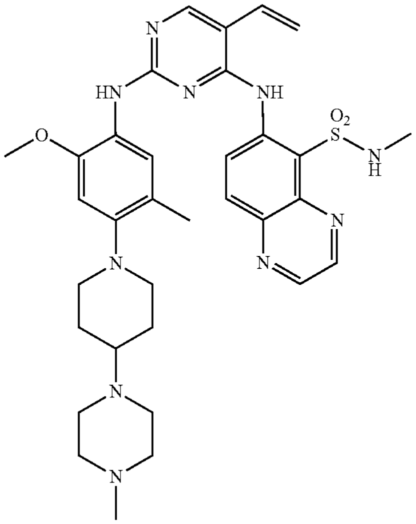 |
| IV-3 | 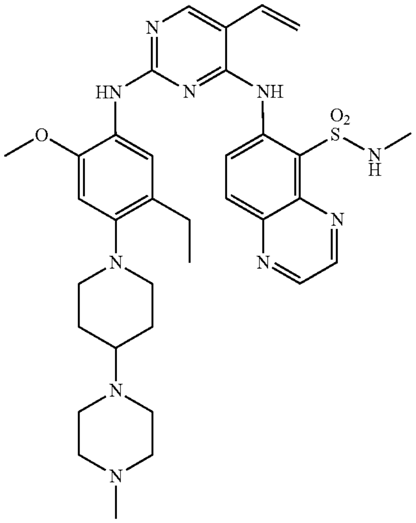 |
| IV-4 | 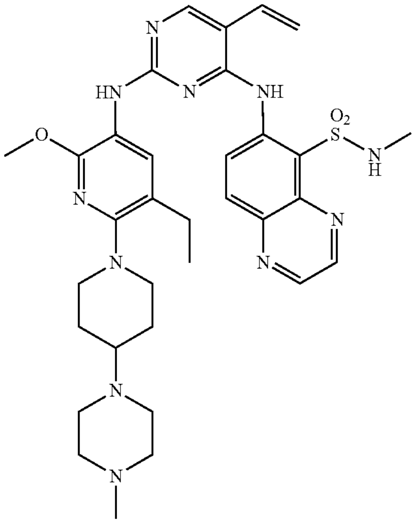 |
| IV-5 | 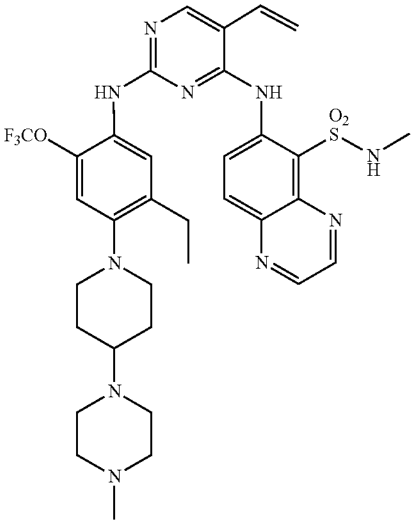 [SMILES: C=Cc1cnc(Nc2cc(CC)c(N3CCC(N4CCN(C)CC4)CC3)cc2OC(F)(F)F)nc1Nc1ccc2nccnc2c1S(=O)(=O)NC] |
| IV-6 | 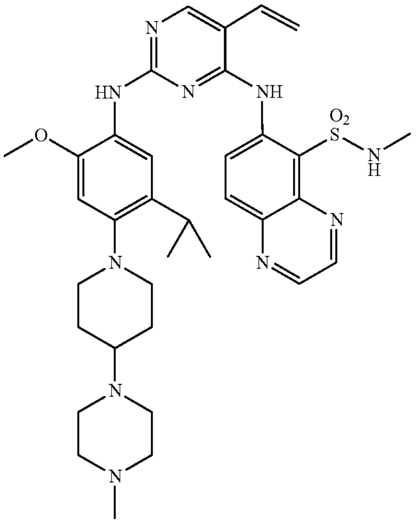 |
| IV-7 | 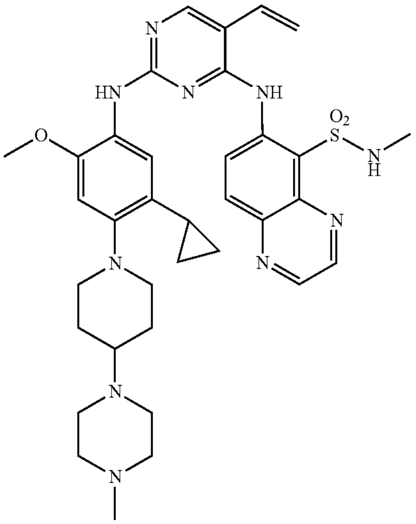 |

-continued
| No. | Structure |
|---|---|
| IV-8 | 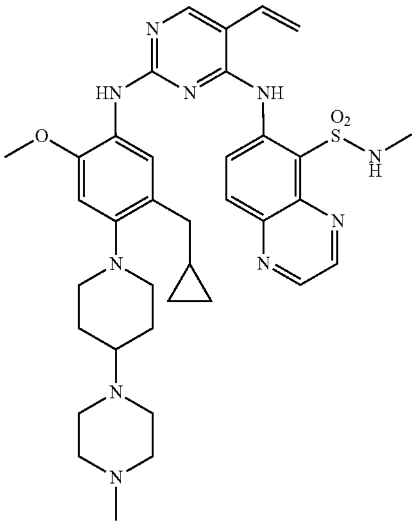 |
| IV-9 | 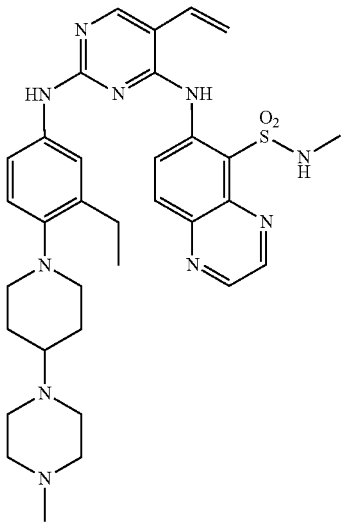 [SMILES: C=Cc1cnc(Nc2ccc(N3CCC(N4CCN(C)CC4)CC3)c(CC)c2)nc1Nc1ccc2nccnc2c1S(=O)(=O)NC] |
| IV-10 | 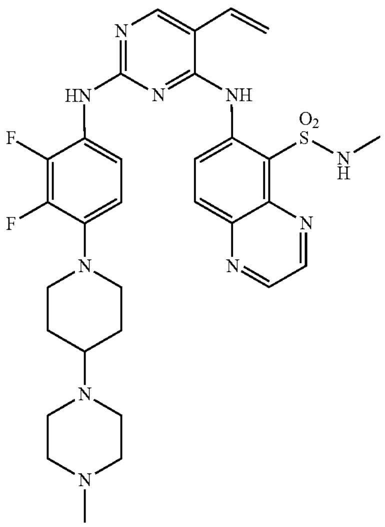 [SMILES: C=Cc1cnc(Nc2ccc(N3CCC(N4CCN(C)CC4)CC3)c(F)c2F)nc1Nc1ccc2nccnc2c1S(=O)(=O)NC] |
-continued
| No. | Structure |
|---|---|
| IV-11 | 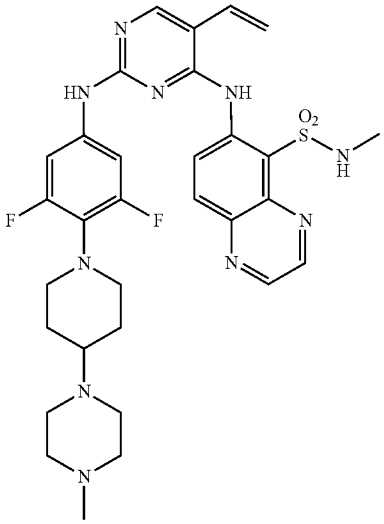 [SMILES: C=Cc1cnc(Nc2cc(F)c(N3CCC(N4CCN(C)CC4)CC3)c(F)c2)nc1Nc1ccc2nccnc2c1S(=O)(=O)NC] |
| IV-12 | 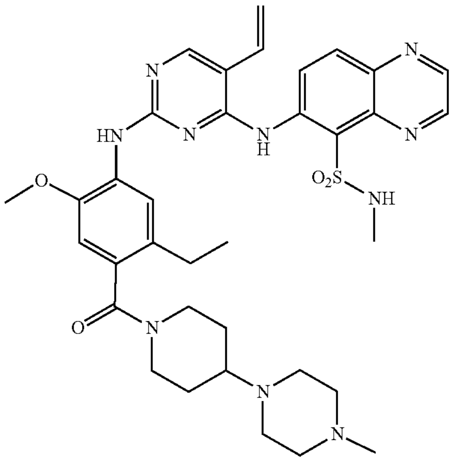 [SMILES: C=Cc1cnc(Nc2cc(CC)c(C(=O)N3CCC(N4CCN(C)CC4)CC3)cc2OC)nc1Nc1ccc2nccnc2c1S(=O)(=O)NC] |
| IV-13 | 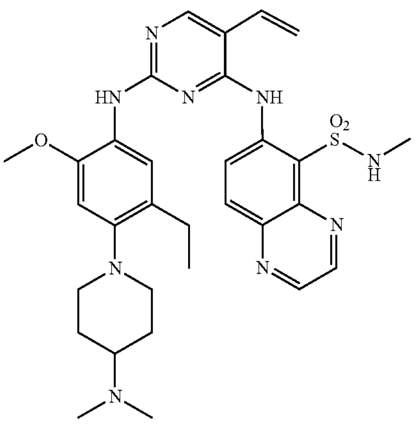 |

-continued
| No. | Structure |
|---|---|
| IV-14 | 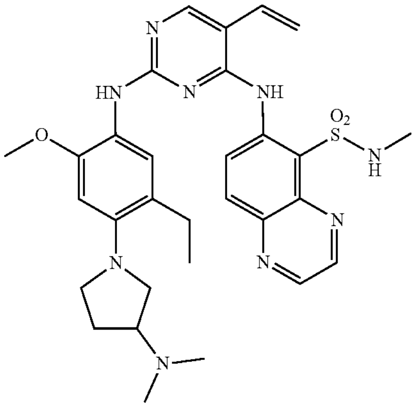 |
| IV-15 | 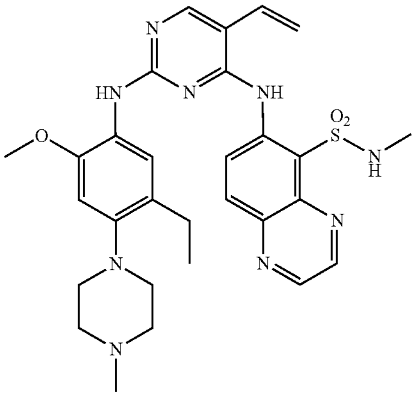 |
| IV-16 | 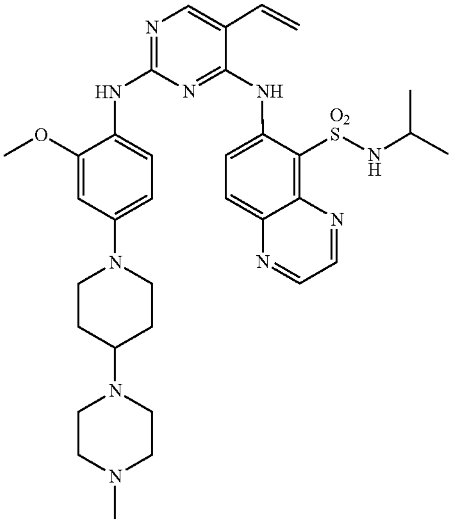 [SMILES: C=Cc1cnc(Nc2ccc(N3CCC(N4CCN(C)CC4)CC3)cc2OC)nc1Nc1ccc2nccnc2c1S(=O)(=O)NC(C)C] |
-continued
| No. | Structure |
|---|---|
| IV-17 | 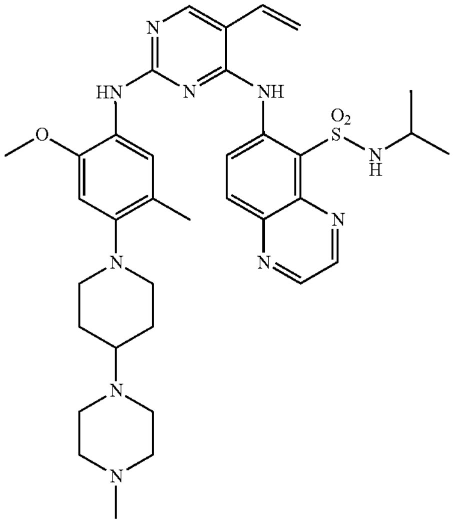 [SMILES: C=Cc1cnc(Nc2cc(C)c(N3CCC(N4CCN(C)CC4)CC3)cc2OC)nc1Nc1ccc2nccnc2c1S(=O)(=O)NC(C)C] |
| IV-18 | 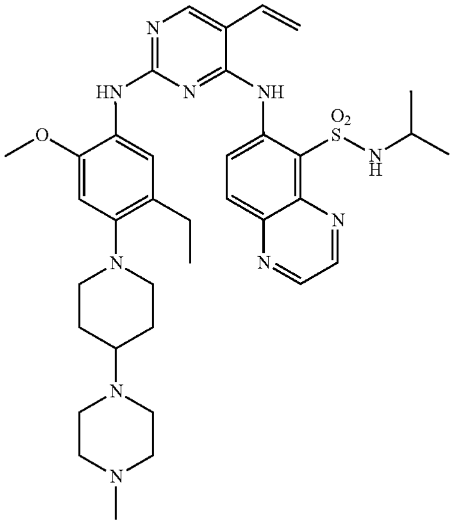 [SMILES: C=Cc1cnc(Nc2cc(CC)c(N3CCC(N4CCN(C)CC4)CC3)cc2OC)nc1Nc1ccc2nccnc2c1S(=O)(=O)NC(C)C] |
| I-25 | 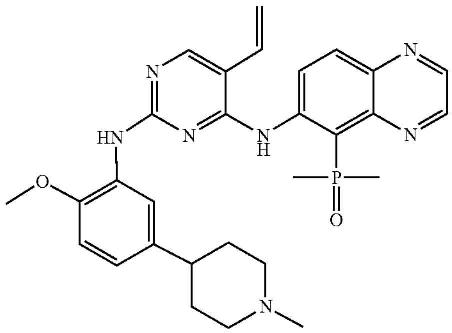 [SMILES: C=Cc1cnc(Nc2cc(C3CCN(C)CC3)ccc2OC)nc1Nc1ccc2nccnc2c1P(C)(C)=O] |
or stereoisomers, pharmaceutically acceptable salts or pharmaceutically acceptable solvates of the above compounds.
5. A compound having the following general formula or a stereoisomer, a pharmaceutically acceptable salt or a pharmaceutically acceptable solvate thereof:

(I)

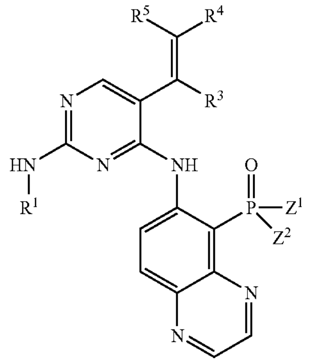

wherein:

$R^1$ is selected from:

1)

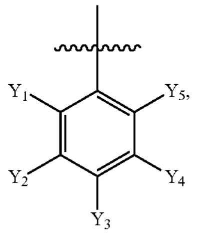

wherein:

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, methyl, ethyl, isopropyl, cyclopropyl, methoxy, trifluoromethoxy, cyclopropylmethylene, N-methylpiperazinyl, 3-(N,N-dimethylamino)tetrahydropyrrolyl, 4-N,N-dimethylaminopiperidyl, 4-(N-methylpiperazinyl-1-) piperidyl, or N-methyl-4-piperidyl;

2)

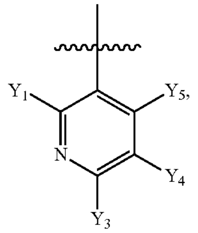

wherein:

$Y_1$, $Y_3$, $Y_4$, $Y_5$ each are independently selected from H, methyl, ethyl, methoxy, or 4-(N-methylpiperazinyl-1-) piperidyl, and $Y_1$, $Y_3$, $Y_4$, $Y_5$ are not hydrogen at the same time,

3)

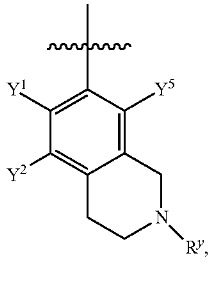

wherein, $Y_1$ is F, $Y_2$, $Y_5$ are H, $R^y$ is methyl;

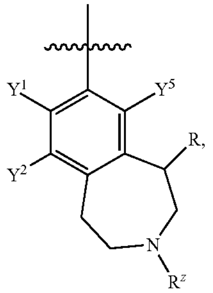

wherein, $Y_1$, $Y_2$, $Y_5$ are H, $R^z$ is methyl, R is H;

$Z_1$, $Z_2$ each are independently selected from C1-$C_6$ alkyl;

$R^3$, $R^4$, $R^5$ each are independently selected from:

1) H, $C_1$-$C_6$ alkyl, $C_1$-$C_6$ alkoxy, C3-$C_6$ cycloalkyl;

2) substituted or unsubstituted aryl, the substituents being selected from halogen, $C_1$-$C_6$ alkyl, or $C_3$-$C_8$ cycloalkyl;

3) $R^3$, $R^4$ and carbon atoms linked thereto together form

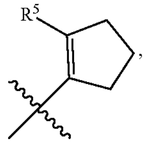

$R^5$ being selected from H, or $C_1$-$C_6$ alkyl; and wherein the compound having the general formula (I) does not include

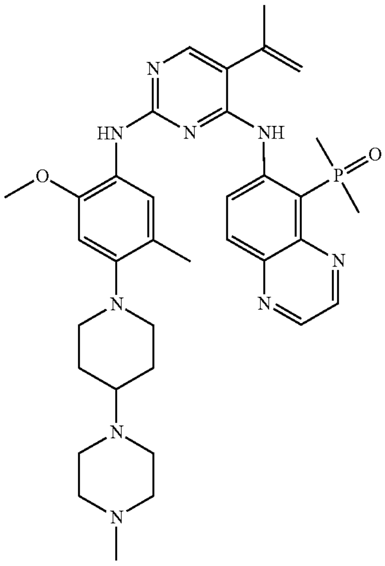

6. The compound according to claim 1 or a stereoisomer, a pharmaceutically acceptable salt or a pharmaceutically acceptable solvate thereof, wherein:

$R^1$ is selected from:

1)

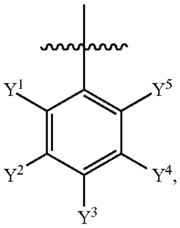

wherein:

$Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, trifluoromethoxy, cyclopropylmethylene, benzyl, N-methylpiperazinyl, 3-(N,N-dimethylamino)tetrahydropyrrolyl, 4-N,N-dimethylaminopiperidyl 4-(N-methylpiperazinyl-1-)piperidyl, 4-(N-methyl-1-piperazinyl) piperidyl-1-formyl, 2-hydroxyethylamino, 2-N, N-dimethylaminoethylamino, N-methyl-N-(2-N,N-dimethylamino)ethylamino, 4-(piperazinyl-1-) piperidyl, N—(N-methyl-4-piperidyl) piperazinyl, 4-(N-methyl-azetidin-3-yl) piperazinyl,

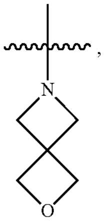,

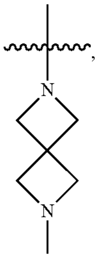,

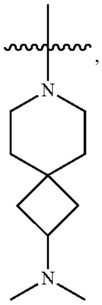, or

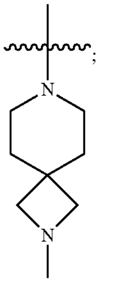;

2)

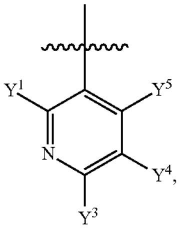

wherein:

$Y_1$, $Y_3$, $Y_4$, $Y_5$ each are independently selected from H, ethyl, methoxy, or 4-(N-methylpiperazinyl-1-) piperidyl, and $Y_1$, $Y_3$, $Y_4$, $Y_5$ are not hydrogen at the same time,

3)

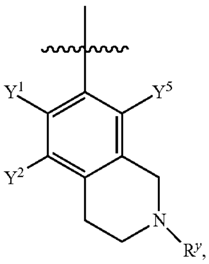

wherein, $Y_1$ is selected from H, methyl, methoxy, F, Cl, or trifluoromethoxy, $Y_2$, $Y_5$ are H, $R^y$ is methyl;

4)

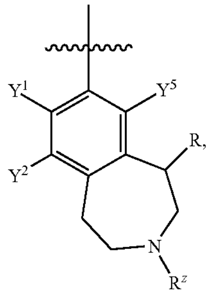

wherein, $Y_1$, $Y_2$, $Y_5$ are H, $R^z$, R are methyl;

5) 3-pyrazolyl, 1-ethyl-3-pyrazolyl, 1-isopropyl-3-pyrazolyl, 1,5-dimethyl-3-pyrazolyl, 1-methyl-5-ethyl-3-pyrazolyl, 4-pyrazolyl, 1-methyl-4-pyrazolyl, 1-ethyl-4-pyrazolyl, 1-isopropyl-4-pyrazolyl, 1-ethyl-3-methyl-4-pyrazolyl.

7. The compound according to claim 1 or a stereoisomer, a pharmaceutically acceptable salt or a pharmaceutically acceptable solvate thereof, wherein: $R^3$, $R^4$, $R^5$ each are independently selected from H, methyl, cyclopropyl, or phenyl; or, $R^3$, $R^4$ and carbon atoms linked thereto together form

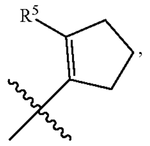

$R^5$ being H.

8. The compound according to claim 2 or a stereoisomer, a pharmaceutically acceptable salt or a pharmaceutically acceptable solvate thereof, wherein: $R^1$ is selected from:

1)

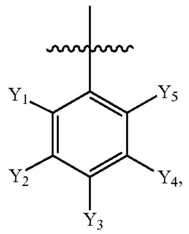

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, trifluoromethoxy, cyclopropylmethylene, N-methylpiperazinyl, 3-(N,N-dimethylamino)tetrahydropyrrolyl, 4-N,N-dimethylaminopiperidyl, 4-(N-methylpiperazinyl-1-) piperidyl, or 4-(N-methyl-1-piperazinyl) piperidyl-1-formyl;

2)

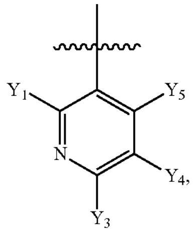

wherein:

$Y_1$, $Y_3$, $Y_4$, $Y_5$ each are independently selected from H, ethyl, methoxy, or 4-(N-methylpiperazinyl-1-) piperidyl, and $Y_1$, $Y_3$, $Y_4$, $Y_5$ are not hydrogen at the same time.

9. The compound according to claim 2 or a stereoisomer, a pharmaceutically acceptable salt or a pharmaceutically acceptable solvate thereof, wherein: $R^3$, $R^4$, $R^5$ are H.

10. The compound according to claim 3 or a stereoisomer, a pharmaceutically acceptable salt or a pharmaceutically acceptable solvate thereof, wherein: $R^1$ is selected from:

1)

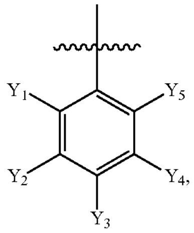

wherein, $Y_1$, $Y_2$, $Y_3$, $Y_4$, $Y_5$ each are independently selected from the following groups, and $Y_1$, $Y_2$, $Y_3$, $Y_4$, $Y_5$ are not hydrogen at the same time:

H, F, methyl, ethyl, isopropyl, cyclopropyl, methoxy, trifluoromethoxy, cyclopropylmethylene, N-methylpiperazinyl, 3-(N,N-dimethylamino)tetrahydropyrrolyl, 4-N,N-dimethylaminopiperidyl, 4-(N-methylpiperazinyl-1-) piperidyl, or 4-(N-methyl-1-piperazinyl) piperidyl-1-formyl;

2)

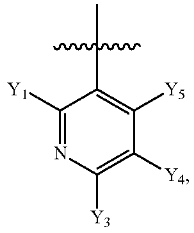

wherein:

$Y_1$, $Y_3$, $Y_4$, $Y_5$ each are independently selected from H, ethyl, methoxy, or 4-(N-methylpiperazinyl-1-) piperidyl, and $Y_1$, $Y_3$, $Y_4$, $Y_5$ are not hydrogen at the same time.

11. The compound according to claim 3 or a stereoisomer, a pharmaceutically acceptable salt or a pharmaceutically acceptable solvate thereof, wherein: $R^3$, $R^4$, $R^5$ are H.

* * * * *